United States Patent
Elbaz et al.

(10) Patent No.: US 12,263,063 B2
(45) Date of Patent: Apr. 1, 2025

(54) INTRAORAL SCANNING APPARATUS

(71) Applicant: Align Technology, Inc., San Jose, CA (US)

(72) Inventors: Gilad Elbaz, Tel Aviv (IL); Erez Lampert, Rehovot (IL); Yossef Atiya, Maccabim (IL); Avi Kopelman, Palo Alto, CA (US); Ofer Saphier, Rehovot (IL); Maayan Moshe, Ramat HaSharon (IL); Shai Ayal, Shoham (IL); Michael Sabina, Campbell, CA (US); Eric Kuo, San Jose, CA (US); Assaf Weiss, Yavne (IL); Doron Malka, Tel Aviv (IL); Eliahou Franklin Nizard, Jerusalem (IL); Ido Tishel, Kfar Bilu (IL)

(73) Assignee: Align Technology, Inc., San Jose, CA (US)

(*) Notice: Subject to any disclaimer, the term of this patent is extended or adjusted under 35 U.S.C. 154(b) by 0 days.

(21) Appl. No.: 18/536,966

(22) Filed: Dec. 12, 2023

(65) Prior Publication Data
US 2024/0115361 A1   Apr. 11, 2024

Related U.S. Application Data

(63) Continuation of application No. 18/295,254, filed on Apr. 3, 2023, now Pat. No. 11,883,259, which is a continuation of application No. 17/146,474, filed on Jan. 11, 2021, now Pat. No. 11,628,046, which is a continuation of application No. 16/814,906, filed on Mar. 10, 2020, now Pat. No. 10,888,400, which is a
(Continued)

(51) Int. Cl.
*A61C 9/00*   (2006.01)
*A61B 1/00*   (2006.01)
(Continued)

(52) U.S. Cl.
CPC ........ *A61C 9/0053* (2013.01); *A61B 1/00009* (2013.01); *A61B 1/00016* (2013.01);
(Continued)

(58) Field of Classification Search
None
See application file for complete search history.

(56) References Cited

U.S. PATENT DOCUMENTS

RE49,605 E   8/2023   Kopelman
11,806,210 B2   11/2023   Moalem
(Continued)

FOREIGN PATENT DOCUMENTS

CN   101689309 A   3/2010
EP   2166303 A1   3/2010
(Continued)

OTHER PUBLICATIONS

Angelino et al. Near-Infrared Imaging for Detecting Caries and Structural Deformities in Teeth, Digital Object Identifier 10.1109/JTEHM.2017.2695194 (Year: 2017).*

*Primary Examiner* — Yingchun He
(74) *Attorney, Agent, or Firm* — Shay Glenn LLP

(57) ABSTRACT

Methods and apparatuses for generating and displaying a model of a subject's teeth. Described herein are intraoral scanning methods and apparatuses for generating a three-dimensional model of a subject's intraoral region (e.g., teeth). These methods and apparatuses may be used for identifying and evaluating lesions, caries and cracks in the teeth.

21 Claims, 54 Drawing Sheets

Related U.S. Application Data continuation of application No. 16/706,461, filed on Dec. 6, 2019, now Pat. No. 11,357,603, which is a continuation of application No. 16/410,949, filed on May 13, 2019, now Pat. No. 10,507,087, which is a continuation-in-part of application No. 16/258,516, filed on Jan. 25, 2019, now Pat. No. 10,390,913, and a continuation-in-part of application No. 15/662,250, filed on Jul. 27, 2017, now Pat. No. 10,380,212.

(60) Provisional application No. 62/758,503, filed on Nov. 9, 2018, provisional application No. 62/622,798, filed on Jan. 26, 2018, provisional application No. 62/517,467, filed on Jun. 9, 2017, provisional application No. 62/477,387, filed on Mar. 27, 2017, provisional application No. 62/367,607, filed on Jul. 27, 2016.

(51) Int. Cl.
- A61B 1/04 (2006.01)
- A61B 1/06 (2006.01)
- A61B 1/24 (2006.01)

(52) U.S. Cl.
CPC ...... *A61B 1/00045* (2013.01); *A61B 1/00194* (2022.02); *A61B 1/046* (2022.02); *A61B 1/0638* (2013.01); *A61B 1/24* (2013.01)

(56) References Cited

U.S. PATENT DOCUMENTS

| | | |
|---|---|---|
| D1,026,227 S | 5/2024 | Ginzburg et al. |
| 12,033,742 B2 | 7/2024 | Farkash et al. |
| 12,127,814 B2 | 10/2024 | Elbaz et al. |
| 2014/0199650 A1 | 7/2014 | Moffson et al. |
| 2015/0305669 A1 | 10/2015 | Hultgren |
| 2016/0015246 A1 | 1/2016 | Clausen et al. |
| 2017/0231721 A1 | 8/2017 | Akeel et al. |
| 2020/0315754 A1 | 10/2020 | Ciriello et al. |
| 2021/0321872 A1 | 10/2021 | Saphier et al. |
| 2022/0233078 A1 | 7/2022 | Fridman et al. |
| 2022/0323190 A1 | 10/2022 | Kopelman et al. |
| 2022/0369910 A1 | 11/2022 | Gorfinkel et al. |
| 2023/0021695 A1 | 1/2023 | Atiya et al. |
| 2023/0025243 A1 | 1/2023 | Atiya et al. |
| 2023/0042643 A1 | 2/2023 | Saphier et al. |
| 2023/0068727 A1 | 3/2023 | Saphier et al. |
| 2023/0309800 A1 | 10/2023 | Farkash et al. |
| 2023/0346514 A1 | 11/2023 | Coslovsky et al. |
| 2023/0380942 A1 | 11/2023 | Fain et al. |
| 2023/0414331 A1 | 12/2023 | Saphier |
| 2024/0024076 A1 | 1/2024 | Fridman |
| 2024/0033057 A1 | 2/2024 | Saphier et al. |
| 2024/0036448 A1 | 2/2024 | Atiya et al. |
| 2024/0115196 A1 | 4/2024 | Moshe et al. |
| 2024/0122446 A1 | 4/2024 | Fridman et al. |
| 2024/0164624 A1 | 5/2024 | Shalev et al. |
| 2024/0197448 A1 | 6/2024 | Saphier et al. |
| 2024/0202921 A1 | 6/2024 | Alkabetz et al. |
| 2024/0245495 A1 | 7/2024 | Moalem et al. |
| 2024/0285379 A1 | 8/2024 | Saphier et al. |

FOREIGN PATENT DOCUMENTS

| | | |
|---|---|---|
| EP | 2363094 A2 | 9/2011 |
| JP | 2016174903 A | 10/2016 |

\* cited by examiner

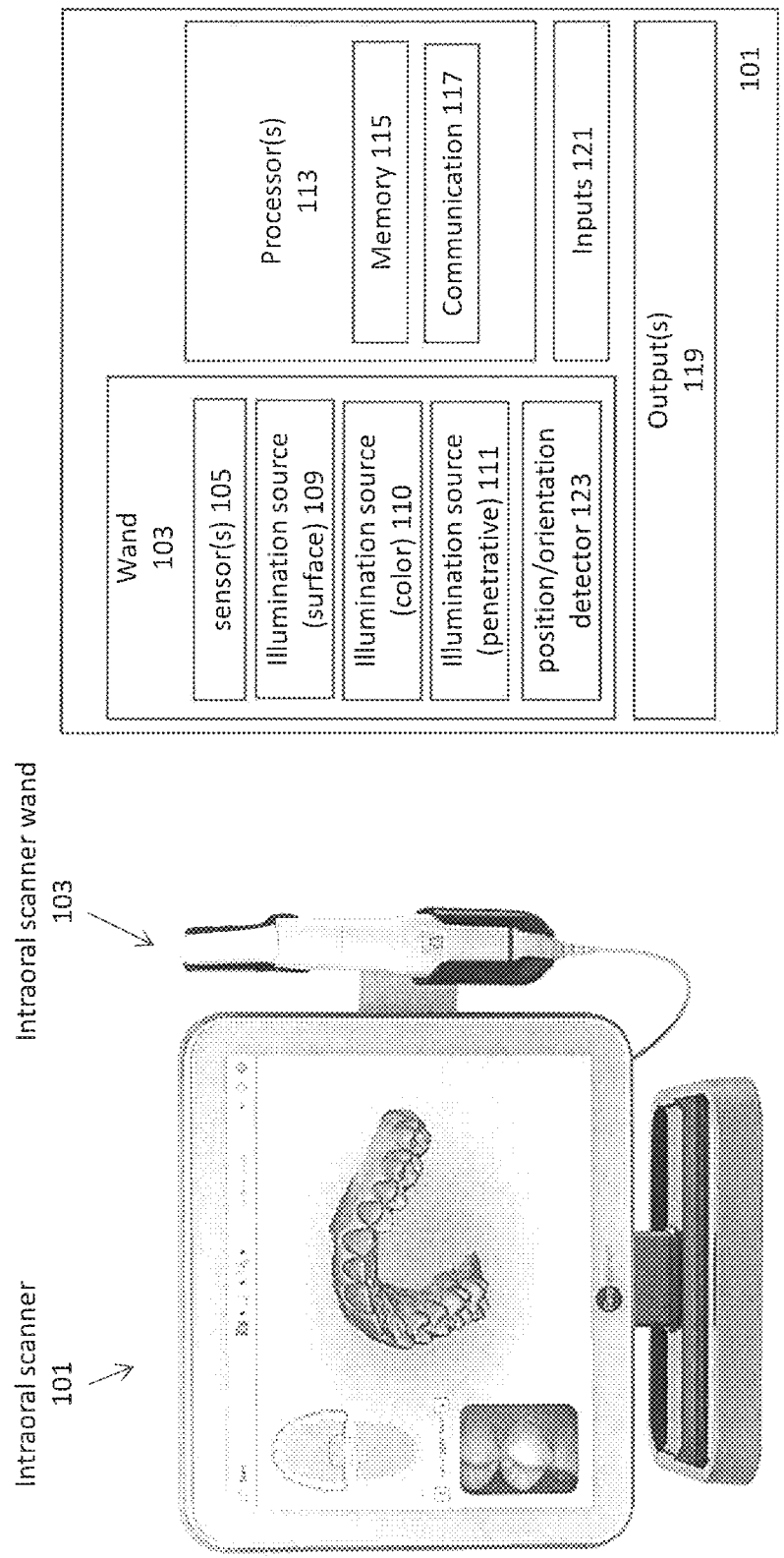

180° configuration

90° configuration

Right LED on – left camera capture

Left LED on – right camera capture

Both LEDs on – wand's sensor capture

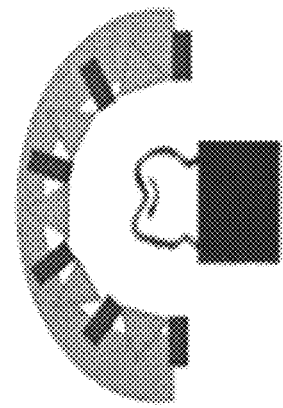
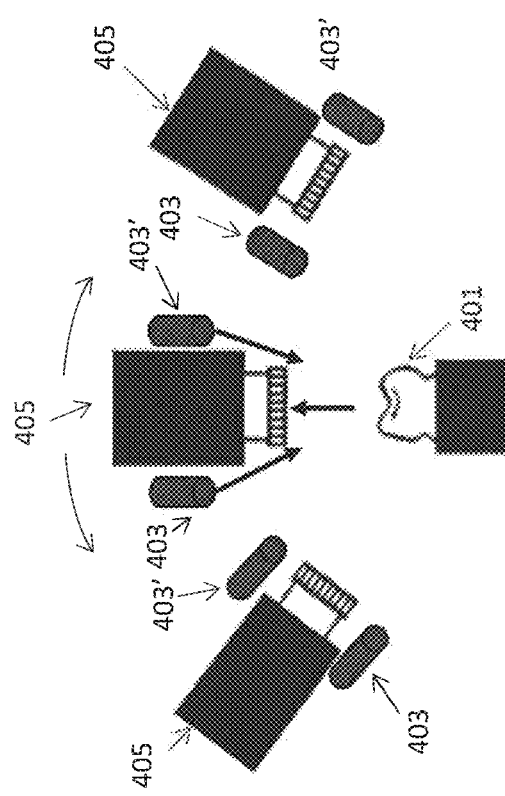
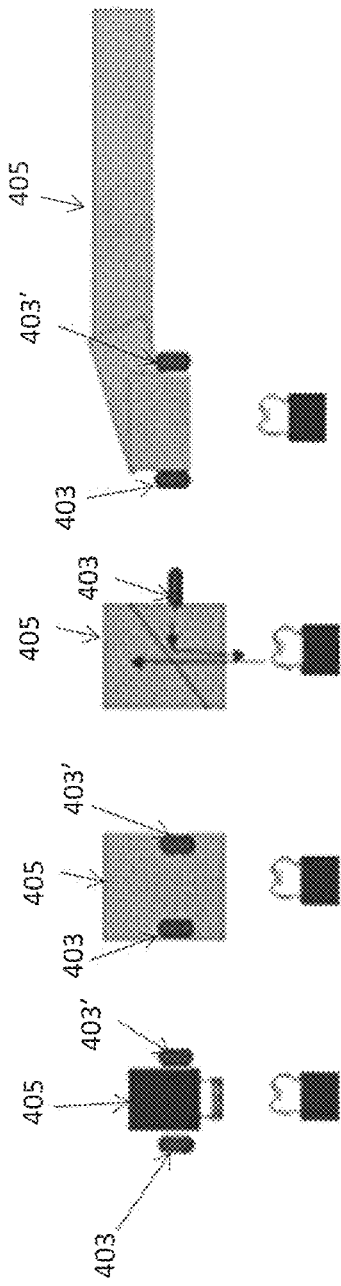

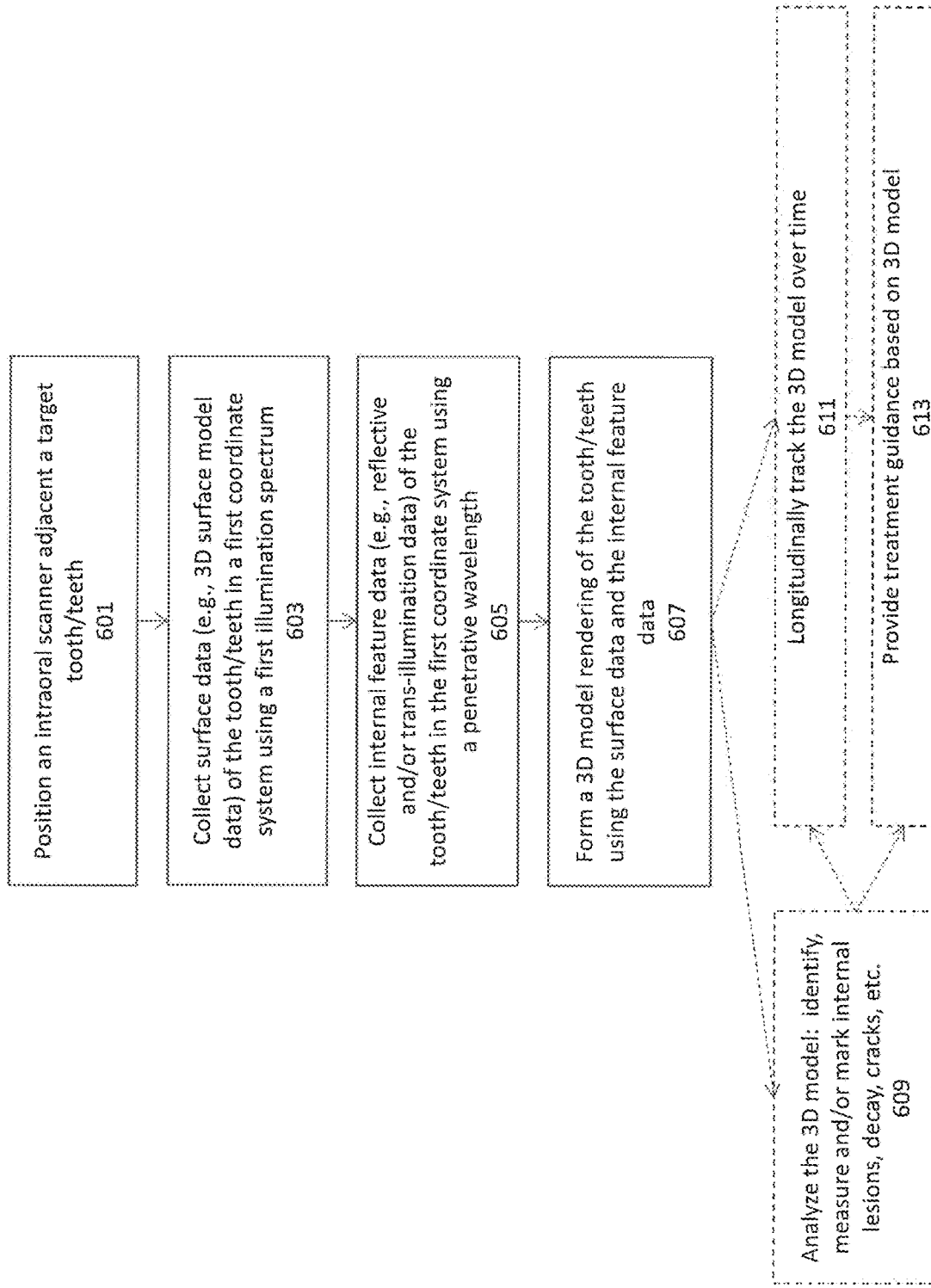

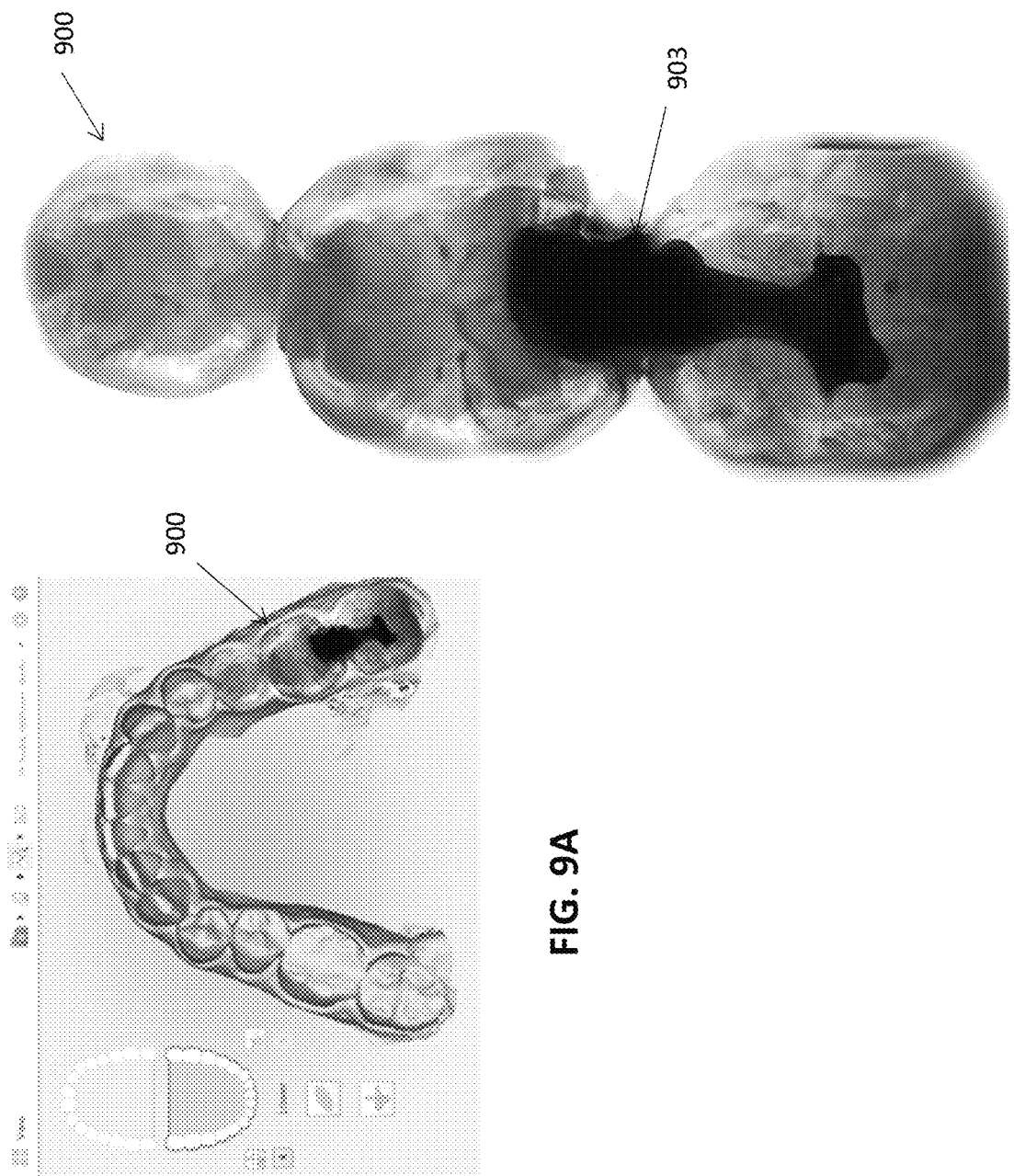

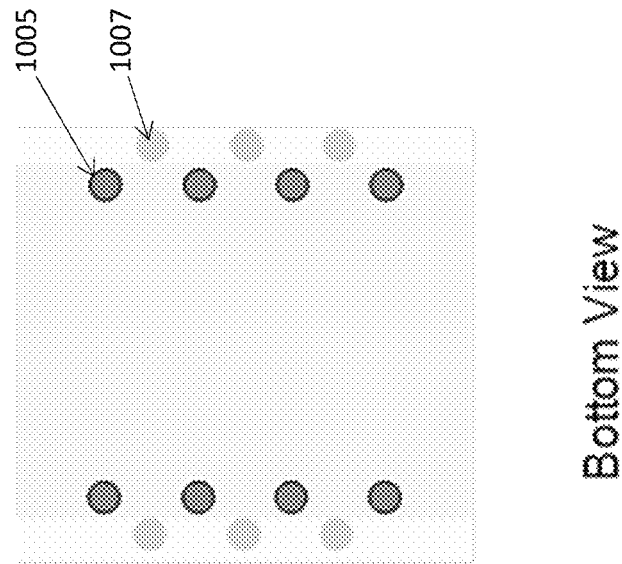
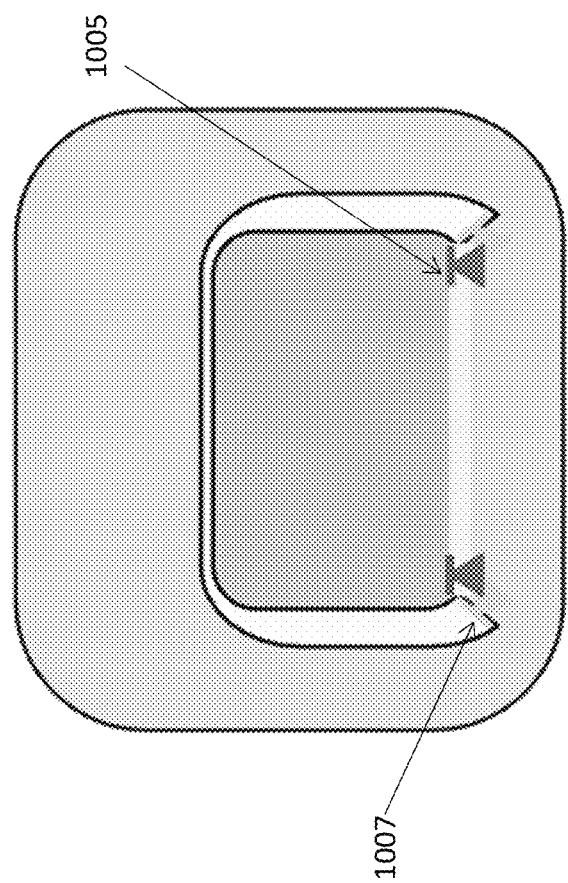
FIG. 10B
FIG. 10A

FIG. 11B
FIG. 11A
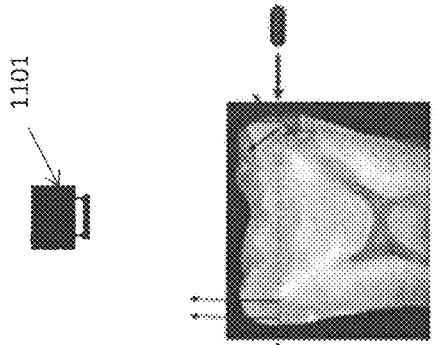
FIG. 11C
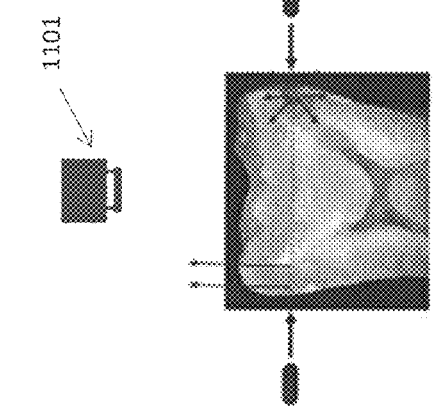
Above lesion
FIG. 11F
Mid-lesion
FIG. 11E
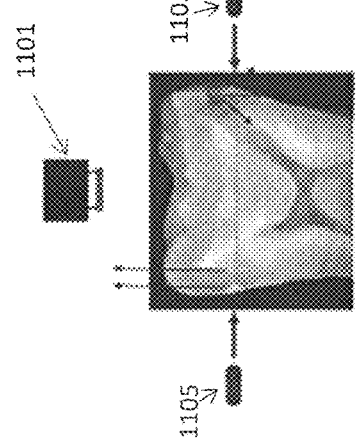
Bellow lesion
FIG. 11D
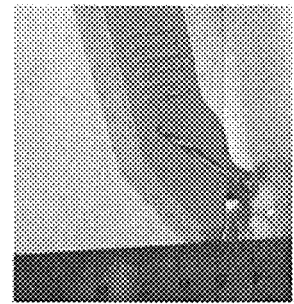
FIG. 11I
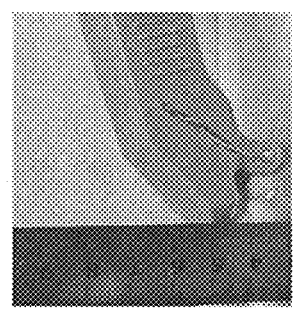
FIG. 11H
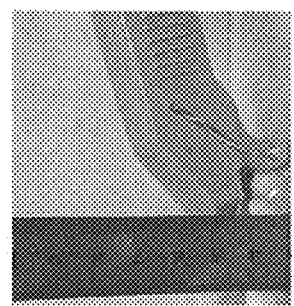
FIG. 11G

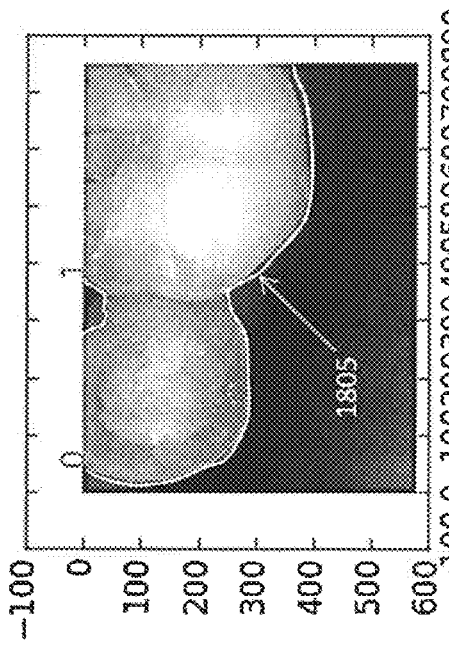
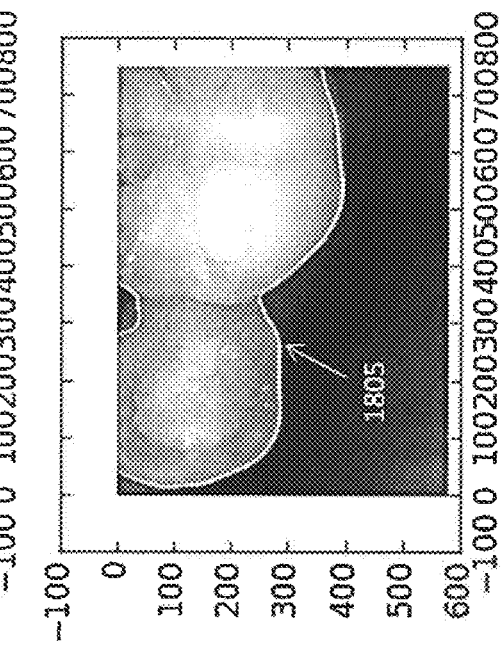
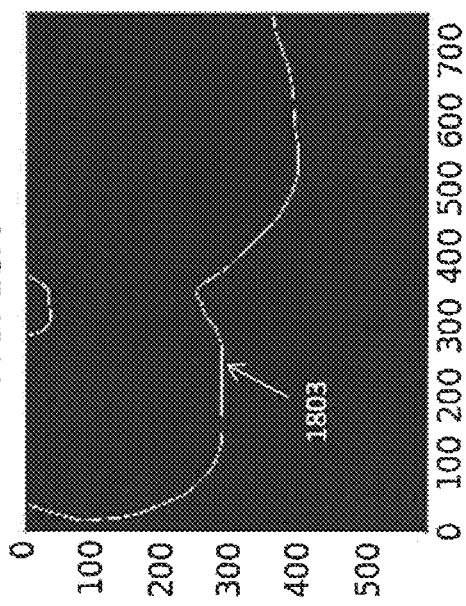
FIG. 18A
FIG. 18B
FIG. 18C

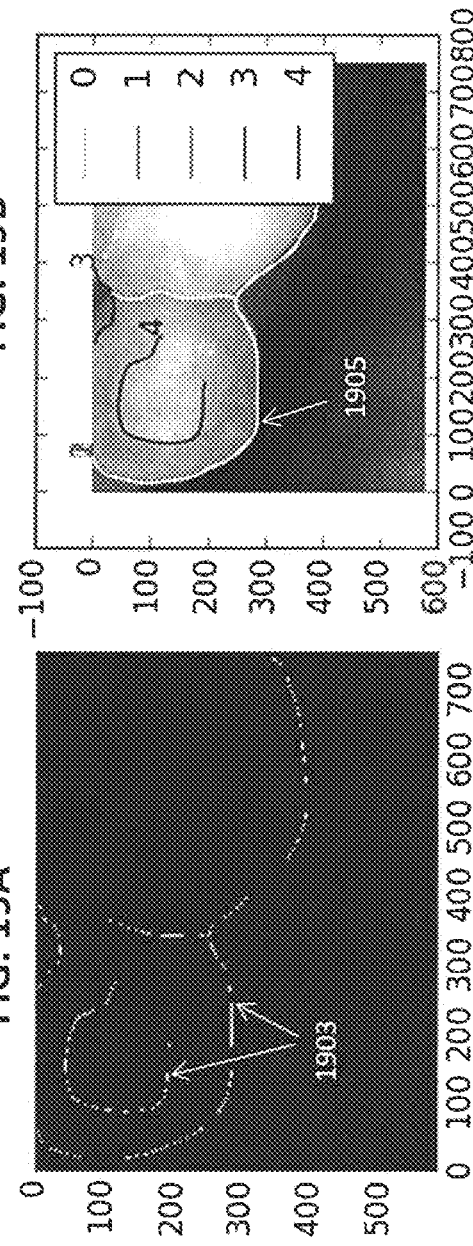
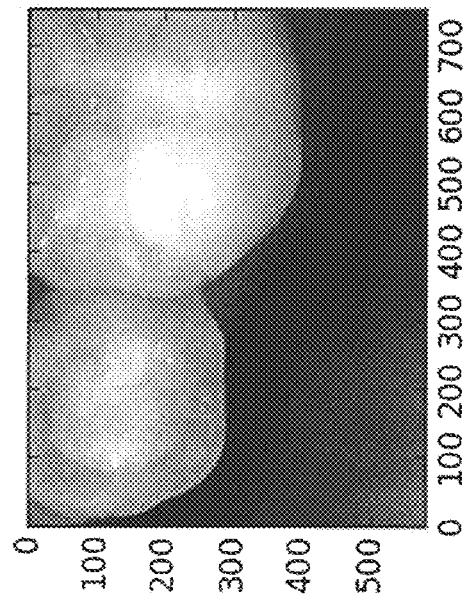
FIG. 19A  FIG. 19B  FIG. 19C

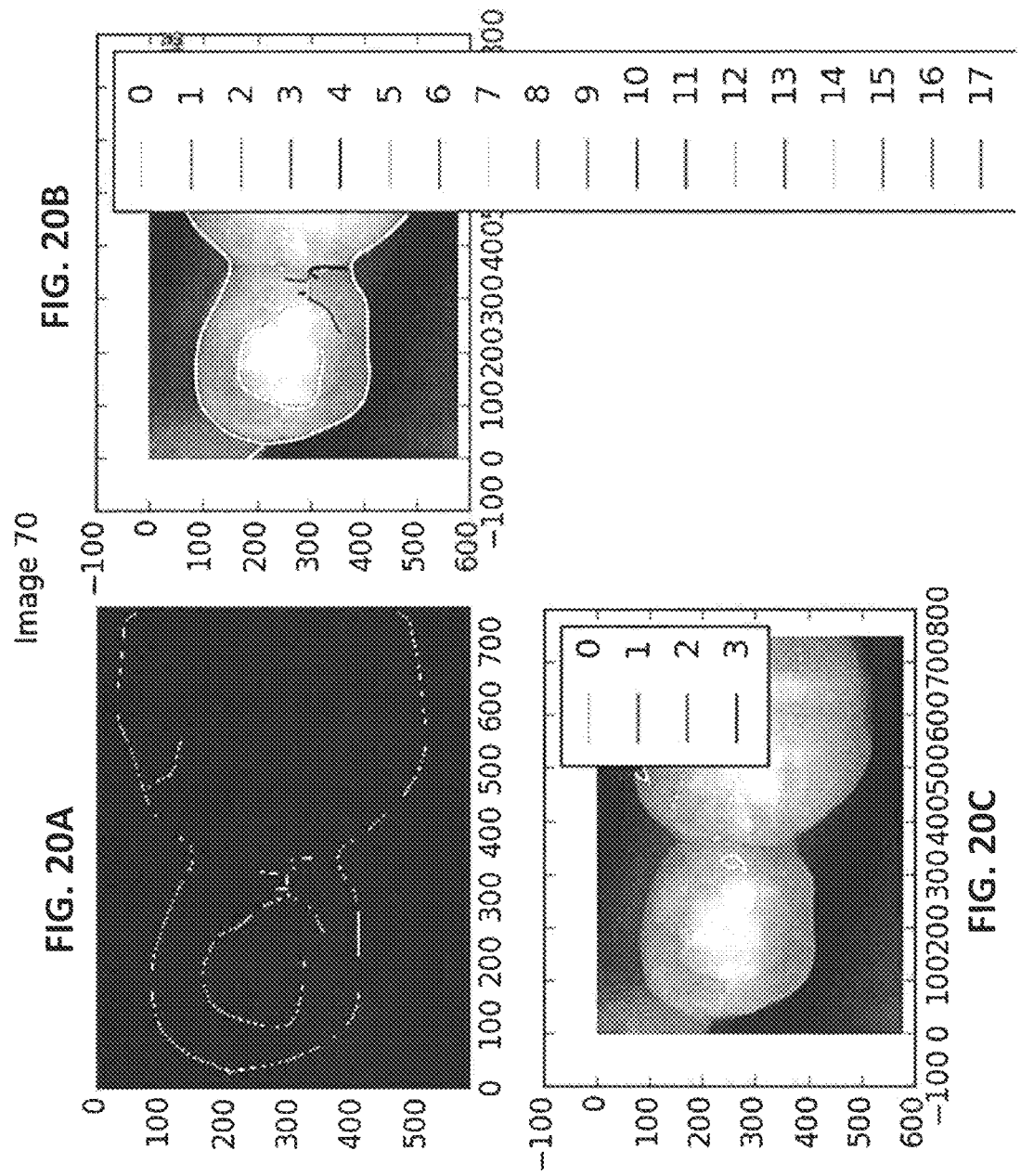

Image 161

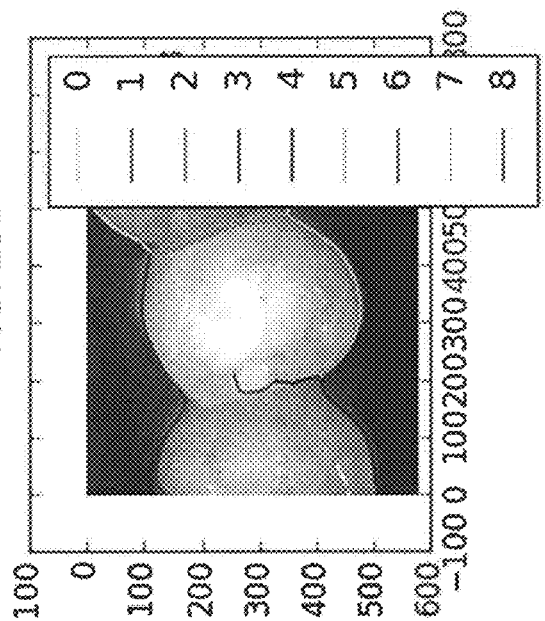
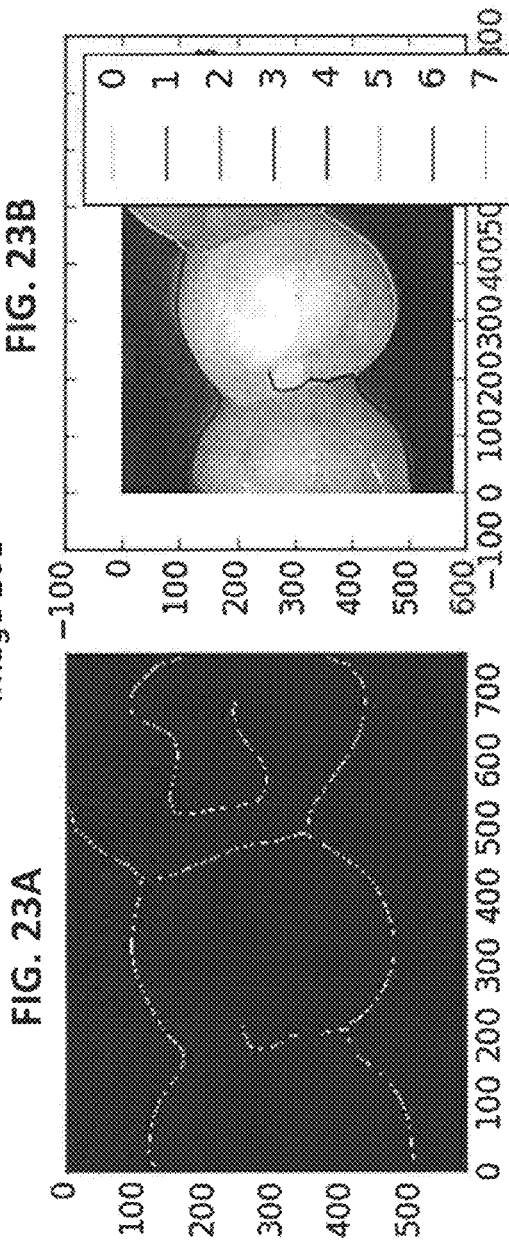
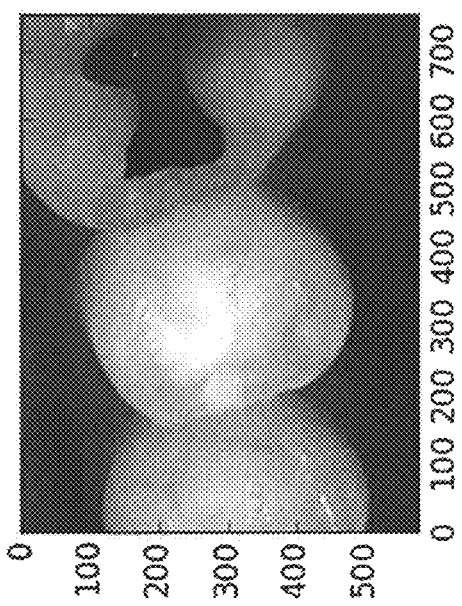
FIG. 23B
FIG. 23A
FIG. 23C

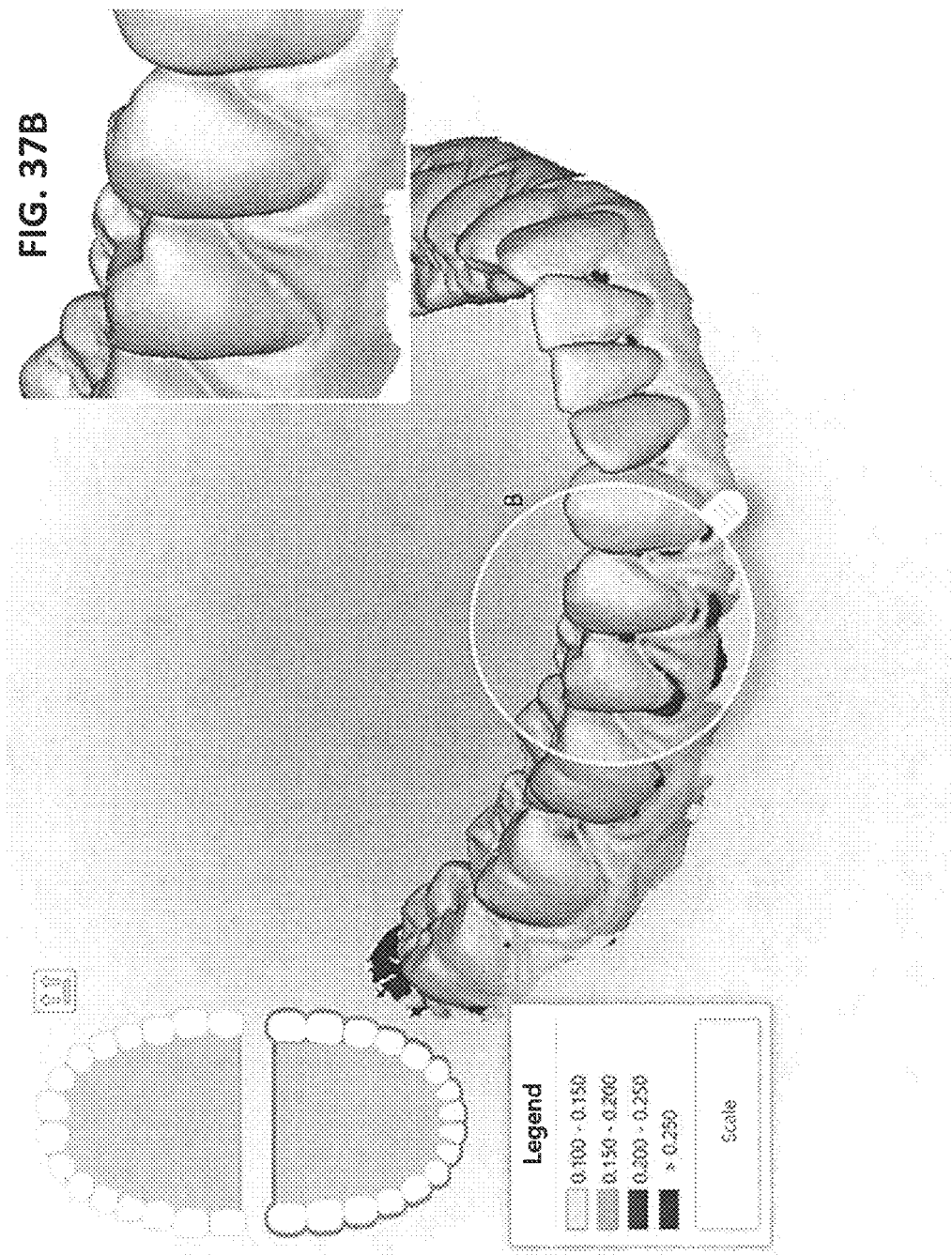

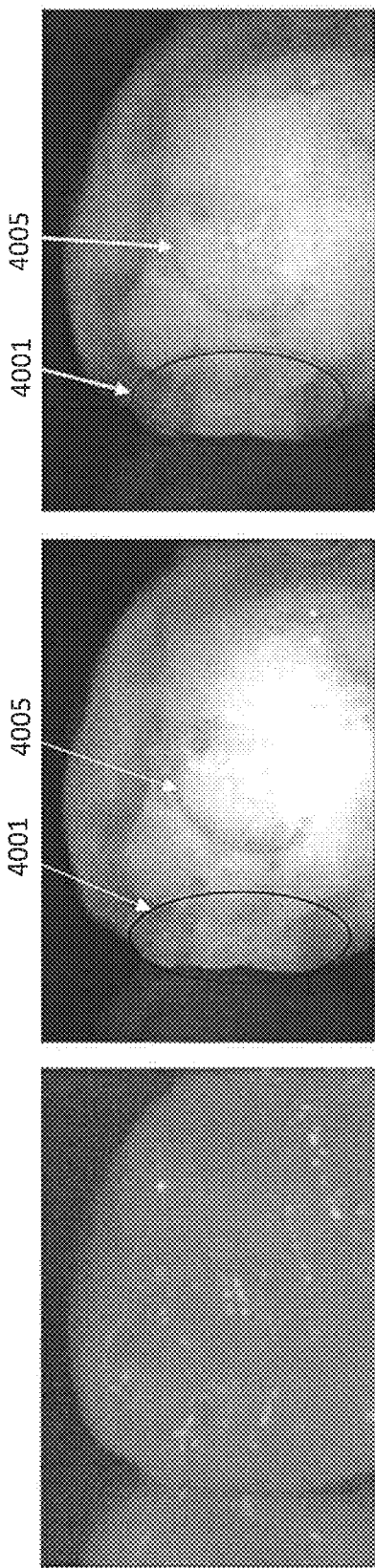

4600

Identify one or more actionable dental features from one or more records (e.g., one or more images or sets of images of the patient's teeth taken with different imaging modalities)
4601

Flag and/or record (e.g., in a collection of putative actionable dental features) each actionable dental feature identified, including recording a location of the actionable dental feature (e.g., on the originating record) and/or one or more of: type of actionable dental features, grade/degree of confidence of the actionable dental feature, etc.
4603

Map the putative actionable dental features to corresponding regions of one or more additional records (e.g., using a 3D volumetric model, by direct mapping, etc.)
4605

Adjust or determine a confidence score for each potential actionable dental features identified, based on the appearance at the corresponding location in the additional record(s)
4607

Filter and/or threshold the composite rank/score (e.g., confidence level) for each of the potential actionable dental feature(s) after comparing across records
4609

Store, present and/or transmit any of the potential actionable dental features above threshold (e.g., display for a dental practitioner)
4611

FIG. 46

INTRAORAL SCANNING APPARATUS

CLAIM OF PRIORITY

This patent application is a continuation of U.S. patent application Ser. No. 18/295,254, filed Apr. 3, 2023, titled "INTRAORAL SCANNING APPARATUS," now U.S. Patent Application Publication No. 2023/0240819, which is a continuation of U.S. patent application Ser. No. 17/146,474, filed Jan. 11, 2021, titled "METHODS AND APPARATUSES FOR FORMING A MODEL OF A SUBJECT'S TEETH," now U.S. Pat. No. 11,628,046, which is a continuation of U.S. patent application Ser. No. 16/814,906, filed Mar. 10, 2020, titled "METHODS AND APPARATUSES FOR FORMING A THREE-DIMENSIONAL VOLUMETRIC MODEL OF A SUBJECT'S TEETH," now U.S. Pat. No. 10,888,400, which is a continuation of U.S. patent application Ser. No. 16/706,461, filed Dec. 6, 2019, titled "METHODS AND APPARATUSES FOR FORMING A THREE-DIMENSIONAL VOLUMETRIC MODEL OF A SUBJECT'S TEETH," now U.S. Pat. No. 11,357,603, which is a continuation of U.S. patent application Ser. No. 16/410,949, titled "METHODS AND APPARATUSES FOR FORMING A THREE-DIMENSIONAL VOLUMETRIC MODEL OF A SUBJECT'S TEETH," filed May 13, 2019, now U.S. Pat. No. 10,507,087, which is a continuation-in-part of U.S. patent application Ser. No. 15/662,250, titled "METHODS AND APPARATUSES FOR FORMING A THREE-DIMENSIONAL VOLUMETRIC MODEL OF A SUBJECT'S TEETH," filed Jul. 27, 2017, now U.S. Pat. No. 10,380,212, which claims priority to each of: U.S. Provisional Patent Application No. 62/367,607, titled "INTRAORAL SCANNER WITH DENTAL DIAGNOSTICS CAPABILITIES," and filed on Jul. 27, 2016; U.S. Provisional Patent Application No. 62/477,387, titled "INTRAORAL SCANNER WITH DENTAL DIAGNOSTICS CAPABILITIES," filed on Mar. 27, 2017; and U.S. Provisional Patent Application No. 62/517,467, titled "MINIMAL VALUE LIFTING TO FORM A VOLUMETRIC MODEL OF AN OBJECT," filed on Jun. 9, 2017. Each of these is herein incorporated by reference in its entirety.

U.S. patent application Ser. No. 16/410,949 is also a continuation-in-part of U.S. patent application Ser. No. 16/258,516, titled "DIAGNOSTIC INTRAORAL SCANNING," filed Jan. 25, 2019, now U.S. Pat. No. 10,390,913, which claims priority to U.S. Provisional Patent Application No. 62/622,798, titled "DIAGNOSTIC INTRAORAL SCANNERS," filed on Jan. 26, 2018, and U.S. Provisional Patent Application No. 62/758,503, titled "DIAGNOSTIC INTRAORAL SCANNERS," and filed Nov. 9, 2018, each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The methods and apparatuses described herein may relate to optical scanners, and particularly for generating three-dimensional representations of objects. In particular, described herein are methods and apparatuses that may be useful in scanning, including 3D scanning, and analyzing the intraoral cavity for diagnosis, treatment, longitudinal tracking, tooth measurement, and detection of dental caries and cracks. These methods and apparatuses may generate volumetric models of the internal structure of the teeth, and/or may include color scanning.

BACKGROUND

Many dental and orthodontic procedures can benefit from accurate three-dimensional (3D) descriptions of a patient's dentation and intraoral cavity. In particular, it would be helpful to provide a three-dimensional description of both the surface, and internal structures of the teeth, including the enamel and dentin, as well as caries and the general internal composition of the tooth volume. Although purely surface representations of the 3D surfaces of teeth have proven extremely useful in the design and fabrication of dental prostheses (e.g., crowns or bridges), and treatment plans, the ability to image internal structures including the development of caries and cracks in the enamel and underlying dentin, would be tremendously useful, particularly in conjunction with a surface topographical mapping.

Historically, ionizing radiation (e.g., X-rays) have been used to image into the teeth. For example, X-Ray bitewing radiograms are often used to provide non-quantitative images into the teeth. However, in addition to the risk of ionizing radiation, such images are typically limited in their ability to show features and may involve a lengthy and expensive procedure to take. Some intraoral features such as soft tissues, plaque and soft calculus may not be easily visualized via x-ray because of their low density. Other techniques, such as cone beam computed tomography (CBCT) may provide tomographic images, but still require ionizing radiation.

Thus, it would be beneficial to provide methods and apparatuses, including devices and systems, such as intraoral scanning systems, that may be used to model a subject's tooth or teeth and include both external (surface) and internal (within the enamel and dentin) structures and composition using non-ionizing radiation. The model of the subject's teeth may be a 3D volumetric model or a panoramic image. In particular, it would be helpful to provide methods and apparatuses that may use a single apparatus to provide this capability. There is a need for improved methods and systems for scanning an intraoral cavity of a patient, and/or for automating the identification and analysis of dental caries.

SUMMARY OF THE DISCLOSURE

Described herein are methods and apparatuses (e.g., devices and systems) that apply scans of both external and/or internal structures of teeth. These methods and apparatuses may generate and/or manipulate a model of a subject's oral cavity (e.g. teeth, jaw, palate, gingiva, etc.) that may include both surface topography and internal features (e.g., dentin, dental filling materials (including bases and linings), cracks and/or caries). Apparatuses for performing both surface and penetrative scanning of the teeth may include intraoral scanners for scanning into or around a subject's oral cavity and that are equipped with a light source or light sources that can illuminate in two or more spectral ranges: a surface-feature illuminating spectral range (e.g., visible light) and a penetrative spectral range (e.g. IR range, and particularly "near-IR," including but not limited to 850 nm). The scanning apparatus may also include one or more sensors for detecting the emitted light and one or more processors for controlling operation of the scanning and for analyzing the received light from both the first spectral range and the second spectral range to generate a model of the subject's teeth including the surface of the teeth and features within the teeth, including within the enamel (and/or enamel-like restorations) and dentin. The generated mode may be a 3D volumetric model or a panoramic image.

As used herein, a volumetric model may include a virtual representation of an object in three dimensions in which internal regions (structures, etc.) are arranged within the volume in three physical dimensions in proportion and relative relation to the other internal and surface features of the object which is being modeled. For example, a volumetric representation of a tooth may include the outer surface as well as internal structures within the tooth (beneath the tooth surface) proportionately arranged relative to the tooth, so that a section through the volumetric model would substantially correspond to a section through the tooth, showing position and size of internal structures; a volumetric model may be section from any (e.g., arbitrary) direction and correspond to equivalent sections through the object being modeled. A volumetric model may be electronic or physical. A physical volumetric model may be formed, e.g., by 3D printing, or the like. The volumetric models described herein may extend into the volume completely (e.g., through the entire volume, e.g., the volume of the teeth) or partially (e.g., into the volume being modeled for some minimum depth, e.g., 2 mm, 3 mm, 4 mm, 5 mm, 6 mm, 7 mm, 8 mm, 9 mm, 10 mm, 12 mm, etc.).

The methods described herein typically include methods for generating a model of a subject's teeth typically generating a 3D model or rendering of the teeth that include both surface and internal features. Non-ionizing methods of imaging and/or detecting internal structures may be used, such as taking images using a penetrating wavelength to view structures within the teeth by illuminating them using one or more penetrative spectral ranges (wavelengths), including using trans-illumination (e.g., illuminating from one side and capturing light from the opposite side after passing through the object), and/or small-angle penetration imaging (e.g., reflective imaging, capturing light that has been reflected/scattered from internal structures when illuminating with a penetrating wavelength). In particular, multiple penetration images may be taken from the same relative position. Although traditional penetration imaging techniques (e.g., trans-illumination) may be used, in which the angle between the light emitter illumination direction and the detector (e.g., camera) view angle is 90 degrees or 180 degrees, also described herein are methods and apparatuses in which the angle is much smaller (e.g., between 0 degrees and 25 degrees, between 0 degrees and 20 degrees, between 0 degrees and 15 degrees, between 0 degrees and 10 degrees, etc.). Smaller angles (e.g., 0-15°) may be particularly beneficial because the illumination (light source) and sensing (detector(s), e.g., camera(s), etc.) may be closer to each other, and may provide a scanning wand for the intraoral scanner that can be more easily positioned and moved around a subject's teeth. These small-angle penetration images and imaging techniques may also be referred to herein as reflective illumination and/or imaging, or as reflective/scattering imaging. In general penetrating imaging may refer to any appropriate type of penetrating imaging unless otherwise specified, including trans-illumination, small-angle penetration imaging, etc. However, small angles may also result in direct reflection from the surface of the object (e.g., teeth), which may obscure internal structures.

The methods and apparatuses described here are particularly effective in combining a 3D surface model of the tooth or teeth with the imaged internal features such as lesions (caries, cracks, etc.) that may be detected by the use of penetration imaging by using an intraoral scanner that is adapted for separate but concurrent (or nearly-concurrent) detection of both the surface and internal features. Combining surface scanning and the penetration imaging may be performed by alternating or switching between these different modalities in a manner that allows the use of the same coordinate system for the two. Alternatively, both surface and penetrative scanning may be simultaneously viewed, for example, by selectively filtering the wavelengths imaged to separate the IR (near-IR) light from the visible light. The 3D surface data may therefore provide important reference and angle information for the internal structures, and may allow the interpretation and analysis of the penetrating images that may otherwise be difficult or impossible to interpret.

For example, described herein are methods for generating a model of a subject's teeth including the steps of: capturing three-dimensional (3D) surface model data of at least a portion of a subject's tooth using an intraoral scanner; taking a plurality of images into the tooth using a penetrative wavelength with the intraoral scanner; and forming a 3D model of the tooth including internal structure using the 3D surface model data and the plurality of images.

A method for generating a model of a subject's teeth may include: capturing three-dimensional (3D) surface model data of at least a portion of a subject's tooth with an intraoral scanner operating in a first imaging modality, wherein the 3D surface model data has a first coordinate system; taking a plurality of images into the tooth with the intraoral scanner operating in a second imaging modality using a penetrative wavelength, wherein the plurality of images reference the first coordinate system; and forming a 3D model of the tooth including internal structures using the 3D surface model data and the plurality of images. In general, the capturing the first wavelength does not necessarily capture images, but may directly capture a 3D surface scan. The second penetrating modalities may be captured as images processed as described herein.

In general, capturing the 3D surface model data may include determining a 3D surface topology using any appropriate method. For example, determining a 3D surface topology may include using confocal focusing. Capturing the 3D surface model data may comprise using on or more of: confocal scanning, stereo vision or structured light triangulation.

Any of the methods and apparatuses described herein may be used to model, image and/or render a 3D image of a single tooth or region of a tooth, multiple teeth, teeth and gums, or other intraoral structures, particularly from within a subject's mouth.

In general, the methods and apparatuses for performing them described herein include 3D color intraoral scanning/ scanners. For example, the methods may include capturing color intraoral 3D data.

As will be described in greater detail below, the method and apparatuses may control the switching between collecting surface data and collecting penetration imaging (penetrative) data. For example, any of these methods may include taking images using the penetrative wavelength as the 3D surface model data is being captured, e.g., by switching between the first imaging modality and the second (penetrative) imaging modality.

The same sensor or a different sensor may be used to collect the surface and internal feature data. For example, taking the plurality of images may comprise using a same sensor on the intraoral scanner to capture 3D surface model data and the plurality of images using the penetrative wavelength. Alternatively, a separate sensor or sensors may be used. For example, taking the plurality of images may comprise using a different sensor on the intraoral scanner to capture 3D surface model data and the plurality of images using the penetrative wavelength.

As mentioned, taking images of the tooth using the penetrative wavelength (or penetrative spectral range) may include taking penetration images at any angle between the illumination source and the sensor (e.g., detector or camera). In particular, internal feature (e.g., reflective imaging) data may be imaged using a small angle configuration, in which one or preferably more penetration images are taken at different orientations relative to the tooth/teeth. For example, taking the plurality of images may comprise illuminating the tooth at an angle of between 0° and 15° relative to a sensor (e.g., detector, camera, etc.) receiving the illumination from the tooth, reflecting off of the internal composition of the tooth/teeth. Taking the plurality of images (e.g., penetration images such as these small-angle penetration images) generally includes taking one or more (e.g., a plurality, including two or more, three or more, etc.) penetration images at different angles of the intraoral scanner relative to the tooth over the same region of the tooth. Thus, the same internal region of the tooth will appear in multiple different scans from different angles.

In general, any number of sensors may be included on the intraoral scanner, e.g., the wand of the intraoral scanner. Any appropriate sensor for detecting and recording the appropriate spectral range(s) (e.g., of light) may be used. Sensors may be referred to and may include detectors, cameras, and the like. For example, taking a plurality of images may comprise using a plurality of sensors on the intraoral scanner to capture the plurality of images using the penetrative wavelength.

The illumination used to take a penetration image is generally penetrative, so that it may at least partially penetrate and pass through the enamel and dentin of the teeth. Penetrative wavelengths of light may include generally infrared (and particularly near infrared) light. For example, light in the range of 700 to 1090 nm (e.g., 850 nm) may be used. Other wavelengths and ranges of wavelengths may be used, including wavelengths shorter than the visible spectrum. Thus, taking the plurality of images may comprise illuminating the tooth with infrared light. Taking the plurality of images (e.g., penetration images) may include illuminating the tooth with one or more of white light (including but not limited to white light trans-illumination), UV/Blue fluorescence and red light fluorescence.

The illumination used to take a penetration image can be considered semi-penetrative in the sense that internal tooth regions (e.g., points or voxels) may be visible from only a few camera positions and orientations; the point may be obstructed by other structures in some images which include the volume point in their field of view. In that sense, images that include the volume point in their field of view may not image this volume point. Thus, the methods and apparatuses described herein may take into account the high masking of volume points, unlike other penetrative scanning techniques such as CT, which uses X-ray imaging in which no masking occurs.

In general, any appropriate technique may be used to form the 3D models of the tooth including the (combined) surface and internal structures from the penetration imaging. These 3D models may be referred to as combined 3D surface/volume models, 3D volumetric surface models, or simply "3D models," or the like. As mentioned, both the surface data and the penetration imaging data may generally be in the same coordinate system. The two may be combined by using the common coordinate system. In some variations the surface data may be expressed as a surface model and the internal features added to this model. In some variations the data may be reconstructed into a three-dimensional model concurrently (after adding together). One or both datasets may be separately modified (e.g., filtered, subtracted, etc.). For example, forming the 3D model of the tooth including internal structures may comprise combing the 3D surface model data with an internal structure data (including volumetric data). Forming the 3D model of the tooth including internal structures may comprise combining the plurality of penetration images, wherein the plurality of penetration images may be taken from different angles using the intraoral scanner.

In any of the methods and apparatuses configured to perform these methods described herein, the data may be analyzed automatically or manually by the system. In particular, the method and apparatuses described herein may include examining internal features and/or identifying features of interest, including crack and caries. Features may be recognized based on feature-recognition criterion (e.g., dark or light regions in the penetration images), pattern-recognition, machine learning, or the like. Features may be marked, including coloring, labeling or the like. Feature may be marked directly in the 3D model, on the penetration image, or in a data structure that references (e.g., shares a coordinate system with) the 3D model of the tooth formed by the methods and apparatuses described herein.

Also described herein are apparatuses configured to perform any of the methods described. For example, described herein are intraoral scanning systems for generating a model of a subject's teeth that include: a hand-held wand having at least one sensor and a plurality of light sources, wherein the light sources are configured to emit light at a first spectral range and a second spectral range, wherein the second spectral range is penetrative; and one or more processors operably connected to the hand-held wand, the one or more processors configured to: generate a three-dimensional (3D) surface model of at least a portion of a subject's tooth using light from a first spectral range; and generate a 3D model of the subject's tooth including internal structures based on the 3D surface model and on a plurality of images taken at the second spectral range showing internal structures.

An intraoral scanning system for generating a model of a subject's teeth may include: a hand-held wand having at least one sensor and a plurality of light sources, wherein the light sources are configured to emit light at a first spectral range and a second spectral range, further wherein the second spectral range is penetrative; and one or more processors operably connected to the hand-held wand, the one or more processors configured to: determine surface information by using light in the first spectral range sensed by the hand-held wand, using a first coordinate system; generate a three-dimensional (3D) surface model of at least a portion of a subject's tooth using the surface information; take a plurality of images in the second spectral range, wherein the images reference the first coordinate system; and generate a 3D model of the subject's tooth including internal structures based on the 3D surface model and the a plurality of images.

Also described herein are methods of generating a model of a subject's teeth that include both surface and internal structures in which the same intraoral scanner is cycled between different modalities such as between surface scanning and penetration; additional modalities (e.g., laser florescence, etc.) may also alternatively be included. In general, although the examples described herein focus on the combination of surface and penetration, other internal scanning techniques (e.g., laser florescence) may be used instead or in addition to the internal feature imaging described herein.

For example, described herein are methods of generating a model of a subject's teeth including both surface and internal structures including the steps of: using a hand-held intraoral scanner to scan a portion of a subject's tooth using a first modality to capture three-dimensional (3D) surface model data of the tooth; using the hand-held intraoral scanner to scan the portion of the subject's tooth using a second modality to image into the tooth using a penetrative wavelength to capture internal data of the tooth; cycling between the first modality and the second modality, wherein cycling rapidly switches between the first modality and the second modality so that images using the penetrative wavelength share a coordinate system with the 3D surface model data captured in the first modality.

Any of the methods described herein may include automatically adjusting the duration of time spent scanning in first modality, the duration of time spent in the second modality, or the duration of time spent in the first and the second modality when cycling between the first modality and the second modality. For example, any of these methods may include automatically adjusting a duration of time spent scanning in first modality, the duration of time spent in the second modality, or the duration of time spent in the first and the second modality when cycling between the first modality and the second modality based on the captured 3D surface model data, the internal data, or both the 3D surface model data and the internal data. Thus, a method of generating a model of a subject's teeth may include: using a hand-held intraoral scanner to scan a portion of a subject's tooth using a first modality to capture three-dimensional (3D) surface model data of the tooth; using the hand-held intraoral scanner to scan the portion of the subject's tooth using a second modality to image into the tooth using a penetrative wavelength to capture internal data of the tooth; cycling between the first modality and the second modality using a scanning scheme wherein cycling rapidly switches between the first modality and the second modality so that the internal data uses the same coordinate system as the 3D surface model data captured in the first modality; and adjusting the scanning scheme based on the captured 3D surface model data, the internal data, or both the 3D surface model data and the internal data.

The scanning scheme adjustment may comprise adjusting based on determination of the quality of the captured 3D surface model data. Adjusting the scanning scheme may comprise automatically adjusting the scanning scheme, and/or adjusting a duration of scanning in the first modality and/or adjusting a duration of scanning in the second modality.

Any of these methods may include combining the 3D surface model data and the internal data of the tooth to form a 3D model of the tooth.

As mentioned above, capturing the 3D surface model data may include determining a 3D surface topology using confocal focusing/confocal scanning, stereo vision or structured light triangulation.

In general, cycling may comprise cycling between the first modality, the second modality, and a third modality, wherein cycling rapidly switches between the first modality, the second modality and the third modality so that images using the penetrative wavelength share a coordinate system with the 3D surface model captured in the first modality. The third modality may be another penetrative modality or a non-penetrative modality (e.g., color, a visual image the subject's tooth, etc.).

Using the hand-held intraoral scanner to scan the portion of the subject's tooth using the second modality may include illuminating the tooth at an angle of between 0° and 15° relative to a direction of view of the sensor receiving the illumination (e.g., small angle illumination). The step of using the hand-held intraoral scanner to scan the portion of the subject's tooth using the second modality may include taking a plurality of penetration images at a plurality of different angles between an illumination source and a sensor and/or at a plurality of different positions or angles relative to the tooth so that the same internal region of the tooth is imaged from different angles relative to the tooth.

As mentioned, any appropriate penetrative wavelength may be used, including infrared (e.g., near infrared). For example using the hand-held intraoral scanner to scan the portion of the subject's tooth using the second modality may comprise illuminating with one or more of: white light trans-illumination, UV/Blue fluorescence, and red light fluorescence.

Also described herein are intraoral scanning systems for generating a model of a subject's teeth that are configured to cycle between scanning modes. For example, described herein are intraoral scanning systems comprising: a hand-held intraoral wand having at least one sensor and a plurality of light sources, wherein the light sources are configured to emit light at a first spectral range and at a second spectral range, further wherein the second spectral range is penetrative; and one or more processors operably connected to the hand-held intraoral wand, the one or more processors configured to cause the wand to cycle between a first mode and a second mode, wherein in the first mode the wand emits light at the first spectral range for a first duration and the one or more processors receives three-dimensional (3D) surface data in response, and wherein in the second mode the wand emits light at the second spectral range for a second duration and the one or more processors receives image data in response.

An intraoral scanning system for generating a model of a subject's teeth may include: a hand-held intraoral wand having at least one sensor and a plurality of light sources, wherein the light sources are configured to emit light at a first spectral range and at a second spectral range, further wherein the second spectral range is penetrative; and one or more processors operably connected to the wand, the one or more processors configured to cause the wand to cycle between a first mode and a second mode, wherein in the first mode the wand emits light at the first spectral range for a first duration and the one or more processors receives three-dimensional (3D) surface data in response, and wherein in the second mode the wand emits light at the second spectral range for a second duration and the one or more processors receives image data in response; wherein the one or more processors is configured to adjusting the first duration and the second duration based on the received 3D surface data, the received image data, or both the 3D surface data and the image data. In any of the apparatuses described herein, one mode may be the surface scanning (3D surface), which may be, for example, at 680 nm. Another mode may be a penetrative scan, using, e.g., near-IR light (e.g., 850 nm). Another mode may be color imaging, using white light (e.g., approximately 400 to 600 nm).

Penetration imaging methods for visualizing internal structures using a hand-held intraoral scanner are also described. Thus, any of the general methods and apparatuses described herein may be configured specifically for using penetration imaging data to model a tooth or teeth to detect internal features such as crack and caries. For example, a method of imaging through a tooth to detect cracks and caries may include: taking a plurality of penetration images through the tooth at different orientations using a hand-held intraoral scanner in a first position, wherein the intraoral scanner is emitting light at a penetrative wavelength; determining surface location information using the intraoral scanner at the first position; and generating a three-dimensional (3D) model of the tooth using the plurality of penetration images and the surface location information.

Generating a 3D model of the tooth may comprise repeating the steps of taking the plurality of penetration images and generating the 3D model for a plurality of different locations.

Taking the plurality of penetration images through the tooth at different orientations may include taking penetration images in which each penetration image is taken using either or both of: a different illumination source or combination of illumination sources on the intraoral scanner emitting the penetrative wavelength or a different image sensor on the intraoral scanner taking the image.

In some variations taking the plurality of penetration images may comprise taking three or more penetration images.

Taking the plurality of penetration images through the tooth surface at different orientations may comprises taking penetration images using small angle illumination/viewing, for example, wherein, for each penetration image, an angle between emitted light and light received by an image sensor is between 0 and 15 degrees. For example, a method of imaging through a tooth to detect cracks and caries may include: scanning a tooth from multiple positions, wherein scanning comprises repeating, for each position taking a plurality of penetration images through the tooth at different orientations using an intraoral scanner, wherein the intraoral scanner is emitting light at a penetrative wavelength and wherein, for each penetration image, an angle between emitted light and light received by an image sensor is between 0 and 15 degrees, and determining surface location information using the intraoral scanner; and generating a three-dimensional (3D) model of the tooth using the penetration images and the surface location information.

As mentioned above, in addition to the apparatuses (e.g., scanning apparatuses, tooth modeling apparatuses, etc.) and methods of scanning, modeling and operating a scanning and/or modeling apparatus, also described herein are methods of reconstructing volumetric structures using images generated from one or more penetrative wavelengths.

For example, described herein are methods of reconstructing a volumetric structure from an object including semi-transparent strongly scattering regions (e.g., a tooth) for a range of radiation wavelengths. The method may include illuminating the object with a light source that is emitting (e.g., exclusively or primarily radiating) a penetrating wavelength, taking a plurality of images of the object with a camera sensitive to the penetrating wavelength (e.g., recording in the range of radiation wavelengths), receiving location data representing a location of the camera relative to the object for each of the plurality of images, generating for each point in a volume an upper bound on a scattering coefficient from the plurality of images and the location data, and generating an image of the object from the upper bound of scattering coefficients for each point. The penetrating wavelength of light applied to the object may be emitted from substantially the same direction as the camera. The image or images generated may illustrate features within the volume of the object, and the image may also include (or be modified to include) the outer boundary of the object, as well as the internal structure(s).

As used herein, a tooth may be described as an object including semi-transparent strongly scattering region or regions; in general, teeth may also include strong scattering regions (such as dentine), and lightly scattering, highly transparent regions (such as the enamel) at near-IR wavelengths. Teeth may also include regions having intermedia or mixed scattering properties, such as caries. The methods and apparatuses for performing volumetric scans described herein are well suited for mapping these different regions in the tooth/teeth.

A method of reconstructing a volumetric structure from an object including semi-transparent strongly scattering regions for a range of radiation wavelengths may include: taking a plurality of images of the object with a camera in the range of radiation wavelengths, wherein lighting for the plurality of images is projected substantially from a direction of the camera, receiving location data representing a location of the camera relative to the object for each of the plurality of images, generating for each point in a volume an upper bound on a scattering coefficient from the plurality of images and the location data, and generating an image of the object from the upper bound of scattering coefficients for each point.

The range of radiation wavelengths may be infrared or near infrared wavelength(s).

Any of these methods may also include receiving surface data representing an exterior surface of the object, wherein the generating step is performed for each point in the volume within the exterior surface of the object.

The object may comprise a tooth, having an exterior enamel surface and an interior dentin surface. Teeth are just one type of object including semi-transparent strongly scattering regions; other examples may include other both tissues (including soft and/or hard tissues), e.g., bone, etc. These objects including semi-transparent strongly scattering regions may include regions that are typically semi-transparent and strongly scattering for the penetrative wavelengths (e.g., the infrared or near infrared wavelengths), as described herein.

The location data may generally include position and orientation data of the camera at the time of capturing each of the plurality of images. For example, the location data may comprise three numerical coordinates in a three-dimensional space, and pitch, yaw, and roll of the camera.

Generating for each point in the volume the upper bound on scattering coefficients may comprise projecting each point of a 3D grid of points corresponding to the volume of the object onto each of the plurality images using a first calibration, producing a list of intensity values for each projected point, converting each intensity value on the list of intensity values to a scattering coefficient according to a volume response, and storing a minimum scattering coefficient value for each grid point from the list of scattering coefficient values.

For example, the first calibration may comprise a fixed pattern noise calibration to calibrate for sensor issues and image ghosts of the camera. The first calibration may comprise a camera calibration that determines a transformation for the camera that projects known points in space to points on an image.

Also described herein are methods of reconstructing a volumetric structure from a tooth, semi-transparent in a range of radiation wavelengths, the method comprising receiving, in a processor, a representation of a surface of the tooth in a first coordinate system, receiving, in the processor, a plurality of images of the tooth in the range of radiation wavelengths, the plurality of images taken with lighting projected substantially from a direction of a camera, receiving, in the processor, location data representing a location of the camera for each of the plurality of images, projecting each point of a grid of points corresponding to a volume within the surface of the tooth onto each of the plurality images using a first calibration, producing a list of intensity values for each projected point, converting each intensity value on the list of intensity values to a scattering coefficient according to a volume response, and storing a minimum scattering coefficient for each point into a list of minimum scattering coefficients.

Any of these methods may further comprise producing an image from the list of minimum scattering coefficients.

The location data may comprise position and orientation data of the camera (or cameras) at the time of capturing each of the plurality of images.

The first calibration may comprise a fixed pattern noise calibration to calibrate for sensor issues and image ghosts of the camera. In some embodiments, the first calibration may comprise a camera calibration that determines a transformation for the camera that projects known points in space to points on an image.

The method may further comprise receiving surface data representing an exterior surface of the object, wherein the projecting step is performed for each point inside the volume within the exterior surface of the object.

The grid of points may comprise a cubic grid.

Any of the methods described herein may be embodied as software, firmware and/or hardware. For example, any of these methods may be configured as non-transitory computing device readable medium having instructions stored thereon for performing the method.

For example, a non-transitory computing device readable medium having instructions stored thereon for reconstructing a volumetric structure from a tooth that is semi-transparent in a range of radiation wavelengths is described. The instructions may be executable by a processor to cause a computing device to receive a representation of a surface of the tooth in a first coordinate system, receive a plurality of images of the tooth in the range of radiation wavelengths, the plurality of images taken with lighting projected substantially from a direction of a camera, receive location data representing a location of the camera for each of the plurality of images, project each point of a grid of points corresponding to a volume of the tooth onto each of the plurality of images using a first calibration, produce a list of intensity values for each projected point, convert each intensity value on the list of intensity values to a scattering coefficient according to a volume response, and store a minimum scattering coefficient for each point into a list of minimum scattering coefficients, and produce an image from the list of minimum scattering coefficients.

The location data may comprise position and orientation data of the camera at the time of capturing each of the plurality of near-infrared images. The location data may comprise three numerical coordinates in a three-dimensional space, and pitch, yaw, and roll of the camera.

The first calibration may comprise a fixed pattern noise calibration to calibrate for sensor issues and image ghosts of the camera. The first calibration may comprise a camera calibration that determines a transformation for the camera that projects known points in space to points on an image.

The grid of points may be inside the tooth; as mentioned, the grid of points may comprise a cubic grid.

Alternatively or additionally to the use of scattering coefficients, any appropriate method of forming the internal structures of the patient's teeth using the penetrative wavelength images. For example, any of the apparatuses (e.g., systems, devices, software, etc.) and methods described herein may use the two-dimensional penetrative images along with position and/or orientation information about the scanner relative to the object being imaged (e.g., the teeth) to segment the 2D penetrative images to form a three-dimensional model of the teeth including an internal structure from within the teeth. As described, a penetrative image may refer to an images taken with a near-IR and/or IR wavelength), penetrating into the object. The position and/or orientation of the scanner may be a proxy for the position and/or orientation of the camera taking the images which is one the scanner (e.g., on a handheld wand).

For example, described herein are methods of modeling a subject's teeth, comprising: capturing, with an intraoral scanner, a plurality of images of an interior of the subject's teeth and a position and orientation of the intraoral scanner specific to each image of the plurality of images; segmenting the plurality of images to form an internal structure corresponding to a structure within the subject's teeth; using the position and orientation of the plurality of images to project the internal structure onto a three-dimensional model of the subject's teeth; and displaying the three-dimensional model of the subject's teeth including the internal structure.

In any of these methods and apparatuses, the 3D surface model may be concurrently captured using a non-penetrative wavelength (e.g., surface scan) while capturing the penetrative images. For example, capturing may comprise capturing surface images of the subject's teeth while capturing the plurality of images of the interior of the subject's teeth. The method may also include forming the three-dimensional model of the subject's teeth from the captured surface images. For example, forming the three-dimensional model of the subject's teeth may comprise determining a three-dimensional surface topology using confocal focusing. Capturing the surface images of the subject's teeth may comprise using confocal scanning, stereo vision or structured light triangulation.

In general, the same device (e.g., scanner) may model and/or display the 3D representation of the teeth, including the internal structures, alternatively or additionally a separate processor (e.g., remote to the scanner) may be used. Any of these methods may also include storing and/or transmitting plurality of penetrative images and the position and orientation of the intraoral scanner while capturing the plurality of two-dimensional images, including transmitting to a remote processor for performing the segmentation and later steps.

In any of the methods and apparatuses described herein, the 3D model including the internal structure(s) may be displayed while the scanner is operating. This may advantageously allow the user to see, in real-time or near real-time the internal structure(s) in the subject's teeth. Thus, any of these methods may include displaying the three-dimensional model as the images are captured.

Segmenting the plurality of images may comprise applying edge detection to the plurality of images to identify closed boundaries within the plurality of images. Segmenting the plurality of images may comprise forming a volumetric density map from the plurality of images to identify the internal structure. Segmenting the volumetric density map may include segmenting by identifying one or more iso-surfaces within the volumetric density map to identify the internal features. Any of these methods may include segmenting the volumetric density map to identify the internal feature (e.g., cracks, caries, dental fillings, dentin, etc.).

For example, an intraoral scanning apparatus configured to generate a model of a subject's teeth may include: an intraoral scanner having a plurality of light sources and a position and orientation sensor, wherein the light sources are configured to emit light at a first spectral range and at a second spectral range, further wherein the second spectral range is penetrative; and a processor operably connected to the intraoral scanner, the one or more processors configured to cause the scanner to capture a plurality of images and position and orientation of the intraoral scanner corresponding to each of the plurality of images when the intraoral scanner is emitting light at the second spectral range; wherein the processor is further configured to segment the plurality of images to form an internal structures corresponding to a structure within the subject's teeth, and to display or transmit a three-dimensional model of the subject's teeth including the internal structure.

The processors may be configured to segment the plurality of images by applying edge detection to the plurality of images to identify closed boundaries within the plurality of images. The processor may be configured to segment the plurality of images by forming a pixel density map from the plurality of images to identify the internal structure. The processor may be configured to identify closed segments within the pixel density map to identify the internal structure.

Also described herein are non-transitory computing device readable medium having instructions stored thereon that are executable by a processor to cause an intraoral scanning apparatus to: capture a plurality of images using a penetrative wavelength of light and a position and orientation of the intraoral scanner specific to each image of the plurality of images; segment the plurality of images to form an internal structure corresponding to a structure within a subject's teeth; use the position and orientation of the intraoral scanner specific to each image to project the internal structure onto a three-dimensional model of the subject's teeth; and display the three-dimensional model of the subject's teeth including the internal structure.

The non-transitory computing device readable medium having instructions may be further configured to cause the intraoral scanning apparatus to segment the plurality of images by applying edge detection to the plurality of images to identify closed boundaries within the plurality of images. The non-transitory computing device readable medium having instructions may be further configured to cause the intraoral scanning apparatus to segment the plurality of images by forming a pixel density map from the plurality of images to form the internal structure. The non-transitory computing device readable medium having instructions may be further configured to cause the intraoral scanning apparatus to segment the plurality of images by identifying closed segments within the pixel density map to form the internal structure.

Also described herein are non-transitory computing device readable medium having instructions stored thereon that are executable by a processor to cause a computing device to: receive, from a scanner, three-dimensional surface model data of a subject's teeth; receive, from the scanner, a plurality of images of an interior of the subject's teeth and position and orientation of the intraoral scanner specific to each image of the plurality of images; segment the plurality of images to form an internal structure of the subject's teeth; project the internal structure of the subject's teeth onto the three-dimensional surface model; and display the three-dimensional surface model showing the internal structure.

For example, described herein are methods for generating a three-dimensional (3D) volumetric model of a subject's teeth using an intraoral scanner, the method comprising: capturing 3D surface model data of at least a portion of the subject's teeth using an intraoral scanner as the intraoral scanner is moved over the teeth; taking a plurality of images into the teeth using a near-infrared (near-IR) wavelength with the intraoral scanner as the intraoral scanner is moved over the teeth so that multiple images of a same internal region of the teeth are imaged; determining, for each of the plurality of images into the teeth, a position of the intraoral scanner relative to the subject's teeth using the 3D surface model data; and forming the 3D volumetric model of the subject's teeth including internal features using the plurality of images and the position of the intraoral scanner relative to the subject's teeth.

A method for generating a three-dimensional (3D) volumetric model of a subject's teeth using an intraoral scanner may include: capturing 3D surface model data of at least a portion of the subject's teeth using an intraoral scanner as the intraoral scanner is moved over the teeth; taking a plurality of images into the teeth using a near-infrared (near-IR) wavelength as the intraoral scanner is moved over the teeth by emitting a near-IR light from the intraoral scanner in a first polarization, and detecting, in an image sensor in the intraoral scanner, the near-IR light returning to the intraoral scanner, wherein the near-IR light returning to the intraoral scanner is filtered to remove specular reflection by filtering near-IR light in the first polarization from the near-IR light returning to the intraoral scanner before it reaches the image sensor; determining, for each of the plurality of images into the teeth, a position of the intraoral scanner relative to the subject's teeth when each of the plurality of images is captured, using the 3D surface model data; and forming the 3D volumetric model of the subject's teeth including internal features using the plurality of images and the position of the intraoral scanner relative to the subject's teeth.

In any of these methods and apparatuses, the near-IR light returning to the intraoral scanner may be filtered to remove specular reflection by filtering all or nearly all of the near-IR light in the first polarization from the near-IR light returning to the intraoral scanner before it reaches the image sensor.

Also described herein are intraoral scanners scan both surface and internal structures. For example, an intraoral scanning system for generating a three-dimensional (3D) volumetric model of a subject's teeth may include: a handheld wand having at least one image sensor and a plurality of light sources, wherein the light sources are configured to emit light at a first spectral range and a second spectral range, wherein the second spectral range is within near-infrared (near-IR) range of wavelengths; and one or more processors operably connected to the hand-held wand, the one or more processors configured to: capture 3D surface model data of at least a portion of the subject's teeth as the intraoral scanner is moved over the teeth; take a plurality of images into the teeth using light in the second spectral range as the intraoral scanner is moved over the teeth so that multiple images of a same internal region of the teeth are imaged; determine, for each of the plurality of images into the teeth, a position of the hand-held wand relative to the subject's teeth using the 3D surface model data; and form the 3D volumetric model of the subject's teeth including internal features using the plurality of images and the position of the intraoral scanner relative to the subject's teeth.

An intraoral scanning system for generating a three-dimensional (3D) volumetric model of a subject's teeth may include: a hand-held wand having at least one image sensor and a plurality of light sources, wherein the light sources are configured to emit light at a first spectral range and a second spectral range, wherein the second spectral range is within near-infrared (near-IR) range of wavelengths; a filter in front of the image sensor configured to filter light in the second spectral range and the first polarization; and one or more processors operably connected to the hand-held wand, the one or more processors configured to: capture 3D surface model data of at least a portion of the subject's teeth as the intraoral scanner is moved over the teeth; take a plurality of images into the teeth using light in the second spectral as the intraoral scanner is moved over the teeth by emitting a near-IR light from the intraoral scanner in a first polarization, and detecting, in an image sensor in the intraoral scanner, the near-IR light returning to the intraoral scanner, wherein the near-IR light returning to the intraoral scanner is filtered to remove specular reflection by filtering near-IR light in the first polarization from the near-IR light returning to the intraoral scanner before it reaches the image sensor; determine, for each of the plurality of images into the teeth, a position of the hand-held wand relative to the subject's teeth using the 3D surface model data; and form the 3D volumetric model of the subject's teeth including internal features using the plurality of images and the position of the intraoral scanner relative to the subject's teeth.

Also described herein are methods of imaging cracks and caries in teeth. For example, described herein are methods of imaging into a subject's teeth to detect cracks and caries using an intraoral scanner, the method comprising: scanning the intraoral scanner over the subject's teeth; taking a plurality of near-infrared (near-IR) images into the subject's teeth at different orientations using the intraoral scanner emitting both a near-IR wavelength and a non-penetrative wavelength; determining a position of the intraoral scanner relative to the subject's teeth for each location of an image from the plurality of near-IR images using the non-penetrative wavelength; and generating a three-dimensional (3D) volumetric model of the subject's teeth using the plurality of near-IR images and the position of the intraoral scanner relative to the subject's teeth for each near-IR image of the plurality of near-IR images.

Any of these methods may include analyzing the volumetric model to identify a crack or caries (or other internal regions of the teeth).

For example, a method of imaging through a subject's teeth to detect cracks and caries may include: scanning the subject's teeth from multiple positions, wherein scanning comprises repeating, for each position: taking a plurality of near-infrared (near-IR) images into the teeth at different orientations using an intraoral scanner, wherein the intraoral scanner is emitting light at a near-IR wavelength in a first polarization and wherein, for each near-IR image, an angle between emitted light and light received by an image sensor is between 0 and 15 degrees, further wherein received near-IR light is filtered to block near-IR light in the first polarization, and determining a position of the intraoral scanner relative to the subject's teeth for each location of an image from the plurality of near-IR images using; and generating a three-dimensional (3D) volumetric model of the tooth using the penetration images and the surface location information.

Also described herein are methods of using scattering coefficients to generate internal images of tooth based on penetrating images and camera sensor location. For example, a method of forming a three-dimensional (3D) volumetric model of a subject's teeth may include: taking a plurality of near-infrared (near-IR) images of the subject's teeth with a camera sensor, wherein the near-IR lighting for the plurality of near-IR images is projected substantially from a direction of the camera sensor; receiving location data representing a location of the camera relative to the subject's teeth for each of the plurality of near-IR images; generating, for each point in a volume, an upper bound on a scattering coefficient from the plurality of near-IR images and the location data; combining the upper bound of scattering coefficients for each point in a volume to form a 3D volumetric model of the subject's teeth; and outputting the 3D volumetric model of the subject's teeth.

Any of these methods may include forming an iso-surface from the 3D volumetric model of the subject's teeth. The iso-surface may be formed by selecting a threshold or range of values of the scattering coefficients. Sub-ranges may correspond to different internal regions (e.g., structures). For example, outputting may comprise forming an iso-surface corresponding to an interior dentin surface from the 3D volumetric model of the subject's teeth.

A method of reconstructing a volumetric structure from a tooth, wherein the tooth is semi-transparent in a range of radiation wavelengths, may include: receiving, in a processor, a representation of a surface of the tooth in a first coordinate system; receiving, in the processor, a plurality of images of the tooth taken by a camera in the range of radiation wavelengths, the plurality of images taken with lighting projected substantially from a direction of the camera; receiving, in the processor, location data representing a location of the camera for each of the plurality of images; projecting each point of a grid of points corresponding to a volume within the surface of the tooth onto each of the plurality images using a first calibration; producing a list of intensity values for each projected point; converting each intensity value on the list of intensity values to a scattering coefficient according to a volume response; and storing a minimum scattering coefficient for each point into a list of minimum scattering coefficients.

Any of these methods may be embodied in an apparatus, including software, hardware and/or firmware for performing the method. For example, described herein are non-transitory computing device readable medium having instructions stored thereon for reconstructing a volumetric structure from a tooth that is semi-transparent in a range of radiation wavelengths, wherein the instructions are executable by a processor to cause a computing device to: receive a representation of a surface of the tooth in a first coordinate system; receive a plurality of images of the tooth taken by a camera in the range of radiation wavelengths, the plurality of images taken with lighting projected substantially from a direction of the camera; receive location data representing a location of the camera for each of the plurality of images; project each point of a grid of points corresponding to a volume of the tooth onto each of the plurality of images using a first calibration; produce a list of intensity values for each projected point; convert each intensity value on the list of intensity values to a scattering coefficient according to a volume response; and store a minimum scattering coefficient for each point from the scattering coefficients; and output an image produced from the list of minimum scattering coefficients.

Also described herein are methods of forming the internal structures using segmentation. For example, a method of modeling a subject's teeth, may include: capturing, with an intraoral scanner, a plurality of images of an interior of the subject's teeth and a position and orientation of the intraoral scanner specific to each image of the plurality of images; segmenting the plurality of images to form an internal structure corresponding to a structure within the subject's teeth; using the position and orientation of the plurality of images to project the internal structure onto a three-dimensional model of the subject's teeth; and displaying the three-dimensional model of the subject's teeth including the internal structure.

Also described herein are intraoral scanning apparatus configured to generate a model of a subject's teeth, the apparatus comprising: an intraoral scanner having a plurality of light sources and a position and orientation sensor, wherein the light sources are configured to emit light at a first spectral range and at a second spectral range, further wherein the second spectral range is penetrative; and a processor operably connected to the intraoral scanner, the one or more processors configured to cause the scanner to capture a plurality of images and position and orientation of the intraoral scanner corresponding to each of the plurality of images when the intraoral scanner is emitting light at the second spectral range; wherein the processor is further configured to segment the plurality of images to form an internal structures corresponding to a structure within the subject's teeth, and to display or transmit a three-dimensional model of the subject's teeth including the internal structure.

Also described herein are non-transitory computing device readable medium having instructions stored thereon that are executable by a processor to cause an intraoral scanning apparatus to: capture a plurality of images using a penetrative wavelength of light and a position and orientation of the intraoral scanner specific to each image of the plurality of images; segment the plurality of images to form an internal structure corresponding to a structure within a subject's teeth; use the position and orientation of the intraoral scanner specific to each image to project the internal structure onto a three-dimensional model of the subject's teeth; and display the three-dimensional model of the subject's teeth including the internal structure.

Also described herein are methods for forming 3D volumes (including volumetric volumes) of teeth. For example, described herein are methods comprising: receiving data associated with an intraoral scan of a subject; determining, from the received data, at least a portion of a volume of a first internal feature of a tooth of the subject; determining, from the received data, at least a portion of a volume of a second internal feature of the tooth of the subject, the first internal feature differing from the second internal feature; mapping the portion of the volume of the first internal feature with the portion of the volume of the second internal feature; outputting a 3D volume of the portion of the volume of the first internal feature with the portion of the volume of the second internal feature.

The received data may comprise data from tooth surface penetrating intraoral scan of the subject. The received data may further comprise data from a tooth surface intraoral scan of the subject.

The method may also include determining, from the received data, a surface of the tooth of the subject; mapping the surface of the tooth with the portion of the volume of the first internal feature and the portion of the volume of the second internal feature; and outputting the 3D volume with the surface of the tooth with the portion of the volume of the first internal feature and the portion of the volume of the second internal feature.

The received data may further comprise data from a tooth surface color intraoral scan of the subject.

The method may also comprise, determining, from the received data, a color of the surface of the tooth of the subject; mapping the color of the surface of the tooth to the surface of the tooth; and outputting the 3D volume with the surface of the tooth and the color of the surface of the tooth.

The first internal feature of the tooth may comprise a dentin of the tooth and the second internal feature of the tooth comprises an enamel of the tooth. The intraoral scan may comprise a second intraoral scan of the subject; and wherein the method further comprises receiving data associated with a prior intraoral scan of the subject; determining from the received data associated with the prior intraoral scan of the subject, at least a portion of a volume of the enamel or the dentin; and determining a volume change of the enamel or the dentin by comparing the portion of the volume of the enamel or the dentin determined from the received data associated with the second intraoral scan and the portion of the volume of the enamel or the dentin determined from the received data associated with the prior intraoral scan; and outputting the determined volume change.

The method may also include detecting a dental caries of the tooth by comparing the second internal feature and the first internal feature and outputting a signal to the user associated with the detected dental caries. Comparing the second internal feature and the second internal feature may comprise analyzing whether the volume of the second internal feature extends from a surface of the volume of the first internal feature. Analyzing may comprise determining whether the volume of the second internal feature extends from the surface of the volume of the first internal feature and to a portion of the second internal feature associated with the dentin.

The method may also include calculating a volume of the second internal feature that extends from the surface of the volume of the first internal feature and outputting a signal associated with the calculated volume.

Also described are method comprising: receiving data associated with an intraoral scan of a subject; determining, from the received data, a volume of a dental caries of a tooth of the subject; quantifying the volume of the dental caries of the tooth of the subject; and outputting a signal associated with the quantified volume of the dental caries of the tooth of the subject.

The method may also include determining, from the received data, a volume of an enamel of the tooth of the subject; mapping the volume of the enamel to the volume of the dental caries; and outputting a 3D volume of the mapped volumes of the enamel and the dental caries to a user. For example, determining, from the received data, a volume of a dentin of the tooth of the subject; mapping the volume of the dentin to the volume of the enamel and the volume of the dental caries; and outputting the 3D volume of the mapped volumes of the enamel and the dental caries with the volume of the dentin.

The intraoral scan of the subject may comprise a second intraoral scan of the subject and wherein the method further comprises receiving data associated with a prior intraoral scan of the subject; determining, from the received data associated with the prior intraoral scan of the subject, a prior volume of the dental caries of the tooth of the subject; outputting a signal associated with a difference in volume between the volume of the dental caries and the prior volume of the dental caries. The method may also comprise outputting a 3D model of the volume of the dental caries of the tooth of the subject.

Also described herein are trans-illumination adapter sleeve device for an intraoral scanner, the device comprising: a sleeve body configured to fit over a wand of an intraoral scanner, the sleeve body comprising a light-passing region at a distal end of the sleeve body configured to allow near-infrared (near-IR) light to pass through the sleeve; a first wing region extending from the distal end of the sleeve body adjacent to the light-passing region; and a near-IR light source configured to emit near-IR light from the first wing region. The near-IR light source may be configured to emit near-IR light transverse to the light-passing region.

The device may also include a second wing region extending from the distal end of the sleeve body adjacent to the light-passing region having a second near-IR light source configured to emit near-IR light from the second wing region. The device may also include an electrical contact on a proximal end of the sleeve body configured to apply electrical energy to the near-IR light source. The device may also include a flexible circuit coupling the electrical contact to the near-IR light source. Any of these devices may include a camera sensor operably connected to a second wing extending from the distal end of the sleeve body adjacent to the light-passing region.

Described herein are methods and apparatuses for taking, using and displaying dental information including information extracted from three-dimensional (3D) volumetric models of a patient's dental arch. A 3D volumetric model may include surface (e.g., color) information as well as information on internal structure, such as near-infrared (near-IR) transparency values for internal structures including enamel and dentin. In some variations, the 3D volumetric scan may include or be derived from one or more other scanning modalities, including, but not limited to: optical coherence tomography (OCT), ultrasound (US), magnetic resonance imaging (MRI), X-ray, etc.

In particular, described herein are methods and user interfaces for displaying and manipulating (e.g., sectioning, marking, selecting sub-regions, etc.) 3D volumetric models. For example, methods and apparatuses for displaying images from 3D volumetric models are provided, including methods for generating sections though the 3D volumetric model, methods for showing both surface and internal structures, and methods for generating easy to interpret images from the 3D volumetric models, such as pseudo-x-ray images.

Also described herein are methods and apparatuses for marking and tracking regions of interest from a 3D volumetric model of a patient's dental arch. These methods may include automatically, manually or semi-automatically (e.g., with user approval or input) identifying one or more regions from within the 3D volumetric model to mark (including surface features and/or internal features of the dental arch); these regions may be regions in which a caries, crack or other irregularity has developed or may develop. Marked regions may be analyzed in greater detail, and may be tracked over time. Further, marked regions may modify the manner in which subsequent scanning is performed, e.g., by scanning marked regions at higher resolution. The regions of the volumetric model may correspond to one or more voxels, including contiguous voxel regions. These regions may be referred to herein as volumetric regions.

Also described herein are methods and apparatuses for using 3D volumetric models to improve or modify a dental procedure, including modifying treatment planning and/or modifying one or more dental device. For example, described herein are dental tools that include 3D volumetric scanning, or that may be operated in conjunction with 3D volumetric models (including robotic or automated control using 3D volumetric models). Methods of diagnosing one or more conditions (e.g., dental conditions) using a 3D volumetric model, and particularly using 3D volumetric models over time are also described.

A method of displaying images from a three-dimensional (3D) volumetric model of a patient's dental arch, the method comprising: collecting the 3D volumetric model of the patient's dental arch, wherein the 3D volumetric model includes surface color and shade values and near-infrared (near-IR) transparency values for internal structures within the dental arch; selecting, by a user, an orientation of a view of the 3D volumetric model to display; generating a two-dimensional (2D) view into the 3D volumetric using the selected orientation, including the patient's dental arch including a weighted portion of the surface color values and a weighted portion of the near-IR transparency of the internal structures; and displaying the 2D view.

For example, described herein are methods of displaying images from a three-dimensional (3D) volumetric model of a patient's dental arch. The method may include: receiving the 3D volumetric model of the patient's dental arch, wherein the 3D volumetric model includes surface color values and near-infrared (near-IR) transparency values for internal structures within the dental arch; generating a two-dimensional (2D) view through the 3D volumetric model including the patient's dental arch including both surface color values and the near-IR transparency of the internal structures. In any of the methods and apparatuses described herein, a 3D model (including a volumetric 3D model) may be displayed as a voxel view. Thus, the methods described herein may generate one or more voxel views in which each voxel may have a color (or hue) that corresponds to its density and/or translucently. Thus, an of the methods and apparatuses described herein may generate a 3D color map of all or some of the voxels of the 3D model (and display one or more 2D images derived from the 3D color view, such a sections, slices, projections, perspective views, transparent-views in which all or some of the 3D model is rendered transparent, etc.). In some variations, flagged regions (e.g., regions corresponding to one or more irregular regions, and/or regions, e.g., voxels that have changed over time, regions/voxels that should be removed, regions/voxels suspected to be problematic and etc., may be displayed as a 3D and/or 2D view.

Generating the two-dimensional (2D) view through the 3D volumetric may include: including in the 2D view, a weighted portion of the surface color values and a weighted portion of the near-IR transparency of the internal structures. Note that the near-IR transparency may be based on or otherwise calculated from near IR scattering or absorption of the material. The weighted portion of the surface color values may comprise a percentage of the full value of the surface color values, and the weighted portion of the near-IR transparency of the internal structures comprises a percentage of the full value of the near-IR transparency of the internal structures, wherein the percentage of the full value of the surface color values and the percentage of the full value of the near-IR transparency of the internal structures adds up to 100%.

In some variations, the method also includes adjusting, by a user, or in response to user input, the weighted portion of the surface color values and/or the near-IR transparency of the internal structures.

Any of these methods may include the step of scanning the patient's dental arch with an intraoral scanner.

Generating the 2D view may comprise sectioning the 3D volumetric model in a plane through the 3D volumetric model. The user may select a section though the 3D volumetric model to display, and/or an orientation of the 2D view.

For example, a method of displaying images from a three-dimensional (3D) volumetric model of a patient's dental arch may include: receiving the 3D volumetric model of the patient's dental arch, wherein the 3D volumetric model includes surface color values and near-infrared (near-IR) transparency values for internal structures within the dental arch; selecting, by a user or in response to user input, a section though the 3D volumetric model to display; generating a two-dimensional (2D) view through the 3D volumetric using the selected section, including the patient's dental arch, and possibly also including a weighted portion of the surface color values and a weighted portion of the near-IR transparency of the internal structures; and displaying the 2D view.

A method of displaying images from a three-dimensional (3D) volumetric model of a patient's dental arch may include: collecting the 3D volumetric model of the patient's dental arch, wherein the 3D volumetric model includes surface values and near-infrared (near-IR) transparency values for internal structures within the dental arch; generating a two-dimensional (2D) view into the 3D volumetric model including the patient's dental arch including both surface values and the near-IR transparency of the internal structures; and displaying the 2D view.

A method of tracking a region of a patient's dental arch over time may include: receiving a first three-dimensional (3D) volumetric model of the patient's dental arch, wherein the 3D volumetric model includes surface color values and near-infrared (near-IR) transparency values for internal structures within the dental arch; identifying a region within the 3D volumetric model to be marked; flagging the identified region; and displaying one or more images of the 3D volumetric model indicating the marked region.

For example, a method of tracking a region of a patient's dental arch over time, the method comprising: collecting a first three-dimensional (3D) volumetric model of the patient's dental arch, wherein the 3D volumetric model includes surface values and near-infrared (near-IR) transparency values for internal structures within the dental arch; identifying a region of the 3D volumetric model; flagging the identified region; collecting a second 3D volumetric model of the patient's dental arch; and displaying one or more images marking, on the one or more images, a difference between the first 3D volumetric model and the second 3D volumetric model at the flagged region.

Identifying the region may comprise automatically identifying using a processor. For example, automatically identifying may comprise identifying a region having a possible defects including: cracks and caries. Identifying the region having a possible defect may comprise comparing a near-IR transparency value of a region within the 3D model to a threshold value. Automatically identifying may comprise identifying a surface color value outside of a threshold range. Automatically identifying may comprise segmenting the 3D volumetric model to identify enamel regions and identifying regions having enamel thicknesses below a threshold value. Flagging the identified region may comprise automatically flagging the identified regions. Flagging the identified region may comprise manually confirming the identified region for flagging.

Any of these methods may include receiving a second 3D volumetric model of the patient's dental arch and displaying a difference between the first 3D volumetric model and the second 3D volumetric model at the marked region.

Further, any of these methods may include pre-scanning or re-scanning the patient's dental arch wherein the flagged region is scanned at a higher resolution or in other scanning modalities than un-flagged regions.

For example, a method of tracking a region of a patient's dental arch over time may include: receiving a first three-dimensional (3D) volumetric model of the patient's dental arch, wherein the 3D volumetric model includes surface color values and near-infrared (near-IR) transparency values for internal structures within the dental arch; identifying, using an automatic process, a region within the 3D volumetric model to be marked; flagging the identified regions; receiving a second 3D volumetric model of the patient's dental arch; and displaying a difference between the first 3D volumetric model and the second 3D volumetric model at the marked region. In some instances, the second 3D volumetric model of the patient's dental arch may be from a scan of the patient at a subsequent visit to the dental practitioner's office at a later date.

Thus, a method of tracking a region of a patient's dental arch over time may include: collecting a first three-dimensional (3D) volumetric model of the patient's dental arch taken at a first time, wherein the 3D volumetric model includes surface color values and near-infrared (near-IR) transparency values for internal structures within the dental arch; identifying, using an automatic process, a region within the 3D volumetric model to be flagged; flagging the identified regions; collecting a second 3D volumetric model of the patient's dental arch taken at a separate time; and displaying a difference between the first 3D volumetric model and the second 3D volumetric model at the flagged region.

Also described herein are methods of displaying pseudo x-ray images from a three-dimensional (3D) volumetric model of a patient's dental arch. For example, a method may include: receiving the 3D volumetric model of the patient's dental arch, wherein the 3D volumetric model includes near-infrared (near-IR) transparency values for internal structures within the dental arch; generating a two-dimensional (2D) view through the 3D volumetric including the patient's dental arch including the near-IR transparency of the internal structures; mapping the near-IR transparency of the internal structures in the 2D view to a pseudo-X-ray density in which the near-IR transparency values are inverted in value; and displaying the mapped pseudo-X-ray density. Generating the 2D view may comprise sectioning the 3D volumetric model in a plane through the 3D volumetric model. The 3D volumetric model may include surface information.

For example, a method of displaying pseudo x-ray images from a three-dimensional (3D) volumetric model of a patient's dental arch may include: collecting the 3D volumetric model of the patient's dental arch, wherein the 3D volumetric model includes near-infrared (near-IR) transparency values for internal structures within the dental arch; generating a two-dimensional (2D) view into the 3D volumetric model including the patient's dental arch including the near-IR transparency of the internal structures; mapping the near-IR transparency of the internal structures in the 2D view to a pseudo-X-ray density in which the pseudo-X-ray density values in the 2D view are based on the near-IR transparency values that are inverted in value; and displaying the mapped pseudo-X-ray density.

Any of these methods may include identifying a sub-region from the 3D volumetric model prior to generating the 2D view, wherein the 2D view comprises a 2D view of the identified sub-region. The method may also include segmenting the 3D volumetric model into a plurality of teeth, wherein generating the 2D view may comprise a 2D view including just one of the identified teeth.

Mapping the near-IR transparency may include inverting the near-IR transparency values so that enamel within the 2D view is brighter than dentin within the 2D view.

A method of displaying pseudo x-ray images from a three-dimensional (3D) volumetric model of a patient's dental arch may include: receiving the 3D volumetric model of the patient's dental arch, wherein the 3D volumetric model includes surface features and near-infrared (near-IR) transparency values for internal structures within the dental arch in which enamel is more transparent than dentin; generating a two-dimensional (2D) view through the 3D volumetric including the patient's dental arch including the near-IR transparency of the internal structures including dentin and enamel; mapping the near-IR transparency of the internal structures in the 2D view to a pseudo-X-ray density in which the near-IR transparency values are inverted in value so that the enamel is brighter than the dentin; and displaying the mapped pseudo-X-ray density.

For example, a method of displaying pseudo x-ray images from a three-dimensional (3D) volumetric model of a patient's dental arch may include: collecting the 3D volumetric model of the patient's dental arch, wherein the 3D volumetric model includes surface features and near-infrared (near-IR) transparency values for internal structures within the dental arch in which enamel is more transparent than dentin; generating a two-dimensional (2D) view into the 3D volumetric including the patient's dental arch including the near-IR transparency of the internal structures including dentin and enamel; mapping the near-IR transparency of the internal structures in the 2D view to a pseudo-X-ray density in which the near-IR transparency values are inverted in value so that the enamel is brighter than the dentin; and displaying the mapped pseudo-X-ray density.

Also described herein are methods and apparatuses for virtually reviewing (e.g., virtually sectioning, virtually scanning, virtually examining), in real time, a volumetric model of the patient's dental arch(s). These apparatuses may include non-transitory, machine-readable tangible medium storing instructions for causing one or more machines to execute operations for performing any of the methods described herein. In particular, any of these methods and apparatuses may operate on a data set that includes both a 3D model of the patient's dental arch, or in some variations, both of the patient's dental arches. The 3D model may be, but is not limited to, a 3D volumetric model; in some variation the 3D model is a 3D surface model of the arch. This data set may also include a plurality of images of the dental arch, taken from different positions relative to the dental arch, such as different angles between the plane of the image and the dental arch and different sub-regions of the dental arch. Some of these images may be taken from the occlusal surface, some from the gingival side, and some from the lingual side. In some variations the images may be the same (or a subset of) the images used to form the 3D model of the teeth. The data set may include multiple images taken from the same, or nearly the same, region of the dental arch and angle relative to the dental arch. In some variations, the data set may include sets of two or more images (e.g., pairs of images) each taken at approximately the same region of the dental arch and at the same angle relative to the dental arch but using different imaging techniques (e.g., different imaging techniques, such as visible light, IR/near-IR, florescence, X-ray, ultrasound, etc.).

For example, a method may include: displaying a three-dimensional (3D) model of a patient's dental arch; displaying a viewing window over at least a portion of the 3D model of the patient's dental arch; allowing a user to change a relative position between the viewing window and the 3D model of the patient's dental arch; and continuously, as the user changes the relative positions between the viewing window and the 3D model of the patient's dental arch: identifying, from both the 3D model of the patient's dental arch and a plurality of images of a patient's dental arch taken from different angles and positions relative to the patient's dental arch, an image taken at an angle and position that approximates a relative angle and position between the viewing window relative and the 3D model of the patient's dental arch; and displaying the identified image taken at the angle and position that approximates the angle and position between the viewing window relative to the 3D model of the patient's dental arch.

Any of the methods described herein, a data set may include the 3D model of the patient's dental arch and a plurality of images of a patient's dental arch taken from different angles and positions relative to the patient's dental arch. A data set may also or alternatively includes metadata associated with each (or each set) of the figures indicating the angle and/or region of the dental arch at which the image was taken. Additional metadata may be included (e.g., indicating a distance from the dental arch, indicating exposure time, indicating that the image is an average of other images, a quality metric for the image, etc.).

For example, described herein are methods for displaying a 3D model (e.g., surface 3D model) of the patient's teeth and/or volumetric model of the patient's teeth) that a user can virtually scan in greater detail by moving a viewing window over the 3D model of the dental arch. For example, described herein are methods including: displaying a three-dimensional (3D) model of a patient's dental arch; displaying a viewing window over a portion of the 3D model of the patient's dental arch; allowing a user to change a relative position between the viewing window and the 3D model of the patient's dental arch, including one or more of: an angle between a plane of the viewing window and the patient's dental arch, and a portion of the dental arch adjacent to the viewing window; and continuously, as the user changes the relative positions between the viewing window and the 3D model of the patient's dental arch: identifying, from both the 3D model of the patient's dental arch and a plurality of images of a patient's dental arch (e.g., in some variations from a data set comprising both the 3D model of the patient's dental arch and a plurality of images of a patient's dental arch), wherein each image is taken from a different angle and position relative to the patient's dental arch, an image taken at an angle and position that approximates the relative angle and position between the viewing window relative and the 3D model of the patient's dental arch; and displaying the identified image taken at the angle and position that approximates the angle and position of the viewing window relative to the displayed 3D model of the patient's dental arch.

For example, a method may include: displaying a three-dimensional (3D) model of a patient's dental arch; displaying a viewing window over a portion of the 3D model of the patient's dental arch; allowing a user to change a relative position between the viewing window and the 3D model of the patient's dental arch, including one or more of: an angle between the patient's dental arch relative and a plane of the viewing window, and a portion of the dental arch adjacent to the viewing window; and continuously, as the user changes the relative position between the viewing window and the 3D model of the patient's dental arch: identifying, from both the 3D model of the patient's dental arch and a plurality of pairs of images of a patient's dental arch (e.g., optionally from a data set comprising both the 3D model of the patient's dental arch and a plurality of images of a patient's dental arch), wherein each pair of the plurality of pairs includes a first imaging wavelength and a second imaging wavelength each taken at the same angle and position relative to the patient's dental arch, a pair of images taken at an angle and position that approximate the angle and position of the viewing window relative to the displayed 3D model of the patient's dental arch; and displaying at least one of the identified pair of images taken at the angle and position that approximate the angle and position of the viewing window relative to the displayed 3D model of the patient's dental arch.

The methods and apparatuses described herein can be used with a 3D model that is a surface model or any representation of the patient's dental arch(s). It may be, but does not have to be, a 3D volumetric model of the patient's teeth, e.g., constructed from images (e.g., the plurality of images of a patient's dental arch taken from different angles and positions relative to the patient's dental arch). The model may be representative of the patient's actual dentition, abstracted from the patient's dentition, or generic.

As described herein, a method may include: displaying a three-dimensional (3D) model of a patient's dental arch; displaying a viewing window over a portion of the 3D model of the patient's dental arch; allowing a user to change a relative position between the viewing window and the 3D model of the patient's dental arch, including one or more of: an angle between the viewing window and the patient's dental arch, and a portion of the dental arch adjacent to the viewing window; and continuously, as the user changes the relative positions between the viewing window and the 3D model of the patient's dental arch: identifying, both the 3D model of the patient's dental arch and a plurality of near-IR images of a patient's dental arch (e.g., from a data set comprising both the 3D model of the patient's dental arch and a plurality of images of a patient's dental arch), wherein each near-IR image is taken from a different angle and position relative to the patient's dental arch, a near-IR image taken at an angle and position that approximates the relative angle and position between the viewing window relative and the 3D model of the patient's dental arch; and displaying the identified near-IR image taken at the angle and position that approximates the angle and position of the viewing window relative to the displayed 3D model of the patient's dental arch.

In any of these examples, the images may be images taken with a penetrating modality, such as with a near-IR. For example, described herein are methods including: displaying a three-dimensional (3D) model of a patient's dental arch; displaying a viewing window over a portion of the 3D model of the patient's dental arch; allowing a user to change a relative position between the viewing window and the 3D model of the patient's dental arch, including one or more of: an angle between the viewing window and the patient's dental arch, and a portion of the dental arch adjacent to the viewing window; and continuously, as the user changes the relative positions between the viewing window and the 3D model of the patient's dental arch: identifying, from a data set comprising both the 3D model of the patient's dental arch and a plurality of near-IR images of a patient's dental arch, wherein each near-IR image is taken from a different angle and position relative to the patient's dental arch, a near-IR image taken at an angle and position that approximates the relative angle and position between the viewing window relative and the 3D model of the patient's dental arch; and displaying the identified near-IR image taken at the angle and position that approximates the angle and position of the viewing window relative to the displayed 3D model of the patient's dental arch.

Any of these methods may also include identifying and displaying multiple images taken at the same angle and position relative to the dental arch. For example, the images may be both a visible light image and a penetrative image (such as an IR/near-IR image, etc.). For example, described herein are: methods comprising: displaying a three-dimensional (3D) model of a patient's dental arch; displaying a viewing window over a portion of the 3D model of the patient's dental arch; allowing a user to change a relative position between the viewing window and the 3D model of the patient's dental arch, including one or more of: an angle between the patient's dental arch relative and a plane of the viewing window, and a portion of the dental arch adjacent to the viewing window; and continuously, as the user changes the relative position between the viewing window and the 3D model of the patient's dental arch: identifying, from a data set comprising both the 3D model of the patient's dental arch and a plurality of pairs of images of a patient's dental arch, wherein each pair of the plurality of pairs includes a first imaging wavelength and a second imaging wavelength each taken at the same angle and position relative to the patient's dental arch, a pair of images taken at an angle and position that approximate the angle and position of the viewing window relative to the displayed 3D model of the patient's dental arch; and displaying the identified pair of images taken at the angle and position that approximate the angle and position of the viewing window relative to the displayed 3D model of the patient's dental arch.

In any of these methods, identifying may comprise determining a plurality images that approximate the relative angle and position between the viewing window relative and the 3D model of the patient's dental arch and averaging the plurality to form the identified image. For example, there may be multiple images in the data set taken at approximately (e.g., within +/−0.1%, 0.5%, 1%, 2%, 3%, 4%, 5%, 7%, 10%, 15%, 20%, etc.) of the same angle and approximately (e.g., within +/−0.1%, 0.5%, 1%, 2%, 3%, 4%, 5%, 7%, 10%, 15%, 20%, etc.) of the same region of the dental arch; these similar images may be combined to form an average image that may be better than the individual images.

In general, identifying one or more images taken at an angle and position that approximates the relative angle and position between the viewing window relative and the 3D model of the patient's dental arch may be identifying within an acceptable spatial range. For example, an image that was taken at between +/−a few degrees of the same angle (e.g., +/−0.1 degree, 0.2 degree, 0.3 degrees, 0.4 degrees, 0.5 degrees, 0.6 degrees, 1 degree, 1.2 degrees, 1.5 degrees, 1.7 degrees, 1.8 degrees, 2 degrees, 2.2 degrees, 2.5 degrees, 3 degrees, 3.2 degrees, 3.5 degrees, 4 degrees, 5 degrees, etc.) as the plane of the viewing widow and within +/−a range of distance of the dental arch region over which the viewing window is positioned (e.g., +/−0.1 mm, 0.2 mm, 0.3 mm, 0.4 mm, 0.5 mm, 0.6 mm, 0.7 mm, 0.8 mm, 0.9 mm, 1 mm, 1.1 mm, 1.2 mm, 1.5 mm, 1.7 mm, 2.0 mm, 2.2 mm, 2.5 mm, etc.).

Any of these methods may include receiving, in a processor, the data set. The data set may be received directly from an intraoral scanner, and/or stored and retrieved. In some variations the data set may be transmitted and received by the processor, in some variations the processor may read the data set from a memory (e.g., a data store) connected to the processor.

In general, any of these methods may include displaying the viewing window over a portion of the 3D model of the patient's dental arch. The viewing window may be any shape or size, such as a circle, oval, triangle, rectangle, or other polygon. For example, the viewing window may be a loop through which the portion of the 3D model of the patient's dental arch may be viewed. The viewing angle may allow the dental arch to be visualized through at least a portion of the viewing window. The viewing window may be smaller than the dental arch. In some variations the viewing window may be made larger or smaller by the user.

Typically these methods may include displaying via a user interface. For example, the user interface may display on a screen or screens the dental arch 3D model, the viewing window, and/or the image(s) corresponding to the view thorough the viewing window of the dental arch. The user may (e.g., by manipulating the user interface, e.g., via a control such as a mouse, keyboard, touchscreen, etc.) move the viewing window and dental arch independently. This movement, and the image(s) determined to correspond to the image though the viewing window of the region and angle of the viewing window relative to the dental arch, may be displayed in real time, as the user moves the viewing window and/or dental arch relative to each other.

For example, allowing the user to change the relative position between the viewing window and the 3D model of the patient's dental arch may include separately controlling the angle and/or rotation of the 3D model of a patient's dental arch and the portion of the dental arch adjacent to the viewing window. In some variations, allowing the user to change the relative position between the viewing window and the 3D model of the patient's dental arch may comprise allowing the user to move the viewing window over the 3D model of the dental arch.

As mentioned, any of the images identified to as taken from an angle and position corresponding to the angle and position of the viewing window as it is moved over and/or around the dental arch (or as the dental arch is moved relative to the viewing window) may be any one or more modalities. Thus, for example, identifying an image that approximates the relative angle and position between the viewing window relative and the 3D model of the patient's dental arch may include identifying one of: a visible light image, an infrared image, and a florescent image.

Displaying the identified image(s) that approximates the angle and position of the viewing window relative to the displayed 3D model may comprise displaying the identified image in a window adjacent or overlapping with the display of the 3D model of the patient's dental arch. For example, the images may be displayed on a screen alongside the 3D model of the dental arch; a the user moves the dental arch and/or imaging window, the image(s) may be shown in one or more windows changing in real time or near real-time to reflect the relative position of the 3D model of the dental arch and the viewing window.

Also described herein are non-transitory, machine-readable tangible medium storing instructions for causing one or more machines to execute operations for performing any of the methods described herein, including virtually reviewing a patient's dental arch. For example, a non-transitory, machine-readable tangible medium may store instructions for causing one or more machines to execute operations for virtually reviewing a patient's dental arch including: displaying a three-dimensional (3D) model of a patient's dental arch; displaying a viewing window over a portion of the 3D model of the patient's dental arch; allowing a user to change a relative position between the viewing window and the 3D model of the patient's dental arch, including one or more of: an angle between the viewing window and the patient's dental arch, and a portion of the dental arch adjacent to the viewing window; and continuously, as the user changes the relative positions between the viewing window and the 3D model of the patient's dental arch: identifying, from a data set comprising both the 3D model of the patient's dental arch and a plurality of images of a patient's dental arch, wherein each image is taken from a different angle and position relative to the patient's dental arch, an image taken at an angle and position that approximates the relative angle and position between the viewing window relative and the 3D model of the patient's dental arch; and displaying the identified image taken at the angle and position that approximates the angle and position of the viewing window relative to the displayed 3D model of the patient's dental arch.

For example, a non-transitory, machine-readable tangible medium storing instructions for causing one or more machines to execute operations for virtually reviewing a patient's dental arch, comprising: displaying a three-dimensional (3D) model of a patient's dental arch; displaying a viewing window over a portion of the 3D model of the patient's dental arch; allowing a user to change a relative position between the viewing window and the 3D model of the patient's dental arch, including one or more of: an angle between the viewing window and the patient's dental arch, and a portion of the dental arch adjacent to the viewing window; and continuously, as the user changes the relative positions between the viewing window and the 3D model of the patient's dental arch: identifying, from a data set comprising both the 3D model of the patient's dental arch and a plurality of images of a patient's dental arch, wherein each image is taken from a different angle and position relative to the patient's dental arch, an image taken at an angle and position that approximates the relative angle and position between the viewing window relative and the 3D model of the patient's dental arch; and displaying the identified image taken at the angle and position that approximates the angle and position of the viewing window relative to the displayed 3D model of the patient's dental arch.

Also described herein are intraoral scanning systems that are configured to perform the methods described herein. For example, an intraoral scanning system may include a handheld wand having at least one image sensor and a light source configured to emit light at a spectral range within near-infrared (near-IR) range of wavelengths; a display output (e.g., a visual output such as a monitor, screen, virtual reality interface/augmented reality interface, etc.); a user input device (e.g., any control for receiving and transmitting user input, such as, but not limited to: a keyboard, button, joystick, touchscreen, etc. The display output and the user input device may be the same touchscreen); and one or more processors operably connected to the hand-held wand, display and user input device, the one or more processors configured to: display a three-dimensional (3D) model of a patient's dental arch on the display output; display a viewing window over a portion of the 3D model of the patient's dental arch on the display output; change a relative position between the viewing window and the 3D model of the patient's dental arch based on input from the user input device; identify, from both the 3D model of the patient's dental arch and a plurality of images of the patient's dental arch taken from different angles and positions relative to the patient's dental arch, a near-infrared (near-IR) image taken at an angle and position that approximates a relative angle and position between the viewing window relative and the 3D model of the patient's dental arch; and display the identified near-IR image taken at the angle and position that approximates the angle and position between the viewing window relative to the 3D model of the patient's dental arch.

The one or more processors of the intraoral scanning system may be configured to receive the plurality of images of the patient's dental arch taken from different angles and positions relative to the patient's dental arch. For example, the images may be taken by the image sensor(s) on the hand-held wand and transmitted to the one or more processors and/or stored in a memory that is accessed by the one or more processors. The system may also include a controller coordinating the activity of the one or more processors, the wand, and the display output (and user input device). The controller may display the images and/or a 3D model constructed from the images as a user operates the hand-held want to take images at different locations and/or angles relative to the patient's dental arch(es).

The one or more processors may be configured to continuously identify the near-IR image and display the identified near-IR image as the user changes the relative positions between the viewing window and the 3D model of the patient's dental arch. Thus, as the user (using the user input) adjusts the position of the viewing window (e.g., loop) relative to the 3D model of the patient's dental arch on the display output (or, equivalently, adjusts the position of the 3D model of the dental arch on the display output relative to the viewing window), the one or more processors may determine and display a near-IR image of the patient's teeth that most closely approximates the relative positions between the viewing window and the 3D model of the patient's dental arch.

The near-IR image is either one of the images taken by the hand-held wand or an average of the images taken by the hand-held wand. Any of the apparatuses (e.g., intraoral scanning systems) described herein may also determine and/or store the positions and/or orientation of the hand-held wand as it is being operated, and this information may be stored with the image(s) taken from this position. For example, the hand-held wand may include one or more accelerometers. For example, the one or more processors may be configured to identify the near-IR image taken at an angle and position that approximates a relative angle and position between the viewing window relative and the 3D model of the patient's dental arch by determining a plurality images that approximate the relative angle and position between the viewing window relative and the 3D model of the patient's dental arch and averaging the plurality to form the identified near-IR image.

As mentioned, the one or more processors may be configured to change, on the display output, the relative position between the viewing window and the 3D model of the patient's dental arch based on input from the user input device. Specifically, the one or more processor may be configured to change, based on user input into user input device, one or more of: an angle between a plane of the viewing window and the patient's dental arch, and a portion of the dental arch adjacent to the viewing window (e.g., in some variations, visible through the viewing window). As discussed above, the viewing window may be a loop (e.g., circular, oval, square, etc.) through which the 3D model is visible). Thus, the one or more processors may be configured to display the viewing window over a portion of the 3D model of the patient's dental arch comprises displaying as a loop through which the portion of the 3D model of the patient's dental arch may be viewed. The viewing window may be moved and positioned over (including changing which side of the dental arch (buccal, occlusal, lingual, or between these, including moving in x, y, z and/or in rotation, e.g., pitch, roll, yaw) the viewing window is positioned over and/or the 3D model of the patient's teeth may be moved (e.g., rotating in pitch, yaw, roll, moving in x, y, z, etc.). Thus, the one or more processors may be configured to change the relative position between the viewing window and the 3D model of the patient's dental arch based on input from the user input device by changing one or more of: the angle of the 3D model of a patient's dental arch relative to the viewing window (which is equivalent to the angle of the viewing window relative to the 3D model of the patient's dental arch), the rotation of the 3D model of a patient's dental arch relative to the viewing window (which is equivalent to the rotation of the viewing window relative to the 3D model of a patient's dental arch), and the portion of the dental arch adjacent to the viewing window (e.g., the portion of the 3D model visible through the viewing window). For example, the one or more processors may be configured to change the relative position between the viewing window and the 3D model of the patient's dental arch based on input from the user input device by changing the position of the viewing window over the 3D model of the dental arch.

The one or more processors may be configured to identify from both the 3D model of the patient's dental arch and the plurality of images of the patient's dental arch taken from different angles and positions relative to the patient's dental arch, a second image that approximates the relative angle and position between the viewing window relative and the 3D model of the patient's dental arch that is one or more of: a visible light image and a florescent image; and wherein the one or more processors is configured to display the second image concurrently with the near-IR image.

Also described herein are methods of automatically, semi-automatically/semi-manually or manually identifying and grading features by coordinating across multiple imaging modalities. For example, a dental diagnostic method may include: identifying a dental feature in a first record, the first record comprising a plurality of images of a patient's dental arch taken first imaging modality; correlating the first record with a model of the patient's dental arch; identifying, using the model of the patient's dental arch, a region of the dental arch corresponding to the dental feature in one or more different records, wherein each record of the one or more different records is taken with a different imaging modality than the first imaging modality and wherein each of the one or more different records is correlated with the model of the patient's dental arch; determining a confidence score for the dental feature based on the identified regions corresponding to the dental feature in the one or more different records; and displaying the dental feature when the confidence score for the dental feature is above a threshold.

A dental diagnostic method may include: identifying a dental feature in a first record, the first record comprising a plurality of images of a patient's dental arch taken first imaging modality; correlating the first record with a three-dimensional (3D) volumetric model of the patient's dental arch; flagging the dental feature on the 3D volumetric model; identifying, using the model of the patient's dental arch, a region of the dental arch corresponding to the dental feature in one or more different records, wherein each record of the one or more different records is taken with a different imaging modality than the first imaging modality and wherein each of the one or more different records is correlated with the model of the patient's dental arch; determining or adjusting a confidence score for the dental feature based on the identified regions corresponding to the dental feature in the one or more different records; and displaying the dental feature and an indicator of the confidence score for the dental feature when the confidence score for the dental feature is above a threshold.

In any of these methods (or systems for performing them) the dental feature may comprise one or more of: cracks, gum recess, tartar, enamel thickness, pits, caries, pits, fissures, evidence of grinding, and interproximal voids.

Displaying may comprise displaying the dental feature and an indicator of the confidence score for the dental feature.

Correlating the first record with the model of the patient's dental arch may comprise correlating the first record with a three-dimensional (3D) volumetric model of the patient's dental arch. Any of these methods (or systems for performing them) may include flagging the dental feature on the model of the patient's dental arch, and/or collecting the dental feature, including the location of the dental feature, and one or more of: the type of dental feature and a confidence score for the dental feature.

Determining the confidence score may comprise adjusting the confidence score for the dental feature based on the identified regions corresponding to the dental feature in the one or more different records.

In any of these methods or systems, identifying the dental feature may comprise automatically identifying the dental feature.

For example, a dental diagnostic method may include: identifying one or more actionable dental features from one or more records of a plurality of records, wherein each record comprises a plurality of images of a patient's dental arch each taken using an imaging modality, further wherein each record of the plurality of records is taken at a different imaging modality; mapping the actionable dental feature to a corresponding region of the one or more records; recording the one or more actionable dental features, including recording a location of the actionable dental feature; adjusting or determining a confidence score for the one or more actionable dental features based on the corresponding region of the one or more records; and displaying the one or more actionable dental features when the confidence score of the one or more actionable dental features is above a threshold. As mentioned above, the one or more actionable dental feature comprises one or more of: cracks, gum recess, tartar, enamel thickness, pits, caries, pits, fissures, evidence of grinding, and interproximal voids.

Displaying may comprise displaying the one or more actionable dental features and an indicator of the confidence score for the dental feature. Mapping the actionable dental feature to the corresponding region of the one or more records may comprise correlating the first record with a three-dimensional (3D) volumetric model of the patient's dental arch. Recording the one or more actionable dental features may comprise marking the dental feature on the 3D volumetric model of the patient's dental arch. Identifying the dental feature may comprise automatically identifying the dental feature.

Also described herein are systems for performing any of the methods described herein. For example, a system may include: one or more processors; and a memory coupled to the one or more processors, the memory configured to store computer-program instructions, that, when executed by the one or more processors, perform a computer-implemented method comprising: identifying a dental feature in a first record, the first record comprising a plurality of images of a patient's dental arch taken first imaging modality; correlating the first record with a model of the patient's dental arch; identifying, using the model of the patient's dental arch, a region of the dental arch corresponding to the dental feature in one or more different records, wherein each record of the one or more different records is taken with a different imaging modality than the first imaging modality and wherein each of the one or more different records is correlated with the model of the patient's dental arch; determining a confidence score for the dental feature based on the identified regions corresponding to the dental feature in the one or more different records; and displaying the dental feature when the confidence score for the dental feature is above a threshold.

Also described herein are methods and apparatuses (e.g., systems) for tracking one or more regions (e.g., tagged or flagged regions) across different imaging modalities and/or over time. For example, a method of tracking a dental feature across different imaging modalities may include: collecting a first three-dimensional (3D) volumetric model of the patient's dental arch, wherein the 3D volumetric model of the patient's dental arch includes surface values and internal structures within the dental arch; identifying a region of the patient's dental arch from a first record of a plurality of records, wherein each record comprises a plurality of images of a patient's dental arch each taken using an imaging modality, further wherein each record of the plurality of records is taken at a different imaging modality; flagging the identified region in a corresponding region of the 3D volumetric model of the patient's dental arch; correlating the flagged region with each of records of the plurality of records by correlating the 3D volumetric model of the patient's dental arch with each of the records of the plurality of records; and saving, displaying and/or transmitting images including the region of the patient's dental arch. The region of the patient's dental arch may comprise a dental feature comprises one or more of: cracks, gum recess, tartar, enamel thickness, pits, caries, pits, fissures, evidence of grinding, and interproximal voids.

Saving, displaying and/or transmitting may comprise displaying the regions of the patient's dental arch. Any of these methods may include flagging the dental feature on the 3D volumetric model. Identifying the region of the patient's dental arch may comprise automatically identifying the region of the patient's dental arch.

A system for tracking one or more regions (e.g., tagged or flagged regions) across different imaging modalities and/or over time may include: one or more processors; a memory coupled to the one or more processors, the memory configured to store computer-program instructions, that, when executed by the one or more processors, perform a computer-implemented method comprising: collecting a first three-dimensional (3D) volumetric model of the patient's dental arch, wherein the 3D volumetric model of the patient's dental arch includes surface values and internal structures within the dental arch; identifying a region of the patient's dental arch from a first record of a plurality of records, wherein each record comprises a plurality of images of a patient's dental arch each taken using an imaging modality, further wherein each record of the plurality of records is taken at a different imaging modality; flagging the identified region in a corresponding region of the 3D volumetric model of the patient's dental arch; correlating the flagged region with each of records of the plurality of records by correlating the 3D volumetric model of the patient's dental arch with each of the records of the plurality of records; and saving, displaying and/or transmitting images including the region of the patient's dental arch.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 1A illustrates one example of a 3D (color) intraoral scanner that may be adapted for used as described herein to generate a model of subject's teeth having both surface and internal features.

FIG. 1B schematically illustrates an example of an intraoral scanner configured to generate a model of subject's teeth having both surface and internal features.

FIG. 4A illustrates an example of a penetration imaging (e.g., small-angle penetration imaging) configuration of sensors and light (illumination) sources in which the viewing vector between the sensors and light sources is between 0° and 15° at different positions around a tooth; these different positions represent different positions taken at different times, e.g., by moving the wand/scanner around the tooth so that penetrative images may be taken at different angles relative to the tooth.

FIGS. 4B-4F illustrate other variations of penetrative imaging similar to that shown in FIG. 4A, for imaging from a tooth. FIG. 4B shows an example of a multi-camera, multi-light source scanner. FIGS. 4C-4F show alternative small-angle configurations.

In FIGS. 5A-5C the central sensor is active, and either the right (FIG. 5B) or the left (FIG. 5A) or both (FIG. 5C) light sources are illuminating the tooth. Similarly, in FIGS. 5D-5E the right sensor is active, while in FIGS. 5G-5I the left sensor is active.

FIG. 6 is a diagram schematically illustrating one method of generating a model of a subject's tooth or teeth having both surface and internal features.

In FIG. 8, the y-axis indicates the lens position of the 3D confocal scanner (scan amplitude). The durations of each of the scans (e.g., the scanning time for each mode) may be fixed, or it may be adjustable. For example the duration of the penetrative scan (d) may be dynamically adjusted (e.g., increased or decreased) during scanning base on the quality of the images received, the completeness of the 3D reconstruction of internal structures, etc. Similarly, the duration of the surface scan may be dynamically adjusted during scanning based on the quality of the image(s) being scanned (e.g., the prior images and/or the current image, etc.), the completeness of the 3D surface model for the region being scanned, etc.

FIG. 9A illustrates one example of an overlay of the penetration images in on a 3D surface model of the teeth, showing the image penetration panorama (in which penetrating images are stitched together to form the panorama)

FIG. 9B illustrates the portion of the model reconstruction of FIG. 9A including the surface and internal features. Note that in FIGS. 9A and 9B, the overlay showing the internal structures is not a volumetric reconstruction.

FIG. 10A shows an example of a front view of one example of an intraoral scanner front end.

FIG. 10B shows an example of a bottom view of the intraoral scanner, showing the plurality of sensors and light sources.

FIGS. 11A-11C shows projected images looking down through the top of the tooth using a penetrative wavelength (e.g., near-IR).

FIGS. 11D-11F illustrate the movement of the light source relative to the tooth in the z direction, using a penetrative wavelength.

FIGS. 11G-11I show the position of the scanner, such as those illustrated above, scanning the tooth in the z-direction. Note that FIGS. 11A, 11D and 11G correspond to a first depth position, FIGS. 11B, 11E and 11H correspond to a second (higher up the tooth) depth position, and FIGS. 11C, 11F and 11I correspond to a third (even higher up) depth.

FIGS. 18A-18C illustrate one method of automatic segmentation of a near-IR image. FIG. 18A illustrates edge detection from a penetrative scan through the teeth, taken with an intraoral scanner in the near-IR wavelength (e.g., 850 nm). FIGS. 18B and 18C shows segmentation based on the edge detection of FIG. 18A plotted on the penetrative scan.

FIGS. 19A-19C show further segmentation of the near-IR image of FIGS. 18A-18C. FIG. 19A shows edge detection from the near-IR image taken of a subject's teeth shown in FIG. 19C. FIG. 19B shows segmentation of the image of FIG. 19C, in which the segments (5 segments) are drawn on the near-IR image shown in FIG. 19C.

FIGS. 20A-20C illustrate segmentation of a near-IR image of a patient's teeth. FIG. 20A is a figure showing edge detection of a near-IR image. FIG. 20B illustrates segmentation of the near-IR image, showing 18 (overlapping) segments. FIG. 20C illustrates further segmentation of the near-IR image shown in FIG. 20B.

FIG. 21A shows edge detection of the near-IR image of FIG. 21C. FIG. 21B illustrates edge detection of the near-IR image shown in FIG. 21C.

FIG. 22A is a figure showing edge detection of a near-IR image. FIG. 22B illustrates segmentation of the near-IR image, showing 8 (overlapping) segments. FIG. 22C illustrates further segmentation of the near-IR image shown in FIG. 22B.

FIGS. 23A-23C illustrate segmentation of a near-IR image of a patient's teeth. FIG. 23A shows edge detection of the near-IR image of FIG. 23C. FIG. 23B illustrates edge detection of the near-IR image shown in FIG. 23C.

FIG. 30A shows an example of a supporting frame of the sleeve; FIG. 30B shows the support frame with a flex circuit and connectors coupled to the supporting frame. FIG. 30C shows the fully assembled sleeve of FIGS. 30A-30B.

In FIG. 34A, virtual section is pseudo-colored to show enamel; in FIG. 34B, the virtual section is pseudo-colored to show dentin.

FIG. 37A is an example of a display tracking gingival recession over time in using a 3D volumetric model as described herein. FIG. 37B shows an enlarged view of region B in FIG. 37A showing the later time.

FIG. 38A show an example of a 3D volumetric model of a patient's upper jaw (showing teeth and gingiva), from a top view. FIG. 38B shows the same 3D volumetric model, showing the internal features, including the more transparent enamel and the less transparent dentin. The 3D volumetric model may be manipulated to show more or less of the surface and/or internal structures. FIGS. 38C-38G illustrate progressively more transparent views or a region ("C") of the 3D volumetric model of FIG. 38A. FIG. 38C show a 2D image extracted from a region of the 3D volumetric model showing just the outer surface of the teeth (e.g., 100% of the color/outer surface image, 0% near-IR/internal volume). FIG. 38D shows the same region as FIG. 38C, combining the outer surface (color) image and the internal (near-IR based) image (e.g., 75% of the color/outer surface image, 25% near-IR/internal volume). FIG. 38E shows the same region as FIG. 38C, combining the outer surface (color) image and the internal (near-IR based) image (e.g., 50% of the color/outer surface image, 50% near-IR/internal volume). FIG. 38F shows the same region as FIG. 38C, combining the outer surface (color) image and the internal (near-IR based) image (e.g., 25% of the color/outer surface image, 75% near-IR/internal volume). FIG. 38G shows the same region as FIG. 38C showing just the internal (near IR based) image of the teeth (e.g., 0% of the color/outer surface image, 1000% near-IR/internal volume).

FIGS. 40A-40C illustrate another example of a method of displaying 3D volumetric image information by mixing it with surface (non-penetrative) information. FIG. 40A shows a visible light image of a region of a patient's dental arch taken with a scanner that is also configured to take penetrative (near-IR) scans). FIG. 40B show a volumetric model of the reconstructed 3D volumetric model of a patient's tooth showing internal dentin and enamel. Features not visible on the surface scan are apparent in the volumetric scan, including a caries and a bubbled region within the enamel. FIG. 40C shows a hybrid image in which the 3D volumetric image has been combined with the surface scan, showing both surface and internal structures, including the carries and the bubbled region.

In FIG. 43B the image window show a light image of the corresponding region of the dental arch.

In FIG. 43C the image window show a near-IR image of the corresponding region of the dental arch.

FIG. 46 schematically illustrates one example of a method for automatically or semi-automatically identify, confirm and/or characterize one or more actionable dental features that may benefit from detection and/or treatment.

DETAILED DESCRIPTION

Figure 2A:
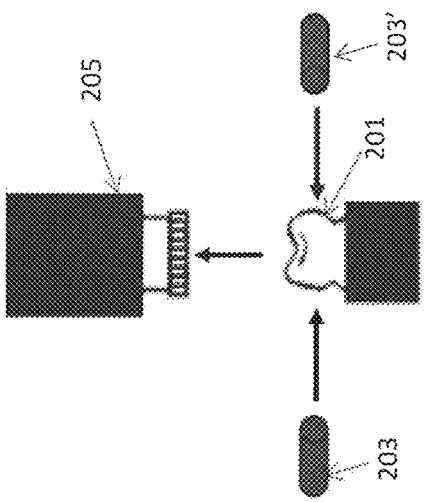
FIG. 2A illustrates trans-illumination imaging through a tooth at 180°.

Described herein are intraoral scanners for generating a three-dimensional (3D) model of a subject's intraoral region (e.g., tooth or teeth, gums, jaw, etc.) which may include internal features of the teeth and may also include a model of the surface, and methods of using such scanners. For example, FIG. 1A illustrates one example of an intraoral scanner 101 that may be configured or adapted as described herein to generate 3D models having both surface and internal features. As shown schematically in FIG. 1B, an exemplary intraoral scanner may include a handle or wand 103 that can be hand-held by an operator (e.g., dentist, dental hygienist, technician, etc.) and moved over a subject's tooth or teeth to scan both surface and internal structures. The wand may include one or more sensors 105 (e.g., cameras such as CMOS, CCDs, detectors, etc.) and one or more light sources 109, 110, 111. In FIG. 1B, three light sources are shown: a first light source 109 configured to emit light in a first spectral range for detection of surface features (e.g., visible light, monochromatic visible light, etc.; this light does not have to be visible light), a second color light source (e.g., white light between 400-700 nm, e.g., approximately 400-600 nm), and a third light source 111 configured to emit light in a second spectral range for detection of internal features within the tooth (e.g., by trans-illumination, small-angle penetration imaging, laser florescence, etc., which may generically be referred to as penetration imaging, e.g., in the near-IR). Although separate illumination sources are shown in FIG. 1B, in some variations a selectable light source may be used. The light source may be any appropriate light source, including LED, fiber optic, etc. The wand 103 may include one or more controls (buttons, switching, dials, touchscreens, etc.) to aid in control (e.g., turning the wand on/of, etc.); alternatively or additionally, one or more controls, not shown, may be present on other parts of the intraoral scanner, such as a foot petal, keyboard, console, touchscreen, etc.

In general, any appropriate light source may be used, in particular, light sources matched to the mode being detected. For example, any of these apparatuses may include a visible light source or other (including non-visible) light source for surface detection (e.g., at or around 680 nm, or other appropriate wavelengths). A color light source, typically a visible light source (e.g., "white light" source of light) for color imaging may also be included. In addition a penetrating light source for penetration imaging (e.g., infrared, such as specifically near infrared light source) may be included as well.

The intraoral scanner 101 may also include one or more processors, including linked processors or remote processors, for both controlling the wand 103 operation, including coordinating the scanning and in reviewing and processing the scanning and generation of the 3D model including surface and internal features. As shown in FIG. 1B the one or more processors 113 may include or may be coupled with a memory 115 for storing scanned data (surface data, internal feature data, etc.). Communications circuitry 117, including wireless or wired communications circuitry may also be included for communicating with components of the system (including the wand) or external components, including external processors. For example the system may be configured to send and receive scans or 3D models. One or more additional outputs 119 may also be included for outputting or presenting information, including display screens, printers, etc. As mentioned, inputs 121 (buttons, touchscreens, etc.) may be included and the apparatus may allow or request user input for controlling scanning and other operations.

Any of the apparatuses and methods described herein may be used to scan for and/or identify internal structures such as cracks, caries (decay) and lesions in the enamel and/or dentin. Thus, any of the apparatuses described herein may be configured to perform scans that may be used to detect internal structures using a penetrative wavelength or spectral range of penetrative wavelengths. Also described herein are methods for detecting cracks, caries and/or lesions or other internal feature such as dental fillings, etc. A variety of penetrative scanning techniques (penetration imaging) may be used or incorporated into the apparatus, including but not limited to trans-illumination and small-angle penetration imaging, both of which detect the passage of penetrative wavelengths of light from or through the tissue (e.g., from or through a tooth or teeth).

Figure 2B:
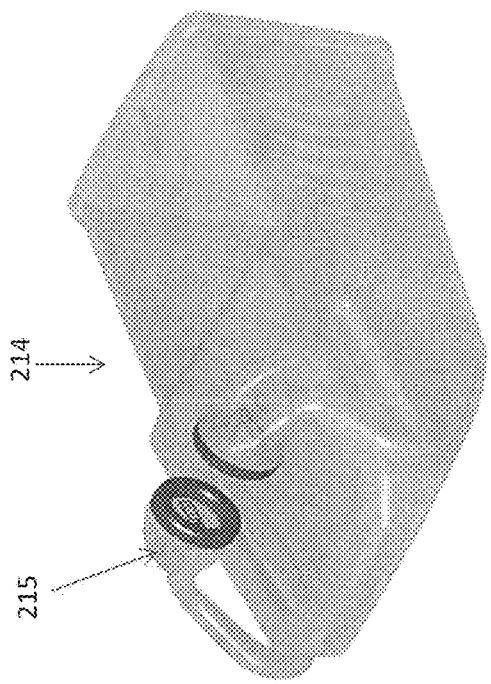
FIG. 2B illustrates trans-illumination imaging through a tooth at 90°.

Trans-illumination is one technique that may be used for seeing internal features of teeth. Traditionally, there are 2 basic configurations for trans-illumination through the teeth. FIGS. 2A and 2B illustrate these: a 180° configuration and a 90° configuration. Both configurations may be used for visualizing inside the teeth, and mainly through the enamel. As shown in FIG. 2A, in the 180° configuration, a penetrative wavelength (including a spectral range of one or more penetrative wavelengths) is emitted from a light source 203 and passed from one side of the tooth 201, and a sensor 205 (e.g., camera) on the opposite side detects the light that has passed through the tooth without being scattered or absorbed. Similarly, in FIG. 2B, the tooth 201 is illuminated by light from light sources (203, 203') on either side of the tooth 201, and the camera 205, which is oriented 90° relative to both light sources, detect light at the right angle to the light source. Typically, trans-illumination has been limited to the use of a single projection type, in order to give an image capture inside the tooth (similar to the use of an x-ray). Described herein are methods and apparatuses for visualization of the enamel-dentin area using a penetrative wavelength (such as between 700 to 1300 nm, 700 to 1090 nm, etc., e.g., 850 nm) and acquiring a plurality of projections or orientations from a single position of the scanner relative to the tooth/teeth and/or for a plurality of angles of the sensor relative to the teeth; in particular three or more orientations or projections may be taken for each internal region being imaged. Taking multiple (e.g., 3 or more) projections may provide better imaging, as it may produce multiple (e.g., 3 or more) images through the tooth from a particular location of the wand relative to the tooth/teeth. The use of one or more 180° projection may be useful as the light travels a shorter distance and is less scattered, however the combination of multiple different projections (orientations) from the same location (e.g., at approximately the same scanning time, within a few milliseconds of each other) may permit the system to build a volumetric model of the enamel-dentin area.

Figure 2C:
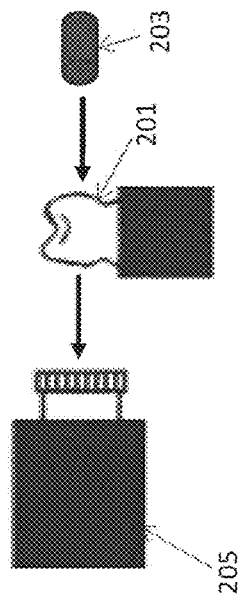
FIGS. 2C and 2D show side and top perspective views, respectively, of an example of a distal end of a wand of an intraoral scanner configured to provide trans-illumination imaging through a tooth at 90° and 180°.
Figure 2D:
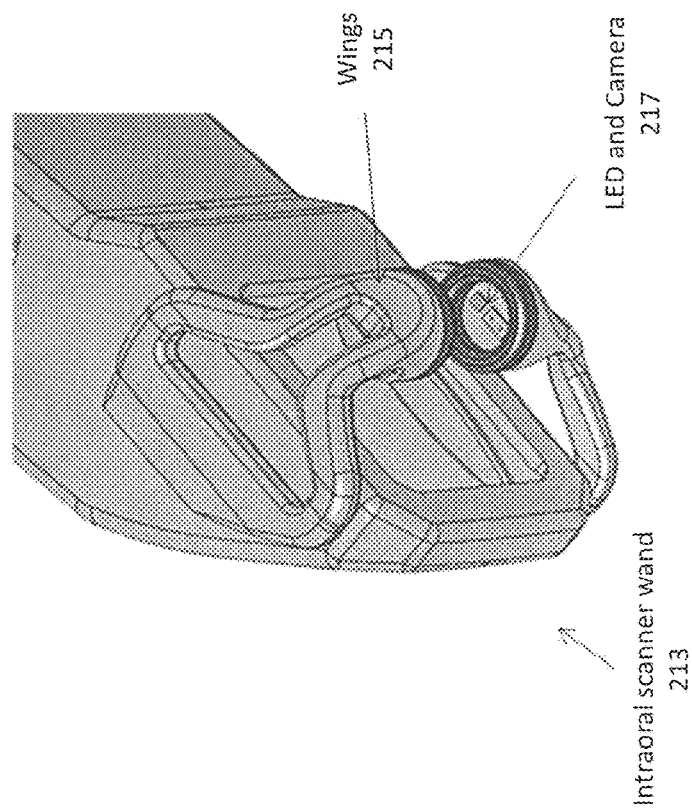
Figure 3A:
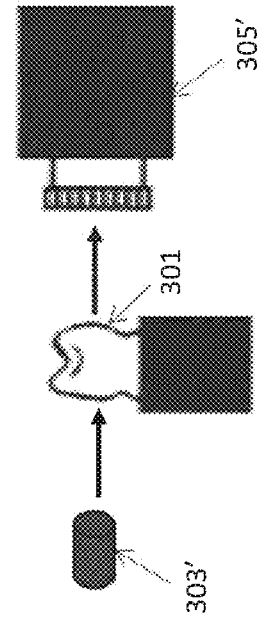
FIGS. 3A, 3B and 3C illustrate exemplary penetration with small angle illumination imaging orientations using an intraoral scanner wand such as the one shown in FIGS. 2C and 2D.
Figure 3B:
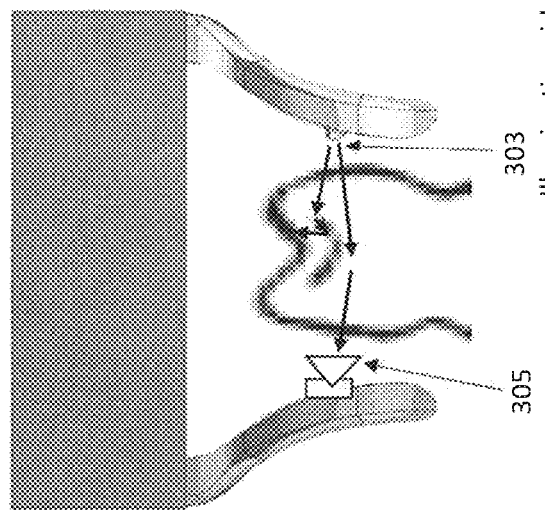
Figure 3C:
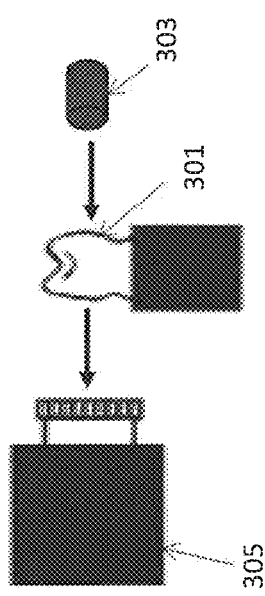
Figure 3D:
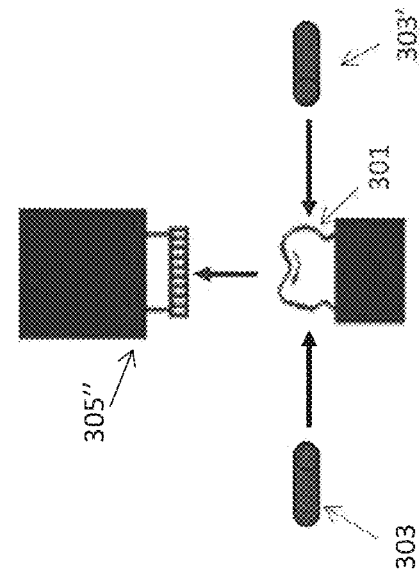
FIG. 3D shows another example (similar to what is shown in FIG. 3A) of illuminating with light (e.g., near-IR) on the right side and imaging from the left side (this orientation may be flipped) to get 180° trans-illumination. Higher and lower scattering is shown by the arrows.
Figure 5C:
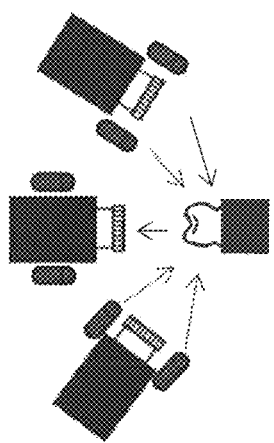
FIGS. 5A-5I illustrate nine alternative penetration imaging orientations that may be used as part of an intraoral scanner such as the ones shown in FIGS. 1A-1B.
Figure 5F:
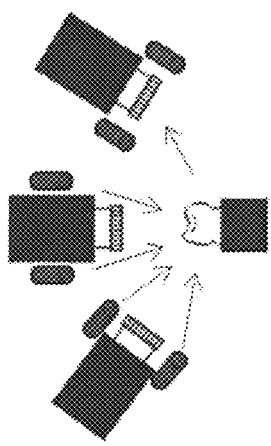
Figure 5I:
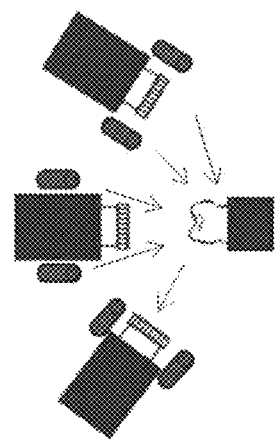
Figure 5B:
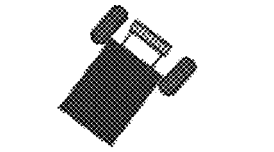
Figure 5E:
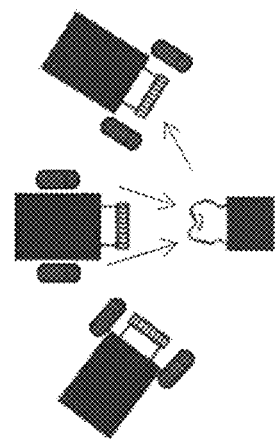
Figure 5H:
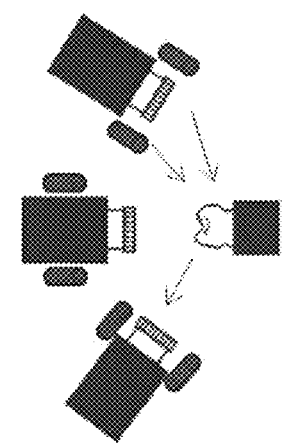
Figure 5A:
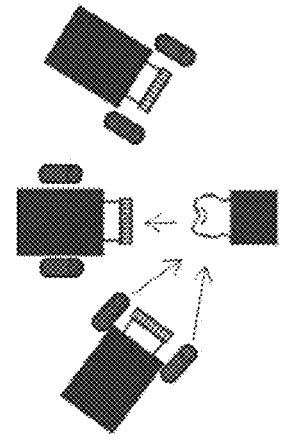
Figure 5D:
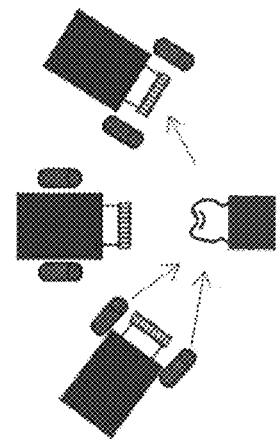
Figure 5G:
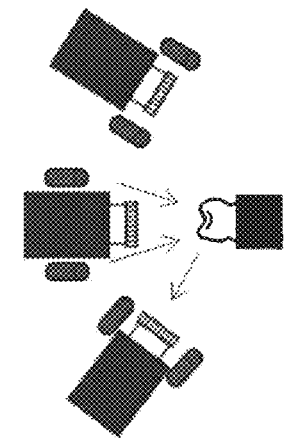

In variations using 90 and/or 180° configuration projections, the intraoral scanner may be adapted to provide trans-illumination imaging in this configuration. For example, FIGS. 2C and 2D illustrate one example of a distal end of a wand of an intraoral scanner adapted to collect trans-illumination images at 90 and 180°, in which the wand 213 includes a pair of projections or wings 215 each housing a light source (LED) and camera combination 217. This distal end portion of the wand may be configured as a sleeve 214, as shown (additional and alternative examples of sleeves are shown in FIGS. 29A-30C, described below). The sleeve may be removably attached onto and/or over the distal end of the wand. In FIGS. 2C and 2D, both wings and the base of the wand may include light sources and sensors (cameras) so that at least three trans-illumination images may be taken from a single position of the wand relative to the teeth, as shown in FIGS. 3A-3C. In FIG. 3A a first orientation is shown, in which the right LED 303 is on, illuminating through the tooth for detection/capture (180°) by the camera 305 on the left. FIG. 3D is similar to FIG. 3A, showing light applied from the right side passing into the tooth (arrows) and either passing through to the camera sensor 305 (also referred to herein as an image sensor, camera, or just "sensor"), or scattered from an internal region. The orientation of the camera sensor and illumination source may be switched. In FIG. 3B the left LED 303' is on, illuminating through the tooth for detection/capture (180°) by the camera 305' on the right. In FIG. 3C, both of the LEDs 303, 303' are on, illuminating from both right and left sides, and a camera 305" located 90° off of the axis of the LEDs captures the trans-illumination image.

In general, the trans-illumination imaging data such as that described above can be combined with, and collected concurrently with, 3D surface data (e.g., 3D surface model data) of the teeth, allowing an additional layer of data on internal structures such as caries and cracks. Further, the use of multiple projections (taken from multiple orientations) as described may enable reconstruction of volumetric models internal structures of the teeth enamel, showing features that would not otherwise be visible.

Although the 90° and 180° configurations of trans-illumination of the teeth may be useful, it may be particularly beneficial to provide penetration imaging configurations in which the angle between the emitted and received rays (vectors) is much smaller, e.g., between 0° and 30°, between 0° and 25°, between 0° and 20°, between 0° and 15°, between 0° and 10°, etc. In particular, angles between 0° and 15° (or between >0° and 15°) may be useful.

Trans-illumination in the 180° configuration and 90° configuration may constrain the movement of the intraoral scanner wand around the teeth due to their camera to light source angle constraint (as shown in FIGS. 2C and 2D). Thus, also described herein are methods and apparatuses for penetration imaging/visualization, e.g., of the enamel-dentin area, using a small angle, including between 0° and 15°. In one example, a light source (LED) emitting a penetrative spectral range (e.g., 850 nm) is used having a viewing vector at a small angle of 0°-15° relative to the camera view angle. As mentioned, this penetration imaging may be combined with concurrent 3D surface modeling of the teeth. The relative positions of the light source(s) and cameras(s) are typically known, and one or more penetration images may be taken at each position of the wand. Because of the small angle of the viewing vectors that may be used by the wand, the intraoral scanning wand may be configured with just a slight curve, allowing it to fit and be easily maneuvered around the intraoral cavity, unlike wands configured to measure 90° and 180° trans-illumination, which may use a device geometry including side wings to hold the LEDs and sensor(s) so that the wand can wrap around the tooth for the imaging (e.g., see FIG. 2C). The use of small-angle reflectance imaging may enable scanning in buccal and lingual directions, whereas the 90 degree (trans-illumination) scanning as described herein may be limited to scanning in the occlusal direction.

The use of a small angle for penetration imaging may include imaging into the tooth using the wand in a way that enables unconstraint movement around the tooth, and may enable capturing the internal structure data while also scanning for 3D (surface) model data, without requiring a dedicated structure and/or mode of operation. However, the use of small angles between the emitting light and the detector(s) may also be complicated by direct reflections. For example, direct reflection may occur in regions on the surface of the tooth in which the angle between the illumination and the imaging angles are approximately equal (e.g., in the cone of light and imaging NA). These direct reflections may be problematic if they saturate the sensor, or if they show surface information but obscure deeper structure information. To overcome these problems, the apparatus and methods of using them described herein may capture and use multiple illumination orientations taken from the same position. As used herein, in the context of a hand-held wand, taking multiple images from the same position may effectively mean taking multiple images at approximately the same time, so that a significant amount of movement has not occurred. For example, the images may be taken within a few milliseconds (less than 500 msec, less than 400 msec, less than 300 msec, less than 200 msec, less than 100 msec, less than 50 msec, etc.) of each other, and/or correcting for small movements.

Alternatively or additionally, the apparatuses and/or methods may reduce or eliminate the problems arising from saturation with direct reflection by using only the non-saturated pixels. In some variations, the surface information may be subtracted from the penetration images as part of the process. For example, visible light images ("viewfinder images") or surface imaging may be used to remove direct surface reflections.

In general, the apparatuses (e.g., systems) described herein may know the position of the wand at all times based on the surface scan, even when taking images at different (even small angle) angles. Thus, when performing surface and penetrating scans concurrently or nearly concurrently (e.g., within 600 ms, 500 ms, 400 ms, etc. of each other), including interleaving these scans with other scanning types, the position of the wand may be known relative to the object(s) being scanned. Based on this information, the apparatus may estimate which part(s) of the multiple images or signals is/are arriving from the surface and what is/are arriving from deeper structures.

FIG. 4A illustrates an example of a configuration of penetrative light sources 403, 403' (e.g., penetrative spectral range light sources) and camera(s) 405 that may be used as part of an intraoral scanner wand, shown in different positions around the target object (tooth 401). In FIG. 4A, three camera positions are shown, and each in each position the camera is flanked by the pair of LEDs (e.g., 403 and 403') for emitting light in the penetrative spectral range (penetrative wavelength). Alternatively a single light source (e.g., LED) may be used instead of a pair. Different images using the penetrative modality may be taken at different wand positions relative to the teeth. Alternatively, the wand may be configured with multiple imaging sensors (cameras) and multiple light sources, allowing multiple penetration images may be taken at approximately the same time, e.g., by turning on multiple sensors when illuminating from one or more LED orientations (e.g., FIGS. 5G and 5E, etc.). In FIGS. 5A-5I, at least nine different orientations of penetration images may be taken, as shown. Alternatively or additionally, multiple orientations may be taken sequentially, including within a very short time period (e.g., within <500 ms, 400 ms, <300 ms, etc.).

FIGS. 4B-4F illustrate other emitters and detectors for use with of any of the penetrating wavelengths that may be used to take images into the object having semi-transparent strongly scattering regions (e.g., teeth). These images typically collect reflective mode (e.g., light at a penetrative wavelength that has passed into the tooth, and been scattered/reflected from internal structures so that it can be collected by the detector. In FIG. 4B a combination of classic (e.g., 90°, 180°) trans-illumination and small-angle illumination angles are included. In FIGS. 4C-4F the angle of the ray of light emitted and collected is very small (e.g., around 0°) and can be collected by placing the emitter 403, 403' and detector 405 assembly (e.g., CMOS, CCD, etc.) adjacent to each other, as shown in FIG. 4C, combined with each other, as shown in FIG. 4D, or simply sharing a common or near-common beam path, as shown in FIGS. 4E and 4F, which may use reflection or waveguides to direct emitted and/or received light, including the use of beam splitters (dichroic beam splitters) and/or filters.

As mentioned above, any appropriate sensor may be used, including CMOS or CCD cameras, or any other sensor that is capable of detecting the appropriate wavelength, such as near-IR wavelength detectors.

Although applying a penetrative illumination from nearby the sensor (camera) may result in the strongest illumination in the region nearest to the camera, and therefore an unequal distribution of illumination, this is surprisingly less problematic then was expected. In penetration imaging conditions, the light generating the captured image has traveled though the object, and the longer the path, the longer the scattering that will occur, resulting in a more smoothed-out illumination when compared to direct illumination. In front illumination, as results with small-angle illumination, the strongest amount of light will be present in the region nearest to the illuminator (e.g., LED), which will back scatter; this nearby region (e.g., the first 1-2 mm) is an important region for detecting caries. However, it may still be desirable to compensate for the resulting non-uniform illumination profile distribution, as discussed above.

The use of penetration imaging, and particularly small angle illumination/imaging, which may also be described as reflective imaging, may provide information about internal regions (such as cracks, caries, lesions, etc.) of the teeth that would not otherwise be available. The internal feature (or internal region) information may be incorporated into a 3D model, which may be particularly powerful when combined with surface information (e.g., the 3D surface model or depth information). This may allow the user to capture the diagnostics data seamlessly during the 3D scanning procedure while allowing unconstrained movement around the teeth to capture data from different angles, providing a 3D model of the tooth interior.

Combining Surface Data with Internal Feature Data

As mentioned above, it may be particularly beneficial to combine and/or coordinate 3D surface data with any of the internal feature data (including, but not limited to, penetration imaging data). For example, internal feature data such as penetration imaging data may be combined with surface data (surface imaging data) collected from the same or approximately the same position of an intraoral scanner so that the same coordinate system may be applied to both types of data.

As described above, a color 3D intraoral scanner such as the one shown in FIG. 1A, may be equipped with illumination devices emitting light at two or more different spectral ranges for capturing a variety of surface and internal features. The data (e.g., surface data and internal feature data) collected may be correlated and combined to form a 3D model including information about lesions, decay, and enamel infractions as well as teeth internal structure. The internal feature data may be gathered by any appropriate penetrative imaging technique, including the reflective (e.g., small-angle) illumination and imaging, and trans-illumination imaging techniques described above or by other techniques known in the art, including, but not limited to UV/blue fluorescence and red light fluorescence.

The internal feature data may be collected (and may include lesion and internal teeth structure images) and combined with the surface data including color 3D surface model data for the teeth. The combination of surface and internal data may be expressed as a 3D model or 3D rendering, which may include a full color 3D data (including models and renderings) of the lesions and tooth internal structure as well as the surface of the teeth, gums and any other scanned portion of the intraoral region. Although in some variations the internal and surface data may be coextensive, in some variations the surface data may be more extensive than the internal data; for example, the 3D model may include internal data for only a portion of the 3D model, while other regions may not include (or may include only incomplete) internal features.

In use, a 3D model of a tooth or teeth including both surface and internal elements may be analyzed either automatically or manually, and internal features may be identified and/or marked. For example, lesions, caries and/or cracks may be labeled, including color coding, e.g., according to their type and level of risk they represent in one or more images that may be provided and/or as part of a data file that is generate to show these images. Alternatively or additionally, a written transcript/description of these findings may be provided.

An intraoral scanner for generating a 3D model including both surface and internal structure as described herein may include one or more image sensors. For example, the image sensor may be configured for capturing color 3D (surface) images or data, and may also capture lesion and teeth internal structure images. Optionally or additionally, the system may have multiple sensors. The surface data may be acquired using an intraoral scanner in any appropriate manner. The intraoral scanner is generally configured to scan (via the wand) in both surface and internal imaging modes, including scanning concurrently. For example, surface data may be captured using a color intraoral 3D scanner by confocal, stereo vision or structured light triangulation or any other 3D surface scanning technology capable of intraoral scanning.

As illustrated in FIGS. 10A and 10B, the illumination light sources (including the lights sources for the first modality (e.g., surface scanning), for the second modality (e.g., penetrative imaging such as penetration imaging), and/or for the third modality (e.g., color scanning) may be located at the front tip of the intraoral scanner wand, e.g., near the scanned objects or inside the scanner head. The front tip illumination configuration may be configurable according to the application needs with or without any particular light source suitable for the desired diagnostics feature by changing the front tip. The light source(s) and the sensors (e.g., cameras) may be arranged in any appropriate manner, including as shown in FIGS. 10A-10B and 4. For example, the light sources and cameras may be adjacent to each other. In some variations the system or method uses miniature sensors 1005, 1007, e.g., located at the front tip in a wrap-around manner, to capture stereoscopic 3D internal feature data (e.g., images) and/or for facilitating penetration imaging in a more efficient fashion.

As mentioned, in some variations, the lesion/internal tooth structure capture methods may be any combination through-tooth penetration imaging, including one or more of: trans-illumination, red light laser fluorescence and blue/UV laser fluorescence, etc. In general, the internal feature data may be used in combination with the surface data, including the coordinate system of the surface data, to reconstruct a 3D representation of the tooth structure. For example a 3D reconstruction of the tooth data may be reconstructed by an algorithm combining several (e.g., multiple) 2D images using the any of the internal feature imaging techniques described herein, typically taken at several different angles or orientations.

Data captured by the intraoral scanner, including in particular the 3D model of the tooth/teeth having both surface and internal features, may be stored by the device and/or transmitted to a physician, medical record, dentist, or the like. For example, any of the data captured by the intraoral scanner, i.e. a color 3D model combining the topography of the teeth lesions and internal teeth structure, may be maintained in a designated patient database for longitudinal monitoring and preservation of patient's oral health. The data may be annotated (including dating and/or markings referencing internal features) or unannotated.

For example, longitudinal comparison in time may be done using the 3D models described herein at one or more levels, including by comparing across time: surface changes, visual color changes, internal/volumetric changes, or any combination of these. For example, each can be shown as before and after e.g., by manual evaluation, or subtracted and compared automatically. In some embodiments, two or more 3D models may be superimposed with one another on a display to highlight differences between the 3D models. The superimposed models may help highlight changes in enamel thickness, dentin volume, color, opacity, and/or decreases/increases in caries size, for example. Optionally, a 3D model of a patient's dentition from an earlier date may be morphed into a 3D model of the patient's dentition at a later date to help highlight any changes in the patient's dentition over time. In some embodiments, a time series of 3D models may be progressively morphed from one to the next to provide a video or animation of the changes in the patient's dentition. Automatic comparison may be done by applying or converting to a common coordinate system, which may in particular be done using surface information (e.g., based on the 3D surface model data that is included as part of the generated 3D volumetric model). Typically, all three types of data (surface, color, volumetric, etc.) are interconnected by the same coordinate system, as already described above. In general the method and apparatuses described herein, including the 3D models, may be used to predict future dental or orthodontic conditions in a patient as described, for example, in U.S. 2016/0135925, incorporated by reference in its entirety.

When comparing scans, including 3D volumetric scans, the scans may be adjusted or normalized relative to each other for automatic, semi-automatic or manual comparison. For example, a scan of the tooth or teeth (e.g., a full jaw scan, partial scan, etc.), may not be 100% repeatable, particularly to a precision higher than the voxel resolution. To compare voxel-by-voxel, a matching and/or morphing function may be applied to one or both scans to allow more direct comparison. For example, a matching and/or morphing function may be used. A morphing function may bring the external surfaces to match and align, allowing a voxel-to-voxel comparison. This may also allow comparison of full scans to partial scans.

As mentioned above, in general, captured data may be stored and saved in the same coordinate system. Thus, surface data (including 3D surface model data) may use a coordinate system (e.g., x, y, z; so that the 3D surface model is S(x,y,z)) and the internal feature data may use or reference the same coordinate system (e.g., so that the internal feature data is I(x, y, z)). Thus, common features or structures may have the same address (coordinates) between both data sets.

FIG. 6 is a diagram illustrating an example of a method for generating a 3D model or rendering of a tooth or teeth using surface data and internal feature data. In this example, a hand-held intraoral scanning wand (scanner) may first be positioned adjacent to a target intraoral region 601 to being scanning Once scanning is initiated, the apparatus may collect surface data (e.g., 3D model surface data) including depth information in a first coordinate system 603. The surface data may typically be collected while illuminating the sample using a first illumination spectrum, such as visible light (e.g., monochromatic or broadband light). Internal feature data may also be collected, e.g., using a second illumination spectrum (which may include just a single wavelength or small range of wavelengths) that is/are penetrative into the tooth/teeth 605. This data may use the same coordinate system as the surface data, which may be accomplished as described in greater detail below. Once collected, the data may be analyzed, and/or filtered (including subtracting, smoothing, etc.), and combined to form a 3D model rendering of the intraoral cavity (e.g., tooth, teeth, gums, jaw, etc.) using both the surface data and the internal feature data 607. For example, when building the 3D geometry of the internal feature data (which is typically two-dimensional in nature), the algorithm may use the reference to the known 3D surface scan to improve the accuracy of the internal feature data.

In general, in any of the apparatuses and methods described herein, the internal feature data collected 605 may be used to reconstruct a volumetric model of the tooth or teeth including the internal features. In particular, tomographic reconstruction (e.g., optical tomography) may be used. A fully volumetric modeling may be used. Typically, every penetrating light ray can either be refracted, reflected, scattered and/or absorbed (including combinations of these), depending on the material properties and the light used. In some variation, the methods and/or apparatus may divide the volume of the tooth into small voxels and for each voxel, estimate these four parameters (refraction index, reflection, scattering, absorption) based on the imaging data collected, using the coordinate system corresponding to the coordinate system of the surface data. More complex models (e.g., based on non-isotropic scattering or complex surface scattering) may also be used. Once a set of parameters for each voxel is estimated, the method or apparatus may compare how well the captured images, fit this model. Thus in some variations the apparatus and/or method may seek to minimize the difference between the captured images and the modeled, predicted image. An initial guess may be built from the 3D surface capture, including estimates of enamel parameters and width.

Alternatively or additionally, multi-surface modeling may be used. Multi-surface modeling assumes a set of material (and in some cases uniform) in optical properties, such as properties for air, dentin, and enamel (but may include more than these three). This technique may seek to find the boundaries between the materials. There are multiple ways to accomplish this, including using techniques similar to what is described above for the full volumetric modeling, but without the voxels representation. Alternatively or additionally, a contour line method may be used in which a first (e.g., air-enamel) boundary is given from the 3D surface capture, and then, by finding the edges of regions in the 2D penetrating images, a smooth 3D surface may be approximated that best fits this silhouette. See for example "3D Shape from Silhouette Points in Registered 2D Images Using Conjugate Gradient Method. Andrzej Szymczaka, William Hoffb and Mohamed Mahfouzc," the entire contents of which are incorporated herein by reference. Apart from contours, other features, like points, corners, as known in the art, may be used. These features may be detected from the different viewpoints, and located in 3D by triangulation, and are part of the boundaries.

In practice, recording the surface data and internal feature data in the same coordinate system may be achieved by scanning both the surface and the internal features at the same position and/or time. As mentioned, in a hand-held user controlled intraoral scanning device (e.g., wand) it may be difficult to scan the same region at different times in different wavelengths. Thus, any of the apparatuses and methods described herein may coordinate scanning at the different modalities or modes (e.g., surface data scanning and/or internal features/penetrative data scanning).

Figure 7:
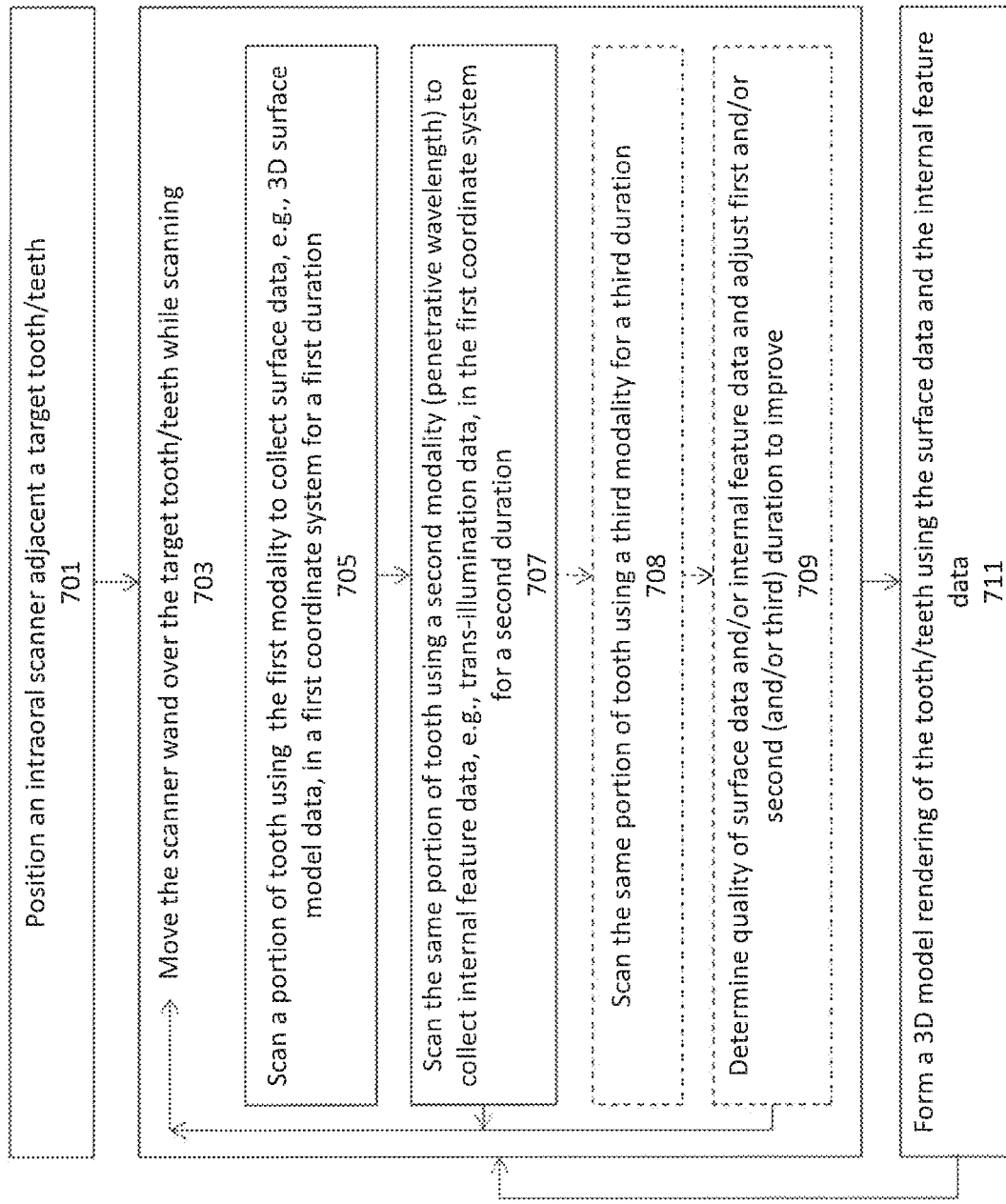
FIG. 7 is a diagram illustrating one variation of a method of generating a model of a subject's teeth when having both surface and internal features by cycling between different scanning modalities (e.g., surface scanning, penetration imaging, etc.).

For example, FIG. 7 illustrates one method in which the intraoral scanner alternates between surface scanning and one or more other scanning modalities (e.g., internal feature scanning, such as penetration imaging scanning). In FIG. 7, after positioning the scanner adjacent to the target intraoral structure to be modeled 701, the wand may be moved over the target while the apparatus automatically scans 703 the target for both surface data and internal data. As part of this method, the system may alternate (switch) between scanning a portion of the tooth using a first modality 705 (e.g., surface scanning, using emitting light in an appropriate wavelength of range of wavelengths) to collect surface data such as 3D surface model data and scanning with a second modality 707

(e.g. a penetrative wavelength). After an appropriate duration in the first modality, the method and apparatus may briefly switch to a second modality (e.g., a penetrative wavelength or range of wavelengths) to collect internal feature data for a brief time period (second duration) 707 over approximately the same region of the object scanned in the surface mode. At the time of the switch, the coordinate system between the two modalities is approximately the same and the wand is in approximately the same position, as long as the second duration is appropriately short (e.g., less than 500 msec, less than 400 msec, less than 300 msec, etc., less than 200 msec, less than 100 msec, less than 50 msec, etc.). Alternatively or additionally, the method and apparatus may extrapolate the position of the wand relative to the surface, based on the surface data information collected immediately before and after collecting the internal data. Thus, in any of the methods described herein, including as shown in step 703 of FIG. 7, the apparatus may interpolate the positions between each scan (e.g., first modality scan, such as a surface scan, a second modality scan, such as a penetrative, e.g., near-IR scan or scan(s) and a third modality scan, such as a color scan, etc.). This interpolation may correct for the small but potentially significant movement of the wand during scanning. In particular, when coordinating between the surface and internal structures, in which the scanning is being manually performed, interpolating (and/or extrapolating) to approximate the more accurate 3D position of the teeth (or of the teeth relative to the scanning wand) for each scanned image. The portion of the teeth scanned using a penetrative wavelength may therefore be interpolated proportionally between the surface scans done before and after the penetrative scan(s). See, e.g., FIG. 8, described below, showing an exemplary relative timing of the scans in each mode. Alternatively or additionally, the position of the teeth and/or wand/scanner during a scan may be extrapolated from the prior surface scan position based on the rate of movement of the scanning wand (e.g., as estimated from the rate of change across the surface from prior surface scans, and/or motion sensor(s) in the wand). Correcting the coordinate system of each scan in this manner (for example, in x, y and z position, and orientations angles) may allow images in different modalities to be tightly registered relative to each other, regardless of how the scanner is manipulated by the user. In penetrative scans, in which multiple scans may be taken from the same relative position and used to reconstruct internal features, the accuracy of the coordinate system may allow higher resolution modeling of the internal features.

In general, when collecting penetrative wavelength images, the light emitted and received may have different polarizations. In the reflective light mode, for example when using small-angle penetration imaging, some of the energy is penetrating, but some is also reflected from the surface. It may be preferable to block this direct surface reflection, which may be done in any appropriate manner, including using polarization. For example, to block the surface reflection the sample (e.g., tooth) may be illuminated with a penetrative wavelength at a specific polarization, and this polarization may be blocked in the imaging path. This polarization may also be helpful to block direct light from the illumination source in trans-illumination (e.g., where there is a direct line of sight to the illuminator as in 180° trans-illumination).

Although many of the methods and apparatuses described herein include switching between modes to distinguish surface and internal structures, in some variations, they may be truly simultaneously detected, for example, using a dichroic beam splitter and/or filter. Thus, by separating out the wavelengths and/or polarization that are penetrative and include internal reflections and/or scattering from those including only (or primarily) surface features, the surface data may be collected and processed separately from the internal features, and these two data sets may be recombined later; this technique may inherently use the same coordinate system.

Figure 2E:
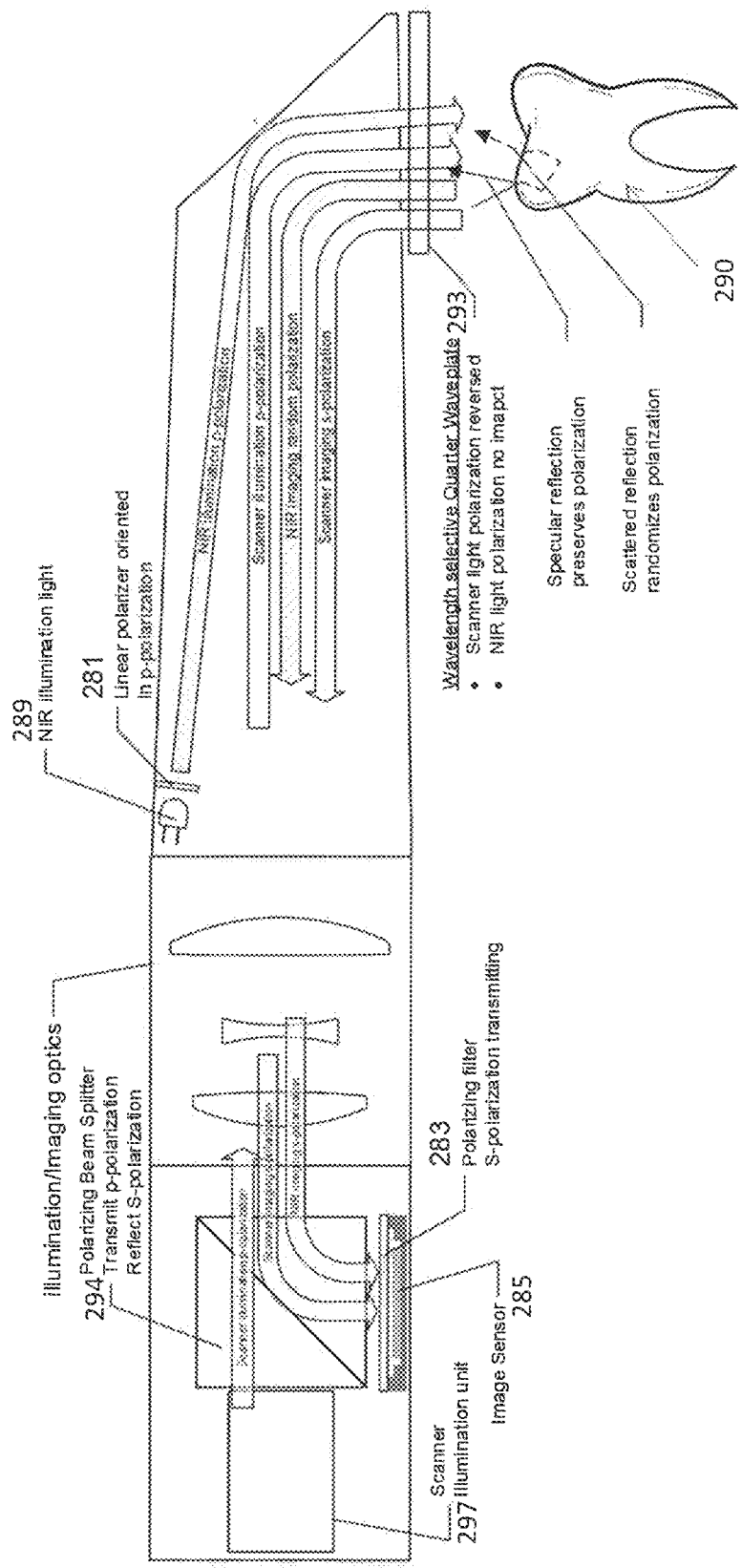
FIG. 2E shows a schematic of an intraoral scanner configured to do both surface scanning (e.g., visible light, non-penetrative) and penetrative scanning using a near infrared (IR) wavelength. The scanner includes a polarizer and filters to block near-IR light reflected off the surface of the tooth while still collecting near-IR light reflected from internal structures.

For example, FIG. 2E shows a schematic of intraoral scanner configured to do both surface scanning (e.g., visible light, non-penetrative) and penetrative scanning using a near infra-red (NIR) wavelength (at 850 nm in this example). In FIG. 2E, the scanner includes a near-IR illumination light 289 and a first polarizer 281 and a second polarizer 283 in front of the image sensor 285 to block near-IR light reflected off the surface of the tooth 290 (P-polarization light) while still collecting near-IR light scattered from internal tooth structures/regions (S-polarization light). The NIR light illuminates the tooth in P-polarization, and specular light reflected from the surface of the tooth, e.g., the enamel, is reflected with specular reflection hence its P-polarization state is conserved. Near-IR light penetrating the internal tooth features, such as the dentin, is scattered resulting in random polarization (S and P). The wavelength selective quarter waveplate 293 does not modify the polarization of the near-IR light (e.g., it leaves the polarization state of the near-IR light being delivered unchanged) but changes the polarization of the returning scan light from P to S such that only surface reflection are captured in the scan wavelength. The returning near-IR light, having a mixture of S and P polarizations, is first filtered through the polarization beam splitter (PBS) 294 and polarizing filter 283 such that only the S-polarization is transmitted to the image sensor. Thus only the near-IR S-polarization light, coming from the tooth internal structures, is captured by the image sensor while specular light, having the original p-polarization, is blocked. Other intraoral scanner configurations with or without polarization filters such as those shown in FIG. 2E may be used as part of the probe.

In FIG. 2E, the surface scan may be performed by illuminating the surface (using the scanner illumination unit 297), illuminating in p-polarization, and the polarization is reversed by the wavelength-selective quarter waveplate 293 (transmitting S-polarization light to the image sensor).

As shown in FIG. 7, the scanning scheme, including the duration of the scanning modalities such as the second scanning modality to determine internal feature data, may be manually or automatically adjusted 709. For example, scanning procedure (time sharing and sequence) may be varied per case and the system may automatically optimize the scanning resources so as to get high-quality scans and/or more complete reconstructions. The method or apparatus may determine the quality of the scanned data 709, such as the quality of the scanned surface data, and may adjust the scanning duration(s) (e.g., the second duration) accordingly. An estimate of quality may be made automatically, for example, based on blurring, over- or under-saturation, etc. For example, the duration of a scanning scheme may be dynamically adjusted (e.g., increased or decreased) based on the quality of the scans in this modality; if the prior x scans in this modality are below a first (e.g., minimum) quality threshold (quantifying one or more of: blurring, over-saturation, under-saturation, etc.) the scan duration for that modality, $d_i$, may be increased. Scan time may be reduced if the duration of the scan is above a minimum duration and the quality is above a second quality threshold (which may be the same as the first quality threshold or greater than the first quality threshold). Reducing the scan duration may allow the duration of other scanning modalities to increase and/or the rate of switching between scanning modalities to increase. Alternatively or additionally, the scan duration for a modality may be adjusted based on the completeness of the 3D model being reconstructed. For example, when scanning a region of the 3D model having a more complete surface model (e.g., regions over which the surface model has already been made), the duration of the surface scan may be decreased, and the duration of the penetrative scan (e.g., a reflective scan using a near-IR wavelength, or a trans-illumination scan using a near-IR wavelength) may be increased to increase the resolution and/or extent of the internal structures. Similarly, the frequency of the scanning in each mode may be adjusted dynamically by the apparatus. Any of the methods and apparatuses described herein may also be configured to give feedback to the user to slow down or add scans from a specific angle by showing these missing regions or angles in the 3D graphical display.

Figure 8:
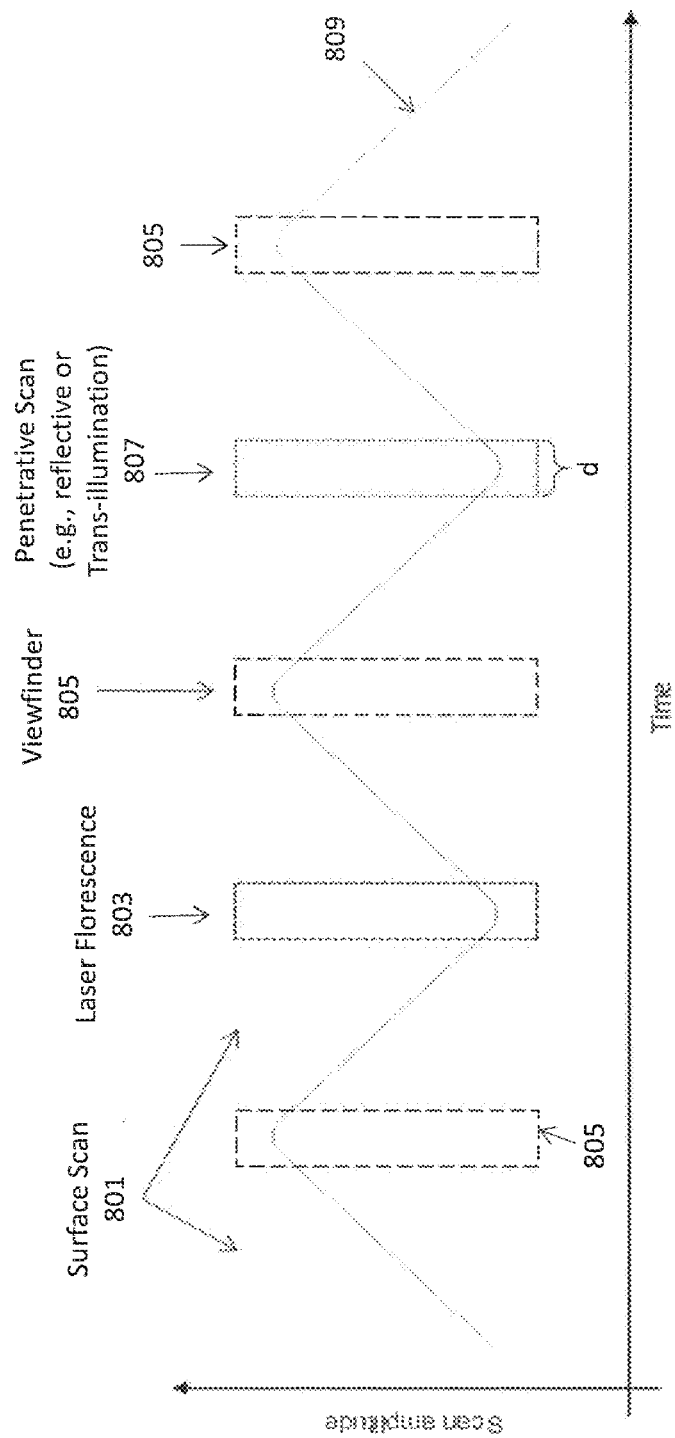
FIG. 8 is a graphical example of one a timing diagram for scanning a sample (e.g., tooth) to generate a model having both surface and internal features cycling between different scanning modalities (showing surface scanning, laser florescence, viewfinder and penetration imaging modalities).

As illustrated in FIG. 7 (e.g., optional step 708) and in FIG. 8, more than two scanning modalities may be used. FIG. 8 illustrates an exemplary method of operating an intraoral scanner so that it switches between different scanning modalities, including surface scanning 801, laser florescence 803, color visible light scan (viewfinder) 805, penetration scanning 807, UV scanning, etc. The system may initially switch between the scanning modalities with a default scanning scheme; as mentioned, the system may then (in real time) analyze the data coming from each of the scanning modalities and may prioritize the scanning modalities that have less complete data, for example, by expanding the frequency and/or duration (d) that they are scanned. In some embodiments, the system may compare the gathered data from the one or more of the scanning modalities to predetermined data resolution thresholds in order to determine which scanning modalities to prioritize. For example, a system may increase the frequency or duration of surface penetrative imaging after determining that sufficient surface data had been gathered with a surface imaging modality and that internal feature data resolution is still insufficient. Alternatively or additionally, in some variations scanning may be done for different modalities simultaneously. Once sufficient scanning area has been completed, the combined 3D model of the intraoral region may be assembled using the scanned data 711; alternatively the 3D model may be continuously assembled as the scanning is ongoing. The frequency of the scanning 809 is shown by the frequency of the scan amplitude in FIG. 8; surface scans are performed at the maximum of the scan amplitude and penetrative scans at the minimum of the scan amplitude as the depth of the confocal scanning increases and decreases. The frequency of the depth scanning 809 may be increased or decreased dynamically during scanning. For example, to allow longer scanning duration scans, or to accommodate for a faster-moving wand/scanner by the user. In some variations the wand may include a motion sensor (e.g., an accelerometer, etc.) to detect movement rates, and the scanning rate(s) and duration(s) may be adjusted based on the detected motion of the scanner.

As shown in FIG. 6, the resulting 3D model including surface and internal structures may be used in a variety of ways to benefit subject (e.g., patient) health care. For example, the 3D model may be used to identify (automatically or manually) and analyze lesions, caries and/or cracks in the teeth. The 3D model may be used, for example, to measure size shape and location of lesion including decay, to assess the type of decay based on translucently, color, shape, and/or to assess the type of surface issues based on surface illumination e.g. cracks, decay, etc. 609.

This 3D data (or data derived from it) may be monitored over time for a particular patient 611. For example, the 3D data may be checked for changes in shape size and type over time either visually or using an algorithm.

In general, the 3D data may be annotated. For example, after a first scan, a clinician may mark areas of interest which may be manually or automatically assessed in following scans. In addition the 3D data may be used to help treat or provide treatment guidance and monitoring 613. For example, if a clinician decides to restore a tooth, the 3D data showing surface and internal regions generated as described herein may be used to provide reduction guidelines for the tooth to ensure the removal of the decayed volume. During the procedure, additional (e.g., intermediate) scans may be made to provide the doctor with further direction and immediate feedback on the reduction.

FIGS. 9A and 9B illustrate one example of a 3D model 900 rendering of an intraoral region of a subject including both surface (total surface is shown in the projection of FIG. 9A) and internal structures, shown in the enlarged region in FIG. 9B. In FIG. 9B, the darker region 903 apparent from the penetration imaging using 850 nm light combined with the 3D surface data, shows a region of interest. The region of interest may be a carious region or a dental filing, or the like. The ability to manipulate images like this to rotate, zoom, section and otherwise view the 3D model or regions of the 3D model may greatly enhance the treatment and understanding of a subject's dental needs.

Depth Scanning

FIGS. 11A-11I illustrates one example of volumetric modeling of internal tooth structure using a penetrative wavelength such as near-IR trans-illumination ("TI"). In this example, a lesion in the tooth may be detected when light is bellow lesion or at the level of the lesion. When the light is below the lesion, the lesion absorbs the light, thus lesion appears as dark spot in the image. In FIG. 11D, a tooth having a lesion is shown with a scanner sensor 1101 above the tooth (positioned above the occlusive surface of the tooth). The scanner includes one or (as illustrated in FIGS. 11D-11F) two light sources (emitters) 1105, 1105', emitting near-IR light, as shown by the arrows. The light penetrates the tooth and the sensor 1101 detects the occlusion of light due to the lesion, as shown in FIG. 11A.

Moving the scanner with the light source upwards (i.e., moving the wand of the scanner higher along the tooth) will produce a change in the lesion image as shown in FIG. 11B. The corresponding position of the light sources relative to the tooth is shown in FIG. 11E schematically, and in the illustration of FIG. 11H. As the scanner is moved further up the tooth, the dark spot representing the lesion 1113 will start shrinking until completely disappearing, turning into light saturation. Finally, when the light source 1105, 1105' is above the lesion, the dark spot is no longer present (e.g., FIG. 11C) and only the central occlusive region (the dentin) is shown. As already discussed above, the outer surface of the tooth and gingiva may be concurrently scanned using a separate light source, providing the 3D outer surface of the tooth, and therefore the distance from the tooth to the scanner. This information, as described above, may be used to map the lesion's depth and/or shape.

Such depth scanning may be manually or automatically performed, and may be useful for providing a backup and/or alternative to volumetric modeling (e.g., 0-degree volumetric modeling) of the tooth/teeth. Indeed this vertical scanning of the teeth (which may be performed in any direction (bottom to top of tooth, top to bottom, etc.) may be used as one type or sub-type of volumetric scanning that may provide information on shape and position of dentin and/or lesions.

For example, the method of vertically (z-axis) scanning of the teeth/tooth with an intraoral scanner, particularly one having both a penetrative (e.g., near-IR) and surface scanning wavelength(s), may provide an alternative method of volumetric scanning. In general, data may be acquired by scanning up or down (in the z-axis) the tooth/teeth.

As discussed above, one configuration for the scanning devices described may optically image the inside region of a tooth/teeth using, e.g., trans-illumination (through the sides) at an angle, such as a 90° angle, between light source and camera. When a dental caries is present in the tooth, viewing the tooth with a penetrative wavelength, e.g., in trans-illumination, from above (occlusion view) may reveal the caries as an occlusive region. Depending on the relative z (depth) position of the light source with respect to the caries, an occluded region corresponding to the caries will be present in the x,y image. Thus scanning through the z-axis (depth) as described above may be used to determine one or both of z-position and shape of the caries. In some variations, a method for scanning using a penetrative wavelength (or a penetrative and surface scanning) may begin with illuminating from the sides and imaging from above and placing light as close as possible to gum line. The method may then proceed to move up along the z axis of tooth, moving away from the tooth's occlusive surface. This may allow the light to hit a lesion from different depths (in the z-axis). As illustrated in FIGS. 11A-11C, a caries will be initially present, and as the scanner is drawn upwards, may shrink in the imaging plane (x,y) until it is no longer blocking the light. Any of these methods may also calculate or determine the z-position along the tooth as the scanner is moved upwards, so that the relative depth on the tooth is known, and therefore the depth of the lesion is from the enamel layer. From this information, the dimensions of the lesion may also be determined (e.g., an estimate of how far along the z-position the lesion extends), as well as the breadth and extent (e.g., how far it extends in x,y) may also be determined. Along with the surface 3D model, showing the outer shape of the tooth, this information may be used to provide a model of the tooth and the overall lesion.

Thus, using both a penetrative wavelength (e.g., near IR) and the non-penetrative (surface scanning) wavelength, a model of both the external and internal structures of the tooth may be determined. Depth scans (even non-contiguous scans) along the z-axis of the tooth may be particularly useful for determining the depths and/or dimensions of internal structures within the tooth/teeth. In any of the methods described herein, as discussed above, a 3D scan of the tooth may be performed concurrently with the penetrative (including depth) scanning.

Thus, in any of the methods of scanning a tooth as described herein, the method may include determining a depth (z) dimension for each scan, showing the relative depth of the light source(s), e.g., the near-IR light source(s) relative to the tooth. This information may be provided by the 3D surface scan corresponding/correlating to the penetrative scan. Depth information (e.g., knowing how much the scanner has been moved in the z-axis) may provide substantial volumetric information.

As mentioned above, the depth (z) scanning described herein may be performed manually or automatically. For example, this scanning may be performed by manually scanning the wand up and along the teeth. During scanning both concurrent 3D surface modeling and internal modeling/imaging may be continuously performed during scanning. Any appropriate scanning rate (e.g., 20 scans per second) may be done. Thus, a user may scan at a reasonable speed, and output may be done in real-time, including displaying a lesion, and/or lesions (and any other internal structures) may be displayed later following analysis by the software. In one example, concurrent scanning may be performed so that the surface scanning (using a laser) may be done for an approximately 35 ms period, followed by a window of 15 ms for other types of imaging, including color, near IR, etc., and repeated during the scanning period. In some examples, the near-IR scanning may be done for 5 ms within the 15 ms window. Shorter sampling may be beneficial (e.g., shorter than 20 ms, shorter than 15 ms, shorter than 12 ms, shorter than 10 ms, shorter than 7 ms, shorter than 5 ms, etc.), as it may reduce smearing of the image. However, shorter scan times may require higher energy, e.g., more power/current to the penetrative light source. Imaging data may be collected throughout. Alternatively, scanning may be done for longer or shorter periods of time (e.g., surface scanning, near IR scanning, color scanning, etc.), and/or at the same time (e.g., laser surface scanning and near-IR concurrently, using different emitters/detectors, for example). In this manner, e.g., concurrent or rapid alternating (within 200 ms, within 150 ms, within 100 ms, within 50 ms, etc.) of surface and penetrative scanning, or any other different types of scanning, may permit coordination between the surface (e.g., 3D) molding and internal structures as described above.

Imaging Internal Structures Using Scattering Coefficients

Also described herein are methods and apparatuses for generating images of internal structures from within a tooth or other semi-transparent, strongly scattering object) based on a plurality of penetrative images (also referred to herein as "penetrating images") through the object in which the position of the camera (relative to the object) is provided. These methods and apparatuses may therefore generate images, including three-dimensional models, of internal structures without requiring a model of the external surface.

For example, described herein are methods and apparatuses, including computing device readable media, for reconstructing a volumetric structure from an object including semi-transparent strongly scattering regions, such as a tooth. More specifically, these apparatuses (e.g., systems) and methods may provide techniques for reconstructing an inner structure of an object, such as the dentin in the teeth.

Generally, objects that are semi-transparent and strongly scattering to a specific wavelength can be imaged according to the methods (and using any of the apparatuses) described herein. If the location and orientation of the camera with respect to the object is known, the inner structure of the object can be reconstructed with a low computational complexity proportional to the volume being reconstructed and the number of images.

Any of the intraoral scanners that take images through a subject's intraoral region (e.g., tooth or teeth, gums, jaw, etc.) described herein and also provide information on the relative position of the scanner (e.g., the camera of the scanner taking the image), may be used. For example, returning to FIGS. 1A and 1B, FIG. 1A illustrates one example of an intraoral scanner 101 that may be configured or adapted as described herein to generate 3D models having both surface and internal features. As shown schematically in FIG. 1B, an exemplary intraoral scanner may include a wand 103 that can be hand-held by an operator (e.g., dentist, dental hygienist, technician, etc.) and moved over a subject's tooth or teeth to scan both surface and internal structures. The wand may include one or more sensors 105 (e.g., cameras such as CMOS, CCDs, detectors, etc.) and one or more light sources 109, 110, 111.

In FIG. 1B, two separate light sources are shown: a first light source 109 configured to emit light in a first spectral range for detection of surface features (e.g., visible light, monochromatic visible light, etc.) and a second light source 111 configured to emit light in a second spectral range for detection of internal features within the tooth (e.g., by trans-illumination, small-angle penetration imaging, laser florescence, etc., which may generically be referred to as penetration imaging). Although separate illumination sources are shown in FIG. 1B, in some variations a selectable light source may be used. The light source may be any appropriate light source, including LED, fiber optic, etc. The wand 103 may include one or more controls (buttons, switching, dials, touchscreens, etc.) to aid in control (e.g., turning the wand on/of, etc.); alternatively or additionally, one or more controls, not shown, may be present on other parts of the intraoral scanner, such as a foot petal, keyboard, console, touchscreen, etc.

In addition, the wand 103 may also include one or more position and/or orientation sensors 123, such as an accelerometer, magnetic field sensor, gyroscope sensors, GPS etc. Alternatively or additionally, the wand may include an optical sensor, magnetic sensor, or other some combination thereof, for detecting the relative position of the wand, and particularly of the camera(s) with respect to the object being imaged (e.g., a tooth or teeth). Alternatively or additionally, the apparatus may detect the relative position of the wand based on the surface images (e.g., surface scanning) and/or viewfinding scan taken as described above.

In general, any appropriate light source may be used, in particular, light sources matched to the mode being detected. For example, any of these apparatuses may include a visible light source or other light source for surface detection (e.g., at or around 680 nm or other appropriate wavelengths), a visible light source (e.g., white light source of light) for traditional imaging, including color imaging, and/or a penetrating light source for penetration imaging (e.g., infrared and/or near infrared light source).

The relative positions of the light source(s) and camera(s) are typically known, and one or more penetration images may be taken at each position of the wand. The positions of the light source(s) and camera(s) can include three numerical coordinates (e.g., x, y, z) in a three-dimensional space, and pitch, yaw, and roll of the camera.

The intraoral scanner 101 may also include one or more processors, including linked processors or remote processors, for both controlling the wand 103 operation, including coordinating the scanning and in reviewing and processing the scanning and generation of the 3D model including surface and internal features. As shown in FIG. 1B the one or more processors 113 may include or may be coupled with a memory 115 for storing scanned data (surface data, internal feature data, etc.). Communications circuitry 117, including wireless or wired communications circuitry may also be included for communicating with components of the system (including the wand) or external components, including external processors. For example the system may be configured to send and receive scans or 3D models. One or more additional outputs 119 may also be included for outputting or presenting information, including display screens, printers, etc. As mentioned, inputs 121 (buttons, touchscreens, etc.) may be included and the apparatus may allow or request user input for controlling scanning and other operations.

Any of the apparatuses and methods described herein may be used to scan for and identify internal structures such as cracks, caries (decay) and lesions in the enamel and/or dentin. Thus, any of the apparatuses described herein may be configured to perform scans to detect internal structures using a penetrative wavelength or spectral range of penetrative wavelengths. Although a variety of penetrative scanning techniques (penetration imaging) may be used or incorporated into the apparatus, trans-illumination and small-angle penetration imaging, both of which detect the passage of penetrative wavelengths of light through the tissue (e.g., through a tooth or teeth), may be of particular interest.

The methods and apparatuses for visualization of the enamel-dentin area using a penetrative wavelength (such as, for example, 850 nm) described herein may acquire a plurality of projections or orientations from a single position of the scanner relative to the tooth/teeth; in particular three or more orientations or projections may be taken at each position. Taking multiple (e.g., 3 or more) projections may provide better imaging, as it may produce multiple (e.g., 3 or more) images through the tooth from a particular location of the wand relative to the tooth/teeth.

Figure 12:
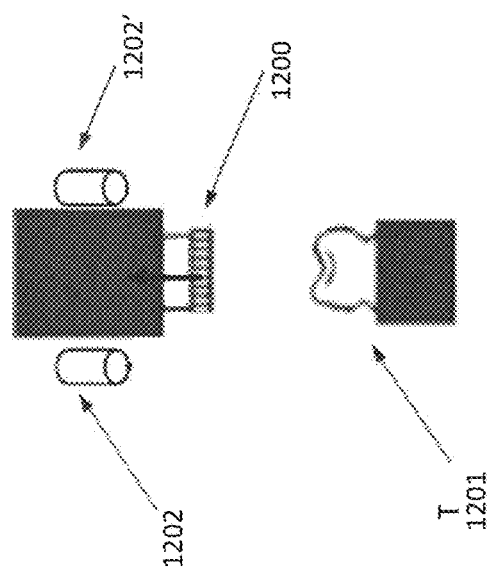
FIG. 12 illustrates an example of a configuration of penetration light sources (e.g., penetrative spectral range light) and cameras that may be used as part of an intraoral scanner wand.

FIG. 12 illustrates an example of a portion of a scanner configured to include penetration light sources 1202, 1202' (e.g., penetrative spectral range light) and cameras that may be used as part of an intraoral scanner wand. In FIG. 12, a camera 1200 is shown that is flanked by a pair of LEDs 1202, 1202' for emitting light in the penetrative spectral range in substantially the same direction as the camera towards a target T (such as a tooth 1201). A single light source 1202 (e.g., LED) may be used instead of a pair. In general according to this disclosure, the light sources of the wand are projected in substantially the same direction as the camera, but in some embodiments the light sources can vary +/−15 degrees from the direction of the camera, as described above.

Figure 13:
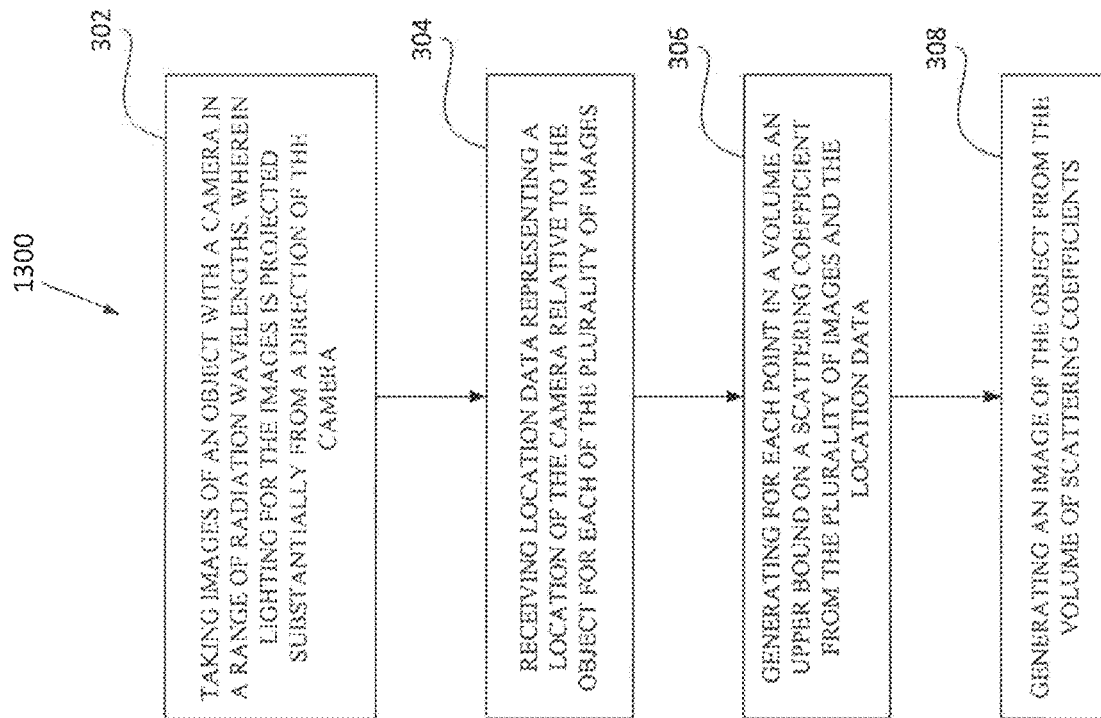
FIG. 13 shows a flowchart that describes one method for reconstructing a volumetric structure from an object including semi-transparent strongly scattering regions for a range of radiation wavelengths.

FIG. 13 shows a flowchart 1300 that describes one method for reconstructing a volumetric structure from an object having semi-transparent strongly scattering regions for a range of radiation wavelengths. The object having semi-transparent strongly scattering regions can be, for example, a tooth comprising an exterior enamel surface and an interior dentin surface.

At step 302 of flowchart 1300, the method comprises taking a plurality of images of the object with a camera in the range of radiation wavelengths, wherein lighting for the plurality of images is projected substantially from a direction of the camera. In some embodiments, the range of radiation wavelengths is an infrared or near infrared wavelength. The infrared or near infrared wavelength can be used, for example, to penetrate the semi-transparent object. In one embodiment, the lighting for the plurality of images can vary +/−15 degrees from the direction of the camera. The plurality of images can be stored in computer memory coupled to the camera.

Any of these methods may also include receiving location data representing a location of the camera relative to the object for each of the plurality of images. Generally, the location data includes the position and orientation of the camera with respect to the object. This location data can be determined from the plurality of images, or alternatively or additionally, the position and orientation can be measured with sensors 123 on the wand (e.g., gyroscope sensors, accelerometers, GPS, etc.). Alternatively or additionally, the position and orientation can be computed by registration of scanned surface data. In some embodiments, the location data comprises three numerical coordinates in a three-dimensional space (e.g., x, y, and z in a Cartesian coordinate system), and pitch, yaw, and roll of the camera. The location data can also be quantified as vector metrics (e.g., rotation metrics and vector position).

At step 306 of flowchart 1300, the method further comprises generating for each point in a volume an upper bound on a scattering coefficient from the plurality of images and the location data. Each of the plurality of images may be a projection from the real world (a 3D environment) onto a 2D plane (the image), during which process the depth is lost. Each 3D point corresponding to a specific image point may be constrained to be on the line of sight of the camera. The real world position of each 3D point can be found as the intersection of two or more projection rays through the process of triangulation.

In step 306, an upper bound on a scattering coefficient is determined for each point in a volume that represents the object being scanned. The upper bound is selected from the plurality of images for each point using the location data from the camera to triangulate the position of each point. The plurality of images produces an intensity for each point that is a result of the amount of light reflected by the object. This intensity for each point is used to generate the scattering coefficient for each point. The upper bound on the scattering coefficient for each point can be stored in memory coupled to the camera.

Generating, for each point in the volume an upper bound on the scattering coefficients may include projecting each point of a 3D grid of points corresponding to the volume of the object onto each of the plurality images using a first calibration, producing a list of scattering coefficient values for each projected point, correcting each scattering coefficient value on the list of scattering coefficient values according to a volume response, and storing a minimum scattering coefficient value for each grid point from the list of scattering coefficient values.

A number of calibrations can be performed to facilitate projecting each point of the 3D grid of points onto each of the plurality of images. For example, in one embodiment, the first calibration may comprise a fixed pattern noise calibration to calibrate for sensor issues and image ghosts of the camera. In another embodiment, the first calibration comprises a camera calibration that determines a transformation for the camera that projects known points in space to points on an image. In some embodiments, all of the calibrations described above can be performed prior to projecting the points onto the images.

When generating an upper bound on a scattering coefficient from the penetrative images and location data, the upper bound on the scattering coefficient(s) may only be determined for points within an exterior surface of the object being imaged. For example, the methods described herein can further include receiving surface data representing an exterior surface of the object (e.g., scan data representing an exterior or enamel surface of a tooth). With the exterior surface data, only points within this exterior surface (e.g., internal points) can be used to generate scattering coefficients. This may allow the imaging to focus only on, for example, a dentin surface within an enamel surface of teeth.

Finally, any of these methods may comprise generating an image of the object from the upper bound of scattering coefficients for each point 308. Example of generating these images are provided herein, and may include forming a line and/or surface based on threshold values of the scattering coefficients or values based on the scattering coefficients.

Figure 14:
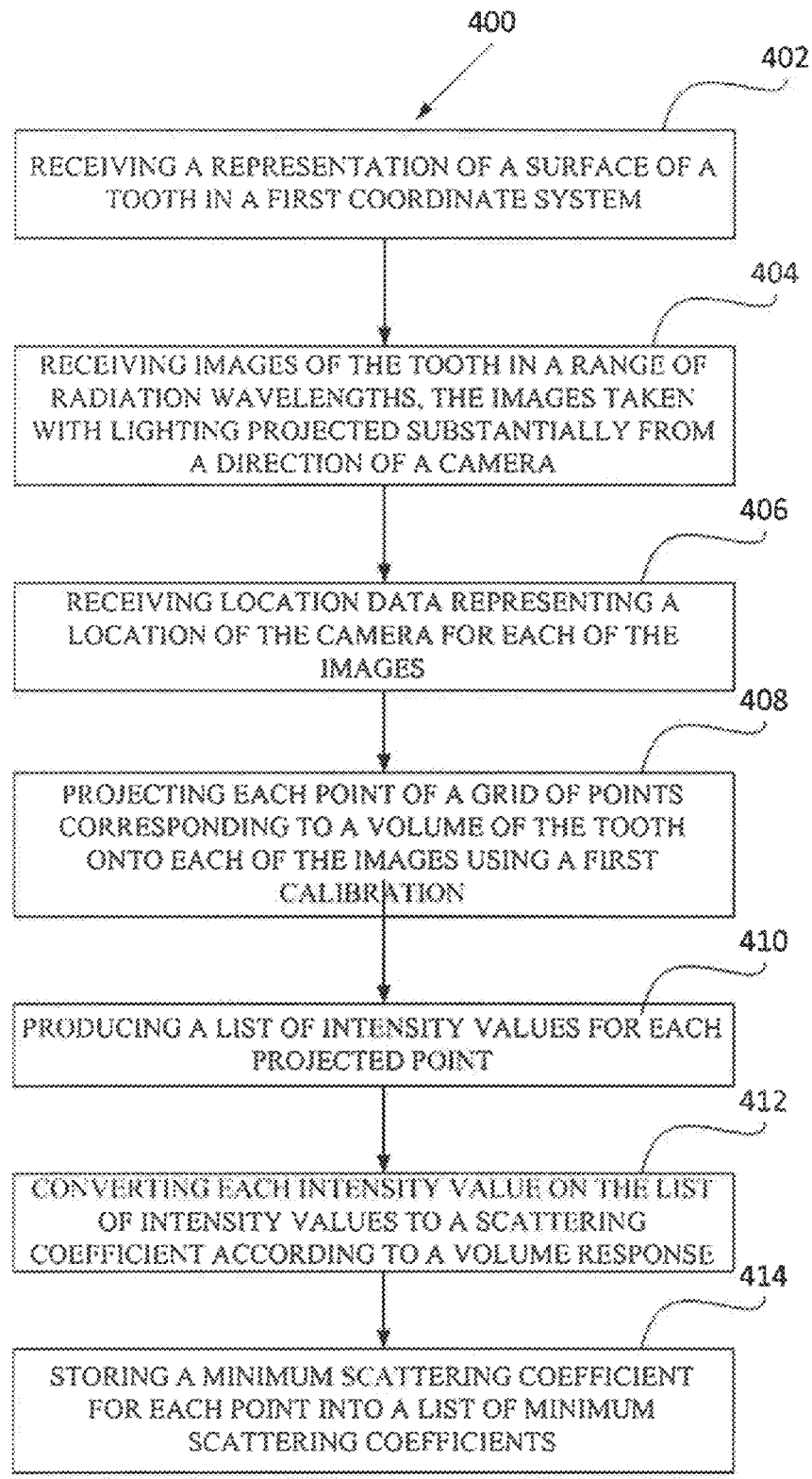
FIG. 14 illustrates another flowchart that provides method steps for reconstructing a volumetric structure from a tooth.

FIG. 14 is a flowchart 400 that illustrates a method for reconstructing a volumetric structure from a tooth. The tooth can be semi-transparent in a range of radiation wavelengths. At step 402, which is optional, the method comprises receiving, in a processor, a representation of a surface of the tooth in a first coordinate system. The representation of the surface of the tooth can be, for example, a 3D model of the tooth that is produced either by scanning the teeth or by taking a mold of the teeth.

The method may also include receiving, in the processor, a plurality of images of the tooth in the range of radiation wavelengths, the plurality of images taken with lighting projected substantially from a direction of a camera 404. In some embodiments, the wavelength is a penetrative wavelength of the infrared or near infrared region or a range within the IR/near IR. The infrared (IR) or near infrared wavelength can be used, for example, to penetrate the tooth. The lighting for the plurality of images can vary +/−15 degrees from the direction of the camera. The plurality of images can be stored in computer memory coupled to the camera.

At step 406 the method further comprises receiving, in the processor, location data representing a location of the camera for each of the plurality of images. Generally, the location data includes the position and orientation of the camera with respect to the object. This location data can be determined from the plurality of images, or alternatively, the position and orientation can be measured with sensors on the camera (e.g., gyroscope sensors, accelerometers, GPS, etc.). Alternatively or additionally, the position and orientation can be computed by registration of scanned surface data. In some embodiments, the location data comprises three numerical coordinates in a three-dimensional space (e.g., x, y, and z in a Cartesian coordinate system), and pitch, yaw, and roll of the camera. The location data can also be quantified as vector metrics (e.g., rotation metrics and vector position).

The method may also include projecting each point of a grid of points corresponding to a volume within the surface of the tooth onto each of the plurality images using a first calibration 408. The grid of points that is produced may be inside of the exterior surface of the tooth. The grid can sit on a cubic grid, for example. Each grid point can be projected onto each of the plurality of images using a calibration. A number of calibrations can be performed to facilitate projecting each point of the grid onto each of the plurality of images. For example, the calibration may comprise a fixed pattern noise calibration to calibrate for sensor issues and image ghosts of the camera. In another embodiment, the calibration may comprise a camera calibration that determines a transformation for the camera that projects known points in space to points on an image. In some embodiments, all of the calibrations described above can be performed prior to projecting the points onto the images.

The method may further include producing a list of intensity values for each projected point 410. The plurality of images produces an intensity for each point that is a result of the amount of light reflected by the object. This intensity value for each point may be stored.

At step 412 the method may further comprise converting each intensity value on the list of intensity values to a scattering coefficient according to a volume response. This step may be performed to calibrate the intensity value for each pixel. The process calculates a scattering coefficient that would produce such an intensity value for each point relative to the position of the camera. The output is a scattering coefficient which normalizes the intensity according to a volume response.

Finally, in FIG. 14, the method may further include storing a minimum scattering coefficient for each point into a list of minimum scattering coefficients 414. The method may further comprise producing an image from the list of minimum scattering coefficient for each point.

Figure 15A:
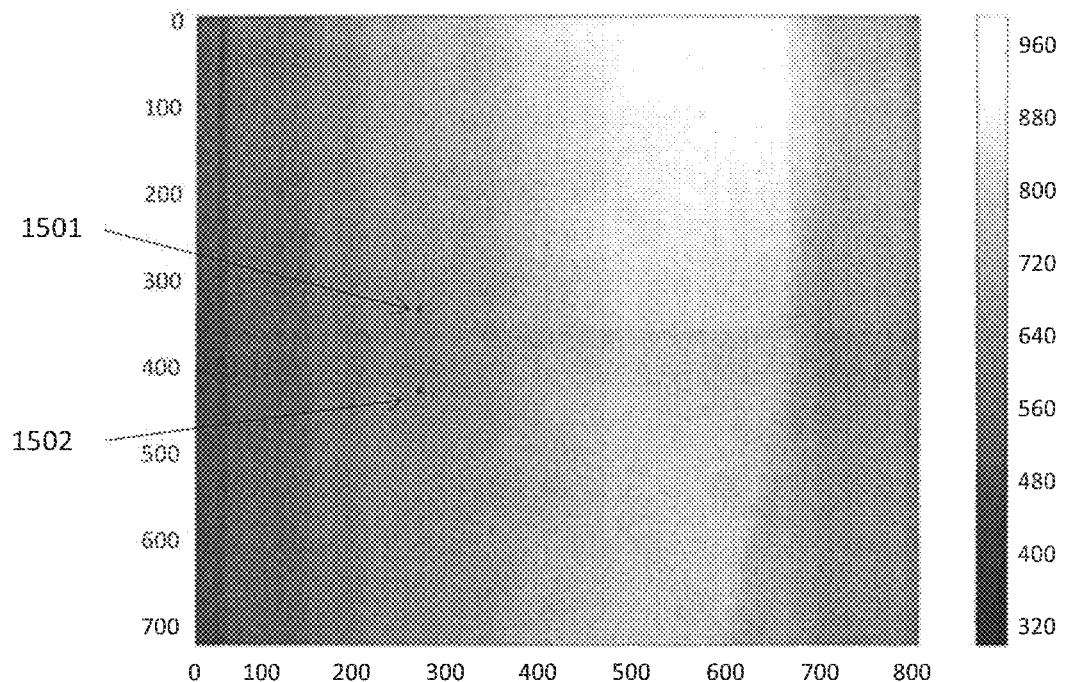
FIGS. 15A-15E show one example of an image fixed pattern noise calibration and illumination non-uniformity calibration, which gives a constant response for a uniform plane target.
Figure 15B:
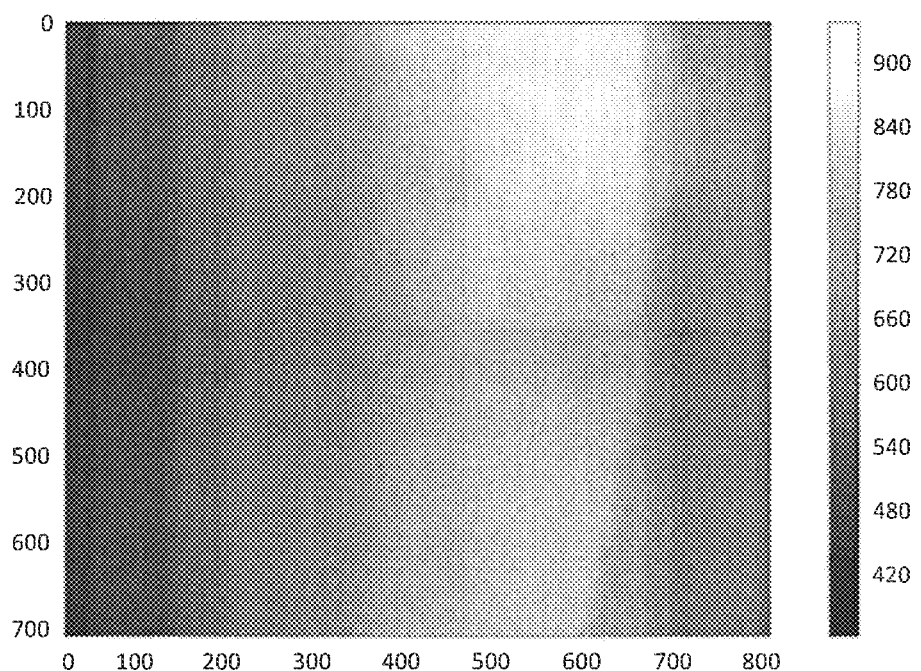
Figure 15C:
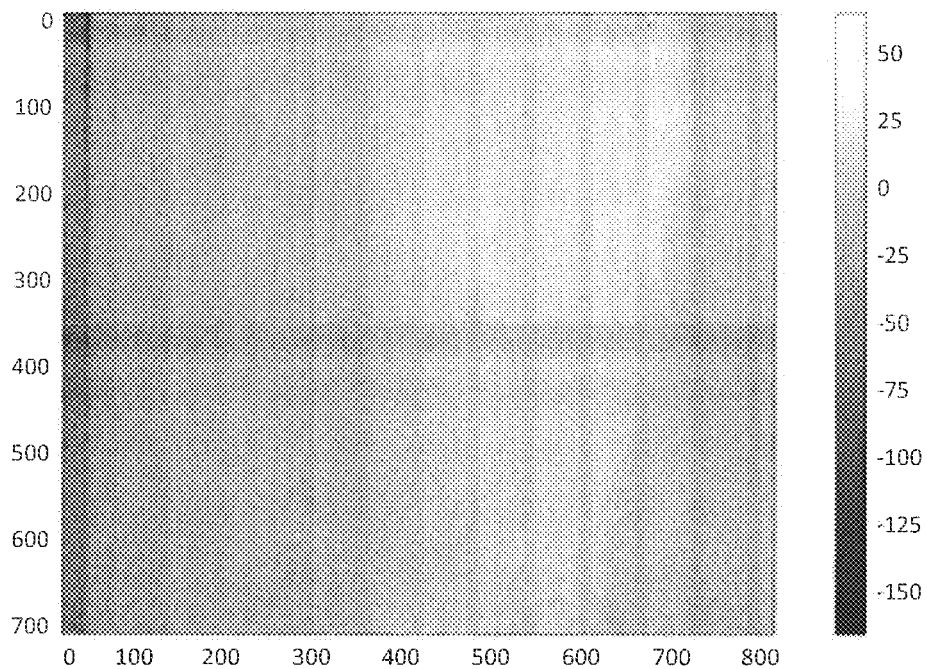
Figure 15D:
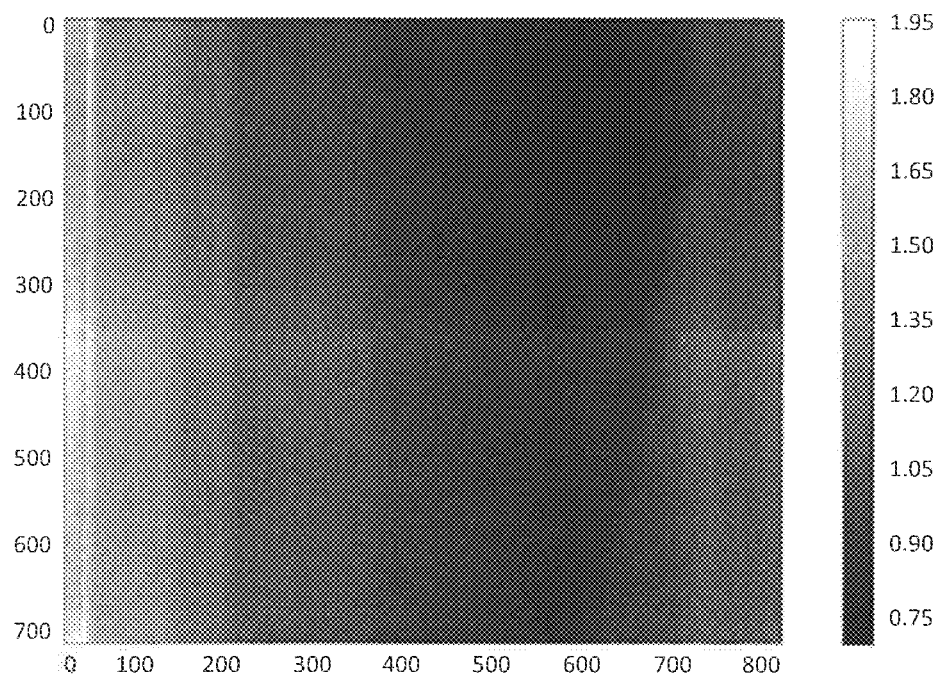
Figure 15E:
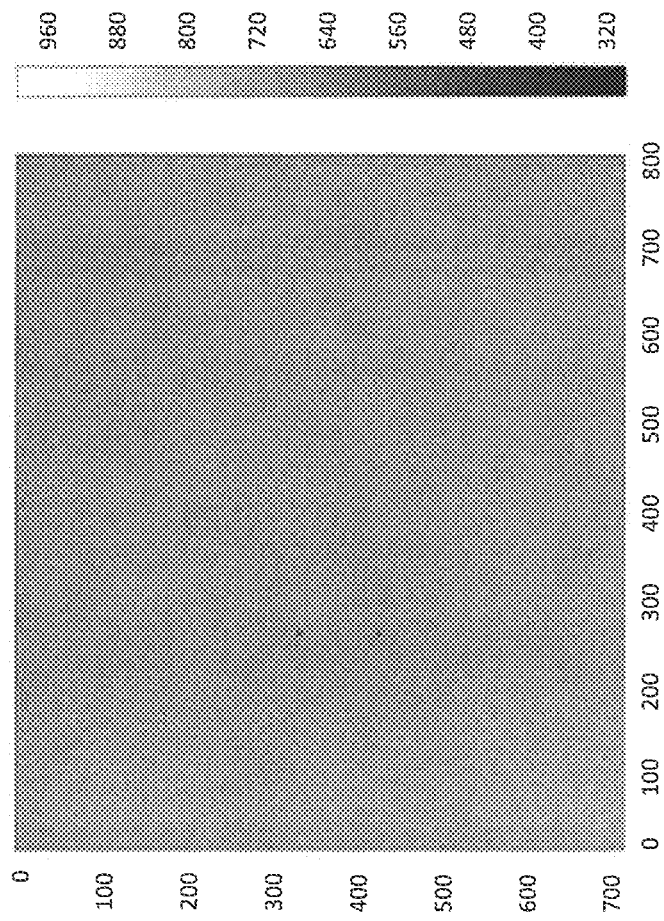

As described above, the methods and techniques can include a plurality of calibrations to project points from the real world into the plurality of images. One such calibration is an image fixed pattern noise calibration (PRNU) which addresses sensor issues and system ghosts that do not depend on the object being scanned. FIGS. 15A-E show one example of an image fixed pattern noise calibration, which gives a constant response for a uniform plane target. FIG. 15A shows an original image of a plane uniform target, including two particles 1501, 1502 in the middle of the image. FIG. 15B shows the median image after moving the target parallel to the plane. This causes the two particles to "disappear" from the image. FIG. 15C shows the image after applying a bias coefficient figure for each pixel, which creates strong electronic noise in the image. In FIG. 15D, a slope has been applied to each pixel, resulting in a smooth pattern given by the optics. Finally, FIG. 15E shows the final image after response equalization.

Another calibration that may be applied is called a camera calibration, which allows the projection of real world (3D) points to 2D image pixels. The camera calibration determines a transformation for the camera that projects known points in space to points on an image.

A volumetric response calibration that gives a scattering coefficient for all points in the world given an intensity in the image within a field of view of the camera may also be applied. This calibration brings a standard scattering coefficient to constant response anywhere in the field of view.

Finally, a scan to world camera calibration may be applied that is a rigid body transformation that converts from the scan coordinate system (of the 3D scan of the object) to the camera calibration coordinate system (of the 2D images of the object).

Other techniques may be used to determine the volumetric scattering coefficients from the penetrative images and camera positions. For example in some variations, back propagation may be used. Back propagation may include estimating (e.g., tracing) rays going through the tooth volume and entering the camera. The actual intensities reaching the sensor for each ray may be taken from the penetrative images and camera positions and orientations. For each ray the damping of the intensity due to scattering in the volume it passes may be estimated. For example, the transmission of light through a strongly scattering and weakly absorbing material may be modeled using a hybrid calculation scheme of scattering by the Monte Carlo method to obtain the temporal variation of transmittance of the light through the material. A set of projection data may be estimated by temporally extrapolating the difference in the optical density between the absorbing object and a non-absorbing reference to the shortest time of flight. This technique may therefore give a difference in absorption coefficients. For example, see Yamada et al., "Simulation of fan-beam-type optical computed-tomography imaging of strongly scattering and weakly absorbing media," Appl. Opt. 32, 4808-4814 (1993). The volumetric scattering may then be estimated by solving for the actual intensities reaching the sensor.

Figure 16:
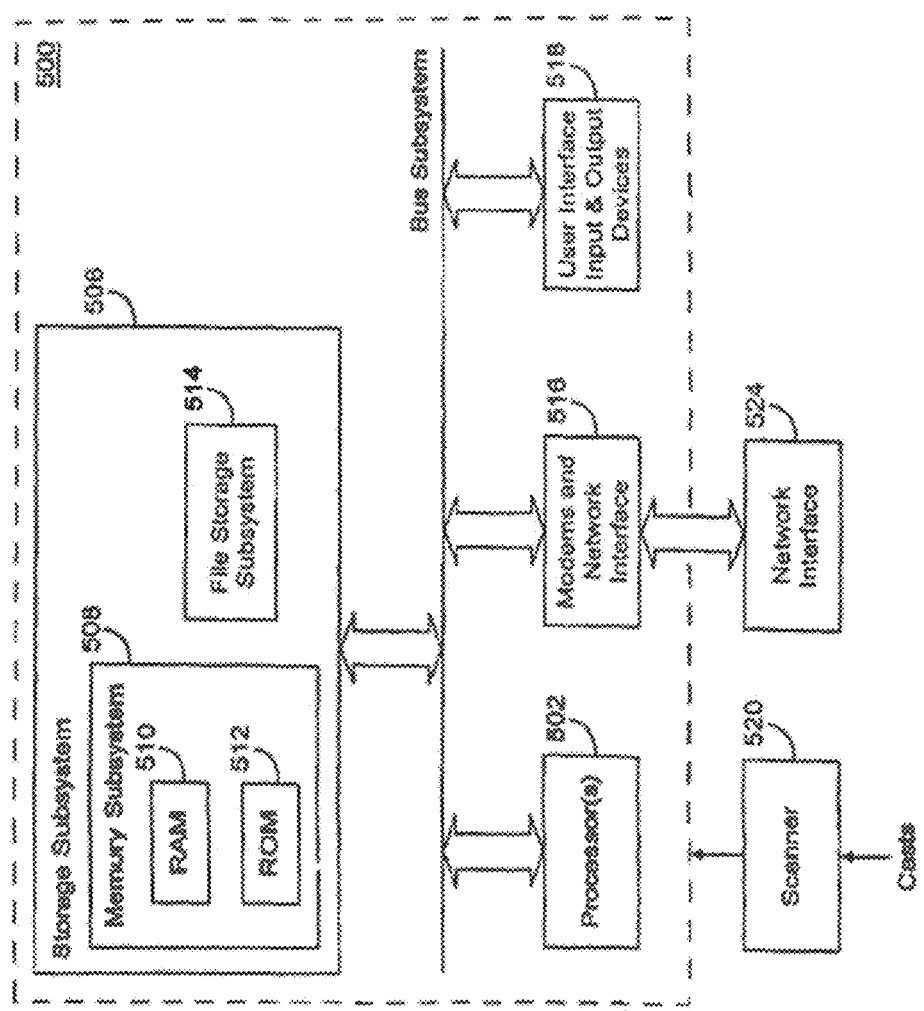
FIG. 16 is a simplified block diagram of a data processing system which can be used to perform the methods and techniques described herein.

Any of the methods described herein may be performed by an apparatus including a data processing system (or subsystem), which may include hardware, software, and/or firmware for performing many of these steps described above, including as part of a processor of an intraoral scanner (see, e.g., FIG. 1B). For example, FIG. 16 is a simplified block diagram of a data processing sub-system 500. Data processing system 500 typically includes at least one processor 502 which communicates with a number of peripheral devices over bus subsystem 504. These peripheral devices typically include a storage subsystem 506 (memory subsystem 508 and file storage subsystem 514), a set of user interface input and output devices 518, and an interface to outside networks 516, including the public switched telephone network. This interface is shown schematically as "Modems and Network Interface" block 516, and is coupled to corresponding interface devices in other data processing systems over communication network interface 524. Data processing system 500 may include a terminal or a low-end personal computer or a high-end personal computer, workstation or mainframe.

The user interface input devices may include a keyboard and may further include a pointing device and a scanner. The pointing device may be an indirect pointing device such as a mouse, trackball, touchpad, or graphics tablet, or a direct pointing device such as a touchscreen incorporated into the display. Other types of user interface input devices, such as voice recognition systems, may be used.

User interface output devices may include a printer and a display subsystem, which includes a display controller and a display device coupled to the controller. The display device may be a cathode ray tube (CRT), a flat-panel device such as a liquid crystal display (LCD), or a projection device. The display subsystem may also provide nonvisual display such as audio output.

Storage subsystem 506 may maintain the basic programming and data constructs that provide the functionality of the present invention. The methods described herein may be configured as software, firmware and/or hardware, and (of software/firmware) may be stored in storage subsystem 506. Storage subsystem 506 typically comprises memory subsystem 508 and file storage subsystem 514.

Memory subsystem 508 typically includes a number of memories including a main random access memory (RAM) 510 for storage of instructions and data during program execution and a read only memory (ROM) 512 in which fixed instructions are stored. In the case of Macintosh-compatible personal computers the ROM would include portions of the operating system; in the case of IBM-compatible personal computers, this would include the BIOS (basic input/output system).

File storage subsystem 514 may provide persistent (non-volatile) storage for program and data files, and may include at least one hard disk drive and at least one floppy disk drive (with associated removable media). There may also be other devices such as a CD-ROM drive and optical drives (all with their associated removable media). Additionally, the system may include drives of the type with removable media cartridges. One or more of the drives may be located at a remote location, such as in a server on a local area network or at a site on the Internet's World Wide Web.

In this context, the term "bus subsystem" may be used generically so as to include any mechanism for letting the various components and subsystems communicate with each other as intended. With the exception of the input devices and the display, the other components need not be at the same physical location. Thus, for example, portions of the file storage system could be connected over various local-area or wide-area network media, including telephone lines. Similarly, the input devices and display need not be at the same location as the processor, although it is anticipated that the present invention will most often be implemented in the context of PCS and workstations.

Bus subsystem 504 is shown schematically as a single bus, but a typical system has a number of buses such as a local bus and one or more expansion buses (e.g., ADB, SCSI, ISA, EISA, MCA, NuBus, or PCI), as well as serial and parallel ports. Network connections are usually established through a device such as a network adapter on one of these expansion buses or a modem on a serial port. The client computer may be a desktop system or a portable system.

Scanner 520 may correspond to the wand and other components responsible for scanning casts of the patient's teeth obtained either from the patient or from an orthodontist and providing the scanned digital data set information to data processing system 500 for further processing. In a distributed environment, scanner 520 may be located at a remote location and communicate scanned digital data set information to data processing system 500 over network interface 524.

Various alternatives, modifications, and equivalents may be used in lieu of the above components. Additionally, the techniques described here may be implemented in hardware or software, or a combination of the two. The techniques may be implemented in computer programs executing on programmable computers that each includes a processor, a storage medium readable by the processor (including volatile and nonvolatile memory and/or storage elements), and suitable input and output devices. Program code is applied to data entered using an input device to perform the functions described and to generate output information. The output information is applied to one or more output devices. Each program can be implemented in a high level procedural or object-oriented programming language to operate in conjunction with a computer system. However, the programs can be implemented in assembly or machine language, if desired. In any case, the language may be a compiled or interpreted language. Each such computer program can be stored on a storage medium or device (e.g., CD-ROM, hard disk or magnetic diskette) that is readable by a general or special purpose programmable computer for configuring and operating the computer when the storage medium or device is read by the computer to perform the procedures described. The system also may be implemented as a computer-readable storage medium, configured with a computer program, where the storage medium so configured causes a computer to operate in a specific and predefined manner.

Figure 26A:
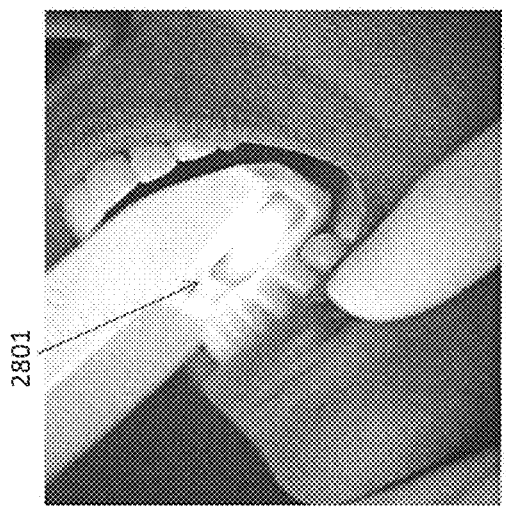
FIGS. 26A-26C illustrate a method of forming a 3D surface that may be used to generate a volumetric model (showing both surface and internal structures) of a patient's teeth.
Figure 26B:
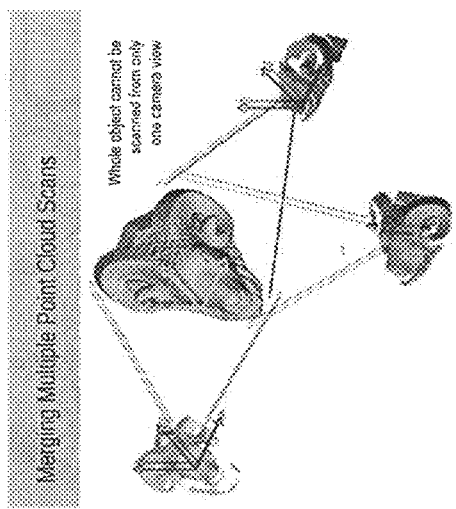
Figure 26C:
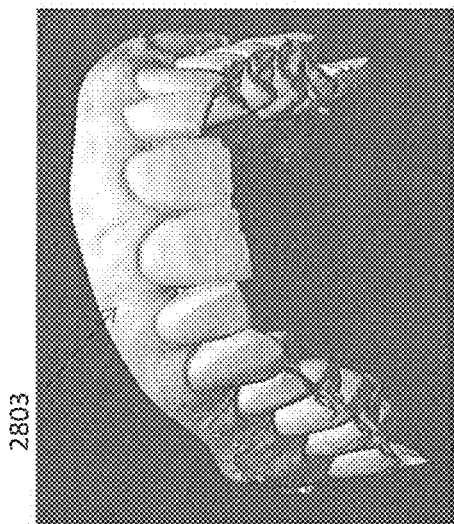

FIGS. 26A-26C and 27A-27G illustrate steps that may form part of a method of forming a 3D volumetric model of a patient's teeth and may be used for one or more treatments using the methods and apparatuses described above. In any of these methods, an intraoral scanner 2801 capable of measuring both surface (including, in some variations color, e.g., R-G-B color) and internal structures may be used to scan the patient's teeth (e.g., taking images and scans of the jaw, including the teeth). The apparatus may scan in different modalities, including surface (non-penetrative or not substantially penetrating, e.g., visible light, white light) and penetrative (e.g., near IR/IR) wavelengths. Scanning typically includes scanning from multiple positions around the oral cavity and assembling the resulting images into a three-dimensional model of the teeth, e.g., by solving the relative position of the scans relative to the jaw (FIG. 26C). The surface scanning may be used to construct a model (e.g., a 3D digital model, and/or renderings) of the outer surface of the jaw/teeth 2803, as shown in FIG. 26C.

Figure 27A:
FIGS. 27A-27G illustrate a method of generating a volumetric model of a patient's teeth using near-IR scanning in addition to surface scanning.
Figure 27B:
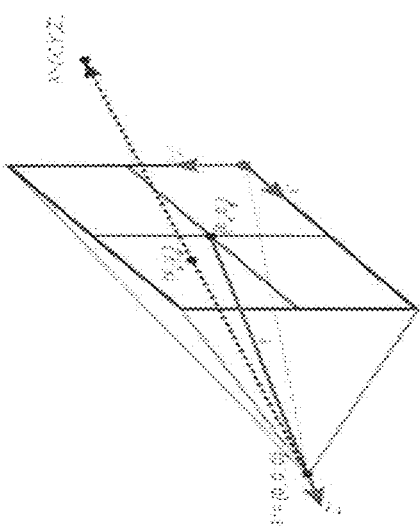
Figure 27C:
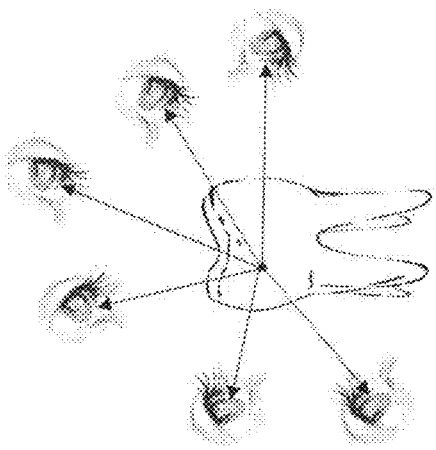
Figure 27E:
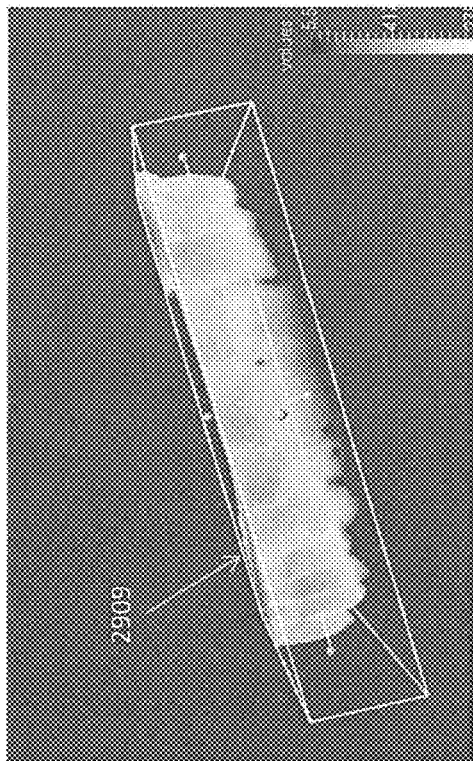
Figure 27F:
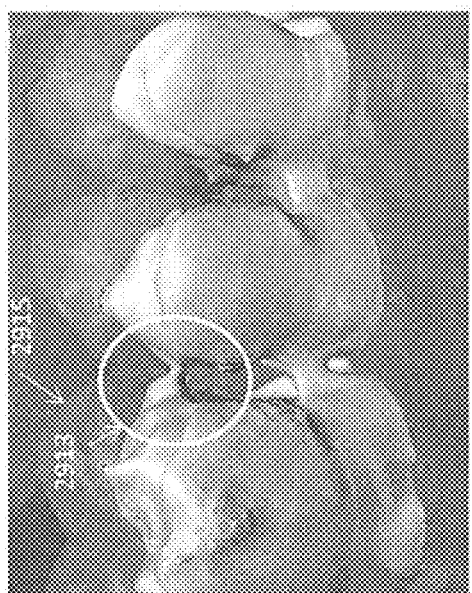
Figure 27D:
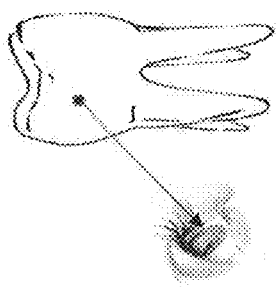
Figure 27G:

In any of these methods and apparatuses described herein, internal structures within the teeth may be formed or modeled to form a volumetric model of the teeth including the internal structures that are extracted from the penetrative scans (e.g., near-IR and/or IR scans), as illustrated in FIGS. 27A-27G. FIGS. 26A-27G describe one method of reconstructing internal structures by using scattering coefficients (other methods may be used alternatively or additionally). In FIG. 27A, a grid is constructed of points representing the inner volume of the jaw/teeth. All of the grid points are projected onto the penetrative (e.g., near-IR) images taken, and all pixel positions may be saved for each of the grid points, as shown in FIG. 27B. For each pixel position and grid position, the apparatus may calculate the scattering coefficient which would result in the gray level of pixel observed, as graphically illustrated in FIG. 27C. In the figures (e.g., FIG. 27C), the eye may represent the viewing angle of the sensor (e.g., camera). For each grid point, the apparatus may take the minimal scattering coefficient that is calculated (FIG. 27D). The grid of points with corresponding minimal scattering coefficients may then provide a volume 2909 that may be sampled at the grid points based on thresholds or correlations (e.g., iso-surfaces) of minimal scattering values, as shown in FIG. 27E. FIG. 27G shows an iso-surface 2911 created by identifying a constant value of the density function sampled. FIG. 27F is an enlarged view of the same region of the teeth, showing both the iso-surface from FIG. 27G as well as a ghosted image (partially transparent) of the enamel 2915 around the iso-surface. This iso-surface may represent dentin and (as described below) dental caries extending from the outer surface of the tooth toward the dentin.

In the example shown in FIG. 27F, the iso-surface shows the dentin-enamel transition 2911 visible beneath the enamel 2915. The example in FIG. 27F also indicates a dental caries shown in circled region 2913. In this example, the dental caries (similar to the dentin) appears as an iso-surface within or surrounded by the enamel. The dental caries may be distinguished because it extends from the inner, dentin region to an outer surface of the tooth. Since the methods and apparatuses described herein may accurately reconstruct both the outer surface and the inner structures, this characteristic configuration (showing an arm or extension extending from the outer surface through the IR/near-IR transparent enamel) may be used to identify dental caries. In FIG. 27F a likely dental caries region is circled 2913, showing an extension or bridge between two teeth in a region where the surface scan shows that the teeth are actually separate. Thus, combining the surface scan with the internal scanning (e.g., from the IR/near-IR images) may allow for corrections in the internal data due to errors that may occur because of the limited view angles or the like. Any of the apparatuses and methods described herein may be configured to automatically or semi-automatically identify these regions or irregularities corresponding to dental caries and the like. They may be highlighted in the model, image or representation of the teeth, and/or a flag, alert or other notification, along with a putative location, may be presented, transmitted and/or stored. Alternatively or additionally, the threshold(s) used to determine the iso-surfaces may be chosen to distinguish between the one or more internal features such as the dentin, caries, fillings, cracks, etc.

Alternatively or additionally, the apparatus may automatically (or semi-automatically) determine and distinguish internal structures within the teeth based on the shape of the iso-surfaces and/or their relative position(s) within the teeth. As mentioned above, caries may have a similar densities (e.g., scattering coefficients) compared to dentin. However, the morphology of the caries may distinguish them from dentin. The apparatus may detect 'arms' or appendages of material having a density (e.g., scattering coefficients) similar to that for dentin, but extending from the out surface of the enamel. Since the outer surface of the teeth may be well characterized in addition to the internal structures, the extent of a caries may be determined by mapping the outer surface of the iso-density map for regions extending from the outer surface toward a larger, defined internal dentin pattern. The border between the dentin and the internal extent of the caries may be determined by approximating the continuous surface of the dentin, including the region around the "projecting" region and/or looking at the rate of change of direction of the surface of the dentin. Other internal structures, such as fillings, cracks and the like may be distinguished based on their scattering coefficient value ranges, and/or based on their position or morphology. The apparatus may display them in different colors, annotations, etc.

Thus, in any of these methods and apparatuses, the scanner may see inside the enamel and reconstruct the margin line. In addition, the use of additional wavelengths (e.g., green light) or even different radiation modalities (e.g., ultrasound) imaging through the flesh may be possible, allowing construction of margin lines and even teeth roots, and/or helping to distinguish structures such as dental caries from the dentin or other internal structures.

The resulting volumetric 3D model of the teeth may be used to reconstruct teeth base on the histological teeth. As described, the volumetric model may be used to create dental prosthetics (implants, etc.) that have a more realistic appearance and/or a better fit.

Figure 28B:
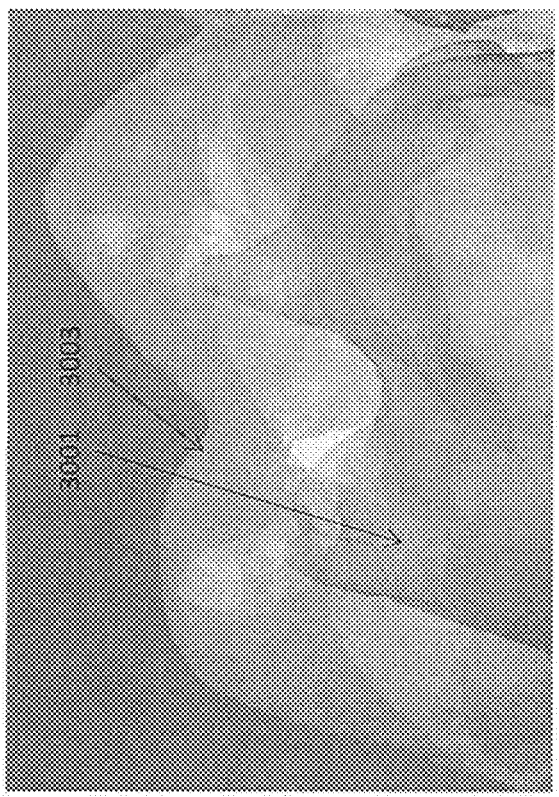
FIGS. 28A and 28B illustrate volumetric models of a patient's teeth formed using an intraoral scanner, showing both surface features, e.g., enamel, and internal (segmented) features, e.g., dentin.
Figure 28A:
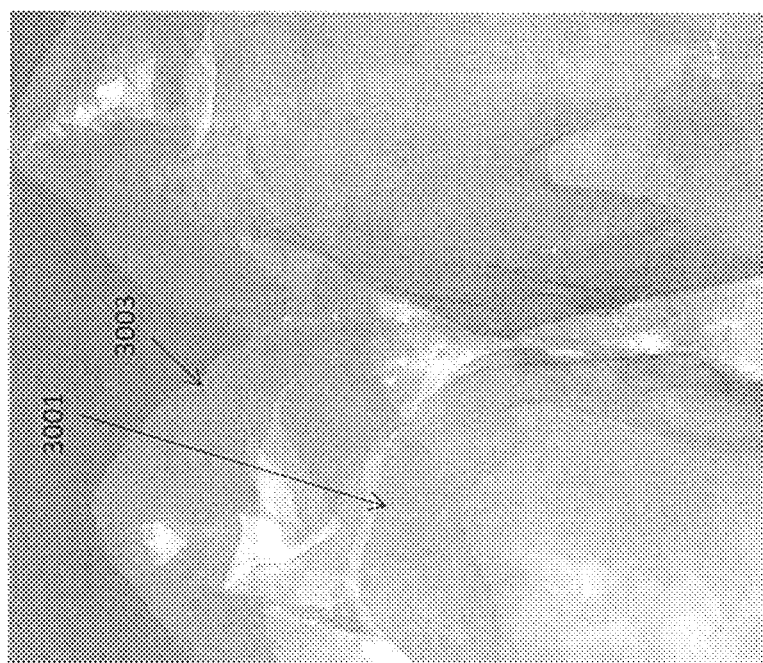

Further, the methods and apparatuses described herein may permit a user (e.g., dentist, physician, dental technician, etc.) to follow the teeth over time, including tracking dentin, caries, etc., and general dental health by comparing models taken over time. For example, time-lapse videos (images) may be constructed. FIG. 28A shows an example of a volumetric reconstruction taken at a first time, showing the dentin 3001 (solid) and enamel 3003 (made slightly transparent). FIG. 28B show another example of a volumetric model of teeth showing the dentin 3001 and enamel 3003.

The volumetric model may include width information may provide estimates of wear over time as well. For example, changes in the enamel width over time and over different regions of the teeth may be easily tracked. By knowing the enamel width we can estimate the tooth wear and provide a snap shot of the severity of wear.

Segmentation and Classification

Any appropriate method and/or apparatus (e.g., systems, devices, software, etc.) for generating images of internal structures from within a tooth (or other semi-transparent, strongly scattering object) may be used. For example, alternatively or additionally to the use of scattering coefficients as discussed above, any of the apparatuses and methods described herein may use the two-dimensional penetrative images along with position and/or orientation information about the intraoral scanner relative to the object being imaged (e.g., the teeth) to segment the two-dimensional penetrative images and form a three-dimensional model of the teeth including one or more internal structures within the object. A penetrative image may refer to images taken with a near-IR and/or IR wavelength, revealing internal structures within the object (e.g., tooth). The position and/or orientation of the scanner may be a proxy for the position and/or orientation of the camera taking the images which is on the scanner (e.g., on a handheld wand).

The apparatuses and methods described herein may construct a three-dimensional (3D) volumetric model of the teeth from segmented two-dimensional (2D) images. These methods and apparatuses may also segment the 3D model of the teeth.

In general, the methods and apparatuses described herein allow for the direct segmentation of the penetrative images. This may allow for the identification of dentin within the teeth, including the location and morphology of the dentin, as well as the identification and location of cracks, lesions, and/or caries in the teeth, including in the dentin. The use of segmentation may allow for reconstruction of a volumetric model based on the penetrative images and the knowledge of the camera position corresponding to the penetrative images. A volumetric model of teeth can be segmented and these segments (relating to different internal structures of the tooth) may be projected back to the images and/or combined with a surface model of the teeth (e.g., the outer tooth surface), allowing projections onto the surface images and better segmentation of the inner structures of teeth.

Thus, penetrative images taken through the teeth with a penetrative wavelength (e.g., near IR and/or IR), may include inner teeth structures and/or 3D data. These images may be taken using any of the dental scanners described herein, and the teeth volume may be segmented into different regions according to opacity, color, and other properties of the images and 3D data. These regions can be for example: healthy enamel, dentin, lesion, dental filling(s), etc. The segmentation can be done on 2D images or on volumetric models. The segmentation can be used to classify the images and/or the 3D models according to the presence of different segments. A user may be able to detect by this segmentation manually or automatically (or semi-automatically) to classify different internal structures, such as: dental caries, enamel erosion, and other dental issues. Further, the images or models may be used to measure internal regions of a tooth or multiple teeth segments for better dental treatments, including aligning teeth or other treatment planning. For example, a user may be able to locate dental lesion in an accurate fashion to plan accurate filling with minimal enamel extraction. Thus, the use of segmentation as described herein may permit the capture of inner teeth structure without ionizing radiation, as is currently used with X-rays. Dental issues may be presented on 3D volumetric model. Further, as will be described in detail below, segmentation and classification of internal structures may be automatized. Finally, exact measurements of internal structures may be taken for better treatment planning.

Figure 17:
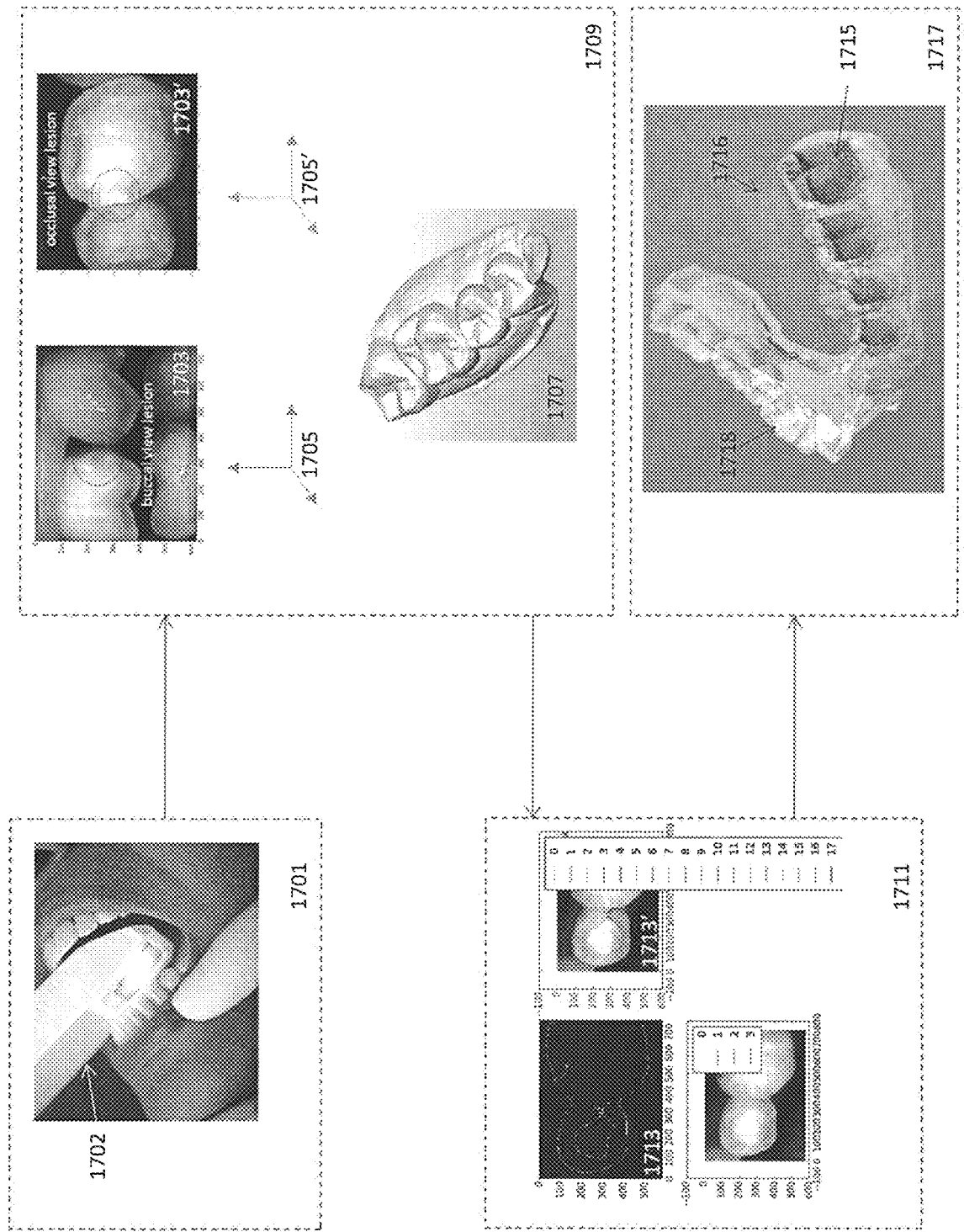
FIG. 17 is an example of a method of scanning teeth with an intraoral scanner to identify internal structures using a penetrative wavelength (e.g., IR and/or near-IR).

FIG. 17 illustrates an example of a data flow for scanning teeth with an intraoral scanner to build a 3D model including internal structures. In FIG. 17, the exemplary method shown may include three parts. First, the teeth may be scanned with an intraoral scanner 1701 (or any other scanner) configured to provide penetrative scans into the teeth using an optical (e.g., IR, near IR, etc.) wavelength or range of wavelengths. Any of these scanners may also concurrently scan to determine a surface features (e.g., via one or more non-penetrative wavelengths), color, etc., as described above. During scanning, a plurality of penetrative scans 1703, 1703' may be taken, and the position of the sensor (e.g., camera) 1705, 1705' (e.g., x,y,z position and/or pitch, roll, yaw angles) may be determined and/or recorded for each penetrative image. In some variations, the surface of the teeth may also and concurrently be imaged, and a 3D surface model of the teeth 1707 determined, as described above. In this example, the patient's teeth may be scanned, for example, with an intraoral 3D scanner 1702 that is capable of imaging the inner teeth structure using, for example, near infra-red imaging. The location and orientation of the camera may be determined, in part, from the 3D scanning data and/or the 3D teeth surface model 1707.

Thereafter, the penetrative images may be segmented 1711. In this example, segmentation may be done in one of two ways. On the inner teeth structure images, the images may be segmented using contour finding 1713, 1713'. Machine learning methods may be applied to further automate this process. Alternatively or additionally, near images (where their camera position is close) may be used to decide on close features, and also project features from the 3D model back to the images in order to locate correctly segments like enamel. The method may also include projecting pixels from the inner teeth images back to the teeth and calculating a density map of inner teeth reflection coefficient. Enclosing surfaces of different segments may be found or estimated by using iso-surfaces or thresholds of the density map and/or by machine learning methods. In addition, segmenting the images and projecting the segments back to a model (such as the 3D surface model, e.g., projecting back to the world), may be used to find a segment by the intersection of the segment projections and the teeth surface.

The results may be displayed 1717, transmitted and/or stored. For example, the results may be displayed by the scanning system during the intraoral scanning procedure. The results may be shown by images with enclosing contours for different segments, a 3D density map, etc. In the example shown in FIG. 17 a density map 1715, representing the dentin beneath the enamel on the outer surface, is shown. This image may be color coded to show different segments. In this example, internal segments (structures) are shown within the 3D surface model (which is shown transparent); not all teeth have been scanned with penetrative images, thus, only some are shown. Alternative views, sections, slices, projections or the like may be provided. In FIG. 17, the example image includes artifacts that are present outside of the teeth 1716; these may be removed or trimmed, based on the surface model 1718.

A segment may mark each pixel on the image. Internal structures, such as dentin, enamel, cracks, lesions, etc. may be automatically determined by segmentation, and may be identified manually or automatically (e.g., based on machine learning of the 3D structure, etc.). Segments may be displayed separately or together (e.g., in different colors, densities, etc.) with or without the surface model (e.g., the 3D surface model).

Thus, in FIG. 17, the patient is initially scanned with a 3D scanner capable of both surface scanning and penetrative scanning (e.g., near IR imaging), and the orientation and/or position of the camera is known (based on the position and/or orientation of the wand and/or the surface scans). This position and orientation may be relative to the tooth surface. The method and apparatus may therefore have an estimate of the camera position (where it is located, e.g., x,y,z position of the camera, and its rotational position).

Figure 21B:
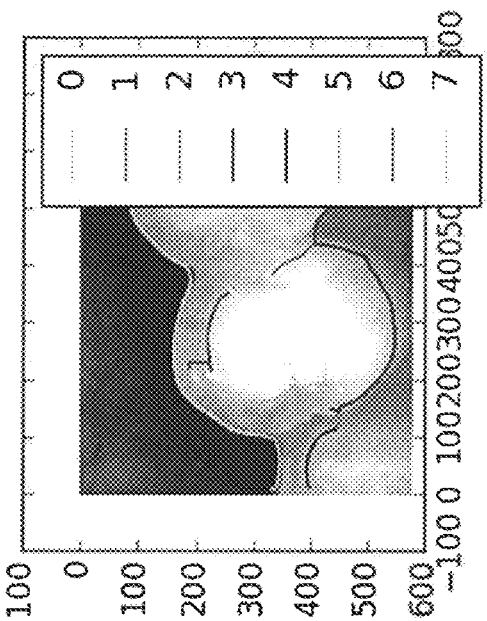
FIGS. 21A-21C illustrate segmentation of a near-IR image of a patient's teeth.
Figure 21A:
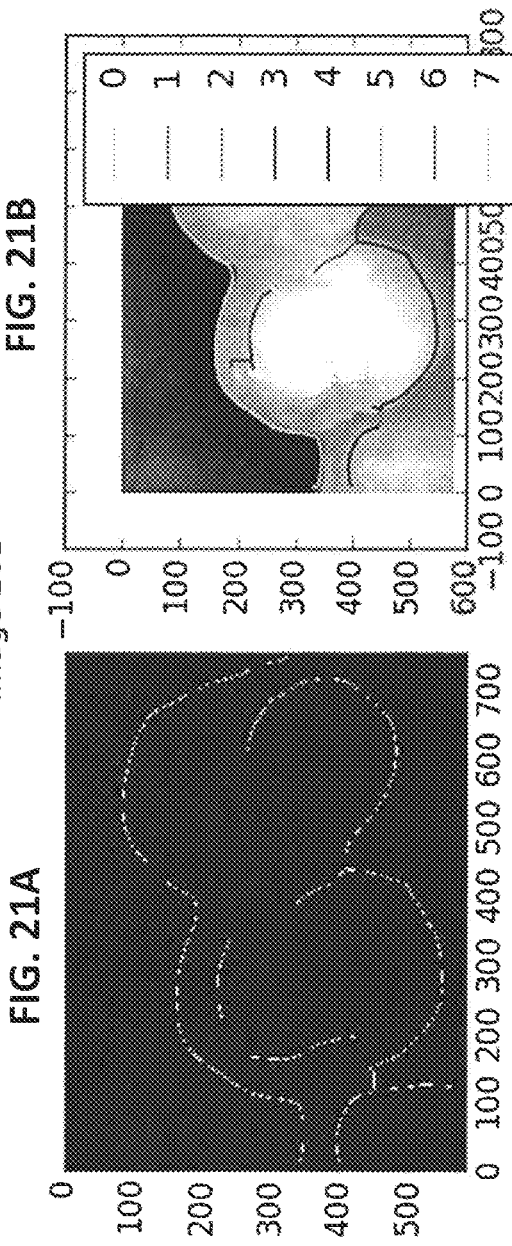
Figure 21C:
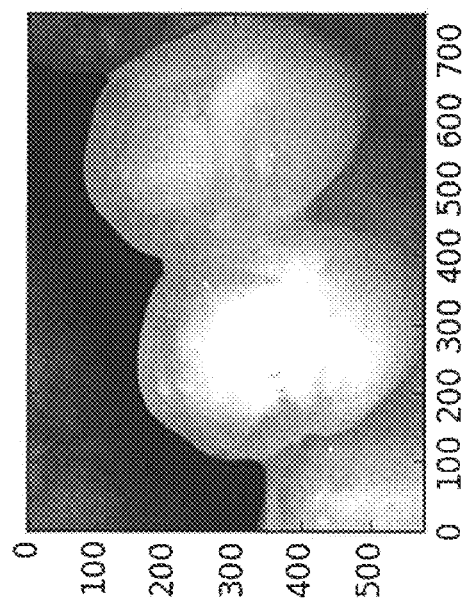
Figures 22A, 22B, 22C:
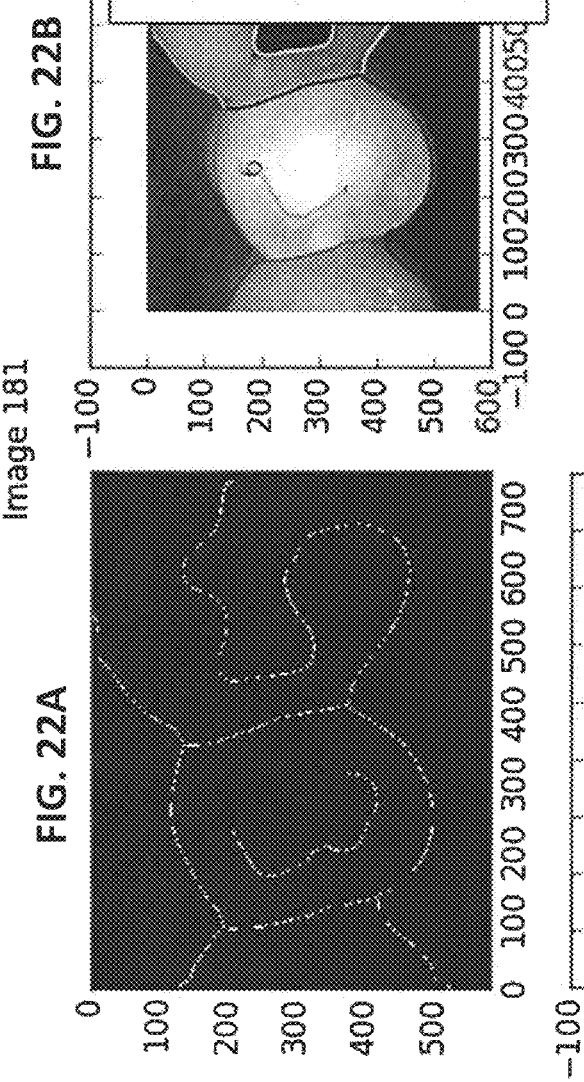
FIGS. 22A-22C illustrate segmentation of a near-IR image of a patient's teeth.

In general, penetrative images (e.g., near IR or IR images) may be segmented automatically. FIGS. 18A-18C illustrate a first example of automatic segmentation of a near-IR image. FIG. 18A, shows a first automatic segmentation of the outer surface of the teeth, determined by, e.g., edge detection. In FIG. 18A, the edges 1803 of the outer perimeter are shown. In this example, only a first level of edge detection was performed, looking for the outer perimeter. In FIGS. 18B and 18C, a continuous edge region 1805 is shown, derived from the edge detection, and mapped onto the near-IR image (original image). FIGS. 19A-19C show the identification and mapping of other edges from the same image. FIG. 19A shows just the edges detected using a threshold setting value from the near-IR image (e.g., FIG. 19C). In FIG. 19B five (overlapping 1905) segments, 0-4, are traced from the detected edges by forming continuous lines. The different segments are shown color coded, and a color key identifying the segments is shown on the right. From the near-IR images the apparatus can automatically segment the images. In FIGS. 18A-18C and 19A-19C, the different segments are marked and may correspond to different regions (or different internal structures) on image. When multiple images are analyzed, these putative segments may be re-projected back to a 3D model and/or shown in the images. FIGS. 20A-20C and 21A-21C illustrate other examples of near-IR images from the same patient shown in FIGS. 18A-19C, illustrating segmentation based on edge detection and identification of presumptive continuous line regions from the detected edges. In FIG. 21A-21C, another region of the teeth from the same patient are shown; eight segments (0-7) have been identified in this image, as shown in FIG. 21B. FIG. 21A shows the edge detection of the original image, shown in FIG. 21C. FIGS. 22A-22C illustrate segmentation of another region of the patient's teeth. FIG. 22A shows the detected edges from the original near-IR image. FIGS. 22B and 22C show eight segments (0-7) identified on the near-IR image. Similarly, FIGS. 23A-23C illustrate segmentation of another region of the patient's teeth; FIG. 23A shows the detection of edges, FIG. 23B shows segments identified from these edges, and FIG. 23C shows the original near-IR image.

Figure 24A:
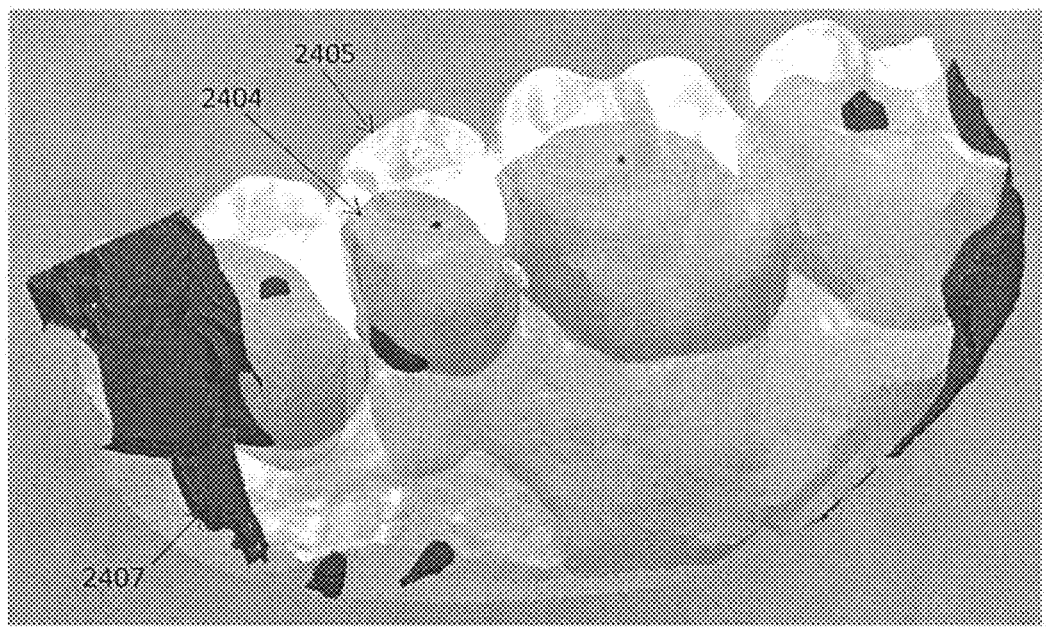
FIG. 24A is a partial three-dimensional model of a patient's teeth formed by segmented images, including those shown in FIGS. 18A-23C.
Figure 24B:
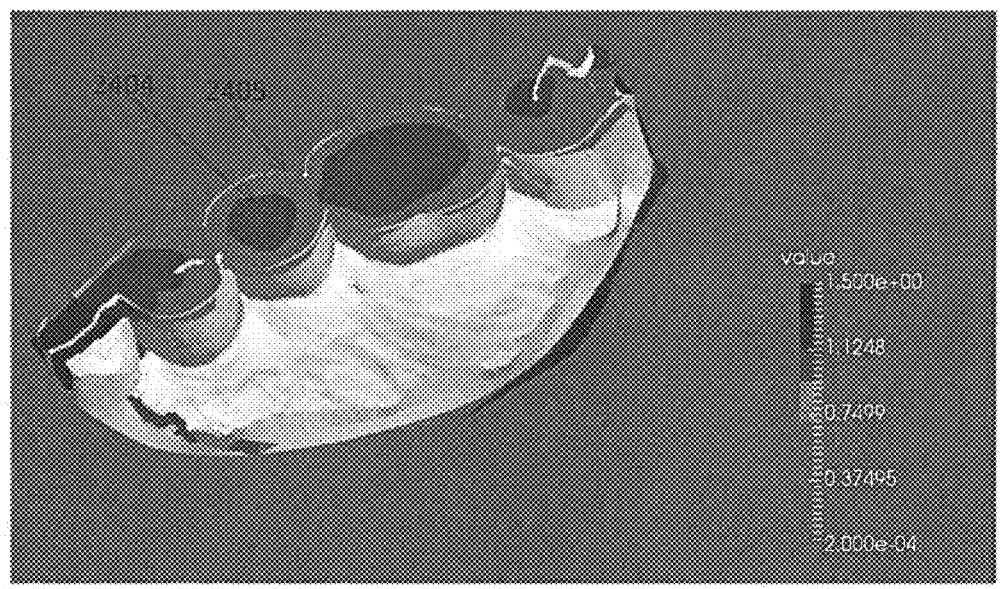
FIG. 24B shows a sectional view through the 3D model of FIG. 24A, showing internal structures, including the dentin.

The segmented images, such as those shown in FIGS. 18A-23C may be used to form a model of the internal structures of the scanned object (e.g., teeth). The surface 3D model may also be used. For example, FIGS. 24A-24B show a three-dimensional model of a region of the patient's teeth formed by segmented images, including those shown in FIGS. 18A-23C. In FIG. 24A, the 3D reconstruction includes the outer surface of the teeth (shown as partially transparent), and different internal segments may be shown in different colors and/or transparencies. For example, In FIG. 24A, the dentin (inner part of teeth) 2404 is shown within the teeth 2405 boundary. In FIG. 24A the segment showing the dentin is a surface (volume in FIG. 24B), but it may also be shown as a density map, as will be illustrated in FIGS. 25A and 25B, below. The resulting 3D volume including the segmented images may be iteratively used to take images through the resulting volume, which may be 'projections' that can be compared directly to the original near-IR images, and this comparison may be used to modify the model. This process may be repeated (iterated) to refine the model, which may provide better segmentation of images.

As described above, segmentation may include edge detection. Any appropriate edge detection method may be used, including machine learning. Segmentation of the plurality of near-IR images may be used in conjunction with the positional information of the camera to reconstruct the volume. Since a plurality of different sections (different conics) are known, and segmented, the resulting segments inside of all of the projections of the conics, from different positions are known and intersections of these segments may therefore be determined. This process may be made easier by using the outer surface boundary of the teeth, which may be provided by the surface imaging and/or the 3D model. As described above, this process may be iterative; the method may use the 3D data to project simulated penetrative (e.g., near-IR) images that may be compared to the original to improve segmentation and derive a second, evolved, model of the internal structures. Similarly, segments or segment regions outside of the teeth surface 2407 may be removed.

The model of the tooth, including internal structures, may be displayed in a variety of ways, as mentioned above. FIG. 24B shows a section through the teeth, showing the internal structures, including the dentin 2404 and the enamel thickness between the outer surface 2405 and the dentin 2404.

Figure 25A:
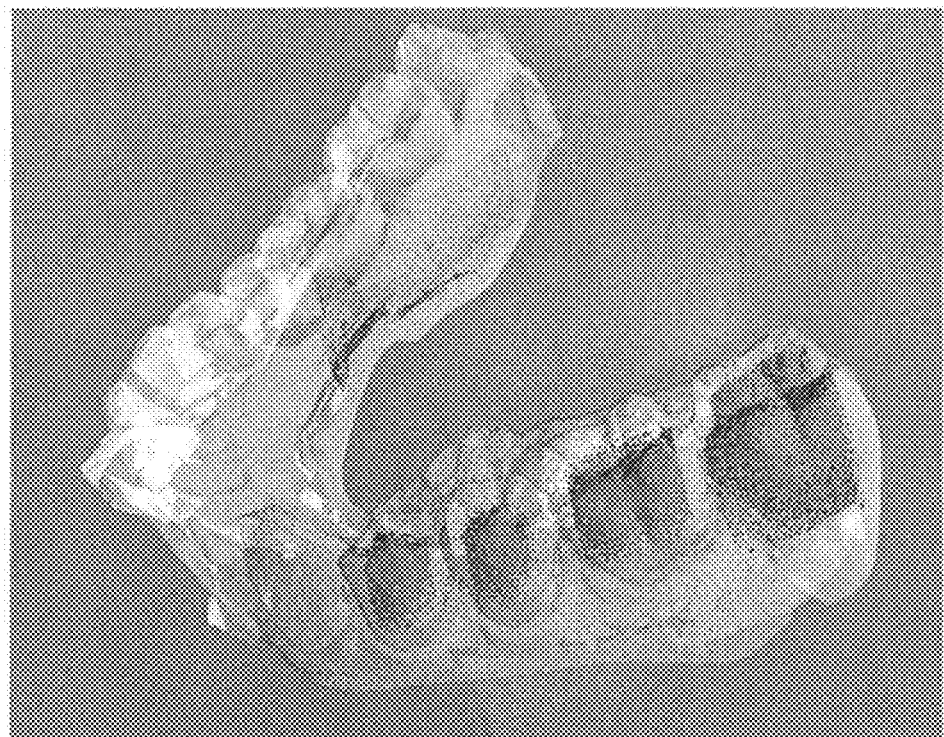
FIG. 25A is an example of a volumetric (or "voxel") model of a patient's jaw and teeth, including internal structures. The internal structures are shown as a density map within the 3D surface model.
Figure 25B:
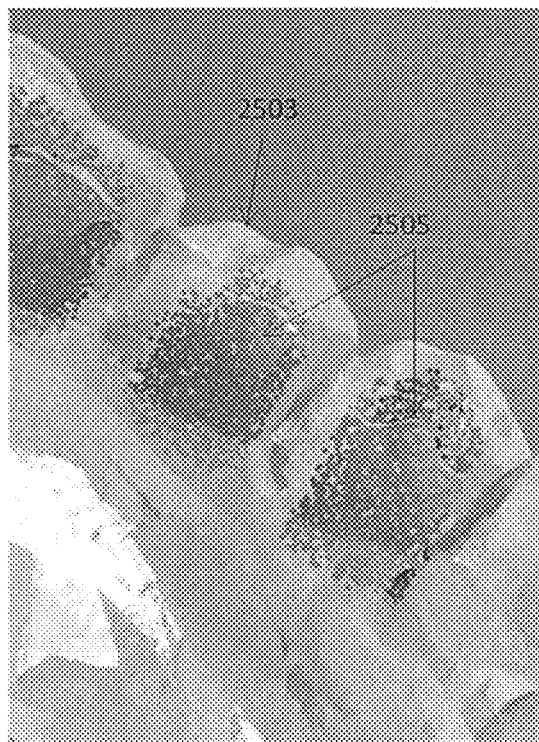
FIG. 25B is an enlarged view of the volumetric model of FIG. 25A.

FIGS. 25A and 25B show an reconstruction of the teeth including internal structures (also shown in FIG. 17, above). In this example, the internal structures are shown by a density mapping (e.g., segments). For example, the dentin 2505 is shown in more detail within a portion of the surface model 2503 in FIG. 25B. The outer surface of the teeth may also be identified as a segment (as shown in FIGS. 25A and 25B), and there is near-perfect agreement between the segmented outer surface and the outer surface as determined from surface imaging in this example.

Sleeves for Intraoral Scanners Having Trans-Illumination

Any of the devices described herein may also include a sleeve or sleeves that is configured to protect the intraoral scanner wand, but may also be configured to extend the functionality and/or adapt the scanner for use with a penetrative wavelength, including trans-illumination. The sleeve illustrated in FIGS. 29A-31B is an example of a sleeve that may be used as a barrier (e.g., sanitary barrier) to prevent contamination of the wand portion of the intraoral scanner, as the scanner may be used with different patients, and also as an adapter for providing trans-illumination by IR/near-IR wavelength imaging. The sleeve in these figures is configured as a trans-illumination sleeve with electrical couplings. For example, the sleeves described herein may include both penetrative wavelength illumination (e.g., near-IR and/or IR LEDs) and one or more sensors (e.g., CCDs) or may use the same cameras already on the wand.

Figures 29A, 29B:
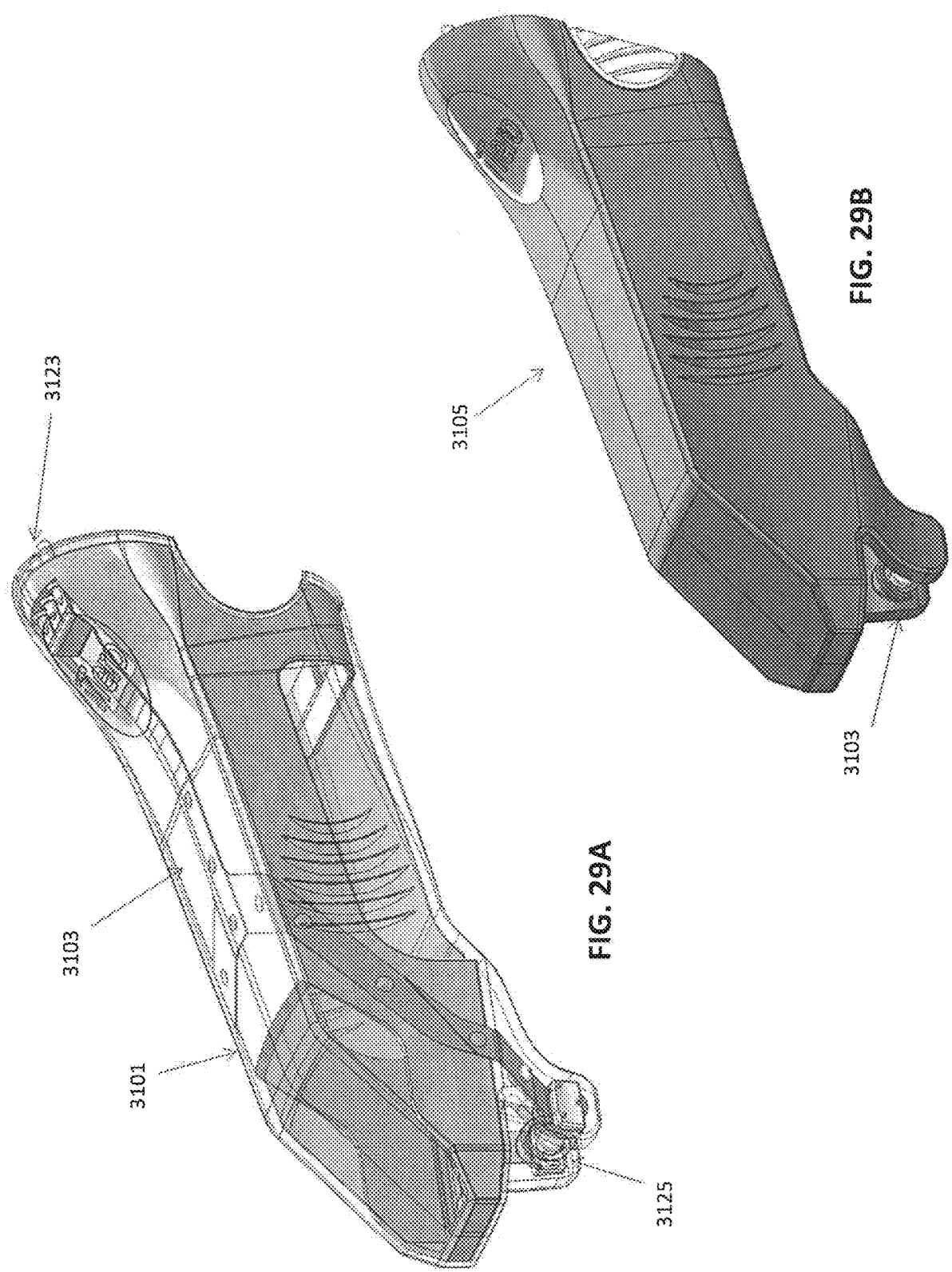
FIG. 29A shows a partially transparent perspective view of a removable/disposable cover configured as a trans-illumination sleeve with electrical couplings.
FIG. 29B is a perspective view of the sleeve of FIG. 29A, shown solid. This sleeve is configured for use with a wand portion of an intraoral scanner; the sleeve is configured to adapt the wand to include trans-illumination with a penetrative (e.g., near-IR) wavelength.

In FIG. 29A, the wand of an intra-oral scanner is shown with a sleeve 3101 disposed around the end of the wand 3105; the sleeve is shown as semi-transparent, so that the internal structures (connectors) are visible. FIG. 29B shows just the sleeve 3105 for the intraoral scanner (wand) shown as solid. In general, the sleeve 3105 slips over the end of the wand so that the light sources and cameras (sensors) already on the wand are able to visualize through the sleeve, and so that the electrical contacts 3123, which may provide control, power and/or data transmission to the LEDs and/or sensors 3125 integrated into or on the sleeve. The sleeve includes a pair of wing regions 3103 on opposite sides, facing each other and extending from the distal end of the wand when the sleeve is placed over the wand.

The sleeve 3101 may be held on the end of the wand by friction or by an attachment (not shown). Consequently, the sleeve may be readily removed from the wand and a new sleeve can be placed on the wand each time the scanner is used on a different patient. In this example, the sleeve may be configured to transmit IR (e.g., near IR), and thus may include one or more wings 3103 (e.g., for trans-illumination, etc.) as shown in FIG. 29B. The electrical contacts and connector integrated into the sleeve may adapt the scanner for IR/near-IR trans-illumination.

Figure 30C:
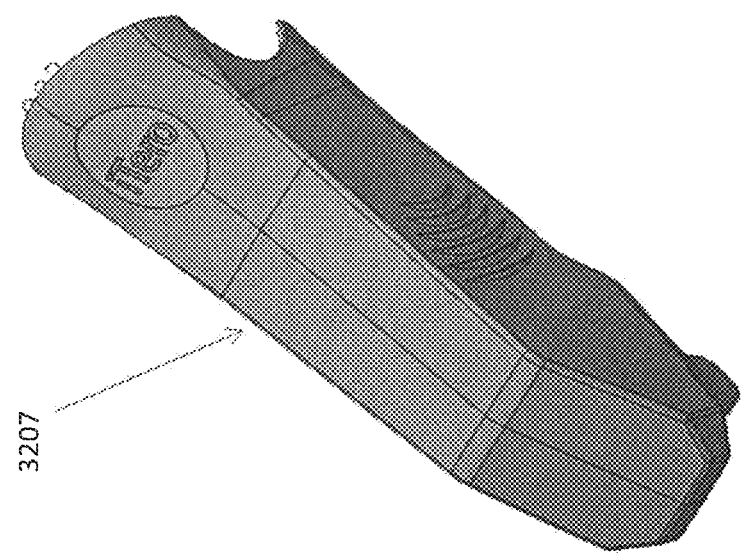
FIGS. 30A-30C illustrate one example of a trans-illumination sleeve with electrical couplings.
Figure 30B:
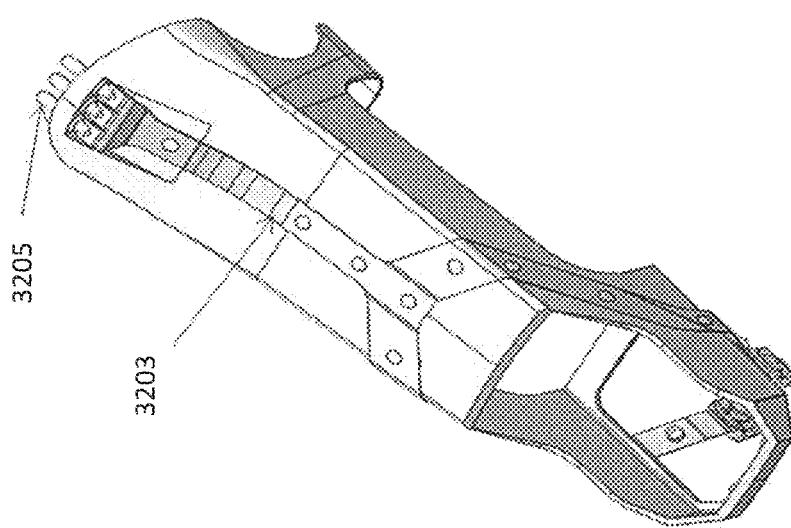
Figure 30A:
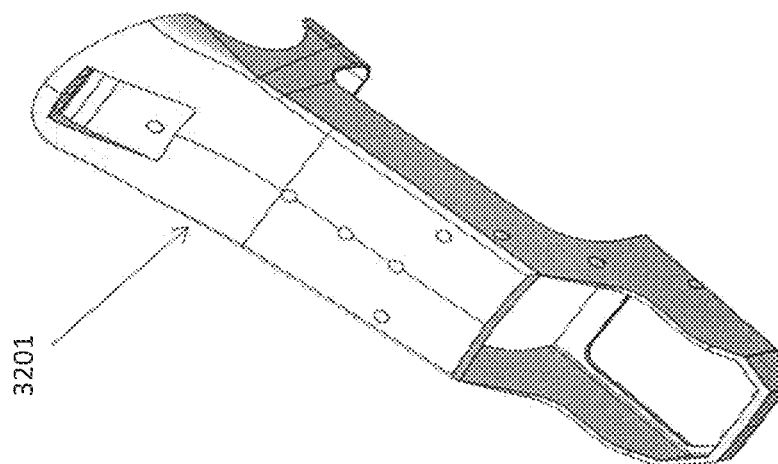

Thus, the sleeve may include circuitry (e.g., flex circuitry) connecting to an LED illumination (IR/near-IR) source and/or one or more sensors, particularly for trans-illumination. FOR example, FIGS. 30A-30C. FIG. 30A shows an example of the frame 3201 of the sleeve, which may be rigid or semi-rigid. The frame may support the flex circuitry 3203 (shown in FIG. 30B) and/or connectors 3205 and may also provide shielding (e.g., blocking light). The frame and circuitry may be covered by a flexible outer sleeve 3207 as shown in FIG. 30C.

The sleeve may be assembled by injection molding of the component parts, including the overall sleeve, windows for illumination and image capture, connectors for the circuitry and one or more LED holding regions (e.g., injection of an IR and visible-light transparent material forming windows through the sleeve, then injection of the rigid sleeve material). The flex circuitry may then be positioned, and LED encapsulation may be placed, using mold locators. The flexible outer sleeve may then be injected.

Figure 31B:
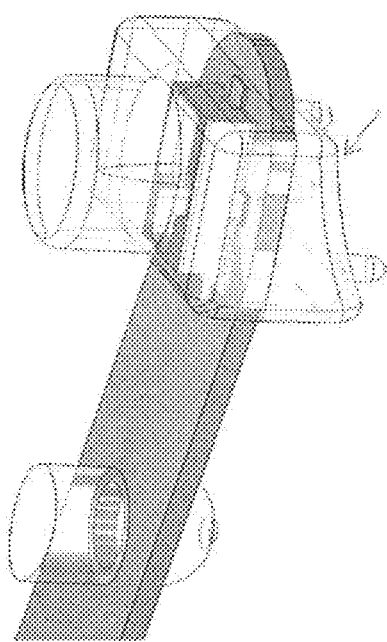
FIG. 31B is an example of a distal end portion of the flex circuit shown in FIG. 31A, including an LED housing.
Figure 31C:
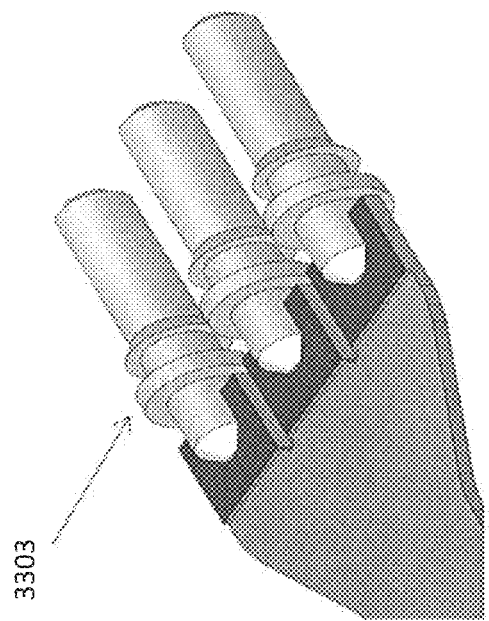
FIG. 31C is an example of a connector portion of a sleeve.
Figure 31A:
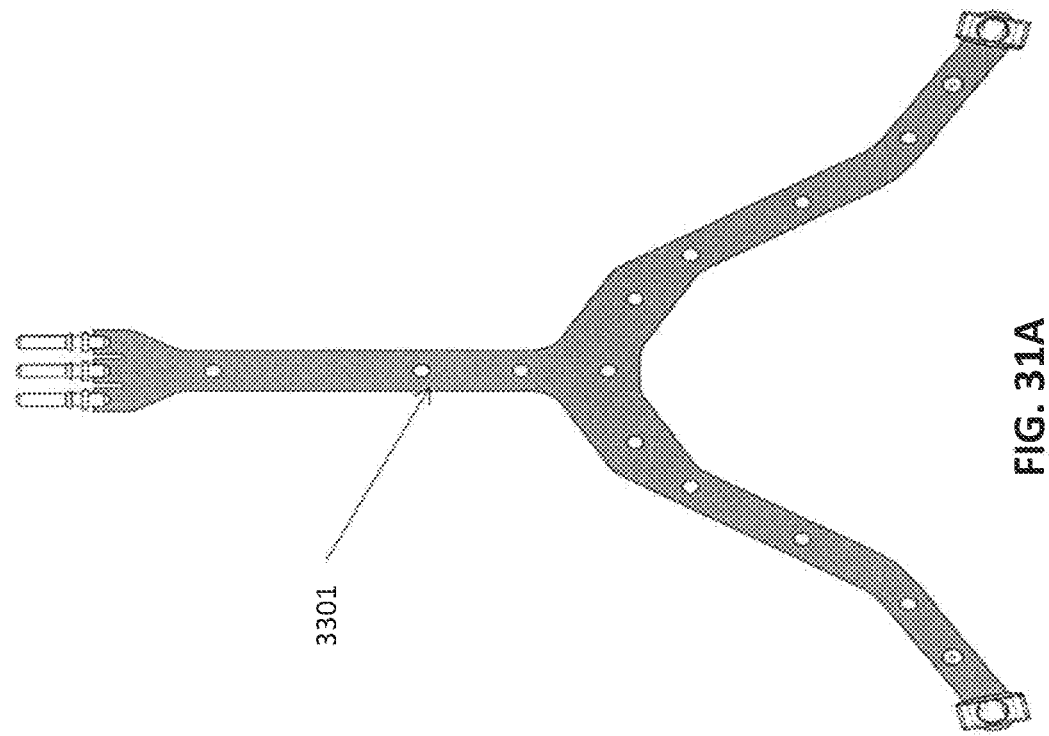
FIG. 31A shows an example of a flex circuit and connectors for use as part of the sleeve shown in FIGS. 29A-30B.
Figure 32B:
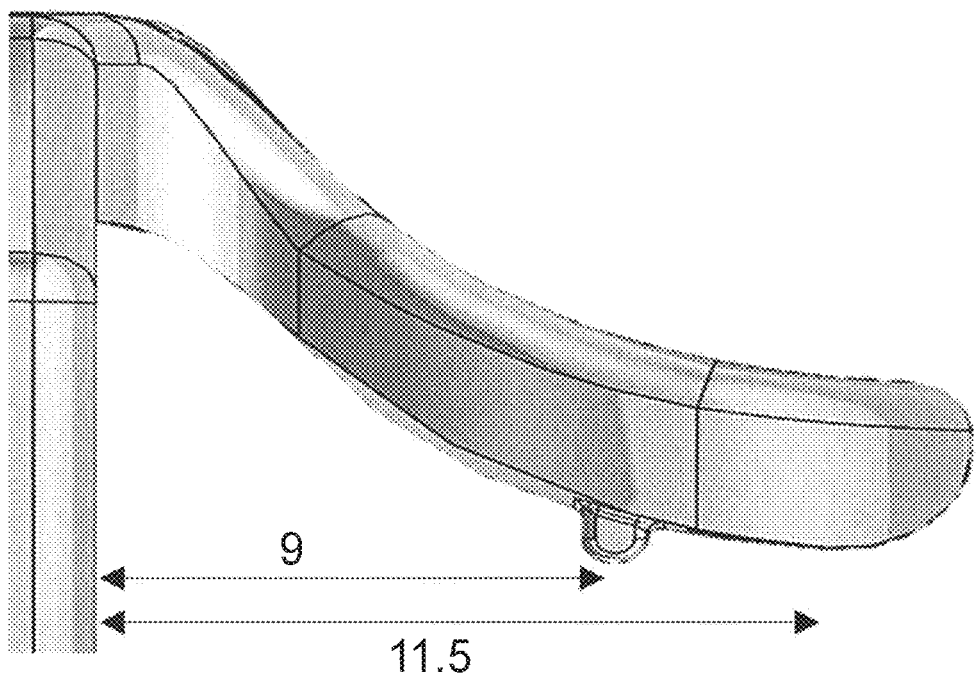
FIGS. 32A and 32B illustrate examples of an LED positioner and light blocker portion of the distal end of a sleeve such as the ones shown in FIGS. 29A-30B.
Figure 32A:
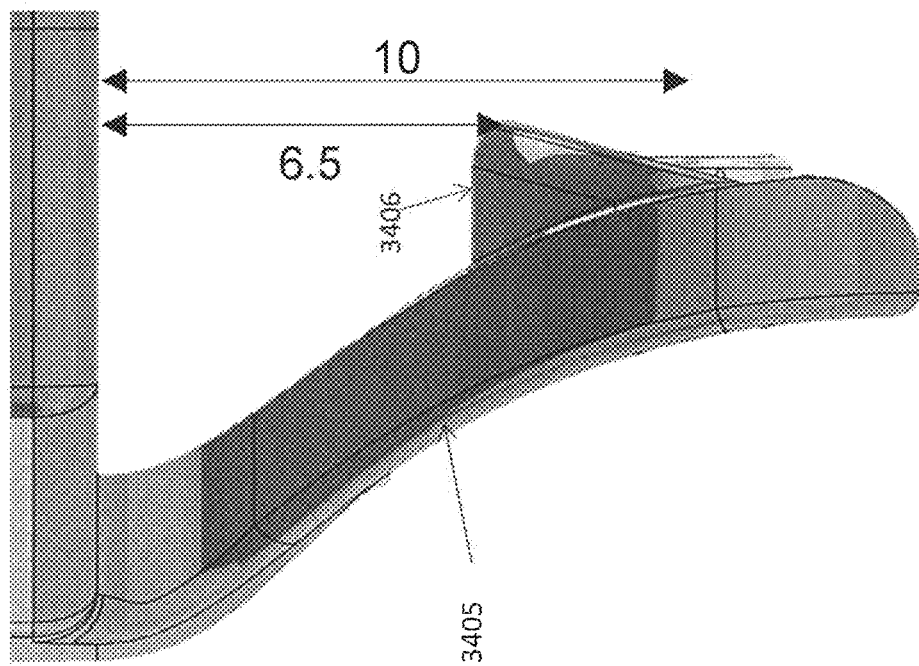

FIGS. 31A-31C illustrate more detailed views of the flex circuitry 3301, connectors 3303 and LED holders/shields 3305. FIGS. 32A-32B illustrate examples of the LED positioner and light blocker portion of the distal end of the sleeve. The example shown in FIG. 32A includes a support frame or arm 3404 that extends down and includes a light shroud or blocker region 3406 encapsulating a portion of the LED. Exemplary dimensions are shown.

User Interface and Display of Volumetric Information

As mentioned above, the penetrative scans described herein may be collected from, for example, an intraoral scanner such as the one illustrated in FIGS. 1A-1B for generating a three-dimensional (3D) model of a subject's intraoral region (e.g., tooth or teeth, gums, jaw, etc.) which may include internal features of the teeth and may also include a model of the surface, and methods of using such scanners. Although in many instances surface scanning (including color scans) may be helpful and useful, the penetrative (IR) scanning may, in some of the variations described herein, be sufficient.

A variety of penetrative scanning techniques (penetration imaging) may be used or incorporated into the apparatuses described herein for performing scans that to detect internal structures using a penetrative wavelength or a spectral range of penetrative wavelengths, including, but not limited, to trans-illumination and small-angle penetration imaging, both of which detect the passage of penetrative wavelengths of light from or through the tissue (e.g., from or through a tooth or teeth). Thus, these apparatuses and techniques may be used to scan intraoral components such as a tooth or one or more teeth, gingiva, palate, etc. and used to generate a model of the scanned area. These models may be generated in real time or after scanning. These models may be referred to as 3D volumetric models of the teeth, but may include other regions of the jaw, including the palate, gingiva and teeth. Although the methods and apparatuses described herein typically relate to 3D volumetric models, the techniques and methods described herein may also be used in some instance with 3D surface models. The surface model information is typically part of the 3D volumetric model.

The collection and analysis of volumetric data from the intraoral cavity may identify features and information from teeth that were previously difficult or impossible to identify from non-volumetric scanning. However, it may be difficult or non-intuitive for a dental practitioner (and/or patient) to analyze three-dimensional volumetric information. Described herein are methods and apparatuses for viewing and interpreting 3D, volumetric data of a patient's oral cavity.

Figure 38B:
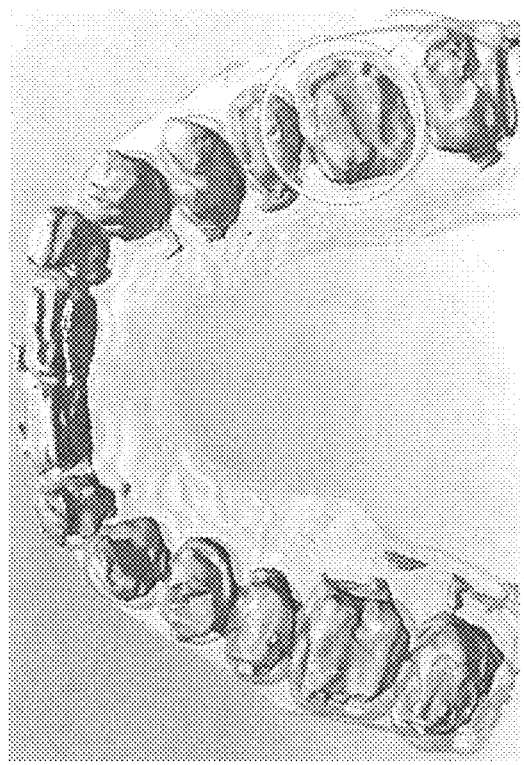
FIGS. 38A-38G illustrate one method of displaying volumetric information from a patient's teeth.
Figure 38A:
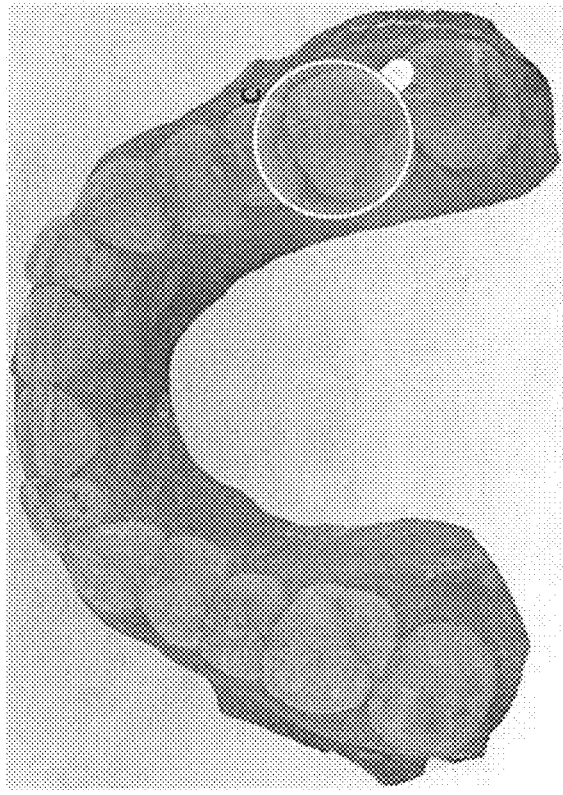

For example, FIGS. 38A-38G illustrate one example of a method for displaying 3D volumetric data. FIG. 38A shows a surface model (which may be a surface model portion of a volumetric model) from a top view of an upper arch, in which external features are visible (e.g., surface features). This view is similar to the surface scan view which may be in color (e.g., taken by visible light). Internal structures, which are present within the model beneath the external surface of the scan, are not readily visible in FIG. 38A. FIG. 38B, the internal structures are shown based on their relative transparency to near-IR light. In FIG. 38B, the enamel is more transparent (and is shown as more transparent) than the dentin, which is shown as less transparent. FIGS. 38B-38F illustrate a transition between the surface view of FIG. 38A and the penetrative, internal 3D view of FIG. 38B for a sub region (circled region "C") shown. For example, a user display may be provided in which the relative surface vs. internal views may be altered to provide a sense of internal structures within the dental arch relative to surface structures. For example, an animated view cycling through image such as FIGS. 38C-38G may be provided. Alternatively, the user may slide a slider 3803 toggling between the surface and internal views. The transition between these two views (which may be made from any angle, may help the user and/or patient to see beneath the surface of the teeth, to visually assess the rich internal data. The 3D volumetric model may be manipulated to show any view, including cross-sectional views, showing internal structures and/or surface features. In FIG. 38A-38G the top view is shown. FIGS. 38C-38G illustrate progressively more transparent views or a region ("C") of the 3D volumetric model of FIG. 38A in which progressively large percentages (from 0% to 100%) of the internal view of FIG. 38B is shown for region C, while progressively less of the surface view (from 100% to 0%) is shown.

Figures 38C, 38D, 38E, 38F, 38G:
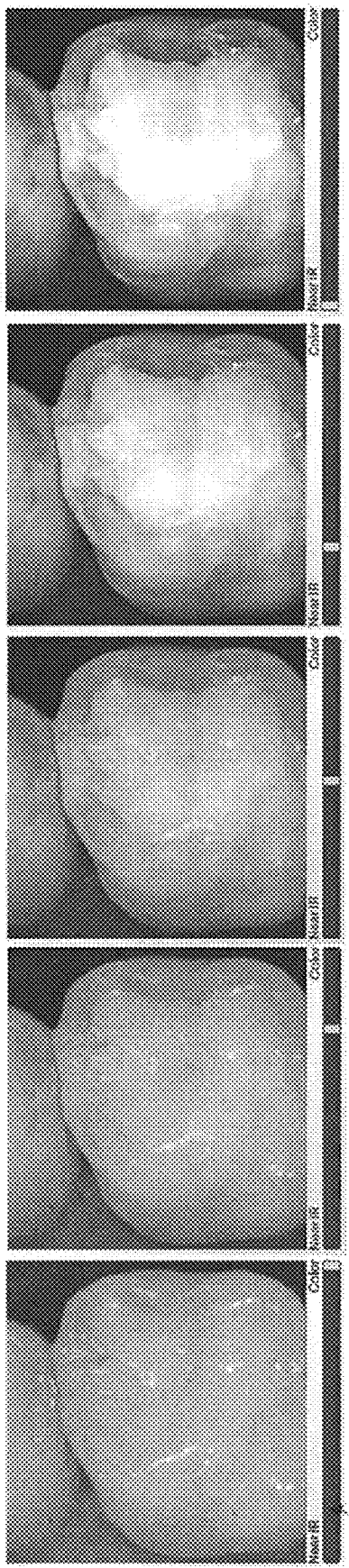

FIGS. 40A-40C illustrate another example, showing a hybrid image that (like FIG. 38E combines and mixes both surface image scanning (e.g., a visible light scan, as shown in FIG. 40A) with a volumetric model taken using a penetrative (e.g., near-IR) wavelength, as shown in FIG. 40B. Features that are present in the tooth enamel and dentin are visible in the volumetric reconstruction (image shown in FIG. 40B) that are not apparent in the image (which may also be a reconstruction) of just the surface shown in FIG. 40A. For example, in FIG. 40B, a carries region 1103 is apparent, which is not visible in FIG. 40A. Similarly a bubbled region of the enamel 1105 is visible in FIG. 40B but is not visible in FIG. 40A. FIG. 40C shows a hybrid image of the 3D volumetric model and surface model (surface image), in which both of these structures, the carries and the bubbled region, are visible.

Figure 33:
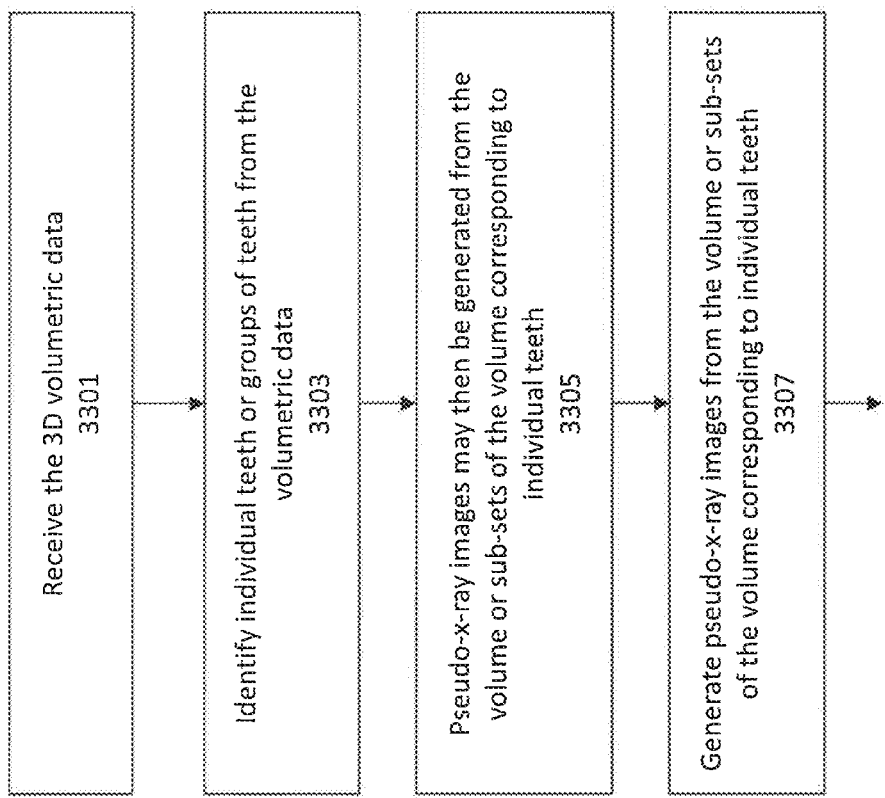
FIG. 33 illustrates one method of generating internal structure (or pseudo x-ray) images from a volumetric data.

In general, described herein are methods and apparatuses for simplifying and displaying volumetric data from a patient's oral cavity (e.g., teeth, gingiva, palate, etc.) in a manner that may be easily understood by a user (e.g., a dental practitioner) and/or a patient. Also described herein are methods of displaying volumetric data taken from a patient's oral cavity in a manner that may be familiar for a user and/or patient to understand. In a first example, the data may be presented as one or a series of x-ray type images, similar from what would be produced by dental x-rays. FIG. 33 illustrates one method of generating x-ray (or pseudo x-ray) images from a volumetric data set taken as described above, e.g., using penetrative light (e.g., near-IR) wavelength(s).

As shown in FIG. 33, a method of displaying 3D volumetric images of a patient's oral cavity may include receiving the 3D volumetric data 3301, e.g., from a scan as described above, either directly or from a stored digital scan, etc. In some variations, individual teeth or groups of teeth may be identified from the volumetric data 3303. The teeth may be identified automatically (e.g., by a segmenting the volume, by machine learning, etc.) or manually. Alternatively, the entire volume may be used. Pseudo-x-ray images may then be generated from the volume or sub-sets of the volume corresponding to individual teeth 3305. For example, an image of the volume may be taken from the 'front' of the tooth or teeth, in which the transparency of the enamel (and/or enamel-like restorations), dentin and other features are kept from the volumetric data. This volumetric data may be based on the absorption coefficients of the material within the oral cavity for the penetrating wavelength of light used. Thus, a projection through the volumetric data may be generated for a fixed direction from the volumetric data to get an image similar to an X-ray, but, in some variations, inverted and showing the density of the dentin (highly absorbing) as "darker" than the density of the enamel (less absorbing and therefore more transparent); caries may also show up as more absorbing (darker) regions. The image may therefore be inverted to resemble an x-ray image in which more dense regions are lighter (e.g., brighter). These pseudo x-ray images may be generated from the same positions as standard dental x-rays and presented to the user. For example, a panel of pseudo x-ray images may be generated from the volumetric model for each of the patient's teeth. Although the penetration of the wavelength of the light (e.g., near IR light) may not be as deep as with traditional x-rays, images generated in this manner may provide a comparable proxy for an x-ray, particularly in the crown and mid-tooth regions above the gingiva.

Other simplified or modified displays may be provided to the user, or customized for display by the user to the patient. For example, in some variations images of the teeth may be generated from the volumetric data in which the image is simplified by pseudo coloring the volumetric data to highlight certain regions. For example, regions that have been previously marked or flagged (as will be described in greater detail, below) may be colored in red, while the enamel may be shown as a more natural white or slightly off-white color. In some variations, enamel-like materials (e.g., from fillings, etc.) may be represented separately and/or marked by a color, pattern, etc.

In some variations, the methods and/or apparatuses may display the teeth in sections through the dental arch. Similarly the individual teeth or groups of teeth may be shown separately and/or labeled (e.g., by standard naming/numbering convention). This may be shown in addition or instead of other displays. In some variations, the teeth and/or internal structures may be pseudo-colored or projecting on to a color image may be used.

Figure 34A:
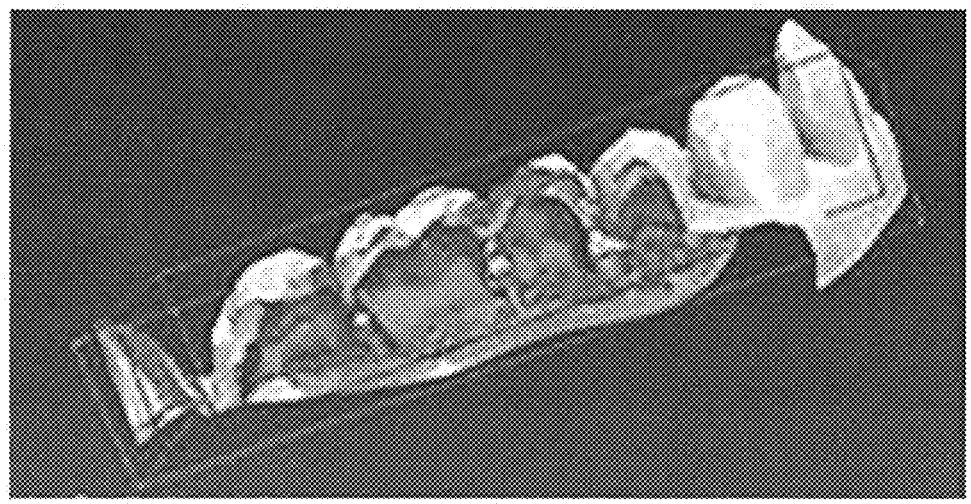
FIGS. 34A and 34B illustrate virtual sections from a volumetric model of the teeth. These virtual sections may be annotated, colored/pseudo-colored, or textured, to show internal features or properties of the teeth.
Figure 34B:
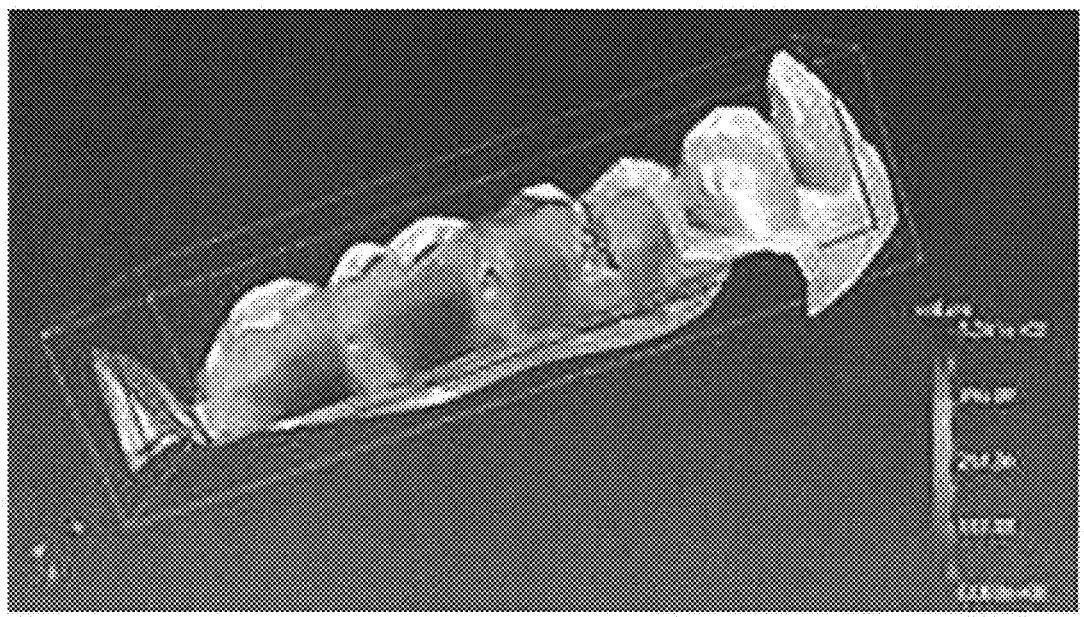

For example, FIGS. 34A and 34B illustrate virtual sections taken through a volumetric model of a patient's teeth generated from an intraoral scan that included near-IR information, and described above. In FIG. 34A, the cross-sectional view may be generated automatically or manually, e.g., by the user, to display regions of interest within teeth, including enamel. The cross-section may show both density sectioning and/or surface sectioning. These images may be pseudo-colored to show different regions, including outer surfaces, enamel, dentin, etc. Internal structures, e.g., within the enamel and/or dentin, may reflect the effect of the near-IR light within the teeth, such as the absorption and/or reflection of light at one or more near-IR/visible wavelengths within the teeth. In FIG. 34B, the section is pseudo-colored with a heat map to show internal features, and a key may be provided, as shown. In any of these variations, 2D projections of the teeth may be generated from the volumetric information, showing one or more features on the tooth and/or teeth. As will be described in greater detail below, additional features, including lesions (e.g., caries/ cavities, cracks, wearing, plaque buildup, etc.) may be displayed as well, and may be indicated by color, texture, etc. While illustrated as sections of the 3D volumetric model, other embodiments may display the 2D section by itself to provide a cross-sectional view of the tooth/teeth similar to a view provided by 2D x-ray images.

Any of the methods and apparatuses for performing them described herein may include displaying one or more (or a continuous) sections through a 3D model of the patient's dental arch, and preferably a 3D volumetric model. For example, a method of displaying images from a three-dimensional (3D) volumetric model of a patient's dental arch may include: collecting the 3D volumetric model of the patient's dental arch, wherein the 3D volumetric model includes near-infrared (near-IR) transparency values for internal structures within the dental arch; generating a two-dimensional (2D) view into the 3D volumetric model including the patient's dental arch including the near-IR transparency of the internal structures; and displaying the 2D view. In any of these methods, the method may optionally (but not necessarily) include scanning the patient's dental arch with an intraoral scanner.

Generating the 2D view may comprises sectioning the 3D volumetric model in a plane through the 3D volumetric model. The user may select the plane's location and/or orientation, and my do this in a continuous manner. For example, any of these methods may include selecting, by a user, a section though the 3D volumetric model to display, wherein selecting comprises continuously selecting sections through the 3D volumetric model as the user scans through the 3D model and continuously displaying the 2D views corresponding to each section. Generating the 2D view may comprises selecting, by a user, an orientation of the 2D view.

In any of these methods, the surface may be included. For example, as described and illustrated above, a method of displaying images from a three-dimensional (3D) volumetric model of a patient's dental arch may include: collecting the 3D volumetric model of the patient's dental arch, wherein the 3D volumetric model includes surface values and near-infrared (near-IR) transparency values for internal structures within the dental arch; generating a two-dimensional (2D) view into the 3D volumetric model including the patient's dental arch including both surface values and the near-IR transparency of the internal structures; and displaying the 2D view. The surface values may comprise surface color values. The surface relative to the internal (volumetric) structures may be weighted. For example, generating the two-dimensional (2D) view through the 3D volumetric may also include including in the 2D view a weighted portion of the surface values and a weighted portion of the near-IR transparency of the internal structures. The weighted portion of the surface values may include a percentage of the full value of the surface values, and the weighted portion of the near-IR transparency of the internal structures comprises a percentage of the full value of the near-IR transparency of the internal structures, wherein the percentage of the full value of the surface values and the percentage of the full value of the near-IR transparency of the internal structures adds up to 100%. For example, the user may adjust the weighted portion of one or more of the surface values and the near-IR transparency of the internal structures.

For example, a method of displaying images from a three-dimensional (3D) volumetric model of a patient's dental arch may include: collecting the 3D volumetric model of the patient's dental arch, wherein the 3D volumetric model includes surface color values and near-infrared (near-IR) transparency values for internal structures within the dental arch; selecting, by a user, an orientation of a view of the 3D volumetric model to display; generating a two-dimensional (2D) view into the 3D volumetric using the selected orientation, including the patient's dental arch including a weighted portion of the surface color values and a weighted portion of the near-IR transparency of the internal structures; and displaying the 2D view.

In addition to displaying qualitative images of the teeth, the methods and apparatuses described herein may quantify, and may provide quantitative information about internal and/or external features. For example, volumetric measurements of one or more lesions may be provided (selectably or automatically) including dimensions (peak or mean length, depth, width, etc.), volume, etc. This may be performed by manually or automatically segmenting the volumetric model to define the regions of interest, including either or both tooth features (enamel, dentin, etc.) and/or irregularities (e.g., caries, cracks, etc.). Any appropriate segmentation technique may be used, such as but not limited to: mesh segmentation (mesh decomposition), polyhedral segmentation, skeletonization, etc. Once the volume has been segmented, these regions may be separately or collectively displayed and/or measured. As will be described below, they may also be marked/flagged and used for further analysis, display and modification of the scanning methods and systems.

In some variations of the user interfaces described herein, a summary report may be generated or created and displayed for the user and/or patient from the volumetric data. For example, summary data may be projected onto a model of the patient's teeth. The model may also be simplified, so that the enamel is opaque, but marked or selected internal features (including automatically selected internal features) are shown in red or some other contrasting color (and/or flashing, blinking, etc.) within the tooth. For example, caries may be shown in this manner. The summary report may be automatically entered into a patient chart.

Any of the images, including the volumetric images, may be animated. For example, virtual sections through the patient's teeth, showing a scanning or traveling cross-section through the patient's dentition may be shown, in some cases with a 3D model showing one or more cutting axes through the volume. The user interface may allow the user to section in one or more planes, showing both external and internal features based on the volumetric scan.

In general, the apparatuses described herein may generate separate view for the user (e.g., physician, dentist, orthodontist, etc.) than the patient. The user may be provided with a 'clinical view' that may include information not present on a separate 'patient view.' The clinical view may be more technical, and may in some cases be closer to the raw images from the volumetric data. The user may select which layers of information to include in the patient view, which may then be presented to the user during or after the scanning or review of the dental scanning Patient educational materials may be appended to the patient view.

For example, in some variations, the user display of volumetric data may include an overlay of the volumetric data in which pseudo coloring of the 3D components within the volumetric data is shown. As will be discussed in more detail below, in any of these displays/images marked or highlight regions may be shown to call attention to potential problem regions (e.g., caries, thin enamel, cracks, etc.). Two-dimensional (2D) color data and 3D near-IR data (e.g., surface and volumetric regions) may be shown, including transitions between the two.

In general, the volumetric information may be annotated (e.g., marked, labeled, etc.) either automatically, manually, or semi-automatically, and this annotation may be displayed. Furthermore, annotations may be used both to annotate future additional scans, and to modify how future scans of the same patient are taken and displayed. An annotation may be, for example, a marker or flag on a region of interest. Regions of interest may correspond to specific regions in which one or more features (cracks, caries, thinning of enamel, buildup of plaque or calculus, etc.) have been observed. Alternatively or additionally, regions of interest may be regions in which there is a change over time, e.g., from one scan to another scan.

As mentioned above any of these methods may include placing one or more markers on the volumetric model of the patient's teeth. Markers (e.g., flags, pins, etc.) may be manually placed by the user, or may be automatically placed by the apparatus, or may be semi-automatically placed (e.g., suggested by the system, configured by the user, etc.). This is described in greater detail below.

Markers may be used to focus attention and/or processing by the system on one or more specific regions of the volumetric model for display, and/or for later follow-up (e.g., in future scans). Markers may modify the manner in which the later scans are taken, e.g., taking future scans of marked regions with greater detail (e.g., higher resolution, different wavelengths, greater scanning frequency or reputations, etc.). Marked regions may be displayed over time to show changes in the marked regions.

For example, a user can mark a digital representation of the patient's teeth (or the patient's actual teeth) with a marker (e.g., a pin, flag, etc.) which can be annotated (e.g., can have notes associated with it). This marker may then be used to track over time between different scans. Later scans can be marked in the corresponding location, the later scan can be modified based on the marked regions. These marked regions may be scanned in greater detail, and analytics may be automatically performed and/or displayed, measuring and/or indicating a change compared to one or more earlier scans. Thus any of the systems described herein may track one or more marked regions from previous scans and give feedback during and/or after a new scan, providing additional detail. This can be done for both surface and/or volumetric information, particularly on the properties of the enamel, and/or by comparison to the enamel, the outer surface of the teeth/tooth, and/or the dentin.

For example, one or more annotation markers from an earlier scan may modify a subsequent scanning of the same patient. Before scanning, the user may enter an identifier of the patient being scanned (alternatively the system may automatically identify the patient based on a database of earlier scans). The system may automatically annotate the new scan based on the prior scan annotations.

In some variations the later scans may be automatically annotated by the system by identifying differences between the prior scan(s) and the current scan. For example, regions showing a change above a threshold compared to the earlier scan may be flagged and presented to the user. The annotation may be done without user oversight (fully automatic) or may be done with some user oversight, for example, by flagging it and indicating to the user why it was flagged, then allowing the user to keep, modify or reject the marking. Reasons for automatically marking the teeth may include a change in the enamel thickness, a change in the surface smoothness, a change in the relative ratio of enamel vs. dentin in a tooth, a change in the position of the tooth (e.g., occlusion), etc. It may also include a change in structures external to the natural tooth, such as increase or decrease in plaque or calculus buildup, or changes to the gingival structures surrounding the tooth, Thus, if the system detects one or more of these conditions, it may automatically flag the relevant region in the volumetric model.

Later scans may be dynamically modified by the flags from earlier scans or by a detection of a change in a region (even unmarked regions) compared to earlier scans. For example, the scanning parameters may be modified to scan at higher resolution (e.g., changing the scan dwell time, requiring the user to scan this region multiple times, etc.), changing the wavelength used for the scanning, etc.

Figure 35:
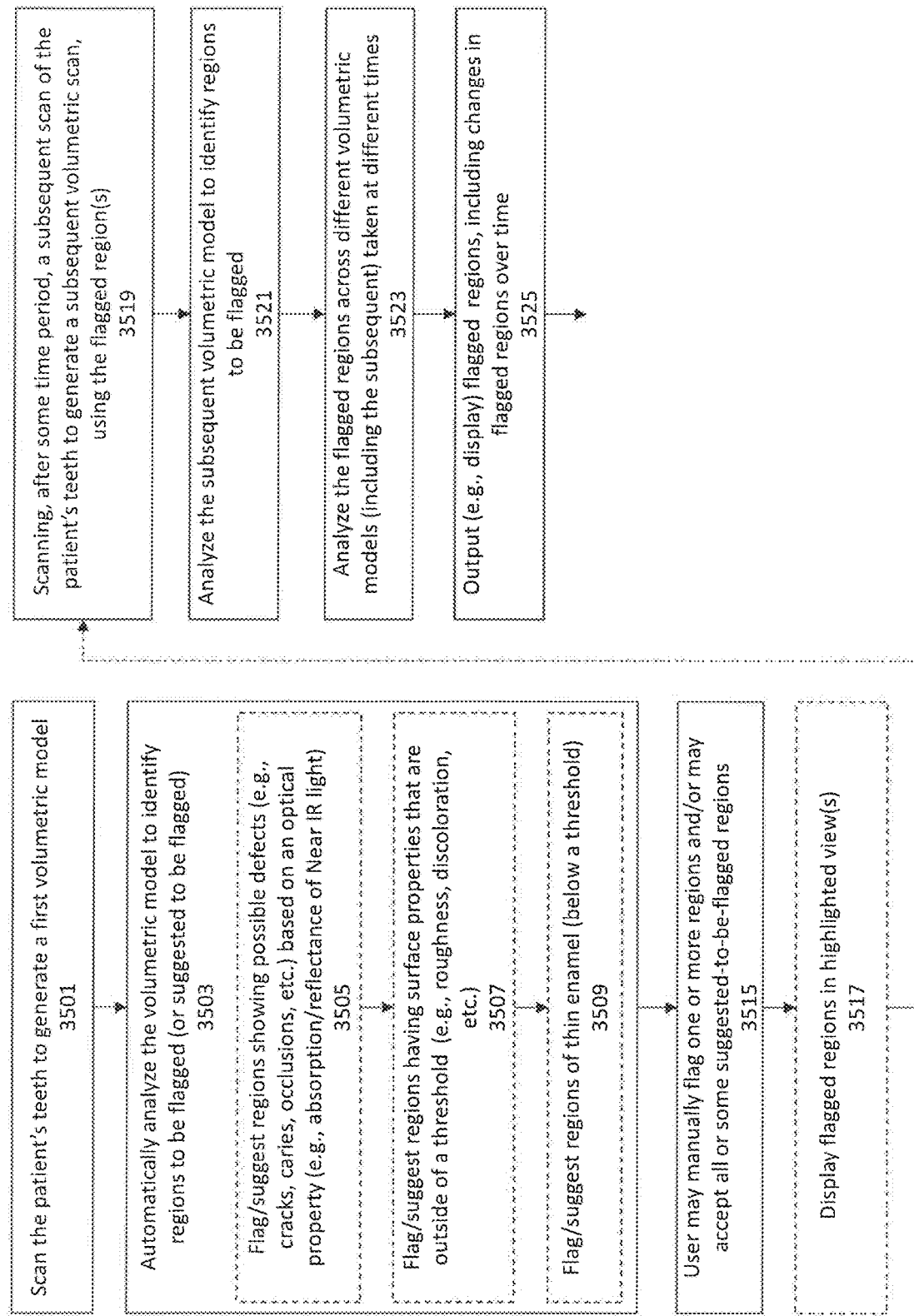
FIG. 35 illustrates one method of marking (e.g., flagging) a volumetric model of a patient's teeth, and/or using the marked regions.

For example, FIG. 35 illustrates a method of automatically selecting a region for marking and/or using the selected regions. A first volumetric model of the patient's teeth is generated from a scan of the patient's teeth 3501. The volumetric model may be generated using any appropriate method, including those described above and discussed in U.S. patent application Ser. No. 15/662,234, filed Jul. 27, 2017, titled "INTRAORAL SCANNER WITH DENTAL DIAGNOSTICS CAPABILITIES", incorporated by reference in its entirety. The first volumetric model may be stored (digitally stored) as part of the patient's dental record. The first volumetric model may concurrently or subsequently (immediately or some time thereafter) be analyzed (e.g., by an apparatus, including an apparatus having a processor that is configured to operate as described herein) to identify any regions that should be flagged 3503. This analysis may therefore be performed automatically, and may examine one or more properties of the patient's teeth from the scan. Automatic (or semi-automatic, etc., automatic but with manual assistance to verify/confirm) may be performed by a microprocessor, including systems that have been trained (e.g., by machine learning) to identify regions of irregularities on the outside and/or internal volume of the teeth. For example, the apparatus may examine the digital model to identify possible defects in the patient's teeth such as (but not limited to): cracks, caries, voids, changes in bite relationship, malocclusions, etc. This may include identifying regions in which there is an optical (e.g., near-IR) contrast near the surface of the tooth indicating a possible crack, caries, occlusion, etc. 3505. Regions that are less transparent (e.g., more absorptive) in the near-IR wavelengths than the rest of the enamel, that are closer to the surface (generally or within specific near-IR wavelengths), may correspond to defects. Alternatively or additionally, surface properties of the teeth may be examined and flagged if they are outside of a threshold 3507. For example, regions of the surface of the teeth in which the tooth surface is rough (e.g., has a smoothness that is below a set threshold, where smoothness may be determined from the outer surface of the enamel) may be flagged. Other surface properties may also be analyzed and used to determine if the region should be marked or presented to the user to confirm marking, including discoloration (based on a color or white-light/surface scan), gingival position (relative to the outer surface of the tooth), etc. The distribution and size of the patient's enamel may also be examined 3509. The enamel thickness may be determined from the optical properties (e.g., comparing absorption/reflectance properties). Regions of putative enamel that are below a threshold thickness, or having a ratio of thickness to tooth dimension (e.g., diameter, width, etc.) below a threshold may be marked or presented to the user to confirm marking.

In some variations, during and/or after automatically analyzing the volumetric model, the use may also manually flag one or more regions of the volumetric model of the patient's teeth 3515. If the automatic analysis of the volumetric model automatically flags the identified volumetric model the user's manually added regions may be added. In some variations, the user may be prompted to flag the regions identified and suggested by the automatic analysis. These regions may be marked and an indication of the reason(s) for their being identified may be provided (e.g., irregular enamel, potential crack, potential caries, potential thinning of the enamel, etc.). In general, the inner boundary (the boundary within the volume of the tooth, for example) may be defined in any of the methods and apparatuses described herein. For example, in variations in which a region of the enamel is thinning, the methods and apparatuses described herein may be used to the entire layer (e.g., layer of enamel, region of the inner structure of the tooth) may be identified and used for qualitative and/or quantitative information.

In some variations the method flagged regions may then be displayed on a digital model of the patient's teeth 3517. The display may emphasize the flagged regions, e.g., by providing a color, animation (e.g., flashing), icon (e.g., arrow, flag, etc.), or the like, including combinations of these. The display may also show enlarged views of any of these. The user may modify the display, e.g., rotating, sectioning, enlarging, etc., the flagged region. Alternatively or additionally, the flagged regions may be enlarged on the display by default. An index or key of the flagged regions may be provided, and may be displayed and/or stored with the digital volumetric model of the patient's teeth.

In some variations, as shown to the right of FIG. 35, the method may include using the flagged regions to modify the future scans, as mentioned above. For example, the method may include scanning ("rescanning") using the flagged regions, after some interim time period of between a first time (e.g., about one day, one week, one month, 2 months, 3 months, 4 months, 5 months, 6 months, 7 months, 8 months, 9 months, 10 months, 11 months, 1 year, 1.2 years, 1.5 years, 2 years, etc.) and a second time (e.g., about one month, 2 months, 3 months, 4 months, 5 months, 6 months, 7 months, 8 months, 9 months, 10 months, 11 months, 1 year, 1.5 years, 2 years, 3 years, 4 years, 5 years, 6 years, 7 years, 8 years, 9 years, 10 years, 11 years, 12 years, 13 years, 14 years, 15 years or more, etc.), or longer than the second time period. The flagged regions may be used to modify the scan by increasing the resolution of the scanned regions during the scan, e.g., by increasing the scan rate, increasing the dwell time in this region, scanning the region in additional wavelengths, scanning this region multiple times, etc. The scanning apparatus may inform the user to adjust the scanning (e.g., moving the wand of an intraoral scanner more slowly in these regions, moving the scanner back over these regions multiple times, etc.) and/or it may automatically adjust the scanning parameters during operation. The scanning apparatus may therefore receive the key or index of flagged regions and/or a marked (flagged) version of the patient's earlier intraoral scan(s). Prior to scanning the scanning apparatus, the user may indicate the identity of the patient being scanned, and this may be used to look up the earlier scan(s). Alternatively or additionally, the apparatus may identify the patient based on the current scan to identify (or confirm the identity) of the patient, to verify or recall the earlier annotated (flagged) scan. Alternatively, the second or subsequent scans may be taken without using the earlier flagged regions.

Following the subsequent (e.g., second, later or follow-up scan or scans), the method or apparatus configured to perform the method may then compare the flagged regions from the subsequent scan with the corresponding regions from the earlier scan(s) 3521. In addition, the volumetric model from the subsequent scan may automatically analyzed to identify any regions of the new (subsequent) scan that can/should be marked/flagged (e.g., repeating the earlier automatic or semi-automatic analysis steps 3503-3515) 3521. Newly identified regions from the subsequent scan may be compared to the previously un-flagged corresponding regions in the earlier volumetric model(s).

The flagged regions may be analyzed over time 3523. Specific sub-regions from the volumetric model including the flagged regions may be generated for display and analysis. The results may be output 3525. For example, these regions may be displayed to the user along with descriptive, analytic information about the scanned region. These regions may also be marked to shows changes over time. The data may be displayed in an animation, for example, showing changes over time. In some variations, the images may be displayed as a time-lapse image (video, loop, etc.), showing changes. Time-lapse images may show the change in the internal and/or external structure over time. Sections (pseudo-sections generated from the volumetric model(s)) may be used to show changes. Color, texture, patterns, and any other highlighting visualization technique may be used. Alternatively or additionally to the display of the flagged regions, these regions (and any accompanying analysis) may be output in other appropriate ways, including digitally outputting (e.g., the patient's dental record), printing a description of the flagged region(s), etc.

Any of the methods of tracking a region of a patient's dental arch described herein may include tracking over time and/or across different imaging modalities (e.g., records) as described in greater detail below. Further, any of these methods may be automated and/or may include automated agents, for example, for identifying one or more regions of interest (e.g., features, defects, including actionable dental features), including for scoring them and/or automating identification, scoring and/or display of such regions. Any of these methods may also include any of the display methods or agents (e.g., for displaying sections, displaying internal structures, for displaying virtual x-rays, for displaying across imaging modalities, etc.).

For example, a method of tracking a region of a patient's dental arch over time may include: collecting a first three-dimensional (3D) volumetric model of the patient's dental arch, wherein the 3D volumetric model includes surface values and near-infrared (near-IR) transparency values for internal structures within the dental arch; identifying a region of the 3D volumetric model; flagging the identified region; collecting a second 3D volumetric model of the patient's dental arch; and displaying one or more images marking, on the one or more images, a difference between the first 3D volumetric model and the second 3D volumetric model at the flagged region.

Any of these methods may also include tracking and/or comparing across different records (e.g., different imaging modalities), so that identifying comprises identifying a region of the patient's dental arch from a first record of a plurality of records, wherein each record comprises a plurality of images of a patient's dental arch each taken using an imaging modality, further wherein each record of the plurality of records is taken at a different imaging modality, further wherein flagging comprises flagging the identified region in a corresponding region of the 3D volumetric model of the patient's dental arch. The method and apparatuses for performing them may also include correlating the flagged region with each of records of the plurality of records by correlating the 3D volumetric model of the patient's dental arch with each of the records of the plurality of records. In some variations the correlation may be used to weight or grade the identified region to determine if it corresponds to a region of interest (e.g., a feature, a defect, including actionable dental features, etc.). For example, the region of the patient's dental arch may comprises a dental feature comprises one or more of: cracks, gum recess, tartar, enamel thickness, pits, caries, pits, fissures, evidence of grinding, and interproximal voids. Identifying the region may comprise comparing a near-IR transparency value of a region within the 3D model to a threshold value.

Where surface values are used, the surface values may comprise surface color values. These methods may be used with stored data and/or with data collected in real time (e.g., thus the method may optionally but not necessarily collect a three-dimensional (3D) volumetric model by scanning the patient's dental arch to generate the 3D volumetric model.

Identifying the region may comprise comprises automatically identifying using a processor. For example, automatically identifying may comprise identifying a surface color value outside of a threshold range. Automatically identifying may comprise segmenting the 3D volumetric model to identify enamel regions and identifying regions having enamel thicknesses below a threshold value.

Flagging the identified region may comprise automatically flagging the identified regions or manually confirming the identified region for flagging.

In any of these method in which regions are flagged, the method may include re-scanning the patient's dental arch wherein the flagged region is scanned at a higher resolution than un-flagged regions.

A method of tracking a region of a patient's dental arch over time may include: collecting a first three-dimensional (3D) volumetric model of the patient's dental arch taken at a first time, wherein the 3D volumetric model includes surface color values and near-infrared (near-IR) transparency values for internal structures within the dental arch; identifying, using an automatic process, a region within the 3D volumetric model to be flagged from a first record of a plurality of records, wherein each record comprises a plurality of images of a patient's dental arch each taken using an imaging modality, further wherein each record of the plurality of records is taken at a different imaging modality; flagging the identified regions; correlating the flagged region with each of the records of the plurality of records by correlating the 3D volumetric model of the patient's dental arch with each of the records of the plurality of records; collecting a second 3D volumetric model of the patient's dental arch taken at a separate time; and displaying a difference between the first 3D volumetric model and the second 3D volumetric model at the flagged region.

Similarly, as summarized and described above, a method of tracking a dental feature across different imaging modalities, the method comprising: collecting a first three-dimensional (3D) volumetric model of the patient's dental arch, wherein the 3D volumetric model of the patient's dental arch includes surface values and internal structures within the dental arch; identifying a region of the patient's dental arch from a first record of a plurality of records, wherein each record comprises a plurality of images of a patient's dental arch each taken using an imaging modality, further wherein each record of the plurality of records is taken at a different imaging modality; flagging the identified region in a corresponding region of the 3D volumetric model of the patient's dental arch; correlating the flagged region with each of the records of the plurality of records by correlating the 3D volumetric model of the patient's dental arch with each of the records of the plurality of records; and saving, displaying and/or transmitting images including the region of the patient's dental arch. Any of these methods may include tracking over time as well, e.g., by comparing the same region(s) to 3D volumetric models at different times.

Figure 39A:
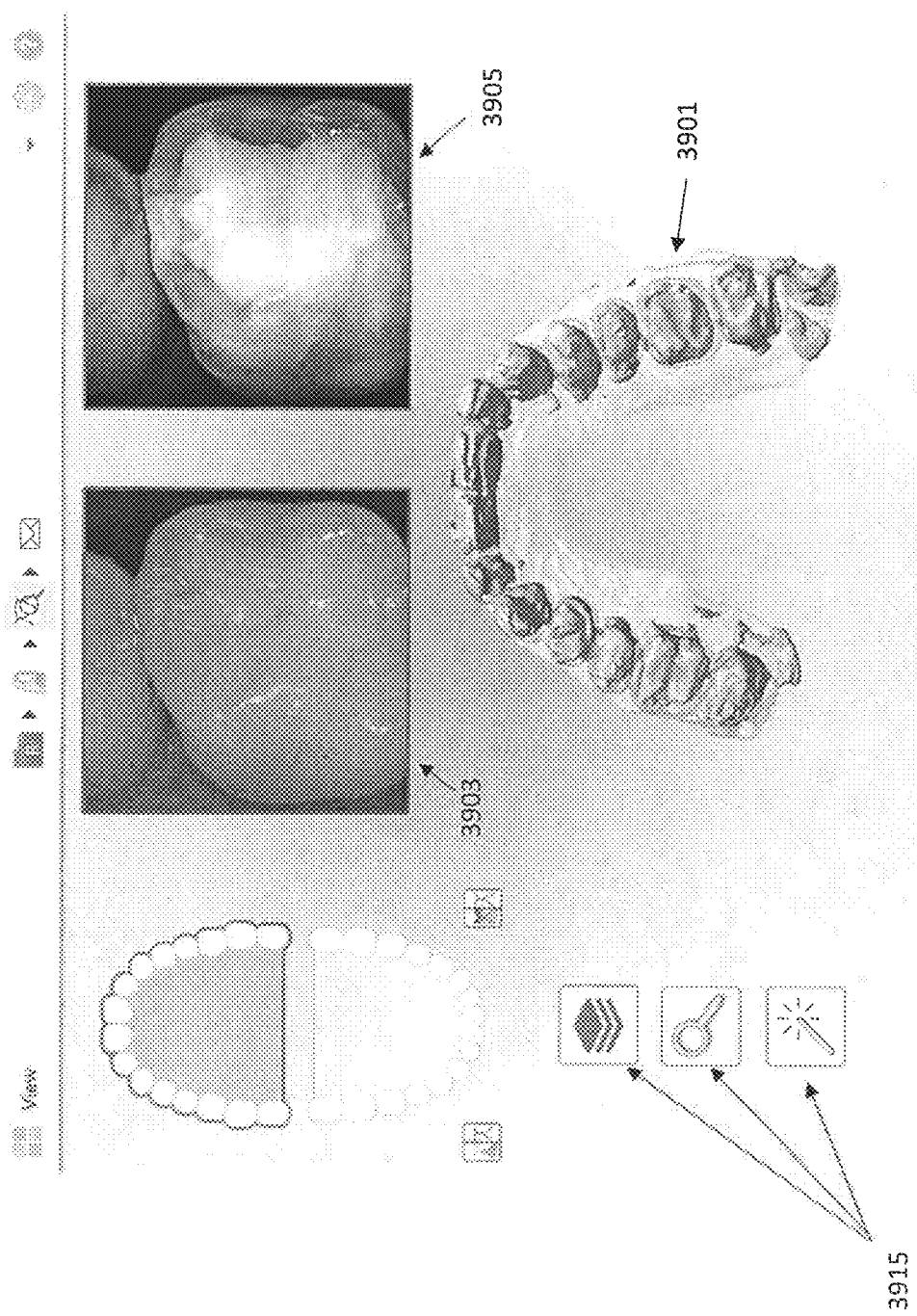
FIG. 39A illustrates an example of a user interface for analysis and/or display of a 3D volumetric model of a patient's teeth, showing a top view of the upper arch, tools that may be used to manipulate the view(s), and two enlarged views showing the outer surface of an enlarged region of the tooth (on the left) and the same view showing internal features of the tooth (showing dentin and enamel within the tooth).
Figure 39B:
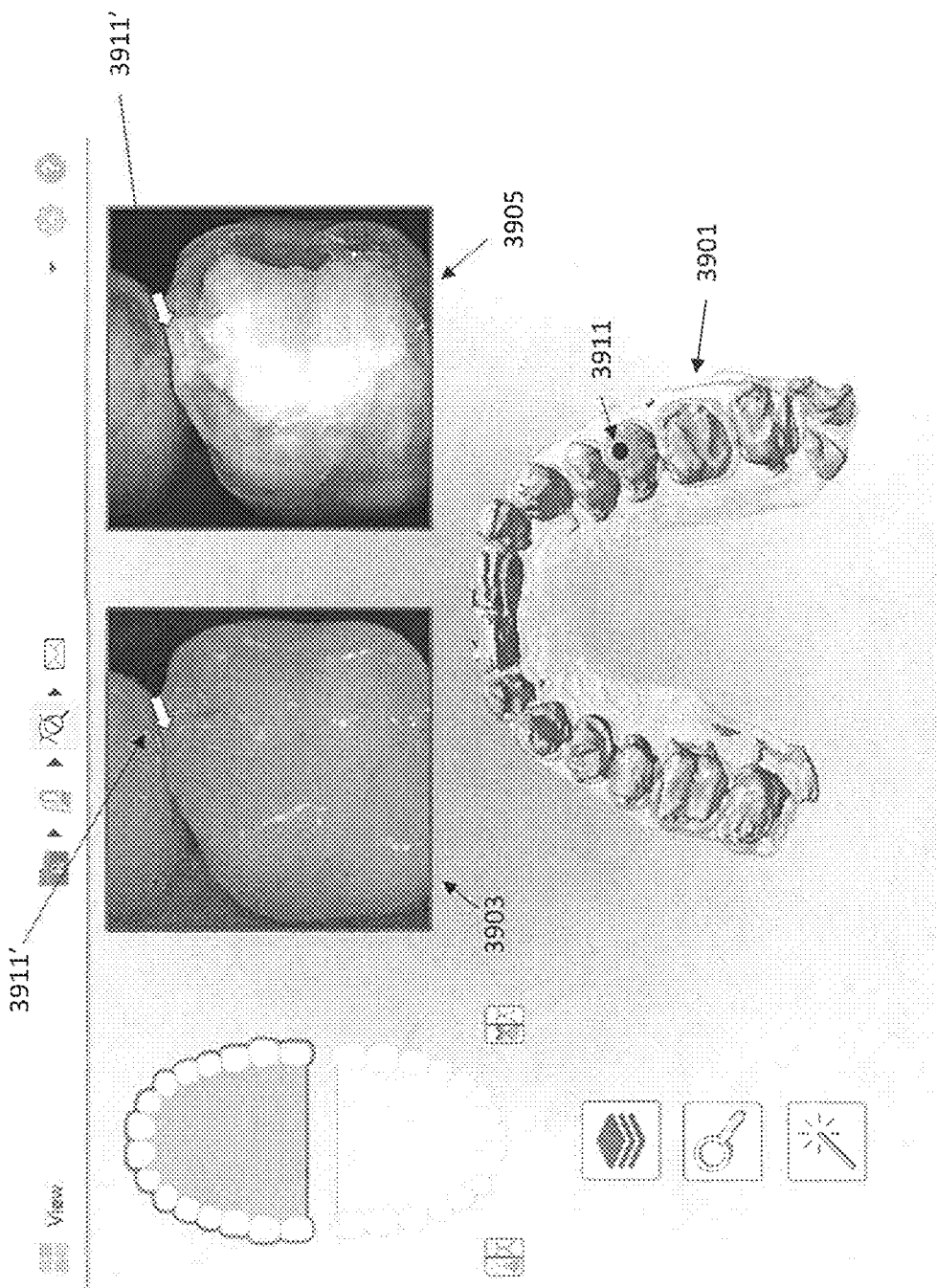
FIG. 39B show the user interface of FIG. 39A in which a region of the teeth has been marked/flagged as described herein.

FIGS. 39A and 39B illustrate a user interface showing marking of a region of interest from a 3D volumetric scan of a patient's oral cavity. In FIG. 39A, the user interface includes an image of the internal features 3901 (e.g., based on the near-IR absorption of the teeth), similar to FIG. 38B, discussed above. This view may be manipulated by user controls 3915, including sectioning tools, rotation, moving tools, etc. In FIG. 39A, two upper windows show a surface view 3903 and a volumetric (internal) view 3905 corresponding to the same region. This region may be selected. FIG. 39B shows the same features of FIG. 39A, but with a region marked or flagged 3911, 3911'. As discussed above, the identification of the region to be flagged may be automatic or manual, or semi-automatic (e.g., confirmed by the user), and may be chosen to select a region for later monitoring. In FIG. 39B, the region may correspond, for example, to possible caries.

Monitoring of one or more internal regions of the teeth over time using the volumetric models of the patient's teeth taken with the devices described herein may be particularly helpful for predicting dental problems, including caries, cracks, tooth loss, gum recession, and the like. In particular, these methods and apparatuses may help the user (e.g., dentist, dental technician, orthodontist, etc.) inform and educate a patient so that the patient may take recommended treatments prior to developing more serious problems. There is a need for effective ways to show changes in teeth over time and to provide patients with information necessary to act early to prevent more complicated and potentially painful problems from developing. Many patients are otherwise reticent to undergo preventive procedures, particularly when there is not currently any associated pain or discomfort. For example, pre-cavitated caries are difficult to identify with current imaging techniques, and it may be particularly difficult to convince a patient to treat even when identified, since they typically present without pain. However, early stage treatment may be critical to avoiding more complicated and dangerous procedures later.

Dental caries are one type of problem that may be identified with the methods and apparatuses described herein. As shown and discussed above, caries may be identified from 3D volumetric models (such as those described herein) that penetrate into teeth using light (e.g., near-IR), one type of non-ionizing radiation. In the 3D volumetric models generated as described herein, e.g., using a near-IR light, typically in combination with a surface scanning (e.g., white light), the absorption coefficients of the internal regions of the teeth may indicate distinctions between dentin and enamel, and may reveal internal structures and flaws, including cracks, caries and the like. For example, regions of enamel that are less transparent than expected in the near-IR wavelengths may (e.g., having different IR optical properties), and particularly those that appear to extend to the surface of the tooth in the volumetric model may be identified manually or automatically as cavities or caries. Other irregularities in the enamel and/or dentin (e.g., based on the internal features of the teeth from the volumetric model) may be identified and may be characteristic of a problem in the teeth. Thus, the techniques described herein may be used for prognosis of dental issues such as caries.

As mentioned, any of the apparatuses and methods described herein may include improved methods for displaying of internal tooth features using the one or more volumetric models of a patient's teeth. For example, the methods and apparatuses described herein may be used to generate an estimate of enamel thickness for one or more of the patient's teeth. These estimates may be visually displayed, showing the outer surface of the teeth or a particular tooth, and may also show internal structures, including in sectional views or 3D internal views showing, e.g., the enamel, including the thickness of the enamel. This information may be used clinically to determine the need for, to help design and to help apply dental prosthetics, including veneers, crowns, and the like. Any of the methods and apparatuses described herein may be used, for example, to help prepare design a dental implant for a particular tooth or teeth.

Plaque and Calculus Detection and Visualization

The method and apparatuses described herein may also be used for the detection and visualization (including quantification) of plaque and calculus on the patient's teeth. Any of the intraoral scanners described herein may be used to detect plaque or calculus on the patient's teeth by using florescence imaging in addition to other imaging/scanning modalities including penetrative (e.g., near-IR) imaging. For example, and intraoral scanner may be cycled between different imaging modalities such as between white light and near-IR, including additional modalities such as florescence (e.g., laser florescence, etc.).

The use of fluorescence capabilities (and/or using current ones) by the intraoral scanner may allow detection of plaque and calculus on the surface of the teeth. In combination with 3D modeling using the data from the intraoral scanner, the plaque/calculus conditions can be modeled and visualized on the 3D model of the teeth, including the 3D volumetric modeling of the teeth. Plaque and/or calculus may be detected and may be displayed and highlighted as described above, and may be used before, during or after treatment. For example, a dental technician (e.g., dental hygienist) may use an intraoral scanner to detect and monitor the condition of the patient and the cleaning treatment. Data on plaque and calculus may also be used by any of the apparatuses described herein to determine and provide predictive models that may indicate plaque and calculus (e.g., tartar) generation rate and/or locations.

In some variations, plaque and calculus may be identified at least in part using florescence information. It has been observed that plaque may fluoresce under blue light (e.g., around about 405 nm). Any of the intraoral scanners described herein may include fluorescence information from which information about plaque and calculus may be used, and incorporated into a 3D model of the patient's teeth. For example, plaque and/or calculus may be visually displayed as a color and/or texture on the 3D model of the patient's teeth.

For example, a fluorescence signal can be obtained from an intraoral scanner using a dichroic filter having a large aperture amplification of fluorescence signal. This amplification may emphasize the fluorescence, thus enabling the detection, visualization and segmentation of plaque and calculus regions using RGB illumination, sensor and image. Alternatively or additionally, the apparatus may include a florescence source (e.g., an LED emitting at 405 nm) and corresponding filter(s) for detection of plaque and/or calculus. This may be integrated in the intraoral scanner, or added (e.g., as a sleeve, accessory, etc.) to be used with the scanner.

Alternatively or additionally, in some variations, depending on the wavelength of near-IR light used, the plaque and calculus may have a different absorption/reflection than enamel. This may allow the calculus and/or plaque to be differentiated from the enamel in the volumetric model. Further, the volumetric model may be used to detect material on the teeth, including calculus and plaque based on the surface smoothness and geometry. In variations in which calculus and/or plaque are not transparent to the near-IR frequencies used, the apparatus may differentiate calculus and/or plaque from the enamel using the volumetric model. Thus, the calculus and/or plaque may be segmented and differentiated from enamel.

The use of an intra-oral scanner to detect plaque and/or calculus may provide quantitative information and digital modeling. This may allow monitoring and comparison of plaque/calculus over time based on registration to 3D model, including real-time registration and/or display.

The acquisition of both fluorescence image and 3D scan on the same time and same position of the intraoral scanner (e.g., the scanning wand) allows for very accurate registration of the plaque/calculus regions and the 3D model. The concurrent scanning is described in greater detail, for example, in U.S. patent application Ser. No. 15/662,234, filed Jul. 27, 2017, and titled "INTRAORAL SCANNER WITH DENTAL DIAGNOSTICS CAPABILITIES". The accurate registration between different scanning modalities, such a white/visible light, penetrative (near-IR) light and/or florescence, may enable the apparatuses to define the borders of the calculus and/or plaque and may permit the apparatus to determine the volume/thickness in high resolution, allowing for both measuring the precise current situation and comparison/tracking relative to previous scans.

The methods and apparatuses described herein may take RGB images of the teeth at the same/similar time with taking 3D scans of the teeth. These scans may then be used to build the 3D model of the teeth/jaw, which may include the volumetric information (3D volumetric model). For example, RGB images may show emphasized signal of fluorescent surfaces, specifically plaque and calculus regions, due to specific characteristic of color and brightness of such surfaces, as mentioned. For example, the image of the outer surface (and in some cases the volumetric model) of the teeth may show regions having optical properties (florescence, brightness, color, etc.) indicative of calculus and/or plaque. In some variations, this emphasized signal may result from the spectral illumination that creates no reflection in visible light, but creates a significant fluorescence signal from plaque and calculus. For example, typical RGB illumination (using a common RGB sensor), may be modified to provide amplification of the fluorescence signal (e.g., in near-IR regions) on the outer surface of the teeth. This amplification can be achieved by, as a non-limiting example, a large aperture that enables IR signals to pass, and small aperture that enables the regular RGB (visible) spectrum to pass. This combination may produce color images with extra emphasis on fluorescent surfaces. Such fluorescence may manifest in characteristic colors and brightness of the desired regions indicating calculus and/or plaque on the teeth.

In any of the method and apparatuses described in which RGB images may be take that include florescence signals (e.g., at a wavelength in which plaque or calculus fluoresces), segmentation of the fluorescent regions may be performed on the image. For example, using the camera positions during acquisition of RGB and 3D scans (e.g., from the intraoral scanner), the fluorescent region may be registered with the 3D model (including the volumetric and/or just surface model) of the patient's teeth. This may result in a definition of relevant plaque and calculus regions on the final 3D model, which may further allow for definition of these regions, such as the borders of the calculus on the teeth, as well as 3D surface & thickness of the plaque.

As already discussed above, regions on the 3D model may be compared with previous/future scans of the same patient, which may show the development of calculus over time, and the effect of the calculus on the patient's teeth. The apparatus may automatically or semi-automatically mark (e.g., flag) these regions for monitoring. Thus, the size and shape of calculus for each tooth may be monitored. Alternatively or additionally, the thickness/depth of calculus may be compared with previous scans. Any of this information may be provided quantitatively and/or qualitatively, as discussed above. The thickness/depth of calculus may be compared with previous scans of clean teeth (including one or more earlier scans following cleaning by a dental professional). This may provide an estimate of the thickness of the calculus in later scans. As mentioned, measurements of the changes in the plaque, and particularly the calculus over time may be made, and this data may be used to monitor plaque and calculus progression on the patient's teeth, and may provide well as visualization of the development.

In general, the monitoring and visualization of the patient's teeth using the methods and apparatuses described herein may be used as part of a dental and/or orthodontic treatment planning. As already mentioned above, monitoring of calculus and plaque may be used to treatments including teeth cleaning. Scans may be performed prior to cleaning, during cleaning and/or after cleaning to provide guidance to the dental practitioner as to what regions to emphasize, focus on, or return to. Other treatments (coatings, caps, etc.) may be proposed based on the progression of plaque and/or calculus over time. Further, monitoring of any other feature or region of interest, including, e.g., caries, cracks, etc., as described above, may also provide treatment planning information. As discussed above, information about cracks and/or caries may be used to suggest treatments including restorations before potential issues develop further. In some variations, a digital model (e.g., surface and/or volumetric model) of the teeth may be modified using the volumetric information, and the modified model(s) used to design an orthodontic appliance or treatment plan. For example, a user may digitally remove plaque and/or calculus from a volumetric scan taken prior or during a treatment. The modified scan may be used to guide treatment, including further cleaning of the teeth, as necessary and to form or modify an appliance, so that the appliance (e.g., a dental aligner) may fit better.

Combination with Dental Tools

The intraoral scanners and volumetric modeling described herein may be used and/or combined with other dental tools (drills, probes, etc.). The combined tool may provide numerous advantages.

For example, described herein are drills that may be used in conjunction or combined with the intraoral scanners, and the use of 3D volumetric models. In some variations, a dental drill and an intraoral scanner may be combined; e.g., incorporating a laser drill or laser-accelerated water drill into an intraoral scanner. This combination may allow the dental professional using the tool to directly visualize the tooth as and before it is drilled, providing real-time feedback to the user. In one example, near-IR light may be applied to the probe head of the drill (e.g., laser drill) to provide imaging into the tooth, which will allow direct forward-looking imaging prior and/or during drilling. The enamel and dentin in the direct path of the drill may be imaged. The density information can be used to inform the clinician when they have reached the dentin layer of a tooth or a certain depth inside the dentin, or when diseased regions have been removed. For example, the density information can be used to provide haptic feedback to the operator, since tactile feedback is much more limited when using a dental laser versus a traditional headpiece.

Figure 36:
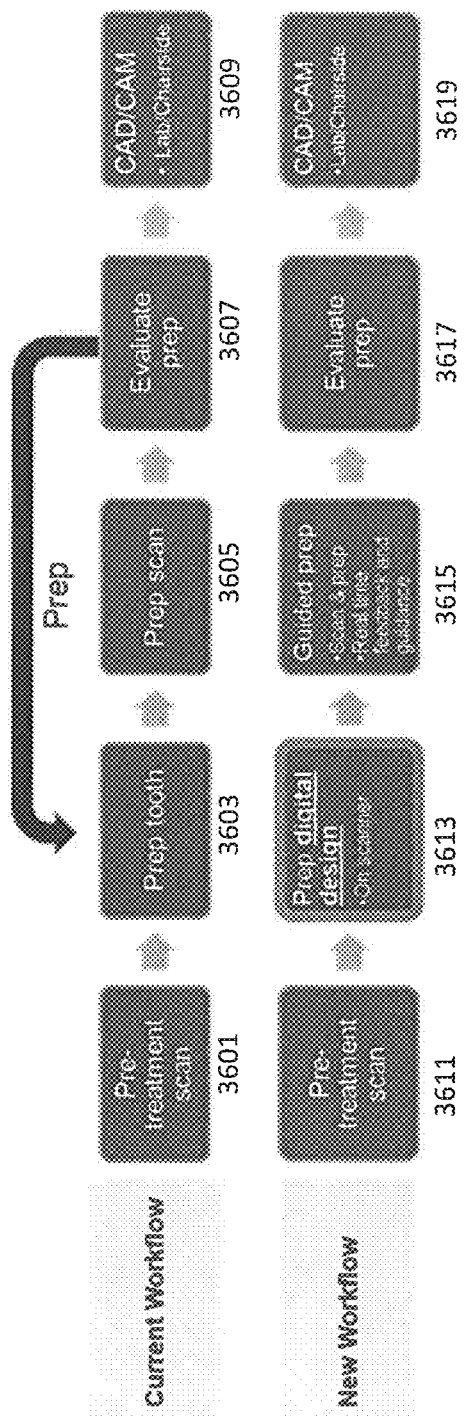
FIG. 36 is a comparison between a typical computer-aided design/computer-aided manufacturing (CAD/CAM) method for dentistry, and a method implementing the 3D volumetric scanning and modeling as described herein.

The methods and apparatuses including intraoral scanners and volumetric modeling as described herein may also be integrated into computer-aided design/computer-aided manufacturing technology for dentistry, as described in FIG. 36. For example, dental implants, such as crowns (e.g., ceramic crowns) may be fabricated for an individual patient using computer-aided design and computer-aided manufacturing (CAD/CAM) apparatuses and procedures. For example, traditionally CAD/CAM laboratory manufacturing ("current workflow" in FIG. 36) may include pre-treatment scanning of the patient's teeth 3601 or an impression of the patient's teeth, such as a caries-free scan of the jaws. The teeth may then be prepared for the crown 3603, and then re-scanned 3605 and evaluated 3607. Finally, the crown may be made using CAD/CAM. The software for the CAD/CAM may receive the scanned information from the scanner and may process it for use in forming the design and performing the manufacture. The use of CAD/CAM software may provide restorations comparable to conventional restorations in all aspects, including in aesthetics, however the current methodologies may require repeated steps for evaluating and preparing the tooth, as shown by FIG. 36, and typically require the user to perform these steps manually.

As shown in the "new workflow" on the bottom of FIG. 36, this method may integrate the 3D volumetric modeling described herein to simplify and improve CAD/CAM of a patient's teeth. For example, the preparation may be digitally designed, and this process may be automated (fully or semi-fully, so that the user may approve and/or modify the process). For example, in FIG. 36, the pre-treatment scan 3611 may be performed using an intraoral scanner that directly communicates with the CAD/CAM apparatus, or the intraoral scanner may include CAD/CAM capabilities. In this example, the tooth preparation 3613 may be fully digitally designed based on the scan performed, and the scanner may guide the preparation of the tooth 3615. This may be done in real time with direct feedback and/or guidance from the apparatus, which may integrate the scanner. The scanner may then be used to evaluate the preparation 3617, on in some cases this step may be integrated fully into the guided prep step 3615, therefore removing the need for the post-prep evaluation. Finally, CAD/CAM may be used to prepare the crown (or other dental appliance) for the correctly prepared tooth 3619.

Root Canal

The methods and apparatuses for 3D volumetric modeling of the patient's oral cavity (e.g., 3D volumetric modeling of the teeth) may also be used to modify a root canal procedure. Typically, root canal procedures require numerous x-rays to provide images into the teeth prior to, during, and/or after the procedure. The methods and apparatuses described herein may remove or reduce the requirement for x-rays in the specific example of root canal procedures. Specifically, as described herein, an intraoral scanner including penetrative wavelengths (e.g., near-IR) may be used to examine within a tooth, including within the root of the tooth during the procedure. This may allow identification and localization of the canal. For example, a tooth may be prepared for the root canal by, for example, drilling a hole through the crown into the tooth. The hole may be drilled with the guidance of the volumetric imaging described herein either during or interposed with the drilling. For example, a tooth (e.g., molar) may have an initial hole drilled into it to expose the camber within the tooth. An intraoral scanner including near-IR may be used to image the tooth, including imaging through the hole that has been drilled into the tooth, to visualize into the pulp chamber. The scanner may be oriented, automatically or manually, to image down into the chamber, which may allow visualization of the roots within the chamber. The initial drilling into the teeth may be limited to penetrate the enamel and expose the inner chamber, and visualizing into the chamber so that regions having different optical properties (at any wavelength, including in particular the near-IR wavelengths) may penetrate into the chamber despite calcifications and/or infection, to allow imaging of the roots from within the tooth itself. The nerve chambers of the root may be identified as being more or less dense than the surrounding regions within the dentin and enamel. By removing the roof of the chamber to expose the inner pulp region of the tooth, the intraoral scanner may visualize through the drilled opening to provide additional volumetric information, including the locations, curvature, and trajectory of the tooth root. Detection of hidden canals and accessory canals may be facilitated by this additional visualization information. This information may then be used to guide the therapy.

For example, in some variations, the method may include taking, using an intraoral scanner as described herein, a 3D volumetric model of the patient's teeth either before or after drilling to form an opening into the target tooth (e.g., for which a root canal will be performed). The drilling may be done with or without guidance from an intraoral scanner, as described above. The inner chamber of the tooth may be visualized using the intraoral scanner, e.g., through an opening drilled from the crown of the tooth. The apparatus may then determine the locations of the horns of the pulp chamber for the tooth. Any of the methods described herein may be used in combination with x-ray information. Treatment planning may be performed by the apparatus to determine the shape and/or location of the pulp horns, pulp chamber, and roots to map out a treatment plan for drilling/tissue removal that avoids overthinking or breaching the lateral sides of the tooth. This treatment plan may then be used to guide the user in drilling on the teeth, and/or for automating the drilling. In some variations the drill may be directly guided by imaging, e.g., using the hybrid drill/intraoral scanner described above. Alternatively or additionally, robotic assistance may be provided using the treatment plan. In some variations, the procedure may be performed manually, and the drilling may be done in small increments, with visualization between drilling steps to confirm the treatment path, and avoid over-drilling, as well as confirming that the entire region has been drilled and infected pulp removed. Additional visualization (including using a contrasting agent) may be used.

In general, any of the methods described herein, including the root canal methods described above, may be used with one or more contrasting agents during imaging. For example, contrasting agent may include material applied to the outside of the tooth (or into a hole or opening in the tooth, including holes drilled into the tooth). Contrast agents that absorb or reflect in the near-IR, or other wavelengths use by the intraoral scanner may be used. Preferably contrast agents may be used that are distinguishable at some of the imaged wavelengths, but not all of them, to provide differential imaging. For example, contrast agents may be visualizable under white light, but not near-IR; alternatively, a contrast agent may be visualizable under near-IR but not white light, or under some wavelengths of near-IR but not others for which images are taken. Contrast agents that preferably attach mix or coat with one or more targets within the teeth or oral cavity may be used. For example, a contrast agent that selectively binds to one or more of: bacteria, plaque, calculus, gingiva, pulp, etc., may be used. In use, the contrast agent may be applied to the teeth/oral cavity, rinsed, then visualized (or visualized without rinsing). For example, a contrast agent that absorbs IR light may be used for inclusion as part of, or mixed in with a material forming, e.g., a dental implant (e.g., to fill a cavity, cap a tooth, fill a root canal, etc.) to create an IR contrasting filler material that may be easily visualized when scanning as described herein.

Also described herein are methods of determining improvements in soft tissue around the teeth using the apparatuses and methods for generating 3D volumetric models of the teeth, as described herein. For example a gum recession may be monitored and/or quantified, and may be observed over time using these methods and apparatuses. In addition to the direct visualization of plaque and/or calculus as described above, the methods and apparatuses described herein may also or alternatively detect the effect on the teeth, including recession of the bone due to plaque and calculus. Diseased regions, may be visualized directly. In some variations a contrast agent may be used to provide additional contrast for the intraoral scanner to detect diseased regions. Scanning of the surface of the gingiva may identify inflamed and/or discolored regions that may be indicative of gum disease. This information may be combined with the 3D volumetric modeling of the teeth, including the location of plaque and/or calculus, as discussed above.

FIGS. 37A and 37B illustrate an example of a monitoring, over time, gum (gingival) recession. In this example, the display may show the 3D model of the teeth and a comparison between the original scan, and a subsequent scan, taken 2-3 years later. In FIG. 37A, the two scans have been aligned and compared, and differences shown by a color indicator, e.g., a heat map. In FIG. 8, darker colors (which may be shown in color, e.g., red) show recession of the gingiva to a greater degree. The circled region B in FIG. 37A is shown in greater detail in FIG. 37B for the later scan. Although FIG. 8 illustrates primarily surface features (e.g., gingiva position), volumetric information may be used to generate this information, e.g., showing changes in gingiva thickness and/or vascularization, enamel thickness, etc.

In addition to guiding the user and/or dental technician based on the scans (e.g., showing plaque, calculus and/or inflammation in particular), these methods and apparatuses may be used by the dental professional to rate, rank or quantify the removal of plaque and/or calculus, either immediately following a treatment, or over time. This may provide a metric against which treatments may be judged. The scan information may also be used to provide information to the patients, including a map or guide for home treatment, including which areas to focus on brushing, flossing, etc. The guide may include one or more images from the 3D volumetric model, for example. Guidance information about what teeth or oral cavity regions to focus home dental care (e.g., brushing) on may be provided to an electronic toothbrush that may also help guide the patient in brushing based on identified regions.

The methods and apparatuses described herein may also be used with patient's already having a dental appliance installed on the teeth, including braces, bridges, and the like.

For example, in some variations the patient may include 3D representations of the dental appliance, and may provide information to help design or modify future dental devices (e.g., retainers, aligners, braces, etc.).

In particular, the methods and apparatuses described herein may be use to provide very accurate volumetric and surface information about the patient's teeth that may be useful for treatment planning of any type of dental treatment. In some variations the methods and apparatuses described herein may be useful for treatment planning of an appliance, such as an aligner or retainer, that is optimally worn in close proximity to the patient's teeth. For example, a method and/or apparatus that includes a 3D volumetric scan of the patient's teeth may be used to subtract out or remove from the 3D model of the teeth, any plaque, calculus and/or food debris that might be present at the time of the 3D scan. By digitally subtracting out any plaque, calculus, and/or food debris present, the volumetric information may be used with a virtual representation of an aligner, retainer, night guard, or other device, and the fit improved prior to fabricating, applying or wearing the apparatus.

The gingival tissue surrounding the teeth, being of different density (or different optical absorption/reflection properties) than the enamel, may also be identified and characterized with greater accuracy, so that the junction between the inner contour and the tooth surface can be identified. By doing this, the shape of the tooth surface beneath the gingival tissue can be accurately characterized so that predictive models of tooth movement can have more accurate representations of the teeth as portions of the teeth not initially visible become gradually exposed as the teeth align. In other words, some parts of the teeth may be initially obscured by the gingival tissue, but as the teeth straighten, the gingival tissue migrates, and the previously-covered regions are exposed. By detecting the tooth regions beneath the gingival tissue accurately, the future state of the teeth after the gingiva has migrated can be more accurately modeled.

The methods and apparatuses described herein may also be sued to detect, diagnose, and/or treat disorders of the oral cavity.

For example, the 3D volumetric scanning and modeling methods and apparatuses described herein may be used to detect and/or treat salivary stones (e.g., plugging of the salivary ducts). These glands, which may be located near the molars and under the patient's tongue, may be scanned using the intraoral scanners described herein. These scans may penetrate the soft tissue and may detect the hard, stone-like formations (i.e., sialoliths, salivary-gland stones, or duct stones) that are calcified structures that may form inside a salivary gland or duct and block the flow of saliva into the mouth. The methods and apparatuses described herein may be used to identify these structures and/or may guide and/or confirm removal of these stones.

In addition to or instead of the use of the apparatuses and methods descried herein to identify, diagnose and/or track regions, including pre-cavitation caries, crack, etc., the methods and apparatuses described herein may also or alternatively be used to identify and manipulate regions that have already been modified. For example, fillings, attachments (for attaching an angler, braces, etc.), braces, retainers, etc. and any other structures may be identified within the volumetric model and/or displayed. For example regions of enamel and/or enamel-like restorations may be displayed differently in the volumetric model. These regions will typically have different optical properties, including different scattering/absorption of the near-IR (and in some cases visible light) compared to each other and/or other regions of the oral cavity, including the dentin. Such regions may be manually, automatically or semi-automatically identified, and may be segmented and/or separately manipulated. For example, in some variations these regions (e.g., attachments/cement, etc. for an aligner or other appliance) on the tooth may be identified for removal by the dental practitioner, and the 3D volumetric model or data (images) taken from it may be provided to guide such treatment. They may also or alternatively be digitally subtracted to provide a better fit for a new appliance once removed. A subtracted view may also or alternatively be provided to a patient.

In some variation the internal structural integrity of an artificial dental structure or modification (e.g., dental bond, filling, etc.) may be determined using the volumetric model(s) described herein. For example, a volumetric model may include internal detail of an artificial dental structure, such as the structural detail within a filling, bond, etc., or the interface between the natural tooth (enamel, dentin, etc.), and this information may be presented or shown to the user in detail to allow an assessment (or to allow automatic assessment) of the condition of such artificial dental structures. This may facilitate their removal, repair and/or replacement.

The 3D volumetric models of the teeth (and method and apparatuses for generating them) may also be used as a diagnostic or detection tool for future tooth sensitivity. For example, an abfraction is a form of non-carious tooth tissue loss that typically occurs along the gingival margin. The abfraction lesion may be a mechanical loss of tooth structure that is not caused by tooth decay that may occur in both the dentin and enamel of the tooth. These are believed to be caused by repetitive stress cycles from the patient's occlusion, and exacerbated by aggressive brushing. The 3D volumetric models of the teeth enhanced by density analysis of the enamel and dentin near the gingival line may provide an early indicator of these lesions. For example, an apparatus may examine the volumetric model to identify the initial stages of formation for these crescent-shaped lesions. Multiple 3D volumetric models taken over time may indicate the rate of progression of these lesions. A system may be configured to automatically or manually identify them; as described above, they may be automatically or semi-automatically flagged.

Thus, the apparatus and methods may identify and alter the user that such a "hotspot" leading the future tooth sensitivity may be occurring, and may provide for treatment plans to slow, stop or reverse the progression of the lesion. Tooth sensitivity can result from these small fractures and the exposed dentin. Detection may be triggered by identifying the characteristic crescent shape that develops in the more mature lesions, however earlier detection may be made by identifying regions of thinning in the enamel and/or dentin (e.g., near the gingival line), which may progress over time. The apparatuses and methods may flag and/or assign risk based on the actual thickness and/or the progression of changes in the thickness.

The methods and apparatuses described herein may also be used to detect the development of acid reflux, based in part on characteristic wear patterns, and/or changes (e.g., over time) in the enamel thickness of the patient. For example, acid reflex while a patient sleeps may result in the gradual erosion of the patient's teeth in a characteristic pattern (e.g., from the back of the teeth, on the lingual side. As similar pattern may develop with bulimia. The volumetric models of the patient's teeth taken, e.g., by near-IR, may provide an accurate mapping of the enamel density and thicknesses of all of the patient's teeth. Thus, a method of detecting acid reflux (or bulimia) may include detecting (including detecting over time) characteristic thinning of the enamel of the patient's teeth in the rear, lingual region. The more proximal, lingual region of the teeth may have an unusually thinner (or thinning) enamel thickness, compared to more anterior (forward) regions on the opposite, buccal, side of the patient's teeth.

The methods and apparatuses described herein may also be used to detect thin enamel regions from occlusal wear due to chronic grinding of the patient's teeth and/or predict tooth sensitivity that may result from this grinding. 3D volumetric models of the patient's teeth may show a snapshot of the occlusal thickness of the patient's enamel and the proximity of the dentin to the occlusal surface. Further, multiple scans taken over time may show the loss of enamel in the occlusal surface. This was mentioned above as one indicator that may be automatically, manually or semi-automatically marked or flagged. For example, a flag can be set whenever a region >0.5 mm$^2$ develops within 0.5 mm of dentin, and the regions of the digital model highlighted. This allows any regions which satisfy the flag criteria to be visualized and/or monitored. Given a patient's age and in some variations gender, as well as the changes in the enamel thickness over time, an estimate of the wear rate over time may be provided, along with proximity to dentin regions, and thus an estimate or prediction of the tooth sensitivity or pain may be made. Grinding of teeth may also be an indicator of other issued, including sleep apnea. For example, sleep apnea may also be detected from 3D volumetric models of the patient's teeth, particularly over time. Many patients with sleep apnea grind their teeth (e.g., in a forward and/or side to side motion), which may result in a pattern of erosion of the teeth. Thus, the methods and apparatuses described herein may be used to help diagnose or confirm sleep apnea.

In general, any of the methods and apparatuses described herein may be used with non-human patients. For example, any of the methods and apparatuses described herein may be used as with veterinary patient's (e.g., animals) to determine, for example, the state of the animals teeth, including wear on the teeth.

The methods and apparatuses described herein may also be used to provide an estimate of risk for the patient in developing fractures in the teeth, and/or the development of tooth sensitivity. For example, a the 3D volumetric models of the teeth described herein may be used to identify malocclusions in the teeth and resulting wear and/or cracking of the teeth, based on the mechanical estimates of the tooth thickness and wear pattern. Functional information such as chewing pattern and articulation forces may also be integrated into the assessment. Wear patterns may be identified and shown as 'hotspots' for example on images generated from the 3D representation of the patient's teeth. This may be displayed to the patient as information, including as information warning of potential risks. High risk regions may be identified to the patient along with an explanation of the potential risk.

In general, the methods and apparatuses, and particularly the monitoring and comparison, over time, of 3D volumetric models including information about the internal structures of the teeth (e.g., enamel and dentin distribution within the teeth) may be used to identify, monitor, diagnose, and guide treatment of a variety of disorders in addition to those mentioned above. For example, dentin dysplasia, enamel dysplasia, etc. These methods also allow the identification of multiple different types of enamel within the patient's teeth, including regions having different amounts hydroxyapatite, amelogenins and/or enamelins, or differently organized regions of these, including regions that are homogenous or non-homogeneous, and that may have different optical properties for the near-IR wavelengths used for imaging.

Interactive Display of 3D Model of a Patient's Dental Arch

As already described (and shown in the figures above), the methods and apparatuses described herein may allow a user to virtually scan a patient's dental arch. In particular a 3D model of the patient's dental arch(s), which may be volumetric, surface, or both (or in some variations an abstracted or generic model), may be used in conjunction with images taken, e.g., using an intraoral scanner, from various positions around the dental arch. These images may be images that were used to generate the 3D model of the dental arch. The images may be tagged and/or arranged in the data structure to indicate their corresponding position or region or angle relative to the 3D dental arch model. In some variations, the 3D model and the images taken may be maintained as a data structure, however it is not necessary that the 3D model be included with the images as a single data structure.

Figure 42:
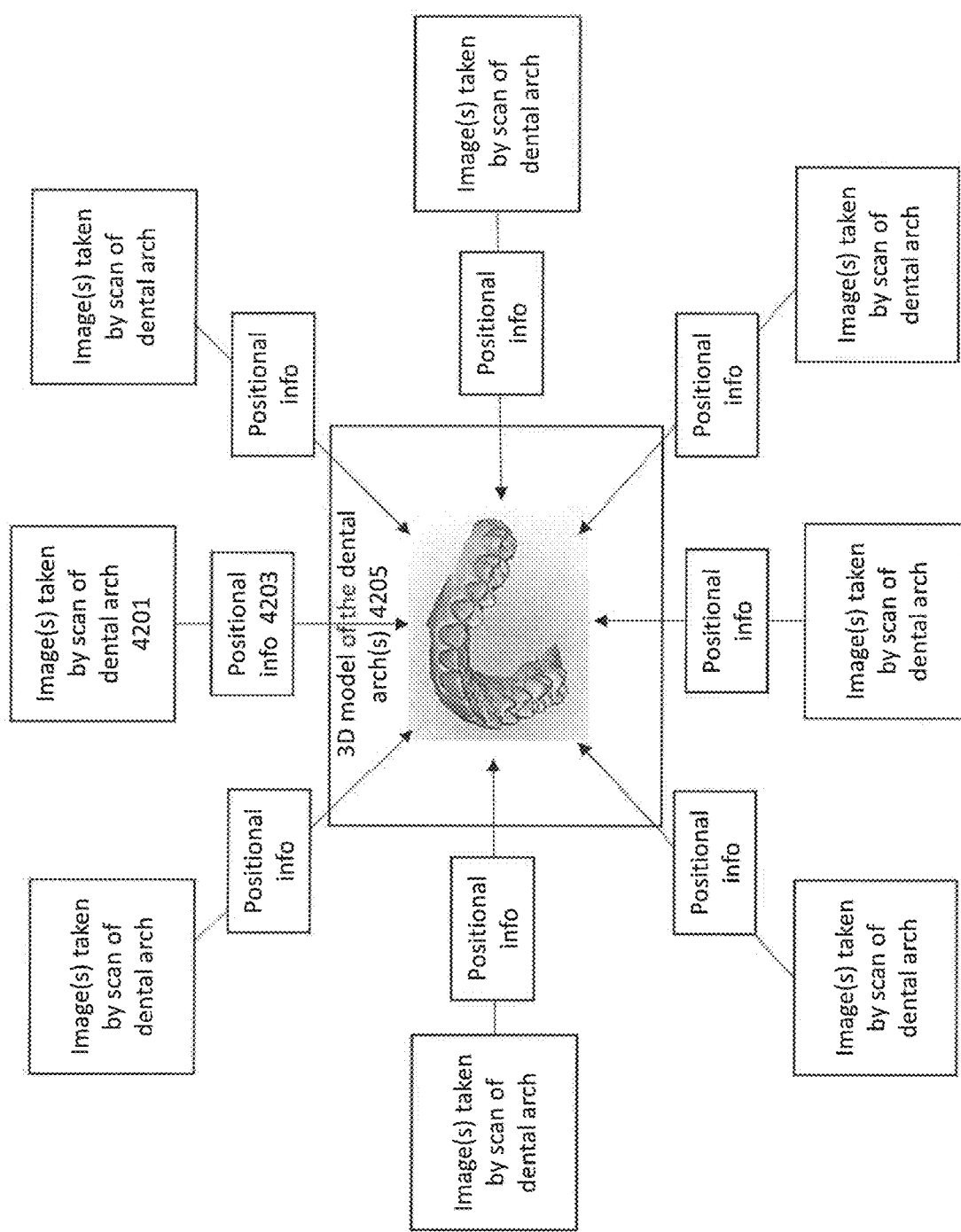
FIG. 42 is a schematic illustration of a data structure including a 3D model of a patient's dental arch(s) and associated 2D images taken (e.g., via intraoral scanner) of the dental arch at a large number of positions around the dental arch.

For example, FIG. 42 is an example of a data structure that includes one or more dental arch models 4205 as well as a plurality (e.g., greater than 50, greater than 100, greater than 200, greater than 500, greater than 750, greater than 1000, greater than 10,000, etc.) of one or more (e.g., sets) of images taken from positions around the patient's dental arch. In some variations both visible light and near-IR (or near-IR and other modalities) images 4201 may be shown and may share positional information. The positional information typically includes the region of the dental arch (e.g., in x, y, z coordinates, such as the coordinate of a center point of the image relative to the dental arch) from which the image was taken, as well as the angle (e.g., roll, pitch and/or yaw, or radial coordinates, etc.) relative to the plane of the dental arch ("positional info" 4201). In some variations the scans may be composites of multiple scans (e.g., averages, blends, etc.) that are combined and stored in the data structure. The 3D model may be formed by virtually "stitching" the scans together to form the 3D model.

The data structure may be stored in a compressed configuration; although it may contain a large amount of data, the compression and organization of the data structure may allow it to be manipulated for display. For example, FIG. 41 illustrates one method of interactively displaying a 3D model of a patient's dental arch using a data structure such as the one schematically shown in FIG. 42.

Figure 41:
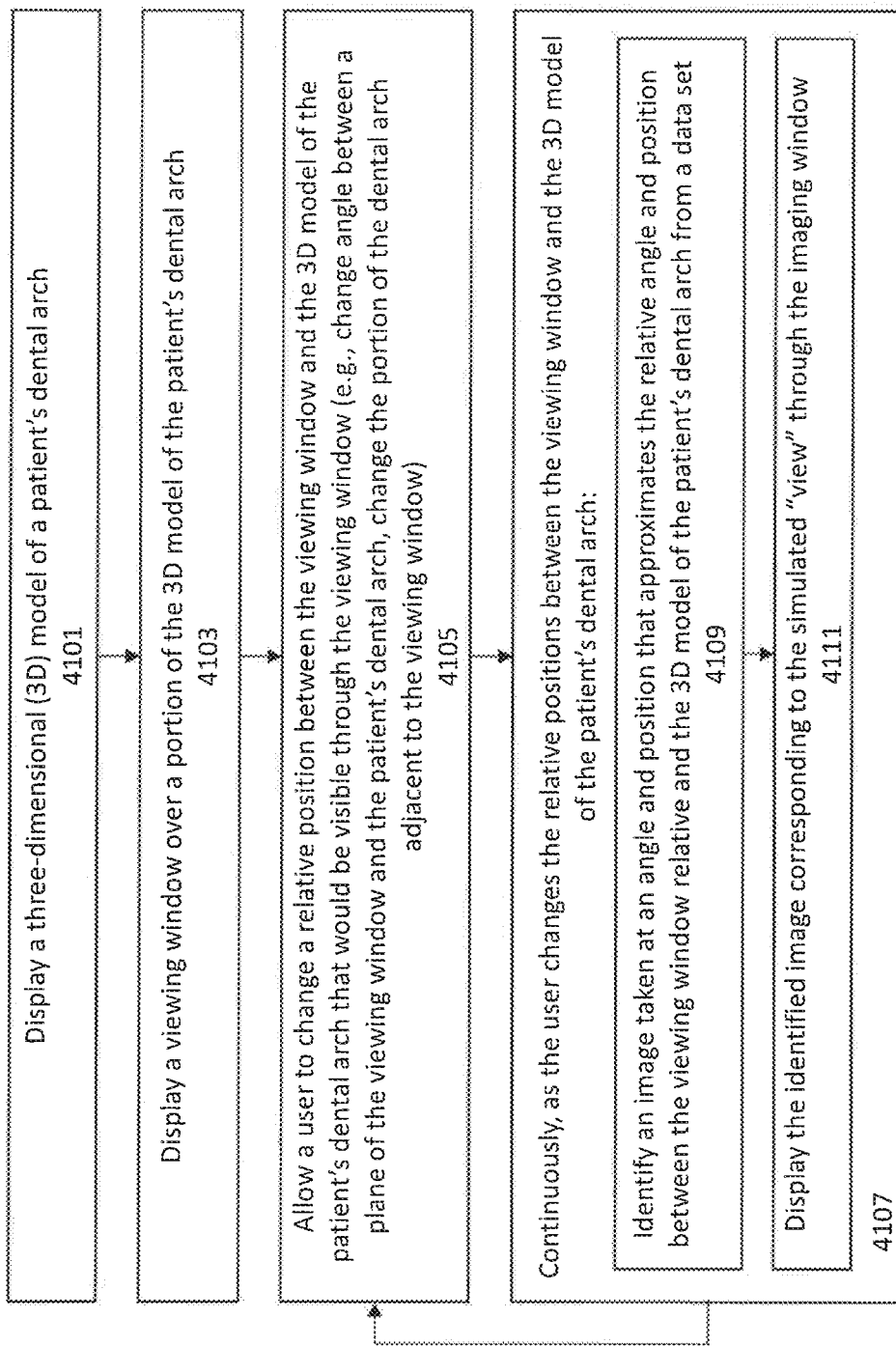
FIG. 41 is an example of a method for allowing a user to virtually scan a patient's dental arch. This method may be performed in real time or near real time.

In FIG. 41, the method includes displaying the 3D model of the patient's dental arch 4101 and displaying on the 3D model a viewing window 4103. The user may then be allowed to continuously move the two (e.g., either or both the viewing window and the 3D model) so that the teeth of the dental arch may be virtually viewed "though" the viewing window in greater detail in a nearby view 4105. The angle of the viewing window as well as the location of the viewing window along the dental arch may be changed by the user, e.g., moving continuously over and/or around the 3D model of the dental arch 4107. As the viewing window/dental arch are moved relative to each other, a corresponding image (or images), such as a near-IR image, taken at a position relative to the dental arch corresponding to the position of the viewing window, may be identified from the data structure/data set (e.g., FIG. 42) 4109. The corresponding image(s) may then be displayed 4111, and this process may be iteratively repeated as the viewing window is moved over and along the 3D dental arch model.

In some variations, the data structure may be configured or arranged topographically or in an indexed topographic manner; thus images of adjacent regions may be linked or ordered in the data structure, simplifying the method.

FIGS. 43A-45C illustrate examples of one variation of a user interface that may allow the user to virtually scan a 3D model of the dental arch, showing corresponding images (e.g., near-IR images) as described in FIG. 41. As mentioned above, the near-IR images may be viewed by the user to identify manually (or in some variations automatically) identify one or more structures/defects and/or actionable dental features, including dental caries, cracks, wear, etc. The display of corresponding 3D dental arch model and visible light images of the same regions may both give perspective and allow for immediate comparison with the patient's teeth, simplifying and powerfully augmenting dental analysis.

Figure 43A:
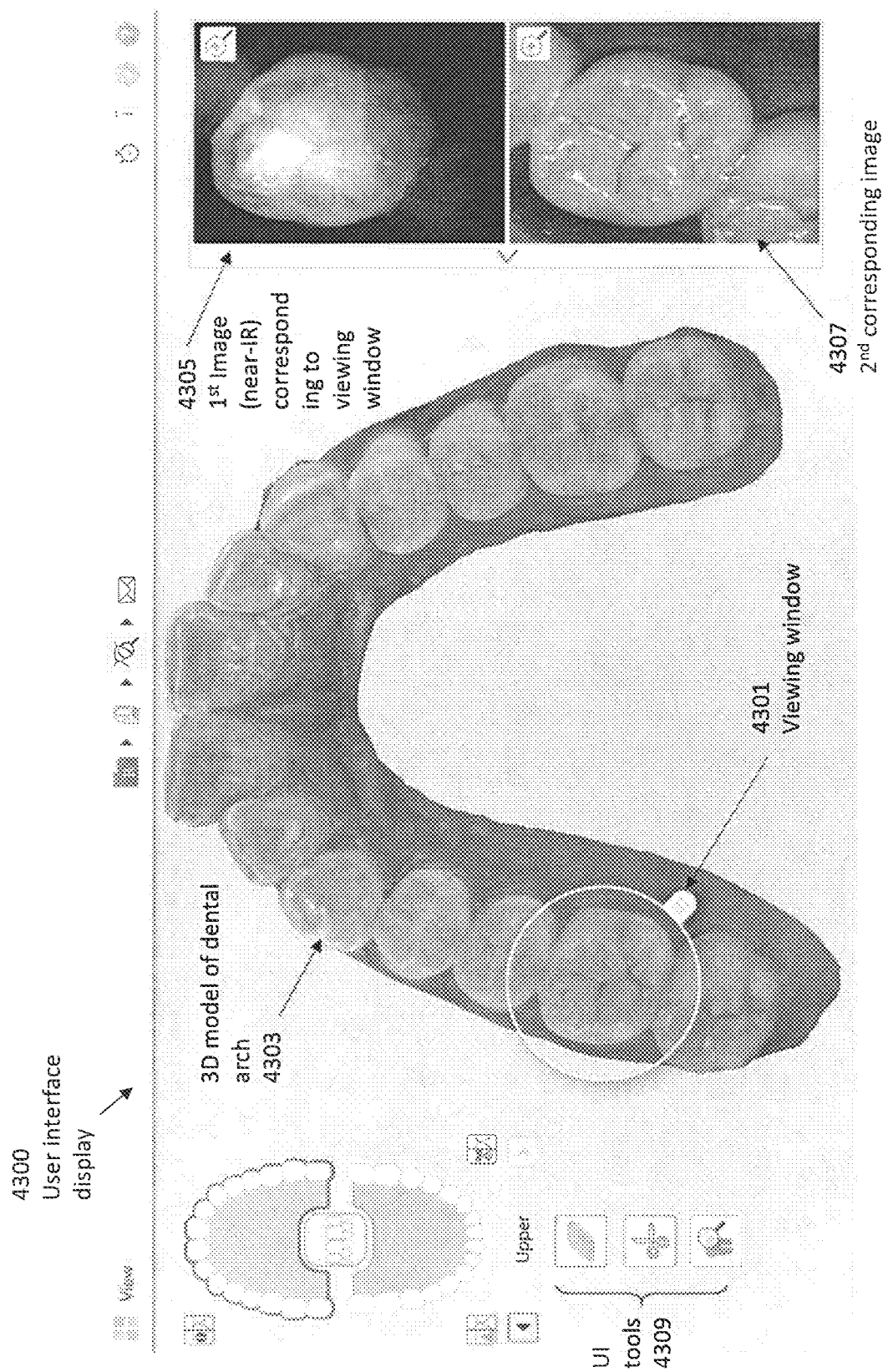
FIG. 43A is an example of a user interface allowing the user to virtually scan over the 3D model of the dental arch, showing corresponding light and near-IR (e.g., external and internal) regions in detail as the user scans over the 3D dental arch; the user may use one or more tools to move the dental arch (e.g., rotate, translate, etc.) and/or the viewing window; the corresponding light and near-IR images may continuously or near-continuously update as the position of the viewing window and dental arch change. A pair of imaging windows are shown adjacent to the view of the 3D model of the dental arch.

For example, in FIG. 43A, the display is shown as a user interface 4300 including a dental arch model 4303 (3D dental arch model) reconstructed form scans of the patient's teeth and stored, along with many or all of these scans, in a data structure. As already mentioned above, it is not necessary, but may be helpful, for the 3D dental arch model to be included in the data structure with the plurality of images. Further, the 3D dental arch model in this example is constructed from the scans of the patient's teeth, however, is should be clear that the 3D dental arch model may be non-representative, and yet may be used to select the 2D views to be displayed, as described herein. A viewing window 4301, shown as a loop or circle, may be moved over or along the 3D model of the dental arch; as the viewing window is moved, each of two image displays 4305, 4307 are updated with images corresponding to the position (both the region of the dental arch and the angle of the dental arch relative to the plane of the viewing window. In FIG. 43A the first (upper) image 4305 is a near-IR image and a corresponding (taken at the same approximate time/location) visible light (e.g., color) image is shown in the bottom image 4307. Alternatively displays are shown in FIGS. 43B and 43C, showing just a single image each; in FIG. 43B an enlarged near-IR display image is shown, while in FIG. 43C a single, enlarged visible light display image of the region corresponding to the imaging window view is shown.

The user interface may also include tools 4309 for manipulating the display (e.g., rotating, moving the dental arch and/or viewing window, modifying, marking, etc., the images and/or 3D model, saving, opening/recalling images, etc.

Figure 44A:
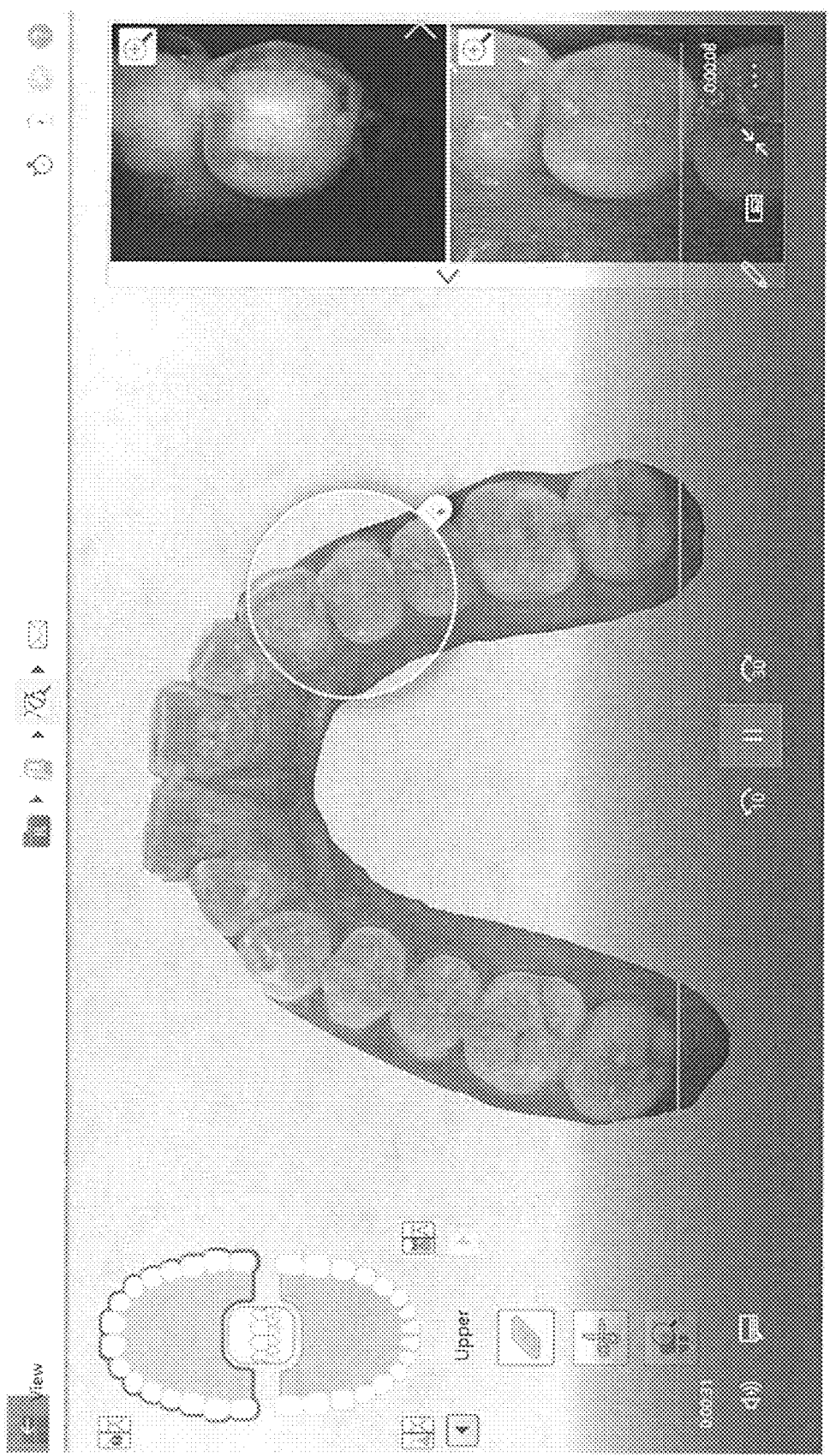
FIG. 44A is similar to FIG. 43A, showing an example of a 3D model of the outer surface of a dental arch, and a viewing window relative to the dental arch. A pair of image display windows are adjacent to the 3D model of the dental arch. The user may move the viewing window over the dental arch (and/or may move the dental arch relative to the viewing window, changing the image(s) shown in the two display windows. The upper display window shows a near-IR image corresponding to the dental arch at the position and angle of the plane of the viewing window; the bottom display window shows a corresponding light image (which may be in color).
Figure 44B:
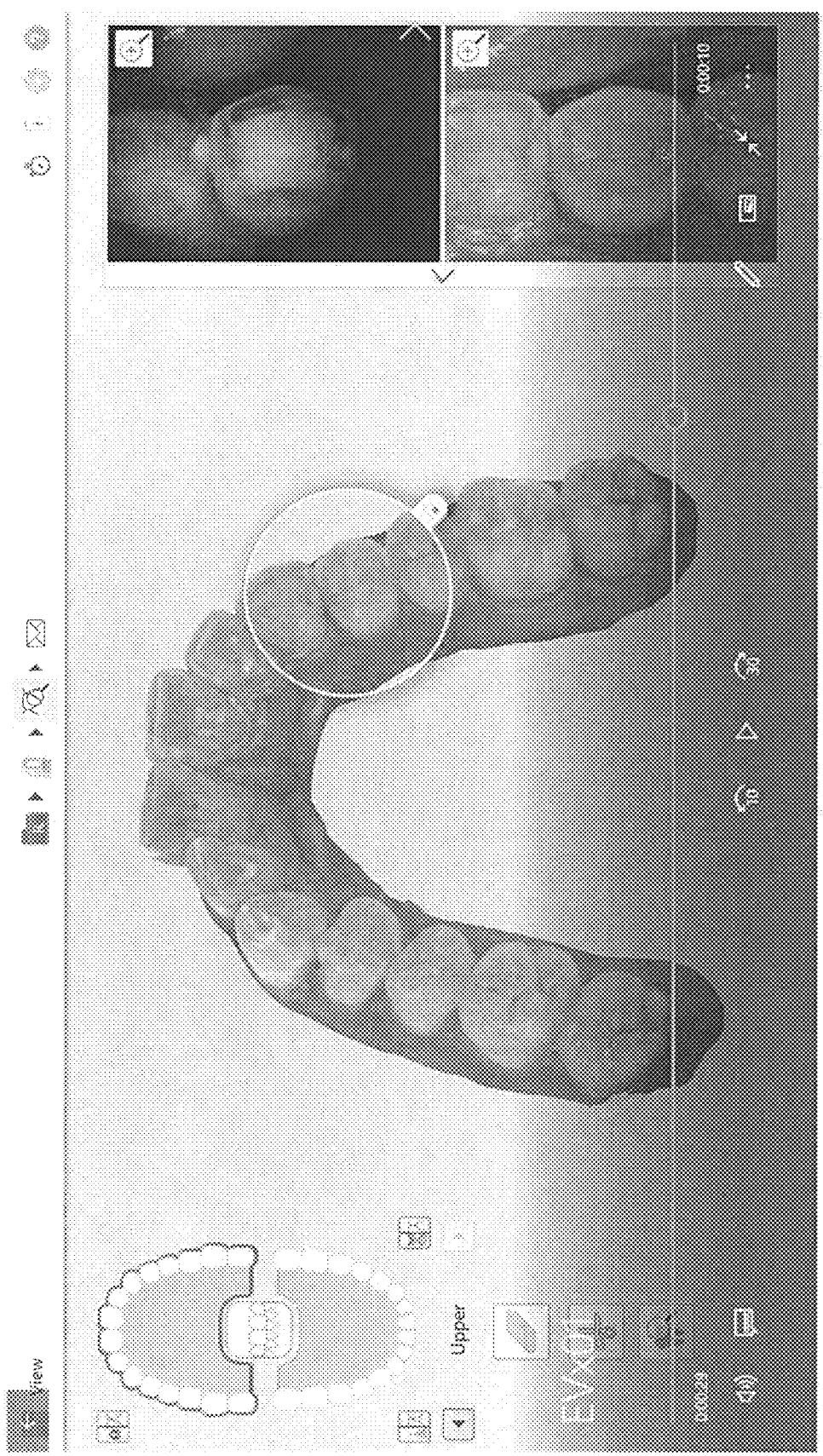
FIG. 44B shows another image of the dental arch shown in FIG. 44A, with the dental arch rotated lingually relative to the viewing window; the corresponding near-IR images (upper right) and visible light (lower right) adjacent to the 3D model of the arch are updated to show the slightly rotated view, allowing the user to virtually scan the dental arch and show both external and internal views in real (or near-real) time.

FIGS. 44A-44B illustrate an example of moving the viewing window over the teeth and changing/updating the corresponding images. FIG. 44A shows the image of the dental arch with corresponding near-IR and light images as "seen" through the viewing window at a middle region of the dental arch. In FIG. 44B the dental arch has been rotated by the user (or alternatively, the viewing window has been rotated relative to the dental arch lingually) so that the viewing window is slightly lingually positioned relative to FIG. 44A; the corresponding views (near IR and visible light) have been updated in real time to show this change of the relative position of the viewing window.

Figure 43B:
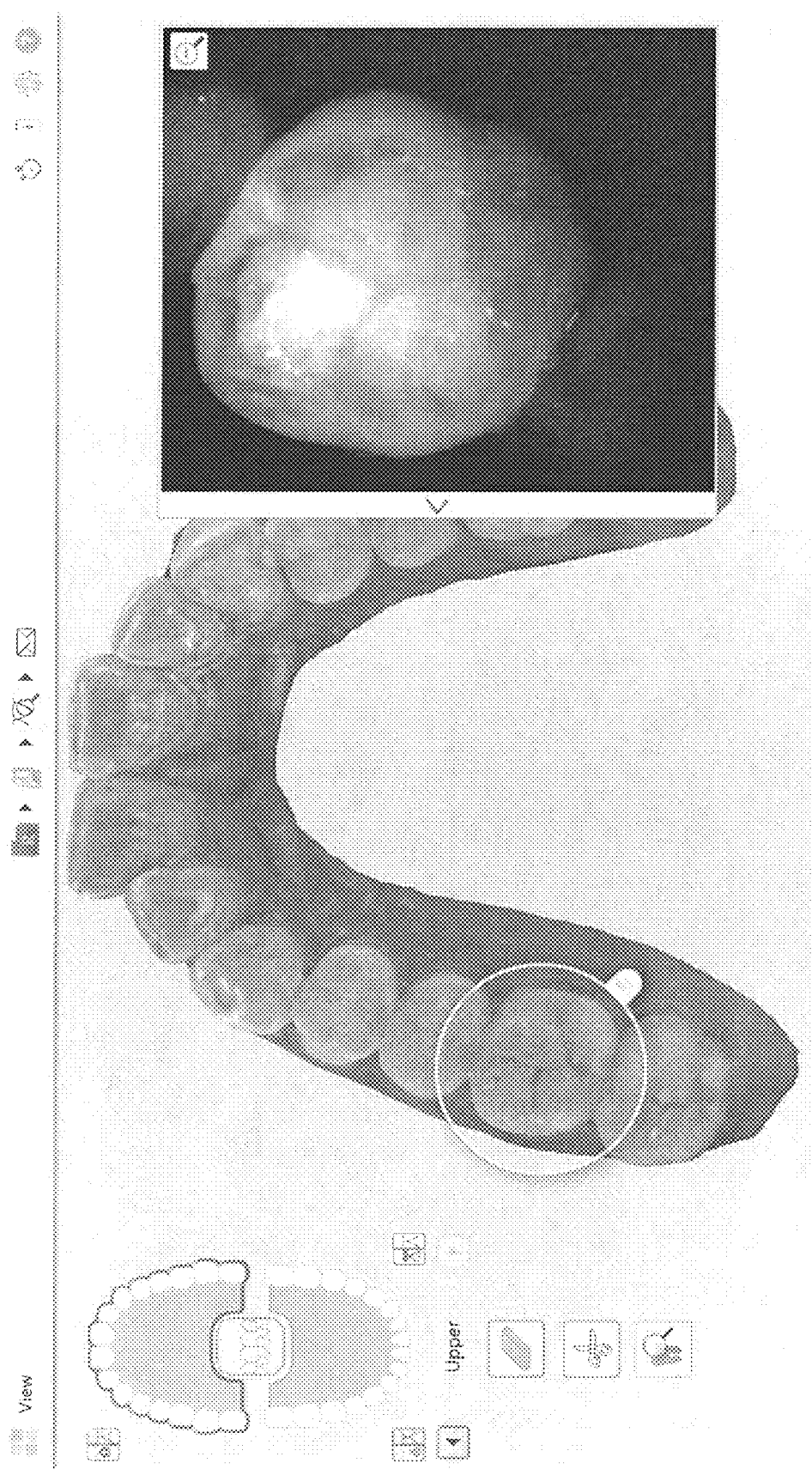
FIG. 43B is an alternative display showing a single large image window over or adjacent to the 3D image of the dental arch.
Figure 43C:
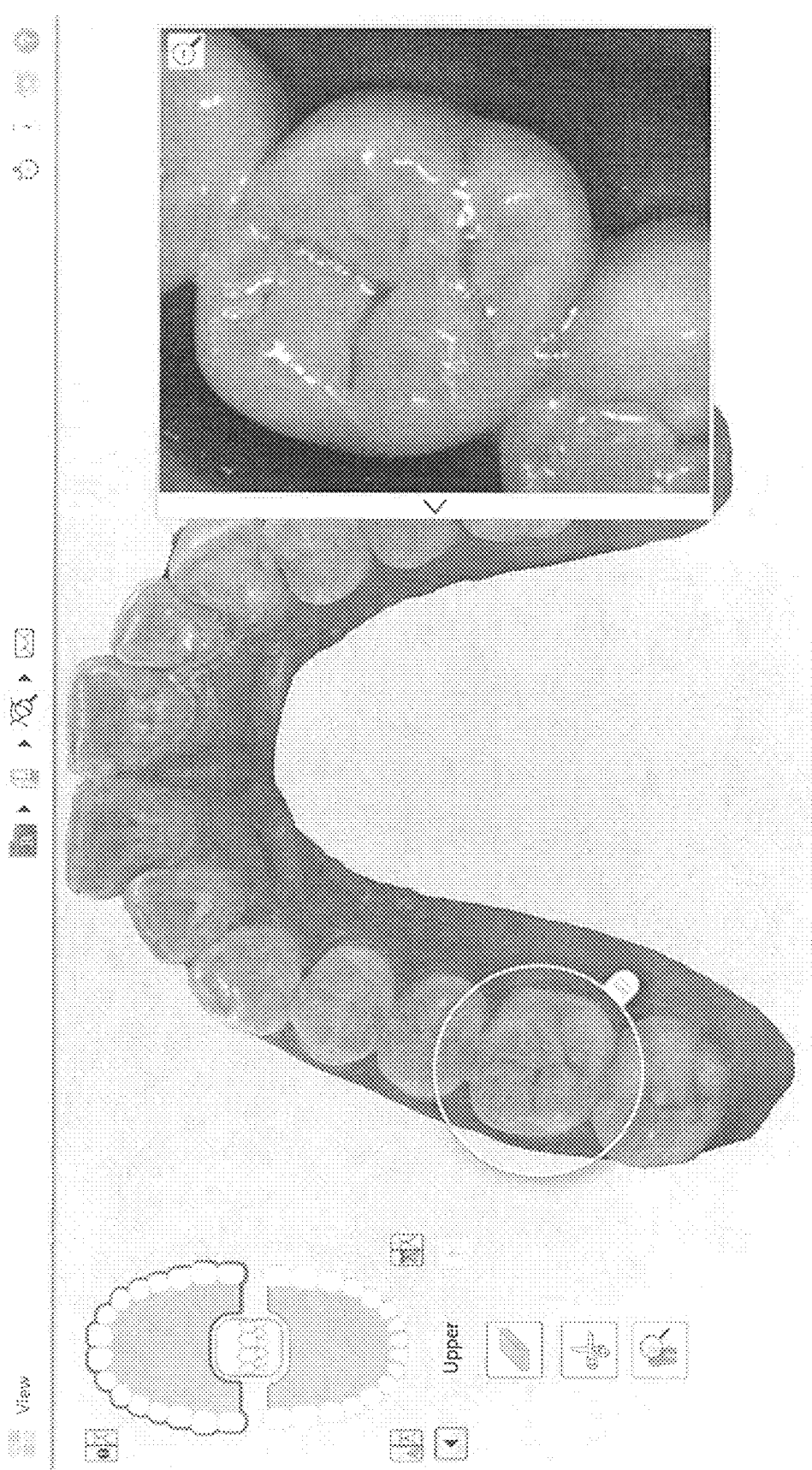
FIG. 43C is an alternative display showing a single large image window over or adjacent to the 3D image of the dental arch.
Figure 45A:
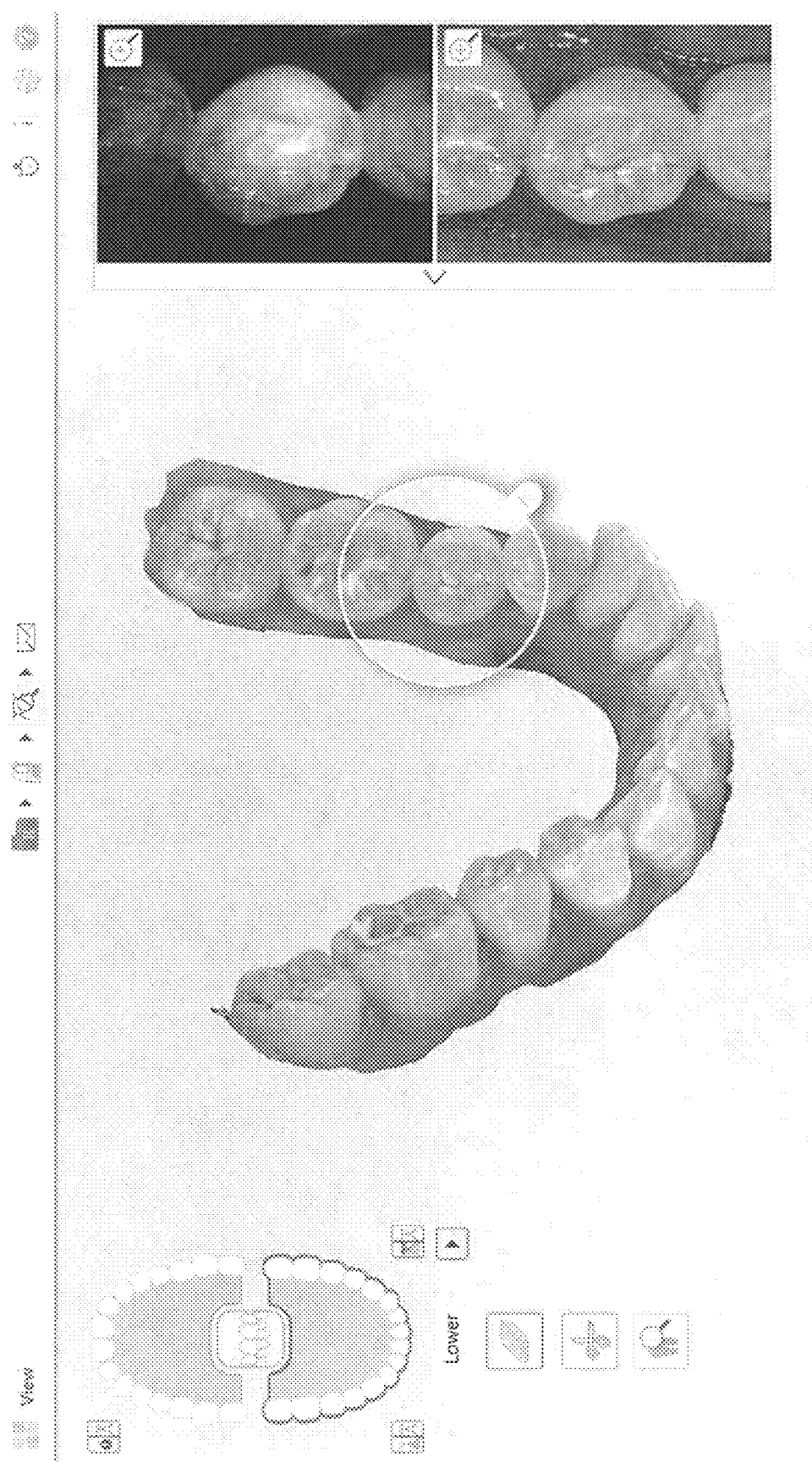
FIG. 45A is another example of a method of showing a 3D model of a dental arch (shown as the lower arch in this example, e.g., by selecting the lower arch display control in the upper left of the user interface) and showing focused views of near-IR and visible light images corresponding to the viewing window region that may be moved over/across, and around (lingual-occlusal-buccal) the model of the patient's arch.
Figure 45B:
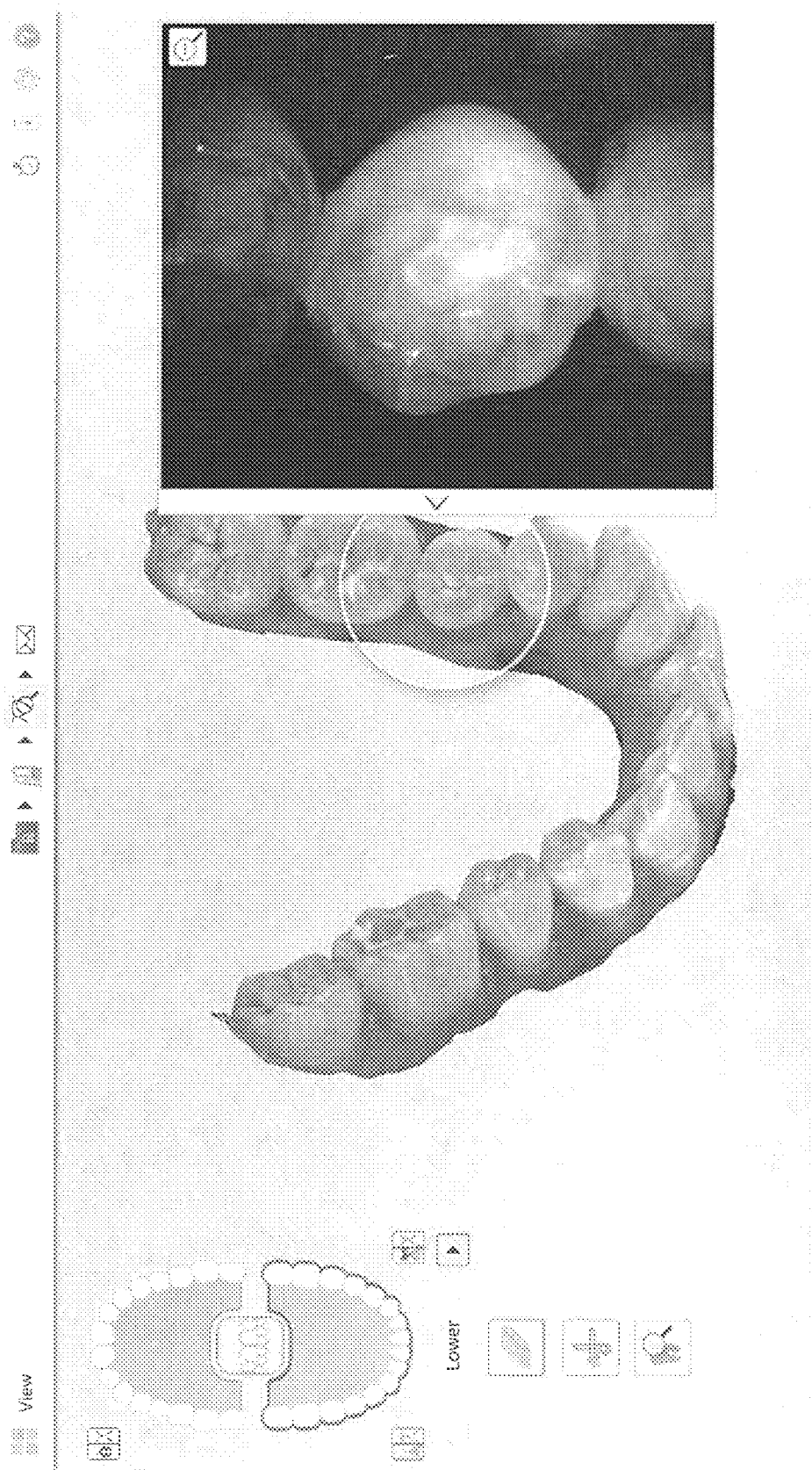
FIG. 45B shows an example of a single window (an enlarged near-IR view into the teeth of the region corresponding to the viewing window loop) similar to FIG. 45A.
Figure 45C:
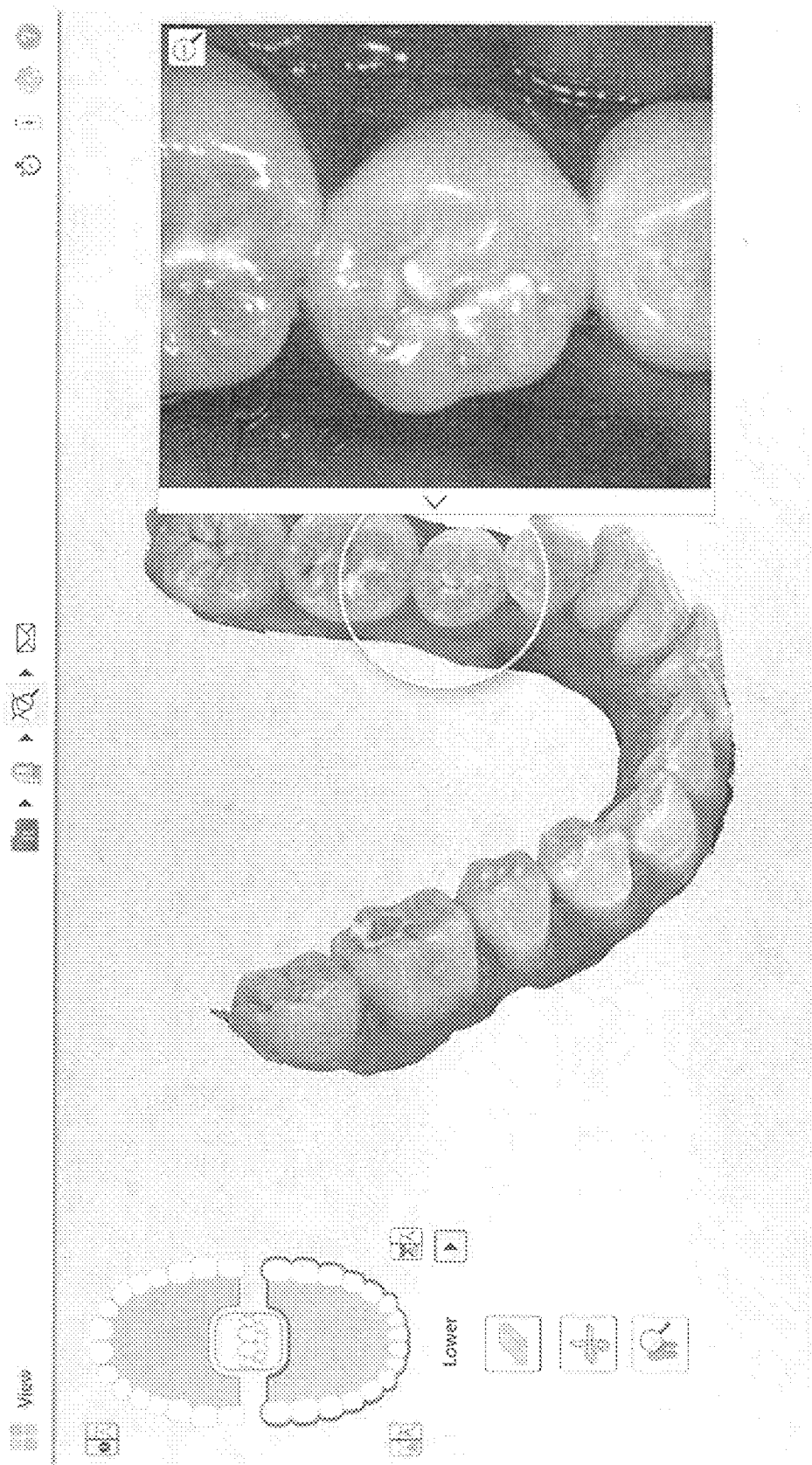
FIG. 45C shows an example of a single window (an enlarged visible light view into the teeth of the region corresponding to the viewing window loop) similar to FIG. 45A.

Similarly, FIGS. 45A-45C shows an example of a 3D model of a patient's lower arch similar to the view shown in FIG. 43A-43C. In use, as the user scans over and along the dental arch by moving the viewing window (and/or the dental arch relative to the viewing window), the display images may change virtually continuously, so that they may update in real or near-real time. The user may identify features in the near-IR image(s), including densities changes in the region of normally IR-transparent enamel, which may indicate carries, cracks, or wearing in the enamel.

The intraoral scanning system shown in FIGS. 1A-1B may be configured as an intraoral scanning system. Returning to FIG. 1A, the intraoral scanning system 101 includes a hand-held wand 103 having at least one image sensor and a light source configured to emit light at a spectral range within near-infrared (near-IR) range of wavelengths, and a display output (screen 102). The screen may be a touch-screen acting as a user input device, or the system may include a separate user input device (e.g., keyboard, touch-pad, joystick, mouse, track ball, etc.). As indicated in FIG. 1B, the system may also include one or more processors that are operably connected to the hand-held wand, display and user input device. The one or more processors may include circuitry and/or software and/or firmware configured to: display a three-dimensional (3D) model of a patient's dental arch on the display output; display a viewing window over a portion of the 3D model of the patient's dental arch on the display output; change a relative position between the viewing window and the 3D model of the patient's dental arch based on input from the user input device; identify, from both the 3D model of the patient's dental arch and a plurality of images of the patient's dental arch taken from different angles and positions relative to the patient's dental arch, a near-infrared (near-IR) image taken at an angle and position that approximates a relative angle and position between the viewing window relative and the 3D model of the patient's dental arch; and display the identified near-IR image taken at the angle and position that approximates the angle and position between the viewing window relative to the 3D model of the patient's dental arch (as shown in FIGS. 43A-45C).

Automatic Characterization of Dental Features

Also described herein are methods and apparatuses (e.g., systems, including software) that is configured to use the 3D models, including but not limited to the volumetric 3D models, of all or a portion of a patient's dental arch to automatically or semi-automatically identify, confirm and/or characterize one or more dental feature. In particular, these methods and apparatuses may be configured to identify, confirm, and/or characterize one or more actionable dental features that may benefit from detection and/or treatment. Actionable dental features may include, but are not limited to cracks, gum recess, tartar, hard tissue and soft tissue oral conditions, etc. Enamel thickness may be another actionable dental feature. For example, the methods and apparatuses described herein may automatically map enamel thickness (e.g., apply color map where enamel is lower than x microns thick, where x may be preset and/or user adjustable). Areas of thin enamel are potential areas where caries may exist. Other potential actionable dental features may include discoloration (e.g., discontinuities in color), pits, fissures, evidence of grinding (thinning, including thinning over time), interproximal voids, etc., or any other similar feature that may be indicate or suggestive of where caries are likely to form.

Any of the methods and apparatuses described herein may use multiple different images or sets of images of the patient's teeth taken with different imaging modalities are used to detect, analyze and/or characterize dental features, and particularly actionable dental features. The multiple different images or sets of images of the patient's teeth taken with different imaging modalities may each be referred to as a "record". Each record may be a different imaging modality, such as dental cone beam computed tomography (CBCT) scanning, three-dimensional (3D) intra-oral scanning, color scanning (one or more of: 3D color scanning, surface color scanning, etc.), two-dimensional (2D) color scanning, near-IR scanning (including, but not limited to one or more of: volumetric near-IR imaging, trans illumination and/or reflective scanning), X-ray (including, but not limited to: cephalometric analysis x-ray scanning, panoramic x-ray scanning, etc.), etc., and may include text or graphic chart information of the patient.

For example, each record may initially be processed independently. One or more dental features, and in particular, one or more actionable dental features, may be identified by this initial scan. A single record (e.g., a single imaging modality) may be used first to identify the one or more actionable dental features, or all of the records, or a subset of the records may be initially processed to identify the one or more actionable dental features. The initial identification of the one or more actionable dental features may be performed manually or automatically or semi-manually. For example, one or more actionable dental features may be identified automatically; a system as described herein may review the record (including the one or more images of the patient's teeth) to flag or identify regions having a characteristic associated with an actionable dental feature. A system may be trained, using machine learning techniques such as supervised learning techniques (e.g., classification, regression, similarity, etc.), unsupervised learning techniques (e.g., density estimation, cluster analysis, etc.), reinforcement learning (e.g., Markov Decision Process techniques, etc.), representation learning techniques and/or principle component analysis, etc., to identify/flag a region of a particular scan in a specified modality that is associated (even loosely associated with) an actionable dental characteristic. Alternatively or additionally, a user (dental professional, technician, etc.) may manually review one or more records (each in a particular imaging modality) and may flag or identify regions suspected to show an actionable dental characteristic. In a semi-automated configuration the system may initially flag one or more regions from a record that the user may then review and confirm/reject.

As the one or more regions are identified, they may be flagged and/or stored in a collection of potential actionable dental features. The location may be relative to (e.g., the location on) the originating record, or relative to a reference model (such as the 3D volumetric model, as will be described in greater detail below). In some variations the collection (e.g., array, data structure, file, etc.) may also include one or more of the type of potential actionable dental features, the extent of the potential actionable dental features, a grade and/or degree of the potential actionable dental features, the originating record and/or the imaging modality of the originating record, etc. In some variations the data structure may be integrated into the originating record (or a copy thereof) and may modify the image(s) of the originating record, e.g., by include a flag or marker at the location of the identified potential actionable dental features and/or any meta text such as the grade and/or degree, etc. The grade and/or degree may refer to the confidence level or score for the potential actionable dental feature, including the confidence level or score that the identified potential actionable dental features is likely 'real'.

This initial identification process to identify potential actionable dental features may be performed across multiple records, or it may be limited to a subset of the records (e.g., including just to one of the records), as mentioned above. In some variations the process may be iteratively performed.

Once one or more potential actionable dental features is identified, it may be cross-referenced to the other one or more records that use(s) other imaging modalities. Thus, the locations of the one or more potential actionable dental features may be examined in particular detail to determine if the same potential actionable dental feature is apparent on these one or more other record. In some variations the entire additional record(s) may be examined during this confirmation portion of the procedure, and any additional potential actionable dental features from the additional one or more records may be likewise flagged as a potential actionable dental feature and the same region of the dental arch may be examined for these other potential actionable dental features (including returning back to records that have already been reviewed, such as the first or originating record).

Comparison across other records may be guided by translating the locations of the dental features (including but not limited to the potential actionable dental features) between the different records. In particular, it may be helpful to coordinate the individual dental record(s) begin examined to a model of the patient's dental arch, such as any of the 3D models, and in particular, the 3D volumetric models, described above. The 3D model of the dental arch may therefore act as a key to translate the locations of the one or more potential actionable dental features and may allow rapid and efficient comparisons between the different records, e.g., different imaging modalities.

Thus, a correlation between each of the different records and, in particular, a correlation between all or some of the different records and a 3D model (e.g., a 3D volumetric model) of the dental arch may be established either before or after the initial scan for potential actionable dental features. Any method of correlating a records and other records and/or a 3D model of the patient's dental arch (or a portion of the dental arch) may be used. For example, one or more easily recognizable features (e.g., tooth edge, shape, segmentation, etc.) may be used to determine landmarks that may translate between the one or more records and/or the one or more records and the 3D model of the patient's dental arch. In some variations a translational dataset may be created that includes a transformation between the records and/or between each record and a 3D volumetric model of the patient's dental arch. For example, a 3D volumetric model of all or a portion of the dental arch may include transformation information for each of the one or more records allowing transformation of the image(s) of the one or more records, such as an estimate of the distance and/or orientation of the imaging modality relative to the record image(s). This allows both forward and reverse translation of position between each record and the 3D model (e.g. volumetric model).

Thus, a translational dataset may include a 3D model and the translational information of each record, so that a portion or region of a record image (or images) may be projected onto the 3D (translational) model, and the same region then back projected onto a second (or more) record taken with another imaging modality so that the same region may be examined. In some variations the process may begin with the collection of all the records and/or an automatic, manual or semi-automatic registration between all the records. For example, the identification of individual teeth, palate, gingiva, etc. regions, may be used to cross-correlate between the different imaging modalities and/or the 3D model. In one example, a record including x-ray images may be correlated with a 3D volumetric model of the patient's teeth by solving (manually or automatically) for the position and/or orientation of the x-ray camera taking the x-ray images corresponding to the record. The volumetric model may be used to determine and/or confirm the location and/or orientation of imaging source for each record. In some variations the record include explicit (e.g., recorded) information about the position and/or orientation and/or imaging parameters used to take the image(s); alternatively or additionally, this information may be derived. As described above one a pseudo-x-ray image may be generated and compared to an actual x-ray image of the record.

Once a region corresponding to the region of the potential actionable dental feature from another record is identified, the system or method may then determine if the same potential actionable dental features is present in this other record. If present, the score (e.g. confidence score, showing the likelihood that the potential actionable dental features is real) may be adjusted, e.g., increased if the same or a similar potential actionable dental feature is present. Depending on the type of record and the type of potential actionable dental features, the absence of a potential actionable dental features may result in adjusting the confidence score. For example, the absence of surface features that are not typically detectable by X-rays, such as discoloration, plaque, gum recession, etc., may not result in lowering the confidence score of the one or more potential actionable dental features. The more occurrences of finding a potential actionable dental features a corresponding location between different records (therefore in different modalities), the more likely that the potential actionable dental features really exists.

In comparing the corresponding locations of the one or more potential actionable dental features the region may be examined manually, automatically or semi-automatically, similar to the original identification techniques discussed above. For example, a region of an additional record corresponding to the location of a potential actionable dental feature in another record may be examined automatically to identify features correlated with the type of potential actionable dental feature. The system may be trained to recognize the potential actionable dental feature in the imaging modality of the additional record and may provide a score indicating the likelihood that the potential actionable dental feature is present in this location. In some variations a user (e.g., technician, dental professional, etc.) may be presented with an image from the additional record(s) and may manually indicate the likelihood (yes/no, graded scale, numeric scale, etc.) that the potential actionable dental feature is present in the one or more additional records.

The final confidence value determined for each potential actionable dental feature may be used by the system: stored, transmitted and/or displayed. For example the potential actionable dental feature(s) may be presented to a dental practitioner in any appropriate manner, including in a list, on a display, such as on 3D model of the dental arch (including the translational 3D dental model) marked, etc. For example, the system may output a display highlights by color, shape, etc. the location of any or all of the potential actionable dental features that are above a threshold confidence level (so likely to be 'real'); the display may also include one or more views (from the one or more records) of the potential actionable dental feature. The user may set of adjust the threshold confidence level, including on the fly (e.g., making the threshold more or less stringent and showing the addition or removal of potential actionable dental features in response.

FIG. 46 illustrates one example of a method 4600 for characterizing dental features across different imaging modalities as just discussed. In FIG. 46, the method (or a system configured to perform it) may identify one or more actionable dental features from one or more records (e.g., one or more images or sets of images of the patient's teeth taken with different imaging modalities) 4601. For example, the one or more actionable dental features may be identified by an agent or engine that is configured to automatically detect one or more actionable dental features. For example, a system performing the method of FIG. 46 may include an actionable dental feature analysis engine, or may include multiple actionable dental feature analysis engines each configured to identify one or more types of actionable dental features or one or more types of imaging modality. The engine (e.g., an actionable dental feature analysis engine) may be part of a computer system. As used herein, an engine includes one or more processors or a portion thereof. A portion of one or more processors can include some portion of hardware less than all of the hardware comprising any given one or more processors, such as a subset of registers, the portion of the processor dedicated to one or more threads of a multi-threaded processor, a time slice during which the processor is wholly or partially dedicated to carrying out part of the engine's functionality, or the like. As such, a first engine and a second engine can have one or more dedicated processors or a first engine and a second engine can share one or more processors with one another or other engines. Depending upon implementation-specific or other considerations, an engine can be centralized or its functionality distributed. An engine can include hardware, firmware, or software embodied in a computer-readable medium for execution by the processor. The processor transforms data into new data using implemented data structures and methods, such as is described with reference to the figures herein.

The engines described herein, or the engines through which the systems and devices described herein can be implemented, can be cloud-based engines. As used herein, a cloud-based engine is an engine that can run applications and/or functionalities using a cloud-based computing system. All or portions of the applications and/or functionalities can be distributed across multiple computing devices, and need not be restricted to only one computing device. In some embodiments, the cloud-based engines can execute functionalities and/or modules that end users access through a web browser or container application without having the functionalities and/or modules installed locally on the end-users' computing devices.

Returning to FIG. 46, the one or more actionable dental features may be identified from one or more records manually or semi-manually. For example, an actionable dental feature analysis engine may initially identify one or more actionable dental features that may then be verified or vetted by a user (e.g., dental technician).

Each actionable dental feature identified may then be flagged and/or recorded, e.g., in a collection of potential actionable dental features 4603. For example a collection of potential actionable dental features may be part of a data structure. Adding the potential actionable dental feature(s) to a collection (e.g., data structure) may include recording a location of the actionable dental feature (e.g., on the originating record) and/or one or more of: type of actionable dental features, grade/degree of confidence of the actionable dental feature, etc. As used herein, a data structure (which may be included as part of a datastore) is intended to include repositories having any applicable organization of data, including tables, comma-separated values (CSV) files, traditional databases (e.g., SQL), or other applicable known or convenient organizational formats. Datastores can be implemented, for example, as software embodied in a physical computer-readable medium on a specific-purpose machine, in firmware, in hardware, in a combination thereof, or in an applicable known or convenient device or system. Datastore-associated components, such as database interfaces, can be considered "part of" a datastore, part of some other system component, or a combination thereof, though the physical location and other characteristics of datastore-associated components is not critical for an understanding of the techniques described herein.

A data structure may be associated with a particular way of storing and organizing data in a computer so that it can be used efficiently within a given context. Data structures are generally based on the ability of a computer to fetch and store data at any place in its memory, specified by an address, a bit string that can be itself stored in memory and manipulated by the program. Thus, some data structures are based on computing the addresses of data items with arithmetic operations; while other data structures are based on storing addresses of data items within the structure itself. Many data structures use both principles, sometimes combined in non-trivial ways. The implementation of a data structure usually entails writing a set of procedures that create and manipulate instances of that structure. The datastores, described herein, can be cloud-based datastores. A cloud-based datastore is a datastore that is compatible with cloud-based computing systems and engines.

The identified "putative" actionable dental features (e.g., "potential actionable dental features") may be mapped to corresponding physical locations in one or more other records 4605. As discussed above, in some variations this may be done using the 3D volumetric model, which may translate between the various different types of records (having different imaging modalities), including projecting a first record onto the 3D model and then back onto a second region.

Thus, the same corresponding regions in other records may be reviewed to determine if the potential actionable dental feature is present or suggested in the additional record(s). In some variations, the method may simply collect all of the different corresponding regions for storage, transmission and/or presentation to a user (e.g., dental professional), e.g., optionally stopping here and allowing the user to review these flagged region from multiple different imaging modalities (records) in parallel. For example, the potential actionable dental feature may be shown for all corresponding views in a side-by-side (e.g., tiled) or sequential view(s).

Alternatively or additionally, the method and/or system may automatically or semi-automatically adjust a confidence score for each of the potential actionable dental features identified. Thus, the system may determine if the additional records indicate that the potential actionable dental feature is more likely to be present or less likely to be present and may adjust (or determine) the confidence score for each of the potential actionable dental features, based on the appearance at the corresponding location in the additional record(s) 4607.

The adjusted confidence levels may then be used to narrow down the potential actionable dental features. For example, the method or system may then filter and/or apply a threshold based on the adjusted confidence level for each potential actionable dental feature 4609. In some variation the threshold may be fixed (e.g., confidence level of greater than x, where x is a numeric value intermediate between zero confidence and 1 (absolute confidence), e.g., 0.1, 0.2, 0.3, 0.4, 0.5, 0.6, 0.7, 0.8, etc. In some variations the threshold value may be manually adjusted by the user and/or may be based on one or more features of the records, such as a quality metric specific to each of the records, etc.

Potential actionable dental feature having a confidence level that is above the threshold value may then be stored, presented and/or transmitted 4611. For example a user may be presented with a final list and/or display (e.g., using the 3D model) including the flagged potential actionable dental features.

Any of the methods and apparatuses (e.g., systems) described herein may be configured to build a data structure including all or part of the multiple records. For example, a data structure may include a 3D volumetric model and all or some of the associated 2D images that were used to construct it, as described above. In addition, the data structure may include additional records, such as images taken by X-ray (e.g., panoramic), and/or CBCT, etc. Metadata, e.g., information, including textual information, about the patient and/or images may also be included, including optionally patient chart information from the patient's health/dental records. Alternatively or additionally, any identified potential actionable dental features (e.g., findings identified from the records) may also be included. The potential actionable dental features may be used to search/find/mark on the other records.

Typically, when compiling the images (e.g., 2D near-IR images) to build the 3D (e.g., volumetric) model, the 2D images that provided information may be marked to indicate the significance to the 3D model. For example, 2D images may be marked as less relevant or more relevant.

As mentioned above, the collection of potential actionable dental features, including their confidence level based on their presence in multiple records may be included as part of the same data structure including the 3D model, or it may be separate. The 3D model may be directly marked (flagged, coded, etc.) to include the potential actionable dental features. Thus, the data structure may be a compilation of all of the different records. The combined/compiled data structure may be referred to as a marked data structure or an actionable dental feature data structure.

Any of the records, including the near-IR 2D images, may be used/scanned to identify the potential actionable dental features. As described above when a suspicious area is identified, either automatically, semi-automatically/semi-manually, or manually (e.g., by a user), in one of the records, the method or system may then search the corresponding area of the dental arch on all or some of the other records and conclude if there is a finding. In some variations, the method or apparatus may update the images on all or some of the records (and/or in the combined data structure) based on the analysis described herein.

In any of the methods and systems described herein, tooth segmentation may be used on all or some of the records and/or the 3D model to enhance performance and usability. Tooth segmentation may be added prior to volumetric modeling to assist and improve volumetric results and model quality. For example, the volumetric 3D model may uses the information of segmentation to potentially enhance performance as additional surface 3D information is added. The segmentation information may also assist in segmenting enamel-dentin-lesions to improve auto detection and suspicious areas marking (e.g., including but not limited to when using an automatic agent to identify potential actionable dental features). Alternatively or additionally, tooth segmentation may be added to the volumetric modeling post-processing to assist in segmenting enamel-dentin-lesions to improve auto detection and suspicious areas marking. For example, segmentation may also or alternatively help with correlating the structures between different imaging modalities, including registering findings on volumetric with other modalities to provide cross-modality visualization. Tooth segmentation may be used to improve records and cross-modality visualization of clinical findings and annotations In any of the methods and apparatuses described herein the confidence level indicated may be a quantitative and/or qualitative index. For example, a quantitative confidence level "score" may be provided (e.g., using a number between, for example, 0-100, 0 to 1.0, −100 to 100, or scaled to any range of numeric values). Qualitative indexes may include "high, medium high, medium, medium low, low", etc. Both qualitative and quantitative confidence levels may be used. A rating system for the confidence level based on the multiple records as described herein may be impactful for insurance claims and/or patient communication.

In any of the methods and system described herein, the morphology of the dental arch may be used to help identify the likely areas of interest or potential issues. Thus, in general, the 3D model (volumetric model) may be used and/or modified as described herein in order to include the regions of potential actionable dental features. A modified 3D model may act as a map that visually indicates areas of areas for risk assessment; this may be used, for example, to guide treatment of the patient, including to promote use of sealants, orthodontic treatment or night guards, etc. In some variations, the modified 3D model may be used to guide a user when additional scans are needed (e.g., when there is a low number of scans in the risk areas). As used herein, a modified 3D model may include a 3D (e.g., volumetric and/or surface) model that has been marked to indicate the locations and/or type and/or confidence level of potential actionable dental features. Thus, in general, the use of additional data sources to guide users to capture potential areas of interest (e.g., when they appear in records, and particularly in records other than near-IR/NIRI scan) may help confirm findings of potential actionable dental features. As mentioned, the results, including a modified 3D model, may help guide the user in scanning or re-scanning (at a future time) the user's dentition. For example, historical scans can be used as a targeting map while scanning (and to confirm adequate coverage in those areas). One or more derived images/presentations may be used in addition or alternatively. For example, tooth segmentation may be used to generate a tooth chart map (e.g., from the 3D volumetric model) that can be used for follow up and auto import into dental practice management software (DPMS). For example, individual records may be lined to match a specified problem to a tooth map.

As described above, an intraoral scanning system may include a hand-held wand configured to operate with one or more sensors to detect infrared and visible light, a sleeve configure to be placed over a distal end of the hand-held wand having a transparent window at a distal end region, and one or more processors operably connected to the hand-held wand, the one or more processors configured to: receive visible light information and infrared information from the one or more sensors; determine, in real time, surface information from the visible light information and generate a three-dimensional (3D) surface model of a subject's teeth using the surface information; display the 3D surface model on a display screen in real time as the hand-held wand is moved; determine, in real time, projections into the subject's teeth from the infrared information, and generate one or more images into the subject's teeth from the projections; and display, in real time on the display screen, one or more images into the subject's teeth as the hand-held wand is moved. As described above, the surface information may be processed and/or displayed concurrently with or separately from the infrared information. For example, in variations in which different sleeves are used for surface and infrared (e.g., transillumination) the images into the subject's teeth may be displayed (in real time) when scanning with the infrared (e.g., near-IR) sleeve on the wand, while the surface images may be displayed with the surface scanning sleeve on the wand. In some variations, the surface and near-IR may be scanned concurrently or alternately (e.g., see FIG. 8, above). For example, a sleeve may be configured for operating with both an infrared light source and a visible light source.

The one or more processors may be configured to: display a viewing window over at least a portion the 3D surface model, receive, from a user, a change in a relative position between the viewing window and the 3D surface model, identify, from both the 3D surface model and a plurality of images of the subject's teeth taken from different angles and positions relative to the subject's teeth, a near-infrared (near-IR) image taken at an angle and position that approximates a relative angle and position between the viewing window relative to the 3D surface model, and display the identified near-IR image taken at the angle and position that approximates the angle and position between the viewing window relative to the 3D surface model.

For example, an intraoral scanning system may include: a hand-held wand configured to operate in a plurality of imaging modes, including a near-infrared (near-IR) imaging mode and a visible light imaging mode; a sleeve configure to be placed on a distal end of the hand-held wand; and one or more processors operably connected to the hand-held wand, the one or more processors configured to: receive visible light information during a visible light imaging mode and near-IR light information during a near-IR imaging mode; determine, in real time, surface information from the visible light information and generate a three-dimensional (3D) surface model of a subject's teeth using the surface information; display the 3D surface model on a display screen in real time as the hand-held wand is moved; determine, in real time, projections into the subject's teeth from the near-IR light information, and generate images into the subject's teeth from the projections; and display, in real time on the display screen, the images into the subject's teeth as the hand-held wand is moved.

For example, as described and illustrated above, an intraoral scanning system may include: a hand-held wand configured to operate in a plurality of imaging modes, including a near-infrared (near-IR) imaging mode and a visible light imaging mode; a sleeve configure to be placed on a distal end of the hand-held wand having a transparent window at a distal end region, wherein the sleeve comprises a pair of wings extending on either side of the transparent window, and a near-IR light source in at least one of the wings configured to project near-IR light between the wings; and one or more processors operably connected to the hand-held wand, the one or more processors configured to: receive visible light information during a visible light imaging mode and near-IR light information during a near-IR imaging mode; determine, in real time, surface information from the visible light information and generate a three-dimensional (3D) surface model of a subject's teeth using the surface information; display the 3D surface model on a display screen in real time as the hand-held wand is moved; determine, in real time, projections into the subject's teeth from the near-IR light information, and generate images into the subject's teeth from the projections; and display, in real time on the display screen, the images into the subject's teeth as the hand-held wand is moved.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An intraoral scanning system comprising:
a hand-held wand having at least one camera image sensor and a plurality of light sources, wherein the light sources are configured to emit light at a first spectral range and a second spectral range, wherein the second spectral range is within near-infrared (near-IR) range of wavelengths; and
one or more processors operably connected to the hand-held wand, the one or more processors configured to:
capture and store three-dimensional (3D) surface model data from the at least one camera image sensor while the hand-held wand is emitting light in the first spectral range corresponding to visible light;
capture and store penetrative scan data from the at least one camera image sensor while the hand-held wand is emitting light in the second spectral range comprising near-IR;
capture and display color visible light viewfinder image data from the at least one camera image sensor while the hand-held wand is emitting color visible light;
display, in real time, the 3D surface model data;
display, in real time, the color visible light viewfinder image data;
display one or more penetrative images from the near-IR data.

2. The system of claim 1, wherein the wand comprises a plurality of camera image sensors.

3. The system of claim 1, wherein the 3D surface model data is displayed concurrently with penetrative images.

4. The system of claim 1, wherein the one or more processors are configured to determine and store the location and position of the at least one camera image sensor while capturing the penetrative scan data.

5. The system of claim 1, further wherein the plurality of light sources and the at least one camera image sensor are arranged on the hand-held wand so that light emitted in the second spectral range is reflected from a tooth and received by the at least camera image sensor at an angle of between 0° and 15°.

6. The system of claim 1, wherein the one or more processors is configured to combine the 3D surface model data and the penetrative scan data to form a volumetric model.

7. The system of claim 1, wherein the penetrative scan data and the 3D surface model data is captured and stored concurrently.

8. The system of claim 1, wherein the one or more processors is configured to segment the penetrative scan data.

9. The system of claim 1, wherein the one or more processors is configured to automatically analyze and mark features.

10. The system of claim 1, further comprising a display in communication with the one or more processors.

11. The system of claim 1, wherein the one or more processors is configured to capture the 3D surface model data using structured light triangulation.

12. An intraoral scanning system comprising:
a hand-held wand having at least one camera image sensor and a plurality of light sources, wherein the light sources are configured to emit light at a first spectral range and a second spectral range, wherein the second spectral range is within near-infrared (near-IR) range of wavelengths; and
one or more processors operably connected to the hand-held wand, the one or more processors configured to:
capture and store three-dimensional (3D) surface model data from the at least one camera image sensor while the hand-held wand is emitting light in the first spectral range corresponding to visible light, wherein the one or more processors generate a 3D surface model from the 3D surface model data as the visible light in the first spectral range is captured;
capture and store penetrative scan data from the at least one camera image sensor while the hand-held wand is emitting light in the second spectral range comprising near-IR;
capture and display color visible light viewfinder image data from the at least one camera image sensor while the hand-held wand is emitting color visible light;
display, concurrently and in real time, the 3D surface model and one or more penetrative images from the near-IR data.

13. The system of claim 12, wherein the wand comprises a plurality of camera image sensors.

14. The system of claim 12, wherein the one or more processors are configured to determine and store the location and position of the at least one camera image sensor while capturing the penetrative scan data.

15. The system of claim 12, further wherein the plurality of light sources and the at least one camera image sensor are arranged on the hand-held wand so that light emitted in the second spectral range is reflected from a tooth and received by the at least one camera image sensor at an angle of between 0° and 15°.

16. The system of claim 12, wherein the one or more processors is configured to combine the 3D surface model data and the penetrative scan data to form a volumetric model.

17. The system of claim 12, wherein the penetrative scan data and the 3D surface model data is captured and stored concurrently.

18. The system of claim 12, wherein the one or more processors is configured to segment the penetrative scan data.

19. The system of claim 12, wherein the one or more processors is configured to automatically analyze and mark features.

20. The system of claim 12, further comprising a display in communication with the one or more processors.

21. The system of claim 12, wherein the one or more processors is configured to capture the 3D surface model data using structured light triangulation.

* * * * *